(12) United States Patent
Altenbach et al.

(10) Patent No.: US 10,047,051 B2
(45) Date of Patent: Aug. 14, 2018

(54) SUBSTITUTED PYRIDINES AND METHOD OF USE

(71) Applicants: AbbVie S.á.r.l., Luxembourg (LU); Galapagos NV, Mechelen (BE)

(72) Inventors: Robert J. Altenbach, Chicago, IL (US); Marlon D. Cowart, Round Lake Beach, IL (US); Tom Roger Lisette De Munck, Mechelen (BE); Sébastien Jean Jacques Cédric Dropsit Montovert, Aulnay sous bois (FR); Gregory A. Gfesser, Lindenhurst, IL (US); Hans Kelgtermans, Mechelen (BE); Sébastien Laurent Xavier Martina, Mechelen (BE); Steven Emiel Van der Plas, Mechelen (BE); Xueqing Wang, Northbrook, IL (US)

(73) Assignees: AbbVie S.á.r.l., Luxembourg (LU); Galapagos NV, Mechelen (BE)

( * ) Notice: Subject to any disclaimer, the term of this patent is extended or adjusted under 35 U.S.C. 154(b) by 0 days.

(21) Appl. No.: 15/164,317

(22) Filed: May 25, 2016

(65) Prior Publication Data
US 2016/0355480 A1      Dec. 8, 2016

Related U.S. Application Data

(60) Provisional application No. 62/169,881, filed on Jun. 2, 2015.

(51) Int. Cl.
| | | |
|---|---|---|
| C07D 213/81 | (2006.01) | |
| C07D 213/76 | (2006.01) | |
| C07D 401/12 | (2006.01) | |
| A61K 31/44 | (2006.01) | |
| A61K 31/4427 | (2006.01) | |
| A61K 31/443 | (2006.01) | |
| A61K 31/4439 | (2006.01) | |
| A61K 31/4545 | (2006.01) | |
| A61K 31/506 | (2006.01) | |
| A61K 31/513 | (2006.01) | |
| A61K 31/5377 | (2006.01) | |
| A61K 45/06 | (2006.01) | |
| C07D 401/06 | (2006.01) | |
| C07D 401/14 | (2006.01) | |
| C07D 405/12 | (2006.01) | |
| C07D 491/107 | (2006.01) | |

(52) U.S. Cl.
CPC ............ *C07D 213/81* (2013.01); *A61K 31/44* (2013.01); *A61K 31/443* (2013.01); *A61K 31/4427* (2013.01); *A61K 31/4439* (2013.01); *A61K 31/4545* (2013.01); *A61K 31/506* (2013.01); *A61K 31/513* (2013.01); *A61K 31/5377* (2013.01); *A61K 45/06* (2013.01); *C07D 401/06* (2013.01); *C07D 401/12* (2013.01); *C07D 401/14* (2013.01); *C07D 405/12* (2013.01); *C07D 491/107* (2013.01)

(58) Field of Classification Search
CPC ... C07D 213/76; C07D 213/81; C07D 401/12
See application file for complete search history.

(56) References Cited

U.S. PATENT DOCUMENTS

2011/0230483 A1    9/2011  Baettig et al.

FOREIGN PATENT DOCUMENTS

WO          2013038390 A1       3/2013

OTHER PUBLICATIONS

International Search Report and Written Opinion of the International Searching Authority issued in International Application No. PCT/IB2016/000821, dated Aug. 24, 2016, 11 pages.
Paul M. Quinton, Cystic fibrosis: a disease in electrolyte transport, The FASEB Journal, Jul. 1990, pp. 2709-2717, vol. 4.
Bat-Sheva Kerem, et al., Identification of the Cystic Fibrosis Gene: Genetic Analysis, Science, Aug. 1989, pp. 1073-1080, vol. 245, No. 4922, American Association for the Advancement of Science, Washington, DC.
Joseph L. Bobadilla, et al., Cystic Fibrosis: A Worldwide Analysis of CFTR Mutations—Correlation With Incidence Data and Application to Screening, Human Mutation, Jun. 2001, pp. 575-606, vol. 19, DOI:10.1002/humu.10041, Wiley-Liss, Inc.
Eva A. Pasyk and J. Kevin Foskett, Mutant (ΔF508) Cystic Fibrosis Transmembrane Conductance Regulator Cl-Channel Is Functional When Retained in Endoplasmic Reticulum of Mammalian Cells*, The Journal of Biological Chemistry, May 1995, pp. 12347-12350, vol. 270, No. 21, The American Society for Biochemistry and Molecular Biology, Inc., USA.

*Primary Examiner* — Samira Jean-Louis
(74) *Attorney, Agent, or Firm* — Quarles & Brady LLP

(57) ABSTRACT

The invention discloses compounds of Formula I

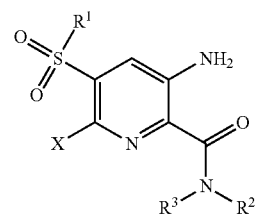

wherein X, $R^1$, $R^2$, and $R^3$ are as defined herein. The present invention relates to compounds and their use in the treatment of cystic fibrosis, methods for their production, pharmaceutical compositions comprising the same, and methods of treating cystic fibrosis by administering a compound of the invention.

47 Claims, No Drawings

SUBSTITUTED PYRIDINES AND METHOD OF USE

CROSS REFERENCE TO RELATED APPLICATIONS

This application claims priority to U.S. Provisional Application No. 62/169,881, filed Jun. 2, 2015, which is incorporated herein by reference in its entirety for all purposes.

BACKGROUND OF THE INVENTION

Technical Field

The invention relates to substituted pyridine compounds that are modulators of the Cystic Fibrosis Transmembrane Conductance Regulator (CFTR) protein, useful in treating diseases and conditions mediated and modulated by CFTR. The invention also relates to compositions containing compounds of the invention, processes for their preparation, and methods of treatment using them.

Description of Related Technology

ABC transporters are a family of homologous membrane transporter proteins regulating the transport of a wide variety of pharmacological agents (for example drugs, xenobiotics, anions, etc.) that bind and use cellular adenosine triphosphate (ATP) for their specific activities. Some of these transporters were found to defend malignant cancer cells against chemotherapeutic agents, acting as multidrug resistance proteins (like the MDR1-P glycoprotein, or the multidrug resistance protein, MRP 1). So far, 48 ABC transporters, grouped into 7 families based on their sequence identity and function, have been identified.

ABC transporters provide protection against harmful environmental compounds by regulating a variety of important physiological roles within the body, and therefore represent important potential drug targets for the treatment of diseases associated with transporter defects, outwards cell drug transport, and other diseases in which modulation of ABC transporter activity may be beneficial.

The cAMP/ATP-mediated anion channel, CFTR, is one member of the ABC transporter family commonly associated with diseases, which is expressed in a variety of cell types, including absorptive and secretory epithelia cells, where it regulates anion flux across the membrane, as well as the activity of other ion channels and proteins. The activity of CFTR in epithelial cells is essential for the maintenance of electrolyte transport throughout the body, including respiratory and digestive tissue (Quinton, P. M., 1990. Cystic fibrosis: a disease in electrolyte transport. FASEB J. 4, 2709-2717).

The gene encoding CFTR has been identified and sequenced (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking.

Cystic fibrosis (CF) is caused by a defect in this gene which induces mutations in CFTR. Cystic fibrosis is the most common fatal genetic disease in humans, and affects ~0.04% of white individuals (Bobadilla, J. L., Macek, M., Jr, Fine, J. P., Farrell, P. M., 2002. Cystic fibrosis: a worldwide analysis of CFTR mutations—correlation with incidence data and application to screening. Hum. Mutat. 19, 575-606. doi:10.1002/humu.10041), for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections.

In cystic fibrosis patients, mutations in endogenous respiratory epithelial CFTR fails to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects with cystic fibrosis suffer from decreased fertility, whilst males with cystic fibrosis are infertile.

A variety of disease causing mutations has been identified through sequence analysis of the CFTR gene of CF chromosomes (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). ΔF508-CFTR, the most common CF mutation (present in at least 1 allele in ~90% of CF patients) and occurring in approximately 70% of the cases of cystic fibrosis, contains a single amino acid deletion of phenylalanine 508.

This deletion prevents the nascent protein from folding correctly, which protein in turn cannot exit the endoplasmic reticulum (ER) and traffic to the plasma membrane, and then is rapidly degraded. As a result, the number of channels present in the membrane is far less than in cells expressing wild-type CFTR. In addition to impaired trafficking, the mutation results in defective channel gating. Indeed, even if ΔF508-CFTR is allowed to reach the cell plasma membrane by low-temperature (27° C.) rescue where it can function as a cAMP-activated chloride channel, its activity is decreased significantly compared with WT-CFTR (Pasyk, E. A., Foskett, J. K., 1995. Mutant (δF508) Cystic Fibrosis Transmembrane Conductance Regulator Cl⁻ Channel Is Functional When Retained in Endoplasmic Reticulum of Mammalian Cells. J. Biol. Chem. 270, 12347-12350).

Other mutations with lower incidence have also been identified that alter the channel regulation or the channel conductance. In case of the channel regulation mutants, the mutated protein is properly trafficked and localized to the plasma membrane but either cannot be activated or cannot function as a chloride channel (e.g. missense mutations located within the nucleotide binding domains), examples of these mutations are G551D, G178R, and G1349D. Mutations affecting chloride conductance have a CFTR protein that is correctly trafficked to the cell membrane but that generates reduced chloride flow (e.g. missense mutations located within the membrane-spanning domain), examples of these mutations are R117H and R334W.

In addition to cystic fibrosis, CFTR activity modulation may be beneficial for other diseases not directly caused by mutations in CFTR, such as, for example, chronic obstructive pulmonary disease (COPD), dry eye disease, and Sjogren's Syndrome.

COPD is characterized by a progressive and non-reversible airflow limitation, which is due to mucus hypersecretion, bronchiolitis, and emphysema. A potential treatment of mucus hypersecretion and impaired mucociliary clearance that is common in COPD could consist in using activators of mutant or wild-type CFTR. In particular, the anion secretion increase across CFTR may facilitate fluid transport into the airway surface liquid to hydrate the mucus and optimize periciliary fluid viscosity. The resulting enhanced mucociliary clearance would help in reducing the symptoms associated with COPD.

Dry eye disease is characterized by a decrease in tear production and abnormal tear film lipid, protein and mucin profiles. Many factors may cause dry eye disease, some of which include age, arthritis, Lasik eye surgery, chemical/thermal burns, medications, allergies, and diseases, such as cystic fibrosis and Sjogrens's syndrome. Increasing anion secretion via CFTR could enhance fluid transport from the corneal endothelial cells and secretory glands surrounding the eye, and eventually improve corneal hydration, thus helping to alleviate dry eye disease associated symptoms. Sjogrens's syndrome is an autoimmune disease where the immune system harms moisture-producing glands throughout the body, including the eye, mouth, skin, respiratory tissue, liver, vagina, and gut. The ensuing symptoms, include, dry eye, mouth, and vagina, as well as lung disease. Sjogrens's syndrome is also associated with rheumatoid arthritis, systemic lupus, systemic sclerosis, and polymyositis/dermatomyositis. The cause of the disease is believed to lie in defective protein trafficking, for which treatment options are limited. As a consequence, modulation of CFTR activity may help hydrating the various organs and help to elevate the associated symptoms.

In addition to CF, the defective protein trafficking induced by the ΔF508-CFTR has been shown to be the underlying basis for a wide range of other diseases, in particular diseases where the defective functioning of the endoplasmic reticulum (ER) may either prevent the CFTR protein to exit the cell, and/or the misfolded protein is degraded (Morello, J.-P., Bouvier, M., Petäjä-Repo, U. E., Bichet, D. G., 2000. Pharmacological chaperones: a new twist on receptor folding. Trends Pharmacol. Sci. 21, 466-469. doi:10.1016/S0165-6147(00)01575-3; Shastry, B. S., 2003. Neurodegenerative disorders of protein aggregation. Neurochem. Int. 43, 1-7. doi:10.1016/S0197-0186(02)00196-1; Zhang, W., Fujii, N., Naren, A. P., 2012. Recent advances and new perspectives in targeting CFTR for therapy of cystic fibrosis and enterotoxin-induced secretory diarrheas. Future Med. Chem. 4, 329-345. doi: 10.4155/fmc.12.1).

A number of genetic diseases are associated with a defective ER processing equivalent to the defect observed with CFTR in CF such as glycanosis CDG type 1, hereditary emphysema (α-1-antitrypsin (PiZ variant)), congenital hyperthyroidism, osteogenesis imperfecta (Type I, II, or IV procollagen), hereditary hypofibrinogenemia (fibrinogen), ACT deficiency (α-1-antichymotrypsin), diabetes insipidus (DI), neurophyseal DI (vasopvessin hormone N2-receptor), neprogenic DI (aquaporin II), Charcot-Marie Tooth syndrome (peripheral myelin protein 22), Perlizaeus-Merzbacher disease, neurodegenerative diseases such as Alzheimer's disease (APP and presenilins), Parkinson's disease, amyotrophic lateral sclerosis, progressive supranuclear palsy, Pick's disease, several polyglutamine neurological disorders such as Huntington's disease, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (prion protein processing defect), Fabry disease (lysosomal α-galactosidase A), Straussler-Scheinker syndrome, chronic obstructive pulmonary disease (COPD), dry eye disease, and Sjogren's Syndrome.

In addition to up-regulation of the activity of CFTR, anion secretion reduction by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Regardless of the cause, excessive chloride transport is seen in all diarrheas, and results in dehydration, acidosis, impaired growth and death. Acute and chronic diarrheas remain a major medical problem worldwide, and are a significant factor in malnutrition, leading to death in children of less than five years old (5,000,000 deaths/year). Furthermore, in patients with chronic inflammatory bowel disease (IBD) and/or acquired immunodeficiency syndrome (AIDS), diarrhea is a dangerous condition.

Accordingly, there is a need for novel compounds able to modulate CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

In one aspect the invention provides for compounds of Formula I

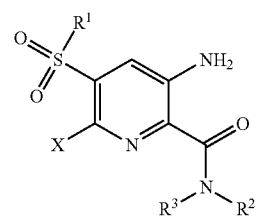

I or a pharmaceutically acceptable salt thereof, wherein:
X is
  H;
  halo;
  $C_{1-4}$ alkyl optionally substituted with one or more independently selected halo;
  $C_{1-4}$ alkoxy optionally substituted with one or more independently selected
    —OH;
    $C_{1-4}$ alkoxy; or
    —$NR^{11A}R^{11B}$;
  —$NR^{12A}R^{12B}$;
  cyclopropyl optionally substituted with one or more independently selected $R^5$ groups;
  phenoxy optionally substituted with one or more independently selected $R^5$ groups; or
  phenyl optionally substituted with one or more independently selected $R^5$ groups;

$R^1$ is
- $C_{1-4}$ alkyl optionally substituted with one or more independently selected
  - —OH;
  - $C_{1-4}$ alkoxy; or
  - 4-6 membered monocyclic heterocycle comprising 1 or 2 heteroatoms independently selected from the group consisting of O, S, and N;
- phenyl optionally substituted with one or more independently selected $R^4$ groups;
- N-linked 4-6 membered monocyclic heterocycle comprising 1, 2, or 3 heteroatoms independently selected from the group consisting of N, O, and S, wherein the monocyclic heterocycle is optionally substituted with one or more independently selected $R^5$ groups;
- N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with one or more independently selected $R^5$ groups;
- $C_{3-7}$ cycloalkyl optionally substituted with one or more independently selected $R^5$ groups; or
- —$NR^6R^7$;

$R^2$ is
- H;
- $C_{1-6}$ alkyl optionally substituted with one or more independently selected
  - —OH;
  - halo;
  - $C_{1-4}$ alkoxy optionally substituted with one or more independently selected
    - halo;
    - $C_{1-4}$ alkoxy;
  - $C_{3-7}$ cycloalkyl optionally substituted with one or more independently selected $R^5$ groups; or
  - 4-6 membered monocyclic heterocycle comprising 1 or 2 heteroatoms independently selected from the group consisting of N, O, and S, wherein the monocyclic heterocycle is optionally substituted with one or more independently selected $R^5$ groups;
  - —C(=O)$NR^{8a}R^{8b}$;
- $C_{3-7}$ cycloalkyl optionally substituted with one or more independently selected
  - —OH;
  - halo;
  - $C_{1-4}$ alkoxy optionally substituted with one or more independently selected halo; or
  - $C_{1-4}$ alkyl optionally substituted with one or more independently selected —OH, halo, or $C_{1-4}$ alkoxy;
- 4-6 membered monocyclic heterocycle comprising 1 or 2 heteroatoms independently selected from the group consisting of N, O, and S, wherein the monocyclic heterocycle is optionally substituted with one or more independently selected
  - —OH;
  - halo;
  - $C_{1-4}$ alkoxy optionally substituted with one or more independently selected halo, or
  - $C_{1-4}$ alkyl optionally substituted with one or more independently selected halo;
- 5-6 membered monocyclic heteroaryl comprising 1, 2, or 3 heteroatoms independently selected from the group consisting of O, S, and N, wherein the monocyclic heteroaryl is optionally substituted with one or more independently selected $R^5$ groups; or
- phenyl optionally substituted with one or more independently selected $R^5$ groups;
- $C_{3-7}$ cycloalkyl optionally substituted with one or more
  - —OH;
  - halo;
  - $C_{1-4}$ alkyl optionally substituted with one or more independently selected halo or —OH; or
  - $C_{1-4}$ alkoxy optionally substituted with one or more independently selected halo;
- 4-6 membered monocyclic heterocycle comprising 1 or 2 heteroatoms independently selected from the group consisting of O, S, and N, wherein the monocyclic heterocycle is optionally substituted with one or more
  - —OH;
  - halo;
  - $C_{1-4}$ alkyl optionally substituted with one or more independently selected halo; or
  - $C_{1-4}$ alkoxy optionally substituted with one or more independently selected halo;
- 4-6 membered monocyclic heterocycle comprising 1 or 2 heteroatoms independently selected from the group consisting of O, S, and N, fused to a phenyl ring, wherein the monocyclic heterocycle and the phenyl are optionally substituted with one or more independently selected $R^5$ groups;
- 5-11 membered spirocyclic heterocycle comprising 1 or 2 heteroatoms independently selected from the group consisting of O, S, and N, wherein the spirocyclic heterocycle is optionally substituted with one or more independently selected $R^5$ groups;
- 5-6 membered monocyclic heteroaryl comprising 1, 2, or 3 heteroatoms independently selected from the group consisting of O, S, and N, wherein the monocyclic heteroaryl is optionally substituted with one or more independently selected $R^5$ groups; or
- —NHC(=O)$R^{13}$;

and $R^3$ is H; or
$R^2$ and $R^3$, together with the nitrogen atom to which they are attached form
- an azetidine or a pyrrolidine ring, wherein the azetidine and the pyrrolidine are optionally substituted with one or more independently selected $R^9$ groups; or
- a 7-11 membered spirocyclic heterocycle comprising one or more heteroatoms independently selected from the group consisting of N, O, and S; wherein the spirocyclic heterocycle is optionally substituted with one or more independently selected $R^5$ groups;

each $R^4$ is independently selected from the group consisting of:
- halo;
- $C_{1-4}$ alkyl optionally substituted with one or more independently selected halo; and
- $C_{1-4}$ alkoxy optionally substituted with one or more independently selected halo;

each $R^5$ is independently selected from the group consisting of:
- —OH;
- halo;
- $C_{1-4}$ alkyl optionally substituted with one or more independently selected
  - $C_{1-4}$ alkoxy;
  - halo; or
  - —OH; and
- $C_{1-4}$ alkoxy optionally substituted with one or more independently selected halo;

$R^6$ is H, $C_{1-4}$ alkyl, or $C_{3-7}$ cycloalkyl wherein the $C_{3-7}$ cycloalkyl is optionally substituted with one or more independently selected $R^5$ groups;

$R^7$ is
$C_{1-4}$ alkyl optionally substituted with one or more independently selected
halo;
phenyl optionally substituted with one or more independently selected
halo;
$C_{1-4}$ alkyl optionally substituted with one or more independently selected halo; or
$C_{1-4}$ alkoxy optionally substituted with one or more independently selected halo;
$C_{1-4}$ alkoxy optionally substituted with one or more independently selected halo; or
4-6 membered monocyclic heterocycle comprising 1 or 2 heteroatoms independently selected from the group consisting of O, S, and N; wherein the monocyclic heterocycle is optionally substituted with one or more independently selected $R^5$ groups;

each $R^{8a}$ and $R^{8b}$ is independently selected from the group consisting of
H;
$C_{1-4}$ alkyl optionally substituted with one or more independently selected halo; and
$C_{3-7}$ cycloalkyl optionally substituted with one or more independently selected $R^5$ groups;

each $R^9$ is independently selected from the group consisting of:
—OH;
halo;
—CN;
$C_{1-4}$ alkyl optionally substituted with one or more independently selected
—OH;
halo; or
$C_{1-4}$ alkoxy;
$C_{1-4}$ alkoxy optionally substituted with one or more independently selected halo;
$C_{3-7}$ cycloalkyl optionally substituted with one or more independently selected $R^5$ groups;
—C(=O)N$R^{10a}R^{10b}$; and
4-6 membered monocyclic heterocycle comprising 1 or 2 heteroatoms independently selected from the group consisting of O, S, and N, wherein the monocyclic heterocycle is optionally substituted with one or more independently selected $R^5$ groups;

each $R^{10a}$ and $R^{10b}$ is independently selected from the group consisting of H and $C_{1-4}$ alkyl;

each $R^{11a}$ and $R^{11b}$ is independently selected from the group consisting of
H; and
$C_{1-4}$ alkyl;

$R^{12a}$ and $R^{12b}$ are independently selected from the group consisting of
H;
$C_{1-4}$ alkyl; and
$C_{3-7}$ cycloalkyl; and $R^{13}$ is independently $C_{1-4}$ alkyl optionally substituted with one or more independently selected
—OH;
halo; or
$C_{1-4}$ alkoxy.

Another aspect of the invention relates to pharmaceutical compositions comprising a compound of the invention, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator activity. In a particular aspect, the pharmaceutical compositions may additionally comprise further therapeutically active ingredients suitable for use in combination with the compounds of the invention. In a more particular aspect, the further therapeutically active ingredient is an agent for the treatment of cystic fibrosis.

Moreover, the compounds of the invention, useful in the pharmaceutical compositions and treatment methods disclosed herein, are pharmaceutically acceptable as prepared and used.

Yet another aspect of the invention relates to a method for treating, or preventing conditions and disorders related to Cystic Fibrosis Transmembrane Conductance Regulator activity in mammals. More particularly, the method is useful for treating or preventing conditions and disorders related to cystic fibrosis, Sjögren's syndrome, pancreatic insufficiency, chronic obstructive lung disease, or chronic obstructive airway disease. Accordingly, the compounds and compositions of the invention are useful as a medicament for treating or preventing Cystic Fibrosis Transmembrane Conductance Regulator modulated disease.

The compounds, compositions comprising the compounds, methods for making the compounds, and methods for treating or preventing conditions and disorders by administering the compounds are further described herein.

In a particular aspect, the compounds of the invention are provided for use in the treatment of cystic fibrosis. In a particular aspect, the compounds of the invention are provided for use in the treatment of cystic fibrosis caused by class I, II, III, IV, and/or VI mutations.

The present invention also provides pharmaceutical compositions comprising a compound of the invention, and a suitable pharmaceutical carrier for use in medicine. In a particular aspect, the pharmaceutical composition is for use in the treatment of cystic fibrosis.

These and other objects of the invention are described in the following paragraphs. These objects should not be deemed to narrow the scope of the invention.

DETAILED DESCRIPTION OF THE INVENTION

Described herein are compounds of Formula I

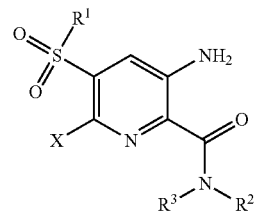

wherein X, $R^1$, $R^2$, and $R^3$ are defined above in the Summary and below in the Detailed Description. Further, compositions comprising such compounds and methods for treating conditions and disorders using such compounds and compositions are also included.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning presented therewith below:

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. In some instances, the number of carbon atoms in an alkoxy moiety is indicated by the prefix "$C_{x-y}$", wherein x is the minimum and y is the maximum number of carbon atoms in the substituent. Thus, for example, "$C_{1-6}$ alkoxy" means an alkoxy substituent containing from 1 to 6 carbon atoms and "$C_{1-4}$ alkoxy" means an alkoxy substituent containing from 1 to 4 carbon atoms.

The term "alkyl" as used herein, means a saturated, straight or branched hydrocarbon chain radical. In some instances, the number of carbon atoms in an alkyl moiety is indicated by the prefix "$C_{x-y}$", wherein x is the minimum and y is the maximum number of carbon atoms in the substituent. Thus, for example, "$C_{1-6}$ alkyl" means an alkyl substituent containing from 1 to 6 carbon atoms and "$C_{1-4}$ alkyl" means an alkyl substituent containing from 1 to 4 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl.

The term "$C_{3-7}$ cycloalkyl" as used herein, means cyclopropyl, cyclobutyl, cyclopentyl, cyclohexyl, and cycloheptyl, each of which is optionally substituted unless otherwise indicated.

The term "$C_{3-6}$ cycloalkyl" as used herein, means cyclopropyl, cyclobutyl, cyclopentyl, and cyclohexyl, each of which is optionally substituted unless otherwise indicated.

The term "$C_{4-6}$ cycloalkyl" as used herein, means cyclobutyl, cyclopentyl, and cyclohexyl, each of which is optionally substituted unless otherwise indicated.

The term "halo" or "halogen" as used herein, means chloro (Cl), bromo (Br), iodo (I), and fluoro (F).

The term "monocyclic heterocycle" or "monocyclic heterocyclic" as used herein, means a three-, four-, five-, six-, seven-, or eight-membered fully saturated monocyclic carbocyclic ring wherein one or more carbon ring atom is replaced by heteroatom independently selected from the group consisting of O, N, and S. 3- and 4-Membered monocyclic heterocycle have one carbon ring atom replaced by a heteroatom selected from the group consisting of O, N, and S. 5-, 6-, 7-, and 8-Membered monocyclic heterocycle may have one, two, or three carbon ring atoms replaced by heteroatoms selected from the group consisting of O, N, and S. Examples of five-membered monocyclic heterocycle include those containing in the ring: 1 O; 1 S; 1 N; 2 N; 3 N; 1 S and 1 N; 1 S, and 2 N; 1 O and 1 N; or 1 O and 2 N. Non-limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, isoxazolidinyl, pyrazolidinyl, pyrazolinyl, pyrrolidinyl, 2-pyrrolinyl, 3-pyrrolinyl, thiazolinyl, and thiazolidinyl. Examples of six-membered monocyclic heterocyclic include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of 6-membered monocyclic heterocyclic groups include tetrahydropyranyl, dihydropyranyl, 1,4-dioxanyl, 1,4-dithianyl, hexahydropyrimidine, morpholinyl, piperazinyl, piperidinyl, 1,2,3,6-tetrahydropyridinyl, tetrahydrothiopyranyl, thiomorpholinyl, thioxanyl, and trithianyl. Representative examples of monocyclic heterocycles include, but are not limited to, azetidinyl, azepanyl, aziridinyl, diazepanyl, 1,4-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl.

The term "4-6 membered monocyclic heterocycle" or "4-6 membered monocyclic heterocyclic" as used herein, means a 4-, 5-, or 6-membered monocyclic heterocycle as defined herein above. Non-limiting examples of 4-6 membered monocyclic heterocycle include azetidinyl, oxetanyl, 1,3-dioxolanyl, pyrrolidinyl, tetrahydrofuranyl, tetrahydropyranyl, 1,4-dioxanyl, piperazinyl, piperidinyl, thiomorpholinyl, and morpholinyl.

The term "3-6 membered monocyclic heterocycle" or "3-6 membered monocyclic heterocyclic" as used herein, means a 3-, 4-, 5-, or 6-membered monocyclic heterocycle as defined herein above. Non-limiting examples of 3-6 membered monocyclic heterocycle include aziridinyl, azetidinyl, oxetanyl, pyrrolidinyl, tetrahydrofuranyl, tetrahydropyranyl, piperazinyl, piperidinyl, thiomorpholinyl, and morpholinyl.

The term "5-11 membered spiro heterocycle" as used herein, means a 3-6 membered monocyclic heterocycle wherein two substituents on the same carbon atom of the 3-6 membered monocyclic heterocycle ring together with said carbon atom form a second ring system; wherein the second ring system is a $C_{3-6}$ cycloalkyl or a 3-6 membered monocyclic heterocycle. Examples of 5-11 membered spiro heterocycle include, but not limited to, 1-oxaspiro[4.4]non-3-yl, and 1-oxaspiro[4.5]decan-3-yl.

The term "7-11 membered spiro heterocycle" as used herein, means a 4-6 membered monocyclic heterocycle wherein two substituents on the same carbon atom of the 4-6 membered monocyclic heterocycle ring together with said carbon atom form a second ring system; wherein the second ring system is a $C_{4-6}$ cycloalkyl or a 4-6 membered monocyclic heterocycle. Particular examples of 7-11 membered spiro heterocycles are 6-oxa-2-azaspiro[3.5]nonyl, 6-oxa-2-azaspiro[3.4]octyl, and 2-oxa-6-azaspiro[3.3]heptyl.

The monocyclic heterocycles and the spiro heterocycles, including the exemplary rings, optionally substituted, and are connected to the parent molecular moiety through any carbon atom or any nitrogen atom contained within the ring systems, unless otherwise indicated. The nitrogen atoms within the heterocycle rings may optionally be oxidized or may optionally be quaternized.

The term "5-6 membered monocyclic heteroaryl" as used herein, means a five- or six-membered monocyclic aromatic ring structure wherein one or more of the ring carbon atoms are replaced with heteroatom(s) independently selected from the group consisting of O, N, and S. The five-membered ring contains two double bonds. The 5 membered ring may also contain one heteroatom selected from the group consisting of O and S; or may contain one, two, three, or four nitrogen atoms and optionally one oxygen or one sulfur atom. The 6-membered ring contains three double bonds and one, two, three or four nitrogen atoms. Representative examples of 5-6 membered monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The 5-6 membered monocyclic heteroaryls, including exemplary rings, are optionally substituted unless otherwise indicated, and are connected to the parent molecular moiety through any substitutable carbon atom or any substitutable nitrogen atom contained within the ring systems. The nitrogen atom in the heteroaryl rings may optionally be oxidized and may optionally be quaternized.

The term "phenoxy" as used herein means a phenyl appended to the parent molecular moiety through an oxygen atom.

The term "heteroatom" as used herein, means a nitrogen (N), oxygen (O), or sulfur (S).

The term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^{3}$H (tritium), $^{14}$C, $^{11}$C, $^{15}$O, $^{18}$F, $^{35}$S, $^{123}$I, and $^{125}$I.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The term 'substituted with one or more' refers to one to four substituents. In one embodiment it refers to one to three substituents. In further embodiments it refers to one or two substituents. In a yet further embodiment it refers to one substituent.

The terms "treat", "treating", and "treatment" refer to a method of alleviating or abrogating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of, or to alleviate to some extent, one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In preferred embodiments, the subject is a human. The terms "human," "patient," and "subject" are used interchangeably herein.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G; G1349D; S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326delTC, or 4279insA mutations. More particularly, Class VI mutation(s) refers to Rescued F508del mutations.

Compounds

Compounds of the invention have the general Formula I as described above.

Particular values of variable groups are as follows. Such values may be used where appropriate with any of the other values, definitions, claims or embodiments defined hereinbefore or hereinafter.

In certain embodiments of Formula I,

X is
  H;
  halo;
  $C_{1-4}$ alkyl optionally substituted with one or more independently selected halo;
  $C_{1-4}$ alkoxy optionally substituted with one or more independently selected
    —OH;
    $C_{1-4}$ alkoxy; or
    —NR$^{11A}$R$^{11B}$;
  —NR$^{12A}$R$^{12B}$;
  cyclopropyl optionally substituted with one or more independently selected R$^5$ groups; phenoxy optionally substituted with one or more independently selected R$^5$ groups; or phenyl optionally substituted with one or more independently selected R$^5$ groups;

R$^1$ is
  $C_{1-4}$ alkyl optionally substituted with one or more independently selected
    —OH;
    $C_{1-4}$ alkoxy; or
    4-6 membered monocyclic heterocycle comprising 1 or 2 heteroatoms independently selected from the group consisting of O, S, and N;
  phenyl optionally substituted with one or more independently selected R$^4$ groups;
  N-linked 4-6 membered monocyclic heterocycle comprising 1, 2, or 3 heteroatoms independently selected from the group consisting of N, O, and S, wherein the monocyclic heterocycle is optionally substituted with one or more independently selected R$^5$ groups;
  N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with one or more independently selected R$^5$ groups;
  $C_{3-7}$ cycloalkyl optionally substituted with one or more independently selected R$^5$ groups; or
  —NR$^6$R$^7$;

R$^2$ is
  $C_{1-6}$ alkyl optionally substituted with one or more independently selected
    —OH;
    halo;
    $C_{1-4}$ alkoxy optionally substituted with one or more independently selected
      halo;
      $C_{1-4}$ alkoxy;
    $C_{3-7}$ cycloalkyl optionally substituted with one or more independently selected R$^5$ groups; or
    4-6 membered monocyclic heterocycle comprising 1 or 2 heteroatoms independently selected from the group consisting of N, O, and S, wherein the monocyclic heterocycle is optionally substituted with one or more independently selected R$^5$ groups;
  —C(=O)NR$^{8a}$R$^{8b}$;
  $C_{3-7}$ cycloalkyl optionally substituted with one or more independently selected
    —OH;
    halo;
    $C_{1-4}$ alkoxy optionally substituted with one or more independently selected halo; or
    $C_{1-4}$ alkyl optionally substituted with one or more independently selected —OH, halo, or $C_{1-4}$ alkoxy;
  4-6 membered monocyclic heterocycle comprising 1 or 2 heteroatoms independently selected from the group consisting of N, O, and S, wherein the monocyclic heterocycle is optionally substituted with one or more independently selected
    —OH;
    halo;
    $C_{1-4}$ alkoxy optionally substituted with one or more independently selected halo, or
    $C_{1-4}$ alkyl optionally substituted with one or more independently selected halo;
  5-6 membered monocyclic heteroaryl comprising 1, 2, or 3 heteroatoms independently selected from the group consisting of O, S, and N, wherein the monocyclic heteroaryl is optionally substituted with one or more independently selected R$^5$ groups; or
  phenyl optionally substituted with one or more independently selected R$^5$ groups;
  $C_{3-7}$ cycloalkyl optionally substituted with one or more
    —OH;
    halo;
    $C_{1-4}$ alkyl optionally substituted with one or more independently selected halo or —OH; or $C_{1-4}$ alkoxy optionally substituted with one or more independently selected halo;

4-6 membered monocyclic heterocycle comprising 1 or 2 heteroatoms independently selected from the group consisting of O, S, and N, wherein the monocyclic heterocycle is optionally substituted with one or more
—OH;
halo;
$C_{1-4}$ alkyl optionally substituted with one or more independently selected halo; or
$C_{1-4}$ alkoxy optionally substituted with one or more independently selected halo;

4-6 membered monocyclic heterocycle comprising 1 or 2 heteroatoms independently selected from the group consisting of O, S, and N, fused to a phenyl ring, wherein the monocyclic heterocycle and the phenyl are optionally substituted with one or more independently selected $R^5$ groups;

5-11 membered spirocyclic heterocycle comprising 1 or 2 heteroatoms independently selected from the group consisting of O, S, and N, wherein the spirocyclic heterocycle is optionally substituted with one or more independently selected $R^5$ groups;

5-6 membered monocyclic heteroaryl comprising 1, 2, or 3 heteroatoms independently selected from the group consisting of O, S, and N, wherein the monocyclic heteroaryl is optionally substituted with one or more independently selected $R^5$ groups; or

—NHC(=O)$R^{13}$;

and $R^3$ is H; or $R^2$ and $R^3$, together with the nitrogen atom to which they are attached form
an azetidine or a pyrrolidine ring, wherein the azetidine and the pyrrolidine are optionally substituted with one or more independently selected $R^9$ groups; or
a 7-11 membered spirocyclic heterocycle comprising one or more heteroatoms independently selected from the group consisting of N, O, and S; wherein the spirocyclic heterocycle is optionally substituted with one or more independently selected $R^5$ groups;

each $R^4$ is independently selected from the group consisting of:
halo;
$C_{1-4}$ alkyl optionally substituted with one or more independently selected halo; and
$C_{1-4}$ alkoxy optionally substituted with one or more independently selected halo;

each $R^5$ is independently selected from the group consisting of:
—OH;
halo;
$C_{1-4}$ alkyl optionally substituted with one or more independently selected
$C_{1-4}$ alkoxy;
halo; or
—OH; and
$C_{1-4}$ alkoxy optionally substituted with one or more independently selected halo;

$R^6$ is H, $C_{1-4}$ alkyl, or $C_{3-7}$ cycloalkyl wherein the $C_{3-7}$ cycloalkyl is optionally substituted with one or more independently selected $R^5$ groups;

$R^7$ is
$C_{1-4}$ alkyl optionally substituted with one or more independently selected
halo;

phenyl optionally substituted with one or more independently selected
halo;
$C_{1-4}$ alkyl optionally substituted with one or more independently selected halo; or
$C_{1-4}$ alkoxy optionally substituted with one or more independently selected halo;
$C_{1-4}$ alkoxy optionally substituted with one or more independently selected halo; or
4-6 membered monocyclic heterocycle comprising 1 or 2 heteroatoms independently selected from the group consisting of O, S, and N; wherein the monocyclic heterocycle is optionally substituted with one or more independently selected $R^5$ groups;

each $R^{8a}$ and $R^{8b}$ is independently selected from the group consisting of
H;
$C_{1-4}$ alkyl optionally substituted with one or more independently selected halo; and
$C_{3-7}$ cycloalkyl optionally substituted with one or more independently selected $R^5$ groups;

each $R^9$ is independently selected from the group consisting of:
—OH;
halo;
—CN;
$C_{1-4}$ alkyl optionally substituted with one or more independently selected
—OH;
halo; or
$C_{1-4}$ alkoxy;
$C_{1-4}$ alkoxy optionally substituted with one or more independently selected halo;
$C_{3-7}$ cycloalkyl optionally substituted with one or more independently selected $R^5$ groups;
—C(=O)NR$^{10a}$R$^{10b}$; and
4-6 membered monocyclic heterocycle comprising 1 or 2 heteroatoms independently selected from the group consisting of O, S, and N, wherein the monocyclic heterocycle is optionally substituted with one or more independently selected $R^5$ groups;

each $R^{10a}$ and $R^{10b}$ is independently selected from the group consisting of H and $C_{1-4}$ alkyl;

each $R^{11a}$ and $R^{11b}$ is independently selected from the group consisting of
H; and
$C_{1-4}$ alkyl;

$R^{12a}$ and $R^{12b}$ are independently selected from the group consisting of
H;
$C_{1-4}$ alkyl; and
$C_{3-7}$ cycloalkyl; and $R^{13}$ is independently $C_{1-4}$ alkyl optionally substituted with one or more independently selected
—OH;
halo; or
$C_{1-4}$ alkoxy.

In one embodiment of Formula I,
X is
H;
halo;
$C_{1-4}$ alkyl optionally substituted with one or more independently selected halo;
cyclopropyl optionally substituted with one or more independently selected $R^5$ groups; or
phenyl optionally substituted with one or more independently selected $R^5$ groups;

$R^1$ is
- phenyl optionally substituted with one or more independently selected $R^4$ groups;
- N-linked 4-6 membered monocyclic heterocycle comprising 1, 2, or 3 heteroatoms independently selected from the group consisting of N, O, and S, wherein the monocyclic heterocycle is optionally substituted with one or more independently selected $R^5$ groups;
- N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with one or more independently selected $R^5$ groups; or
- —$NR^6R^7$;

$R^2$ is
- $C_{1-6}$ alkyl optionally substituted with one or more independently selected
  - —OH;
  - halo;
  - $C_{1-4}$ alkoxy optionally substituted with one or more independently selected
    - halo;
  - $C_{1-4}$ alkoxy;
  - $C_{3-7}$ cycloalkyl optionally substituted with one or more independently selected $R^5$ groups; or
  - 4-6 membered monocyclic heterocycle comprising 1 or 2 heteroatoms independently selected from the group consisting of N, O, and S, wherein the monocyclic heterocycle is optionally substituted with one or more independently selected $R^5$ groups;
- —$C(=O)NR^{8a}R^{8b}$;
- $C_{3-7}$ cycloalkyl optionally substituted with one or more independently selected
  - —OH;
  - halo;
  - $C_{1-4}$ alkoxy optionally substituted with one or more independently selected halo; or
  - $C_{1-4}$ alkyl optionally substituted with one or more independently selected —OH, halo, or $C_{1-4}$ alkoxy;
- 4-6 membered monocyclic heterocycle comprising 1 or 2 heteroatoms independently selected from the group consisting of N, O, and S, wherein the monocyclic heterocycle is optionally substituted with one or more independently selected
  - —OH;
  - halo;
  - $C_{1-4}$ alkoxy optionally substituted with one or more independently selected halo, or
  - $C_{1-4}$ alkyl optionally substituted with one or more independently selected halo;
- 5-6 membered monocyclic heteroaryl comprising 1, 2, or 3 heteroatoms independently selected from the group consisting of O, S, and N, wherein the monocyclic heteroaryl is optionally substituted with one or more independently selected $R^5$ groups; or
- phenyl optionally substituted with one or more independently selected $R^5$ groups;
- $C_{3-7}$ cycloalkyl optionally substituted with one or more
  - —OH;
  - halo;
  - $C_{1-4}$ alkyl optionally substituted with one or more independently selected halo; or
  - $C_{1-4}$ alkoxy optionally substituted with one or more independently selected halo;
- 4-6 membered monocyclic heterocycle comprising 1 or 2 heteroatoms independently selected from the group consisting of O, S, and N, wherein the monocyclic heterocycle is optionally substituted with one or more
  - —OH;
  - halo;
  - $C_{1-4}$ alkyl optionally substituted with one or more independently selected halo; or
  - $C_{1-4}$ alkoxy optionally substituted with one or more independently selected halo;
- 4-6 membered monocyclic heterocycle comprising 1 or 2 heteroatoms independently selected from the group consisting of O, S, and N, fused to a phenyl ring, wherein the monocyclic heterocycle and the phenyl are optionally substituted with one or more independently selected $R^5$ groups; or
- 5-11 membered spirocyclic heterocycle comprising 1 or 2 heteroatoms independently selected from the group consisting of O, S, and N, wherein the spirocyclic heterocycle is optionally substituted with one or more independently selected $R^5$ groups;

and $R^3$ is H; or $R^2$ and $R^3$, together with the nitrogen atom to which they are attached form
- an azetidine or a pyrrolidine ring, wherein the azetidine and the pyrrolidine are optionally substituted with one or more independently selected $R^9$ groups; or
- a 7-11 membered spirocyclic heterocycle comprising one or more heteroatoms independently selected from the group consisting of N, O, and S; wherein the spirocyclic heterocycle is optionally substituted with one or more independently selected $R^5$ groups;

each $R^4$ is independently selected from the group consisting of:
- halo;
- $C_{1-4}$ alkyl optionally substituted with one or more independently selected halo; and
- $C_{1-4}$ alkoxy optionally substituted with one or more independently selected halo;

each $R^5$ is independently selected from the group consisting of:
- halo;
- $C_{1-4}$ alkyl optionally substituted with one or more independently selected halo; and
- $C_{1-4}$ alkoxy optionally substituted with one or more independently selected halo;

$R^6$ is H, $C_{1-4}$ alkyl, or $C_{3-7}$ cycloalkyl wherein the $C_{3-7}$ cycloalkyl is optionally substituted with one or more independently selected $R^5$ groups;

$R^7$ is
- $C_{1-4}$ alkyl optionally substituted with one or more independently selected
  - halo;
  - phenyl optionally substituted with one or more independently selected
    - halo;
    - $C_{1-4}$ alkyl optionally substituted with one or more independently selected halo; or
    - $C_{1-4}$ alkoxy optionally substituted with one or more independently selected halo;
  - $C_{1-4}$ alkoxy optionally substituted with one or more independently selected halo; or
  - 4-6 membered monocyclic heterocycle comprising 1 or 2 heteroatoms independently selected from the group consisting of O, S and N; wherein the monocyclic heterocycle is optionally substituted with one or more independently selected $R^5$ groups;

$R^{8a}$ and $R^{8b}$ are independently selected from the group consisting of

H;

$C_{1-4}$ alkyl optionally substituted with one or more independently selected halo; and $C_{3-7}$ cycloalkyl optionally substituted with one or more independently selected $R^5$ groups;

each $R^9$ is independently selected from the group consisting of:

—OH;

halo;

—CN;

$C_{1-4}$ alkyl optionally substituted with one or more independently selected

—OH;

halo; or $C_{1-4}$ alkoxy;

$C_{1-4}$ alkoxy optionally substituted with one or more independently selected halo;

$C_{3-7}$ cycloalkyl optionally substituted with one or more independently selected $R^5$ groups;

—C(=O)NR$^{10a}$R$^{10b}$; and 4-6 membered monocyclic heterocycle comprising 1 or 2 heteroatoms independently selected from the group consisting of O, S, and N, wherein the monocyclic heterocycle is optionally substituted with one or more independently selected $R^5$ groups; and $R^{10a}$ and $R^{10b}$ are independently selected from the group consisting of H and $C_{1-4}$ alkyl.

In certain embodiments of Formula I, $R^1$ is phenyl optionally substituted with one or more independently selected $R^4$ groups.

In certain embodiments of Formula I, $R^1$ is phenyl optionally substituted with one, two, or three independently selected $R^4$ groups.

In certain embodiments of Formula I, $R^1$ is phenyl which is unsubstituted.

In certain embodiments of Formula I, $R^1$ is phenyl substituted with one or two independently selected $R^4$ groups.

In certain embodiments of Formula I, $R^1$ is phenyl substituted with one $R^4$ group.

In certain embodiments each $R^4$ is independently selected from the group consisting of fluoro, $C_{1-4}$ alkyl optionally substituted with 1, 2, or 3 fluoro; and $C_{1-4}$ alkoxy optionally substituted with 1, 2, or 3 fluoro.

In certain embodiments, each $R^4$ is independently selected from the group consisting of $C_{1-4}$ alkyl optionally substituted with 1, 2, or 3 fluoro; and $C_{1-4}$ alkoxy optionally substituted with 1, 2, or 3 fluoro.

Examples of $R^4$ are F, CH$_3$, —CH(CH$_3$)$_2$, t-Bu, CF$_3$, —OCH$_3$, —OCH(CH$_3$)$_2$, and —OCF$_3$. Particular examples of $R^4$ are F, CF$_3$, and —OCF$_3$. In some embodiments, $R^4$ is F. In some embodiments, $R^4$ is CF$_3$. In some embodiments $R^4$ is —OCF$_3$.

Included herein are compounds of Formula I-a or pharmaceutically acceptable salts thereof

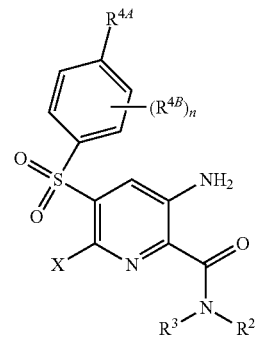

I-a wherein n is 0, 1, or 2, $R^{4A}$ is H, F, CH$_3$, —CH(CH$_3$)$_2$, t-Bu, CF$_3$, —OCH$_3$, —O—CH(CH$_3$)$_2$, or —OCF$_3$, $R^{4B}$ is F or —OCF$_3$, and X, $R^2$, and $R^3$, are as defined in the Summary and embodiments herein below.

Included herein are compounds of Formula I-a or pharmaceutically acceptable salts thereof wherein n is 0, 1, or 2, $R^{4A}$ is H, F, CH$_3$, —CH(CH$_3$)$_2$, t-Bu, CF$_3$, —OCH$_3$, —O—CH(CH$_3$)$_2$, or —OCF$_3$, each $R^{4B}$ is independently F or —OCF$_3$, and X, $R^2$, and $R^3$, are as defined in the Summary and embodiments herein below.

In certain embodiments of Formula I-a, n is 0 or 1. In certain embodiments, n is 0. In certain embodiments, n is 1.

In certain embodiments of Formula I-a, $R^{4A}$ is H, —CH(CH$_3$)$_2$, —O—CH(CH$_3$)$_2$, t-Bu, CH$_3$, —OCH$_3$, F, CF$_3$, or —OCF$_3$.

In certain embodiments of Formula I-a, $R^{4A}$ is H, F, CF$_3$, or —OCF$_3$.

In certain embodiments of Formula I-a, $R^{4A}$ is F, CF$_3$, or —OCF$_3$.

In certain embodiments of Formula I-a, n is 0 or 1, $R^{4A}$ is F, CF$_3$ or —OCF$_3$, and $R^{4B}$ is F.

In certain embodiments, $R^{4A}$ is F.

In certain embodiments, n is 0 and $R^{4A}$ is F.

In certain embodiments, n is 0 and $R^{4A}$ is H.

In certain embodiments of Formula I, $R^1$ is N-linked 4-6 membered monocyclic heterocycle comprising 1, 2, or 3 heteroatoms independently selected from the group consisting of N, O, and S, wherein the monocyclic heterocycle is optionally substituted with 1, 2, or 3 independently selected $R^5$ groups.

In certain embodiments of Formula I, $R^1$ is N-linked 4-6 membered monocyclic heterocycle comprising 1 or 2 heteroatoms independently selected from the group consisting of N and O, wherein the monocyclic heterocycle is optionally substituted with 1, 2, or 3 independently selected $R^5$ groups. In some such embodiments, each $R^5$ is independently selected from the group consisting of F, CH$_3$, t-Bu, CF$_3$, —OCH$_3$, and —OCF$_3$. In some such embodiments, each $R^5$ is independently selected from the group consisting of F, CH$_3$, t-Bu, CF$_3$, —OCH$_3$, —CH$_2$OH, and —OCF$_3$.

In certain embodiments of Formula I, $R^1$ is azetidinyl, pyrrolidinyl, morpholinyl, or piperidinyl, each of which is optionally substituted with 1 or 2 independently selected $R^5$ groups.

In some such embodiments, each $R^5$ is independently selected from the group consisting of F, CH$_3$, t-Bu, CF$_3$, —OCH$_3$, and —OCF$_3$.

In certain embodiments of Formula I, $R^1$ is piperidinyl, which is optionally substituted with 1 or 2 independently selected $R^5$ groups. In some such embodiments, each $R^5$ is independently selected from the group consisting of F, CH$_3$, t-Bu, CF$_3$, —OCH$_3$, and —OCF$_3$. In some such embodiments, R$^1$ is piperidinyl substituted with two fluoro groups. In some such embodiments, R$^1$ is piperidinyl substituted with one fluoro group. In some such embodiments, R$^1$ is piperidinyl substituted with one methyl group. In some such embodiments, R$^1$ is piperidinyl substituted with two methyl groups. In some such embodiments, R$^1$ is piperidinyl substituted with one CF$_3$, group. In some such embodiments, R$^1$ is piperidinyl substituted with one —OCH$_3$, group. In some such embodiments, R$^1$ is piperidinyl substituted with one —OCF$_3$, group. In some such embodiments, R$^1$ is piperidinyl substituted with one t-Bu group.

In certain embodiments of Formula I, R$^1$ is N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with 1, 2, or 3 independently selected R$^5$ groups. In some such embodiments, R$^1$ is 3,4-dihydro-2H-benzo[b][1,4]oxazinyl, optionally substituted with 1, 2, or 3 independently selected R$^5$ groups. In some such embodiments, R$^1$ is unsubstituted 3,4-dihydro-2H-benzo[b][1,4]oxazinyl.

In certain embodiments of Formula I, R$^1$ is C$_{1-4}$ alkyl optionally substituted with one or more independently selected —OH, C$_{1-4}$ alkoxy, or 4-6 membered monocyclic heterocycle comprising 1 or 2 heteroatoms independently selected from the group consisting of O, S, and N. In some such embodiments, R$^1$ is C$_{1-4}$ alkyl which is unsubstituted. In some such embodiments of Formula I, R$^1$ is C$_{1-4}$ alkyl which is substituted with —OH. In some such embodiments of Formula I, R$^1$ is C$_{1-4}$ alkyl which is substituted with C$_{1-4}$ alkoxy. In some such embodiments of Formula I, R$^1$ is C$_{1-4}$ alkyl which is substituted with 4-6 membered monocyclic heterocycle comprising 1 or 2 heteroatoms independently selected from the group consisting of O, S, and N. In some such embodiments of Formula I, R$^1$ is CH$_2$CH$_3$. In some such embodiments of Formula I, R$^1$ is CH$_2$CH$_2$OH. In some such embodiments of Formula I, R$^1$ is —CH(CH$_3$)$_2$. In some such embodiments of Formula I, R$^1$ is CH$_2$CH$_2$OCH$_3$. In some such embodiments of Formula I, R$^1$ is C$_1$ alkyl substituted with tetrahydrofuran.

In certain embodiments of Formula I, R$^1$ is C$_{3-7}$ cycloalkyl optionally substituted with one or more independently selected R$^5$ groups. In some such embodiments of Formula I, R$^1$ is cyclopropyl, cyclobutyl, cyclopentyl, or cyclohexyl. In some such embodiments of Formula I, R$^1$ is cyclopentyl.

In certain embodiments of Formula I, R$^1$ is —NR$^6$R$^7$.
In certain embodiments of Formula I, R$^1$ is —NR$^6$R$^7$; wherein
R$^6$ is H, CH$_3$, or cyclopropyl; wherein the cyclopropyl is optionally substituted with 1 or 2 independently selected R$^5$ groups; and
R$^7$ is
C$_{1-4}$ alkyl;
C$_{1-4}$ alkyl substituted with 1, 2, or 3 fluoro;
C$_{1-4}$ alkyl substituted with one phenyl wherein the phenyl is optionally substituted with 1, 2, or 3 independently selected
fluoro;
C$_{1-4}$ alkyl optionally substituted with 1, 2, or 3 fluoro; or
C$_{1-4}$ alkoxy optionally substituted with 1, 2, or 3 fluoro;
C$_{2-4}$ alkyl substituted with one C$_{1-4}$ alkoxy; or
C$_{1-4}$ alkyl substituted with one 4-6 membered monocyclic heterocycle comprising 1 or 2 heteroatoms independently selected from the group consisting of O, S, and N; wherein the monocyclic heterocycle is optionally substituted with 1, 2, or 3 independently selected R$^5$ groups.

In certain embodiments of Formula I, R$^1$ is —NR$^6$R$^7$; wherein
R$^6$ is H, CH$_3$, cyclobutyl or cyclopropyl; wherein the cyclobutyl and cyclopropyl are optionally substituted with 1 or 2 independently selected R$^5$ groups; and
R$^7$ is
C$_{1-4}$ alkyl;
C$_{1-4}$ alkyl substituted with 1, 2, or 3 fluoro;
C$_{1-4}$ alkyl substituted with one phenyl wherein the phenyl is optionally substituted with 1, 2, or 3 independently selected
fluoro;
C$_{1-4}$ alkyl optionally substituted with 1, 2, or 3 fluoro; or
C$_{1-4}$ alkoxy optionally substituted with 1, 2, or 3 fluoro;
C$_{2-4}$ alkyl substituted with one C$_{1-4}$ alkoxy; or
C$_{1-4}$ alkyl substituted with one 4-6 membered monocyclic heterocycle comprising 1 or 2 heteroatoms independently selected from the group consisting of O, S, and N; wherein the monocyclic heterocycle is optionally substituted with 1, 2, or 3 independently selected R$^5$ groups.

In certain embodiments, R$^7$ is C$_{1-4}$ alkyl substituted with one phenyl wherein the phenyl is optionally substituted with 1, 2, or 3 independently selected CF$_3$, fluoro, or C$_{1-4}$ alkoxy.

In certain embodiments of Formula I, X is H; halo; C$_{1-4}$ alkyl optionally substituted with one or more independently selected halo; C$_{1-4}$ alkoxy optionally substituted with one or more independently selected —OH, C$_{1-4}$ alkoxy, or —NR$^{11A}$R$^{11B}$; —NR$^{12A}$R$^{12B}$; optionally substituted cyclopropyl; optionally substituted phenoxy; or optionally substituted phenyl.

In certain embodiments, X is H, halo, optionally substituted cyclopropyl, or optionally substituted phenyl.

In certain embodiments of Formula I, X is H, halo, or unsubstituted cyclopropyl.

In certain embodiments, X is H.

In certain embodiments of Formula I, X is bromo, —NR$^{12A}$R$^{12B}$, alkoxy, cyclopropyl, phenoxy, or phenyl; wherein the cyclopropyl, phenoxy, and phenyl are optionally substituted with 1, 2, or 3 independently selected R$^5$ groups, and the C$_{1-4}$ alkoxy is optionally substituted with one or more independently selected —OH, C$_{1-4}$ alkoxy, or —NR$^{11A}$R$^{11B}$. In some such embodiments of Formula I, the cyclopropyl is unsubstituted. In some such embodiments of Formula I, the phenyl and phenoxy are substituted with F.

In certain embodiments, X is bromo, cyclopropyl, or phenyl; wherein the cyclopropyl and the phenyl are optionally substituted with 1, 2, or 3 independently selected R$^5$ groups. In some such embodiments, the cyclopropyl is unsubstituted.

In certain embodiments, X is bromo.

In certain embodiments, X is cyclopropyl, or phenyl; wherein the cyclopropyl and the phenyl are optionally substituted with 1, 2, or 3 independently selected R$^5$ groups. In some such embodiments, the cyclopropyl is unsubstituted.

In certain embodiments of Formula I, X is cyclopropyl, phenoxy, or phenyl; wherein the cyclopropyl, phenoxy, and phenyl are optionally substituted with 1, 2, or 3 independently selected R$^5$ groups. In some such embodiments of Formula I, the cyclopropyl is unsubstituted.

In certain embodiments, X is unsubstituted cyclopropyl or phenyl substituted with one fluoro.

In certain embodiments of Formula I, X is unsubstituted cyclopropyl, phenyl substituted with one fluoro, or phenoxy substituted with one fluoro.

In certain embodiments, X is unsubstituted cyclopropyl.

In certain embodiments, X is phenyl substituted with one fluoro.

In certain embodiments of Formula I, X is phenoxy substituted with one fluoro.

In certain embodiments of Formula I, X is $C_{1-4}$ alkoxy optionally substituted with one or more independently selected —OH, $C_{1-4}$ alkoxy, or —$NR^{11A}R^{11B}$. In some such embodiments of Formula I, $R^{11A}$ and $R^{11B}$ are H or $C_{1-4}$ alkyl. In some such embodiments of Formula I, $R^{11A}$ and $R^{11B}$ are both $CH_3$.

In certain embodiments of Formula I, X is $C_{1-4}$ alkoxy which is unsubstituted. In some such embodiments of Formula I, X is —$OCH_3$.

In certain embodiments of Formula I, X is $C_{1-4}$ alkoxy which is substituted with $C_{1-4}$ alkoxy. In some such embodiments of Formula I, X is —$OCH_2CH_2OCH_3$.

In certain embodiments of Formula I, X is $C_{1-4}$ alkoxy which is substituted with —$NR^{11A}R^{11B}$. In some such embodiments of Formula I, $R^{11A}$ and $R^{11B}$ are H or $C_{1-4}$ alkyl. In some such embodiments of Formula I, $R^{11A}$ and $R^{11B}$ are both $CH_3$.

In certain embodiments of Formula I, X is —$NR^{12A}R^{12B}$. In some such embodiments of Formula I, $R^{12A}$ and $R^{12B}$ are H, $C_{1-4}$ alkyl, or $C_{3-7}$ cycloalkyl. In some such embodiments of Formula I, $R^{12A}$ and $R^{12B}$ are both $CH_3$. In some such embodiments of Formula I, $R^{12A}$ is H and $R^{2B}$ is cyclopropyl.

In certain embodiments of Formula I, $R^2$ and $R^3$ are H.

In certain embodiments, $R^2$ is $C_{1-6}$ alkyl optionally substituted with 1, 2, or 3 independently selected
- —OH;
- fluoro;
- $C_{1-4}$ alkoxy optionally substituted with 1, 2, or 3 independently selected
  - fluoro;
  - $C_{1-4}$ alkoxy;
  - $C_{3-7}$ cycloalkyl optionally substituted with 1, 2, or 3 independently selected $R^5$ groups; or
  - 4-6 membered monocyclic heterocycle comprising 1 or 2 heteroatoms independently selected from the group consisting of N, O, and S, wherein the monocyclic heterocycle is optionally substituted with 1, 2, or 3 independently selected $R^5$ groups;
- 4-6 membered monocyclic heterocycle comprising 1 or 2 heteroatoms independently selected from the group consisting of N, O, and S, wherein the monocyclic heterocycle is optionally substituted with 1, 2, or 3 independently selected
  - —OH;
  - fluoro;
  - $C_{1-4}$ alkoxy optionally substituted with 1, 2, or 3 fluoro, or
  - $C_{1-4}$ alkyl optionally substituted with 1, 2, or 3 fluoro; or
- phenyl optionally substituted with 1, 2, or 3 independently selected $R^5$ groups.

In certain embodiments of Formula I, $R^2$ is $C_{1-6}$ alkyl optionally substituted with one or more independently selected
- —OH;
- fluoro;
- $C_{1-4}$ alkoxy optionally substituted with one or more independently selected
  - fluoro;
  - $C_{1-4}$ alkoxy;
  - $C_{3-7}$ cycloalkyl optionally substituted with one or more independently selected $R^5$ groups; or
  - 4-6 membered monocyclic heterocycle comprising 1 or 2 heteroatoms independently selected from the group consisting of N, O, and S, wherein the monocyclic heterocycle is optionally substituted with one or more independently selected $R^5$ groups;
- —$C(=O)NR^{8a}R^{8b}$;
- $C_{3-7}$ cycloalkyl optionally substituted with one or more independently selected
  - —OH;
  - fluoro;
  - $C_{1-4}$ alkoxy optionally substituted with one or more independently selected halo; or
  - $C_{1-4}$ alkyl optionally substituted with one or more independently selected —OH, fluoro, or $C_{1-4}$ alkoxy;
- 4-6 membered monocyclic heterocycle comprising 1 or 2 heteroatoms independently selected from the group consisting of N, O, and S, wherein the monocyclic heterocycle is optionally substituted with one or more independently selected
  - —OH;
  - fluoro;
  - $C_{1-4}$ alkoxy optionally substituted with one or more independently selected fluoro, or
  - $C_{1-4}$ alkyl optionally substituted with one or more independently selected fluoro;
- 5-6 membered monocyclic heteroaryl comprising 1, 2, or 3 heteroatoms independently selected from the group consisting of O, S, and N, wherein the monocyclic heteroaryl is optionally substituted with one or more independently selected $R^5$ groups; or
- phenyl optionally substituted with one or more independently selected $R^5$ groups.

In certain embodiments, $R^2$ is $C_{3-6}$ alkyl substituted with one or two —OH, and optionally further substituted with 1, 2, or 3 fluoro; or optionally further substituted with one $C_{1-4}$ alkoxy optionally substituted with
- 1, 2, or 3 fluoro;
- one $C_{1-4}$ alkoxy; or
- one $C_{3-7}$ cycloalkyl optionally substituted with 1, 2, or 3 independently selected $R^5$ groups.

In certain embodiments of Formula I, $R^2$ is $C_{2-6}$ alkyl substituted with one or two —OH, and optionally further substituted with 1, 2, or 3 fluoro; or optionally further substituted with one $C_{1-4}$ alkoxy optionally substituted with
- 1, 2, or 3 fluoro;
- one $C_{1-4}$ alkoxy; or
- one $C_{3-7}$ cycloalkyl optionally substituted with 1, 2, or 3 independently selected $R^5$ groups.

In certain embodiments, $R^2$ is $C_{3-6}$ alkyl substituted with one —OH, and optionally further substituted with 1, 2, or 3 fluoro or optionally further substituted with one $C_{1-4}$ alkoxy wherein the $C_{1-4}$ alkoxy is optionally substituted with one cyclopropyl or 1, 2, or 3 fluoro. In some such embodiments, the optional substituents are independently selected from the group consisting of $CF_3$, —$OCH_3$, —$OCH_2CH_3$, —$OCH_2CH(CH_3)_2$, —$OC(CH_3)_3$, —$OCH(CH_3)_2$, —$OCH_2CF_3$, and —$OCH_2$-cyclopropyl. In some such embodiments of Formula I, the optional substituents are independently selected from the group consisting of F, —$OCH_3$, —$OCH_2CH_3$, —$OCH_2CH_2OCH_2CH_3$, —OCH$_2$CH$_2$OCH$_3$, —OCH$_2$CH(CH$_3$)$_2$, —OC(CH$_3$)$_3$, —OCH(CH$_3$)$_2$, —OCH$_2$CF$_3$, and —OCH$_2$-cyclopropyl.

In certain embodiments, R$^2$ is C$_{3-6}$ alkyl substituted with one —OH, and optionally further substituted with 1, 2, or 3 fluoro or optionally further substituted with one C$_{1-4}$ alkoxy wherein the C$_{1-4}$ alkoxy is optionally substituted with 1, 2, or 3 fluoro.

In certain embodiments, R$^2$ is C$_{3-5}$ alkyl substituted with one —OH, and optionally further substituted with 1, 2, or 3 fluoro.

In certain embodiments, R$^2$ is C$_{3-4}$ alkyl substituted with one —OH and 3 fluoro.

In certain embodiments of Formula I, R$^2$ is C$_{3-5}$ alkyl substituted with one —OH.

In certain embodiments of Formula I, R$^2$ is C$_{4-5}$ alkyl substituted with one —OH.

In certain embodiments of Formula I, R$^2$ is C$_3$ alkyl substituted with one —OH.

In certain embodiments, R$^2$ is

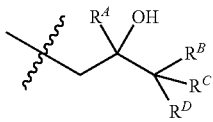

wherein
R$^A$ is H or CH$_3$, and
R$^B$, R$^C$, and R$^D$ are H; or
R$^B$, R$^C$, and R$^D$ are fluoro; or
R$^B$ and R$^C$ are H, and R$^D$ is C$_{1-4}$ alkoxy, —OCH$_2$-cyclopropyl, or —OCH$_2$CF$_3$.

In certain embodiments, R$^A$ is H.

In certain embodiments, R$^A$ is H, and R$^B$, R$^C$, and R$^D$ are fluoro; or R$^B$ and R$^C$ are H, and R$^D$ is —OCH$_3$, —OCH$_2$CH$_3$, —OCH(CH$_3$)$_2$, —OC(CH$_3$)$_3$, —OCH$_2$-cyclopropyl, or —OCH$_2$CF$_3$.

In certain embodiments of Formula I, R$^A$ is H, and R$^B$, R$^C$, and R$^D$ are fluoro; or R$^B$ and R$^C$ are H, and R$^D$ is —OCH$_3$, —OCH$_2$CH$_3$, —OCH$_2$CH$_2$OCH$_2$CH$_3$, —OCH$_2$CH$_2$OCH$_3$, —OCH$_2$CH(CH$_3$)$_2$, —OC(CH$_3$)$_3$, —OCH(CH$_3$)$_2$, —OCH$_2$CF$_3$, or —OCH$_2$— cyclopropyl.

In certain embodiments, R$^A$ is H, and R$^B$, R$^C$, and R$^D$ are fluoro.

In certain embodiments, R$^A$ is H, R$^B$ and R$^C$ are H, and R$^D$ is —OCH$_3$, —OCH$_2$CH$_3$, —OCH(CH$_3$)$_2$, —OC(CH$_3$)$_3$, —OCH$_2$-cyclopropyl, or —OCH$_2$CF$_3$.

In certain embodiments of Formula I, R$^A$ is H, R$^B$ and R$^C$ are H, and R$^D$ is —OCH$_3$, —OCH$_2$CH$_3$, —OCH$_2$CH$_2$OCH$_2$CH$_3$, —OCH$_2$CH$_2$OCH$_3$, —OCH$_2$CH(CH$_3$)$_2$, —OC(CH$_3$)$_3$, —OCH(CH$_3$)$_2$, —OCH$_2$CF$_3$, or —OCH$_2$-cyclopropyl.

In certain embodiments, R$^2$ is C$_{1-6}$ alkyl substituted with one substituent wherein the substituent is:
—C(=O)NR$^{8a}$R$^{8b}$;
C$_{3-7}$ cycloalkyl optionally substituted with 1, 2, or 3 independently selected
—OH;
fluoro;
C$_{1-4}$ alkoxy optionally substituted with 1, 2, or 3 fluoro; or
C$_{1-4}$ alkyl optionally substituted with 1, 2, or 3 independently selected —OH, fluoro, or C$_{1-4}$ alkoxy;
4-6 membered monocyclic heterocycle comprising 1 or 2 heteroatoms independently selected from the group consisting of N, O, and S, wherein the monocyclic heterocycle is optionally substituted with 1, 2, or 3 independently selected
—OH;
fluoro;
C$_{1-4}$ alkoxy optionally substituted with 1, 2, or 3 fluoro, or
C$_{1-4}$ alkyl optionally substituted with 1, 2, or 3 fluoro; or
5-6 membered monocyclic heteroaryl comprising 1, 2, or 3 heteroatoms independently selected from the group consisting of O, S, and N, wherein the monocyclic heteroaryl is optionally substituted with 1, 2, or 3 independently selected R$^5$ groups.

In certain embodiments, R$^2$ is C$_{1-6}$ alkyl substituted with one —C(=O)NR$^{8a}$R$^{8b}$ wherein R$^{8a}$ and R$^{8b}$ are independently selected from the group consisting of H; C$_{1-4}$ alkyl optionally substituted with 1, 2, or 3 fluoro; and cyclopropyl optionally substituted with 1, 2, or 3 independently selected R$^5$ groups.

In certain embodiments of Formula I, R$^2$ is C$_{1-6}$ alkyl substituted with one —C(=O)NR$^{8a}$R$^{8b}$ wherein R$^{8a}$ and R$^{8b}$ are independently selected from the group consisting of H; C$_{1-4}$ alkyl; and cyclopropyl.

In certain embodiments, R$^2$ is C$_{1-4}$ alkyl substituted with one C$_{3-5}$ cycloalkyl which is optionally substituted with 1, 2, or 3 independently selected —OH; fluoro; C$_{1-4}$ alkoxy optionally substituted with 1, 2, or 3 fluoro; or C$_{1-4}$ alkyl optionally substituted with 1, 2, or 3 independently selected —OH, fluoro, or C$_{1-4}$ alkoxy. In some such embodiments, R$^2$ is —CH$_2$-cyclopropyl wherein the cyclopropyl is optionally substituted with one —OH. In some such embodiments of Formula I, R$^2$ is —CH$_2$-cyclopropyl wherein the cyclopropyl is optionally substituted with 1, 2, or 3 independently selected —OH, fluoro, —CH$_2$OH, or C$_{1-4}$ alkoxy. In some such embodiments of Formula I, R$^2$ is —CH$_2$-cyclobutyl wherein the cyclobutyl is optionally substituted with 1, 2, or 3 independently selected fluoro, —OH, CH$_2$OH, or CH$_2$OCH$_2$CH$_3$. In some such embodiments of Formula I, R$^2$ is —CH$_2$CH$_2$-cyclopropyl wherein the cyclopropyl is optionally substituted with CH$_3$.

In certain embodiments, R$^2$ is C$_{1-4}$ alkyl substituted with one 4-6 membered monocyclic heterocycle comprising 1 or 2 heteroatoms independently selected from the group consisting of N and O, wherein the monocyclic heterocycle is optionally substituted. In some such embodiments, the monocyclic heterocycle is tetrahydrofuranyl, 1,3-dioxolanyl, tetrahydropyranyl, 1,4-dioxanyl, morpholinyl, or piperidinyl; each of which is optionally substituted. In some such embodiments, the monocyclic heterocycle is tetrahydrofuranyl. In some such embodiments, the monocyclic heterocycles, including the exemplary rings, are optionally substituted with 1, 2, or 3 independently selected —OH; fluoro; C$_{1-4}$ alkoxy optionally substituted with 1, 2, or 3 fluoro; or C$_{1-4}$ alkyl optionally substituted with 1, 2, or 3 fluoro.

In certain embodiments, R$^2$ is C$_{1-4}$ alkyl substituted with one 5-6 membered monocyclic heteroaryl comprising 1, 2, or 3 heteroatoms independently selected from the group consisting of O, S, and N, wherein the monocyclic heteroaryl is optionally substituted with 1, 2, or 3 independently selected R$^5$ groups. In some such embodiments, the monocyclic heteroaryl is furanyl, optionally substituted with 1, 2, or 3 independently selected R$^5$ groups. In some such embodiments of Formula I, the monocyclic heteroaryl is furanyl or pyrimidinyl, wherein the furanyl and pyrimidinyl are optionally substituted with 1, 2, or 3 independently selected R$^5$ groups.

In certain embodiments, $R^2$ is $C_{3-6}$ cycloalkyl optionally substituted with 1, 2, or 3 independently selected —OH; fluoro; $C_{1-4}$ alkyl optionally substituted with 1, 2, or 3 fluoro; or $C_{1-4}$ alkoxy optionally substituted with 1, 2, or 3 fluoro. In some such embodiments, $R^2$ is cyclobutyl, cyclopentyl, or cyclohexyl, each of which is optionally substituted. In some such embodiments, the $C_{3-6}$ cycloalkyl, including the exemplary rings, are optionally substituted with 1 or 2 independently selected fluoro, $CH_3$, $CF_3$, —OH, or —$OCH_3$. In some such embodiments, the $C_{3-6}$ cycloalkyl, including the exemplary rings, are substituted with one —OH.

In certain embodiments of Formula I, $R^2$ is $C_{3-6}$ cycloalkyl optionally substituted with 1, 2, or 3 independently selected —OH; fluoro; $C_{1-4}$ alkyl optionally substituted with —OH or 1, 2, or 3 fluoro; or $C_{1-4}$ alkoxy optionally substituted with 1, 2, or 3 fluoro. In some such embodiments of Formula I, $R^2$ is cyclopropyl, cyclobutyl, cyclopentyl, or cyclohexyl, each of which is optionally substituted. In some such embodiments of Formula I, the $C_{3-6}$ cycloalkyl, including the exemplary rings, are optionally substituted with 1 or 2 substituents independently selected fluoro, $CH_2OH$, $CH_3$, $CF_3$, —OH, or —$OCH_3$. In some such embodiments of Formula I, the $C_{3-6}$ cycloalkyl, including the exemplary rings, are substituted with one —OH.

In certain embodiments, $R^2$ is 4-6 membered monocyclic heterocycle comprising 1 or 2 heteroatoms independently selected from the group consisting of O, S, and N, wherein the monocyclic heterocycle is optionally substituted with 1, 2, or 3 independently selected —OH; fluoro; $C_{1-4}$ alkyl optionally substituted with 1, 2, or 3 fluoro; or $C_{1-4}$ alkoxy optionally substituted with 1, 2, or 3 fluoro. In some such embodiments, $R^2$ is oxetanyl, tetrahydrofuranyl, tetrahydropyranyl, azetidinyl, pyrrolidinyl, or piperidinyl; each of which is optionally substituted. In some such embodiments, $R^2$ is optionally substituted tetrahydrofuranyl or tetrahydropyranyl. In some such embodiments, the monocyclic ring, including the exemplary rings, are optionally substituted with 1 or 2 independently selected fluoro, $CH_3$, $CF_3$, —OH, or —$OCH_3$. In some such embodiments, the monocyclic rings, including the exemplary rings, are substituted with one —OH.

In certain embodiments, $R^2$ is 4-6 membered monocyclic heterocycle comprising 1 or 2 heteroatoms independently selected from the group consisting of O, S, and N, fused to a phenyl ring, wherein the monocyclic heterocycle and the phenyl are optionally substituted with 1, 2, or 3 independently selected $R^5$ groups. In some such embodiments, $R^2$ is optionally substituted chromanyl.

In certain embodiments, $R^2$ is 5-11 membered spirocyclic heterocycle comprising 1 or 2 heteroatoms independently selected from the group consisting of O, S, and N, wherein the spirocyclic heterocycle is optionally substituted with 1, 2, or 3 independently selected $R^5$ groups. In some such embodiments, $R^2$ is optionally substituted 1-oxaspiro[4.4]non-3-yl or optionally substituted 1-oxaspiro[4.5]decan-3-yl.

In certain embodiments, $R^2$ and $R^3$, together with the nitrogen atom to which they are attached form an azetidine or a pyrrolidine ring, wherein the azetidine and the pyrrolidine are optionally substituted with 1, 2, or 3 independently selected $R^9$ groups.

In certain embodiments, $R^2$ and $R^3$, together with the nitrogen atom to which they are attached form an azetidine ring which is substituted with 1, 2, or 3 independently selected $R^9$ groups.

In certain embodiments, $R^2$ and $R^3$, together with the nitrogen atom to which they are attached form an azetidine ring which is substituted with 1 or 2 $R^9$ groups; and each $R^9$ is independently selected from the group consisting of —OH, fluoro, —CN, $CF_3$, optionally substituted cyclopropyl, $C_{1-4}$ alkyl optionally substituted with one —OH or one $C_{1-4}$ alkoxy; and $C_{1-4}$ alkoxy optionally substituted with 1, 2, or 3 fluoro.

In certain embodiments of Formula I, $R^2$ and $R^3$, together with the nitrogen atom to which they are attached form an azetidine ring which is substituted with 1 or 2 $R^9$ groups; and each $R^9$ is independently selected from the group consisting of —C(=O)$NR^{10a}R^{10b}$, —OH, fluoro, —CN, $CF_3$, optionally substituted cyclopropyl, $C_{1-4}$ alkyl optionally substituted with one —OH or one $C_{1-4}$ alkoxy; and $C_{1-4}$ alkoxy optionally substituted with 1, 2, or 3 fluoro. In some such embodiments of Formula I, $R^2$ and $R^3$, together with the nitrogen atom to which they are attached form an azetidine ring which is substituted with —C(=O)$NR^{10a}R^{10b}$, wherein each $R^{10a}$ and $R^{10b}$ is independently selected from the group consisting of H and $C_{1-4}$ alkyl. In some such embodiments of Formula I, $R^2$ and $R^3$, together with the nitrogen atom to which they are attached form an azetidine ring which is substituted with —C(=O)$NR^{10a}R^{10b}$, wherein each $R^{10a}$ and $R^{10b}$ is H. In some such embodiments of Formula I, $R^2$ and $R^3$, together with the nitrogen atom to which they are attached form an azetidine ring which is substituted with —C(=O)$NR^{10a}R^{10b}$, wherein each $R^{10a}$ and $R^{10b}$ is $C_{1-4}$ alkyl.

In certain embodiments, $R^2$ and $R^3$, together with the nitrogen atom to which they are attached form an azetidine ring which is substituted with 1 or 2 $R^9$ groups; and each $R^9$ is independently selected from the group consisting of —OH, fluoro, —CN, $CF_3$, unsubstituted cyclopropyl, $CH_3$, —$CH_2CH_3$, —$CH(CH_3)_2$, —$C(CH_3)_2OH$, —$CH_2OH$, —$CH_2OCH_3$, —$OCH_3$, —$OCHF_2$, and —$OCH_2CHF_2$.

In certain embodiments of Formula I, $R^2$ and $R^3$, together with the nitrogen atom to which they are attached form an azetidine ring which is substituted with 1 or 2 $R^9$ groups; and each $R^9$ is independently selected from the group consisting of —OH, fluoro, —CN, —$CF_3$, unsubstituted cyclopropyl, $CH_3$, —$CH_2CH_3$, —$CH(CH_3)_2$, —$C(CH_3)_2OH$, —$CH_2OH$, —$CH_2OCH_3$, —$OCH_3$, —$OCHF_2$, —$OCH_2CHF_2$, C(=O)$NH_2$, and C(=O)N$(CH_3)_2$.

In certain embodiments, $R^2$ and $R^3$, together with the nitrogen atom to which they are attached form an azetidine ring which is substituted with one —OH, and optionally further substituted with one substituent selected from the group consisting of fluoro, —$CH_3$, —$CH(CH_3)_2$, $CF_3$, and unsubstituted cyclopropyl.

In certain embodiments, $R^2$ and $R^3$, together with the nitrogen atom to which they are attached form a pyrrolidine ring which is optionally substituted with 1, 2, or 3 independently selected $R^9$ groups. In some such embodiments, each $R^9$ is independently selected from the group consisting of —OH, fluoro, $CF_3$, optionally substituted cyclopropyl, $C_{1-4}$ alkyl optionally substituted with one —OH or one $C_{1-4}$ alkoxy; and $C_{1-4}$ alkoxy optionally substituted with 1, 2, or 3 fluoro. In some such embodiments, each $R^9$ is independently selected from the group consisting of —OH, fluoro, and $C_{1-4}$ alkyl optionally substituted with one —OH. In some such embodiments of Formula I, each $R^9$ is independently selected from the group consisting of —OH, fluoro, $CF_3$, optionally substituted cyclopropyl, $C_{1-4}$ alkyl optionally substituted with one —OH or one $C_{1-4}$ alkoxy; $C_{1-4}$ alkoxy optionally substituted with 1, 2, or 3 fluoro; or 4-6 membered monocyclic heterocycle comprising 1 or 2 heteroatoms independently selected from the group consisting of O, S, and N, wherein the monocyclic heterocycle is optionally substituted with one or more independently selected $R^5$ groups. In some such embodiments of Formula I, each $R^9$ is independently selected from the group consisting of —OH, fluoro, $C_{1-4}$ alkyl optionally substituted with one —OH; and morpholinyl.

In certain embodiments, $R^2$ and $R^3$, together with the nitrogen atom to which they are attached form a 7-11 membered spirocyclic heterocycle comprising 1 or 2 heteroatoms independently selected from the group consisting of N and O; wherein the spirocyclic heterocycle is optionally substituted with 1, 2, or 3 independently selected $R^5$ groups. In some such embodiments, $R^2$ and $R^3$, together with the nitrogen atom to which they are attached, is 2-oxa-6-azaspiro[3.3]heptyl, 6-oxa-2-azaspiro[3.4]octyl, or 6-oxa-2-azaspiro[3.5]nonyl; each of which is optionally substituted with 1, 2, or 3 independently selected $R^5$ groups.

Various embodiments of substituents X, $R^1$, $R^2$, and $R^3$ have been discussed above. These substituents embodiments can be combined to form various embodiments of the invention. All embodiments of present compounds, formed by combining the substituent embodiments discussed above are within the scope of Applicant's invention, and some illustrative embodiments of present compounds are provided below.

In one embodiment, the invention is directed to compounds of Formula I wherein
  $R^1$ is phenyl optionally substituted with one, two, or three independently selected $R^4$ groups; and
  $R^2$ is $C_{1-6}$ alkyl optionally substituted with 1, 2, or 3 independently selected
    —OH;
    fluoro;
    $C_{1-4}$ alkoxy optionally substituted with 1, 2, or 3 independently selected
      fluoro;
      $C_{1-4}$ alkoxy;
    $C_{3-7}$ cycloalkyl optionally substituted with 1, 2, or 3 independently selected $R^5$ groups; or
    4-6 membered monocyclic heterocycle comprising 1 or 2 heteroatoms independently selected from the group consisting of N, O, and S, wherein the monocyclic heterocycle is optionally substituted with 1, 2, or 3 independently selected $R^5$ groups;
  4-6 membered monocyclic heterocycle comprising 1 or 2 heteroatoms independently selected from the group consisting of N, O, and S, wherein the monocyclic heterocycle is optionally substituted with 1, 2, or 3 independently selected
    —OH;
    fluoro;
    $C_{1-4}$ alkoxy optionally substituted with 1, 2, or 3 fluoro, or
    $C_{1-4}$ alkyl optionally substituted with 1, 2, or 3 fluoro;
  or
  phenyl optionally substituted with 1, 2, or 3 independently selected $R^5$ groups.

In one embodiment, the invention is directed to compounds of Formula I wherein
  $R^1$ is phenyl optionally substituted with one, two, or three independently selected $R^4$ groups; and
  $R^2$ is $C_{3-6}$ alkyl substituted with one or two —OH, and optionally further substituted with 1, 2, or 3 fluoro; or optionally further substituted with one $C_{1-4}$ alkoxy which is optionally substituted with 1, 2, or 3 fluoro;
  one $C_{1-4}$ alkoxy; or
  one $C_{3-7}$ cycloalkyl optionally substituted with 1, 2, or 3 independently selected $R^5$ groups.

In one embodiment, the invention is directed to compounds of Formula I wherein
  $R^1$ is phenyl optionally substituted with one, two, or three independently selected $R^4$ groups; and
  $R^2$ is $C_{1-6}$ alkyl substituted with one substituent wherein the substituent is
    —C(=O)NR$^{8a}$R$^{8b}$;
    $C_{3-7}$ cycloalkyl optionally substituted with 1, 2, or 3 independently selected
      —OH;
      fluoro;
      $C_{1-4}$ alkoxy optionally substituted with 1, 2, or 3 fluoro; or
      $C_{1-4}$ alkyl optionally substituted with 1, 2, or 3 independently selected —OH, fluoro, or $C_{1-4}$ alkoxy;
    4-6 membered monocyclic heterocycle comprising 1 or 2 heteroatoms independently selected from the group consisting of N, O, and S, wherein the monocyclic heterocycle is optionally substituted with 1, 2, or 3 independently selected
      —OH;
      fluoro;
      $C_{1-4}$ alkoxy optionally substituted with 1, 2, or 3 fluoro, or
      $C_{1-4}$ alkyl optionally substituted with 1, 2, or 3 fluoro;
    or
    5-6 membered monocyclic heteroaryl comprising 1, 2, or 3 heteroatoms independently selected from the group consisting of O, S, and N, wherein the monocyclic heteroaryl is optionally substituted with 1, 2, or 3 independently selected $R^5$ groups.

In one embodiment, the invention is directed to compounds of Formula I wherein
  $R^1$ is phenyl optionally substituted with one, two, or three independently selected $R^4$ groups; and
  $R^2$ is $C_{3-6}$ cycloalkyl optionally substituted with 1, 2, or 3 independently selected —OH; fluoro; $C_{1-4}$ alkyl optionally substituted with 1, 2, or 3 fluoro; or $C_{1-4}$ alkoxy optionally substituted with 1, 2, or 3 fluoro.

In one embodiment, the invention is directed to compounds of Formula I wherein
  $R^1$ is phenyl optionally substituted with one, two, or three independently selected $R^4$ groups; and
  $R^2$ is 4-6 membered monocyclic heterocycle comprising 1 or 2 heteroatoms independently selected from the group consisting of O, S, and N, wherein the monocyclic heterocycle is optionally substituted with 1, 2, or 3 independently selected —OH; fluoro; $C_{1-4}$ alkyl optionally substituted with 1, 2, or 3 fluoro; or $C_{1-4}$ alkoxy optionally substituted with 1, 2, or 3 fluoro.

In one embodiment, the invention is directed to compounds of Formula I wherein
  $R^1$ is phenyl optionally substituted with one, two, or three independently selected $R^4$ groups; and
  $R^2$ and $R^3$, together with the nitrogen atom to which they are attached form an azetidine or a pyrrolidine ring, wherein the azetidine and the pyrrolidine are optionally substituted with 1, 2, or 3 independently selected $R^9$ groups.)

In one embodiment, the invention is directed to compounds of Formula I wherein
$R^1$ is N-linked 4-6 membered monocyclic heterocycle comprising 1, 2, or 3 heteroatoms independently selected from the group consisting of N, O, and S, wherein the monocyclic heterocycle is optionally substituted with 1, 2, or 3 independently selected $R^5$ groups; and
$R^2$ is $C_{3-6}$ alkyl substituted with one —OH and optionally further substituted with 1, 2, or 3 fluoro; or optionally further substituted with one $C_{1-4}$ alkoxy wherein the $C_{1-4}$ alkoxy is optionally substituted with 1, 2, or 3 fluoro.

In one embodiment, the invention is directed to compounds of Formula I wherein
$R^1$ is —$NR^6R^7$; and
$R^2$ is $C_{3-6}$ alkyl substituted with one —OH and optionally further substituted with 1, 2, or 3 fluoro; or optionally further substituted with one $C_{1-4}$ alkoxy wherein the $C_{1-4}$ alkoxy is optionally substituted with 1, 2, or 3 fluoro.

In one embodiment, the invention is directed to compounds of Formula I-a wherein
X is H;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$; and
$R^{4B}$ is F or —$OCF_3$.

In one embodiment, the invention is directed to compounds of Formula I-a wherein
X is H;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$; and
each $R^{4B}$ is independently F or —$OCF_3$.

In one embodiment, the invention is directed to compounds of Formula I-a wherein
n is 0 or 1;
$R^{4A}$ is F, $CF_3$, or —$OCF_3$; and
$R^{4B}$ is F.

In one embodiment, the invention is directed to compounds of Formula I-a wherein
X is H;
n is 0 or 1;
$R^{4A}$ is F, $CF_3$, or —$OCF_3$; and
$R^{4B}$ is F.

In one embodiment, the invention is directed to compounds of Formula I-a wherein
X is cyclopropyl or phenyl, each optionally substituted with 1, 2, or 3 independently selected $R^5$ groups;
n is 0 or 1;
$R^{4A}$ is F, $CF_3$, or —$OCF_3$; and
$R^{4B}$ is F.

In one embodiment, the invention is directed to compounds of Formula I-a wherein
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
$R^{4B}$ is F or —$OCF_3$; and
$R^2$ is $C_{3-6}$ alkyl substituted with one or two —OH, and optionally further substituted with 1, 2, or 3 fluoro; or optionally further substituted with one $C_{1-4}$ alkoxy which is optionally substituted with
1, 2, or 3 fluoro;
one $C_{1-4}$ alkoxy; or
one $C_{3-7}$ cycloalkyl optionally substituted with 1, 2, or 3 independently selected $R^5$ groups.

In one embodiment, the invention is directed to compounds of Formula I-a wherein
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is $C_{3-6}$ alkyl substituted with one or two —OH, and optionally further substituted with 1, 2, or 3 fluoro; or optionally further substituted with one $C_{1-4}$ alkoxy which is optionally substituted with
1, 2, or 3 fluoro;
one $C_{1-4}$ alkoxy; or
one $C_{3-7}$ cycloalkyl optionally substituted with 1, 2, or 3 independently selected $R^5$ groups.

In one embodiment, the invention is directed to compounds of Formula I-a wherein
X is H;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
$R^{4B}$ is F or —$OCF_3$; and
$R^2$ is $C_{3-6}$ alkyl substituted with one or two —OH, and optionally further substituted with 1, 2, or 3 fluoro; or optionally further substituted with one $C_{1-4}$ alkoxy which is optionally substituted with
1, 2, or 3 fluoro;
one $C_{1-4}$ alkoxy; or
one $C_{3-7}$ cycloalkyl optionally substituted with 1, 2, or 3 independently selected $R^5$ groups.

In one embodiment, the invention is directed to compounds of Formula I-a wherein
X is H;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is $C_{3-6}$ alkyl substituted with one or two —OH, and optionally further substituted with 1, 2, or 3 fluoro; or optionally further substituted with one $C_{1-4}$ alkoxy which is optionally substituted with
1, 2, or 3 fluoro;
one $C_{1-4}$ alkoxy; or
one $C_{3-7}$ cycloalkyl optionally substituted with 1, 2, or 3 independently selected $R^5$ groups.

In one embodiment, the invention is directed to compounds of Formula I-a wherein
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
$R^{4B}$ is F or —$OCF_3$; and
$R^2$ is $C_{3-6}$ alkyl substituted with one —OH, and optionally further substituted with 1, 2, or 3 fluoro or optionally further substituted with one $C_{1-4}$ alkoxy wherein the $C_{1-4}$ alkoxy is optionally substituted with one cyclopropyl or 1, 2, or 3 fluoro.

In one embodiment, the invention is directed to compounds of Formula I-a wherein
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is $C_{3-6}$ alkyl substituted with one —OH, and optionally further substituted with 1, 2, or 3 fluoro or optionally further substituted with one $C_{1-4}$ alkoxy wherein the $C_{1-4}$ alkoxy is optionally substituted with one cyclopropyl or 1, 2, or 3 fluoro.

In one embodiment, the invention is directed to compounds of Formula I-a wherein
X is H;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
$R^{4B}$ is F or —$OCF_3$; and
$R^2$ is $C_{3-6}$ alkyl substituted with one —OH, and optionally further substituted with 1, 2, or 3 fluoro or optionally further substituted with one $C_{1-4}$ alkoxy wherein the $C_{1-4}$ alkoxy is optionally substituted with one cyclopropyl or 1, 2, or 3 fluoro.

In one embodiment, the invention is directed to compounds of Formula I-a wherein
X is H;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is $C_{3-6}$ alkyl substituted with one —OH, and optionally further substituted with 1, 2, or 3 fluoro or optionally further substituted with one $C_{1-4}$ alkoxy wherein the $C_{1-4}$ alkoxy is optionally substituted with one cyclopropyl or 1, 2, or 3 fluoro.

In one embodiment, the invention is directed to compounds of Formula I-a wherein
X is unsubstituted cyclopropyl;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
$R^{4B}$ is F or —$OCF_3$; and
$R^2$ is $C_{3-6}$ alkyl substituted with one —OH, and optionally further substituted with 1, 2, or 3 fluoro.

In one embodiment, the invention is directed to compounds of Formula I-a wherein
X is unsubstituted cyclopropyl;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is $C_{3-6}$ alkyl substituted with one —OH, and optionally further substituted with 1, 2, or 3 fluoro.

In one embodiment, the invention is directed to compounds of Formula I-a wherein
X is phenyl substituted with one fluoro;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
$R^{4B}$ is F or —$OCF_3$; and
$R^2$ is $C_{3-6}$ alkyl substituted with one —OH, and optionally further substituted with 1, 2, or 3 fluoro.

In one embodiment, the invention is directed to compounds of Formula I-a wherein
X is phenyl substituted with one fluoro;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is $C_{3-6}$ alkyl substituted with one —OH, and optionally further substituted with 1, 2, or 3 fluoro.

In one embodiment, the invention is directed to compounds of Formula I-a wherein
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
$R^{4B}$ is F or —$OCF_3$; and $R^2$ is $C_{1-6}$ alkyl substituted with one —C(=O)$NR^{8a}R^{8b}$ wherein $R^{8a}$ and $R^{8b}$ are independently selected from the group consisting of H; $C_{1-4}$ alkyl optionally substituted with 1, 2, or 3 fluoro; and cyclopropyl optionally substituted with 1, 2, or 3 independently selected $R^5$ groups.

In one embodiment, the invention is directed to compounds of Formula I-a wherein
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is $C_{1-6}$ alkyl substituted with one —C(=O)$NR^{8a}R^{8b}$ wherein $R^{8a}$ and $R^{8b}$ are independently selected from the group consisting of H; $C_{1-4}$ alkyl optionally substituted with 1, 2, or 3 fluoro; and cyclopropyl optionally substituted with 1, 2, or 3 independently selected $R^5$ groups.

In one embodiment, the invention is directed to compounds of Formula I-a wherein
X is H;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
$R^{4B}$ is F or —$OCF_3$; and
$R^2$ is $C_{1-6}$ alkyl substituted with one —C(=O)$NR^{8a}R^{8b}$ wherein $R^{8a}$ and $R^{8b}$ are independently selected from the group consisting of H; $C_{1-4}$ alkyl optionally substituted with 1, 2, or 3 fluoro; and cyclopropyl optionally substituted with 1, 2, or 3 independently selected $R^5$ groups.

In one embodiment, the invention is directed to compounds of Formula I-a wherein
X is H;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is $C_{1-6}$ alkyl substituted with one —C(=O)$NR^{8a}R^{8b}$ wherein $R^{8a}$ and $R^{8b}$ are independently selected from the group consisting of H; $C_{1-4}$ alkyl optionally substituted with 1, 2, or 3 fluoro; and cyclopropyl optionally substituted with 1, 2, or 3 independently selected $R^5$ groups.

In one embodiment, the invention is directed to compounds of Formula I-a wherein
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
$R^{4B}$ is F or —$OCF_3$; and
$R^2$ is $C_{3-6}$ cycloalkyl optionally substituted with 1 or 2 independently selected fluoro, $CH_3$, $CF_3$, —OH, or —$OCH_3$.

In one embodiment, the invention is directed to compounds of Formula I-a wherein
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is $C_{3-6}$ cycloalkyl optionally substituted with 1 or 2 independently selected fluoro, $CH_3$, $CF_3$, —OH, or —$OCH_3$.

In one embodiment, the invention is directed to compounds of Formula I-a wherein
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;

each $R^{4B}$ is independently F or —$OCF_3$; and $R^2$ is $C_{3-6}$ cycloalkyl optionally substituted with 1 or 2 independently selected fluoro, $CH_2OH$, $CF_3$, —OH, or —$OCH_3$.

In one embodiment, the invention is directed to compounds of Formula I-a wherein X is H;

n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

$R^{4B}$ is F or —$OCF_3$; and $R^2$ is $C_{3-6}$ cycloalkyl optionally substituted with 1 or 2 independently selected fluoro, $CH_3$, $CF_3$, —OH, or —$OCH_3$.

In one embodiment, the invention is directed to compounds of Formula I-a wherein X is H;

n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

each $R^{4B}$ is independently F or —$OCF_3$; and $R^2$ is $C_{3-6}$ cycloalkyl optionally substituted with 1 or 2 independently selected fluoro, $CH_3$, $CF_3$, —OH, or —$OCH_3$.

In one embodiment, the invention is directed to compounds of Formula I-a wherein n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

$R^{4B}$ is F or —$OCF_3$; and $R^2$ is oxetanyl, tetrahydrofuranyl, tetrahydropyranyl, azetidinyl, pyrrolidinyl, or piperidinyl; each of which is optionally substituted with 1 or 2 independently selected fluoro, $CH_3$, $CF_3$, —OH, or —$OCH_3$.

In one embodiment, the invention is directed to compounds of Formula I-a wherein n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

each $R^{4B}$ is independently F or —$OCF_3$; and $R^2$ is oxetanyl, tetrahydrofuranyl, tetrahydropyranyl, azetidinyl, or pyrrolidinyl; each of which is optionally substituted with 1 or 2 independently selected $CH_3$, $CF_3$, or —OH.

In one embodiment, the invention is directed to compounds of Formula I-a wherein X is H;

n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

$R^{4B}$ is F or —$OCF_3$; and $R^2$ is oxetanyl, tetrahydrofuranyl, tetrahydropyranyl, azetidinyl, pyrrolidinyl, or piperidinyl; each of which is optionally substituted with 1 or 2 independently selected fluoro, $CH_3$, $CF_3$, —OH, or —$OCH_3$.

In one embodiment, the invention is directed to compounds of Formula I-a wherein X is H;

n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

each $R^{4B}$ is individually F or —$OCF_3$; and $R^2$ is oxetanyl, tetrahydrofuranyl, tetrahydropyranyl, azetidinyl, pyrrolidinyl, or piperidinyl; each of which is optionally substituted with 1 or 2 independently selected fluoro, $CH_3$, $CF_3$, —OH, or —$OCH_3$.

In one embodiment, the invention is directed to compounds of Formula I-a wherein n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

$R^{4B}$ is F or —$OCF_3$; and $R^2$ and $R^3$, together with the nitrogen atom to which they are attached form an azetidine ring which is optionally substituted with 1, 2, or 3 independently selected $R^9$ groups.

In one embodiment, the invention is directed to compounds of Formula I-a wherein n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

each $R^{4B}$ is independently F or —$OCF_3$; and $R^2$ and $R^3$, together with the nitrogen atom to which they are attached form an azetidine ring which is optionally substituted with 1, 2, or 3 independently selected $R^9$ groups.

In one embodiment, the invention is directed to compounds of Formula I-a wherein X is H;

n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

$R^{4B}$ is F or —$OCF_3$; and $R^2$ and $R^3$, together with the nitrogen atom to which they are attached form an azetidine ring which is substituted with one —OH, and optionally further substituted with one substituent selected from the group consisting of fluoro, —$CH_3$, —$CH(CH_3)_2$, $CF_3$, and unsubstituted cyclopropyl.

In one embodiment, the invention is directed to compounds of Formula I-a wherein X is H;

n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

each $R^{4B}$ is independently F or —$OCF_3$; and $R^2$ and $R^3$, together with the nitrogen atom to which they are attached form an azetidine ring which is substituted with one —OH, and optionally further substituted with one substituent selected from the group consisting of fluoro, —$CH_3$, —$CH(CH_3)_2$, $CF_3$, and unsubstituted cyclopropyl.

In one embodiment, the invention is directed to compounds of Formula I-a wherein n is 0, 1, or 2;

$R^{4A}$ is H, F, $CH_3$, —$CH(CH_3)_2$, t-Bu, $CF_3$, —$OCH_3$, —O—$CH(CH_3)_2$, or —$OCF_3$;

$R^{4B}$ is F or —$OCF_3$; and $R^2$ is

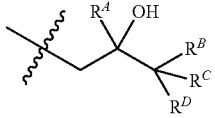

wherein $R^A$ is H or $CH_3$; and $R^B$, $R^C$, and $R^D$ are H; or $R^B$, $R^C$, and $R^D$ are fluoro; or $R^B$ and $R^C$ are H, and $R^D$ is $C_{1-4}$ alkoxy, —$OCH_2$-cyclopropyl, or —$OCH_2CF_3$.

In one embodiment, the invention is directed to compounds of Formula I-a wherein
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is

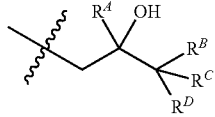

wherein
$R^A$ is H or $CH_3$; and
$R^B$, $R^C$, and $R^D$ are each independently H or fluoro; or
$R^B$ and $R^C$ are H, and $R^D$ is $C_{1-4}$ alkoxy, —$OCH_2$-cyclopropyl, or —$OCH_2CF_3$.

In one embodiment, the invention is directed to compounds of Formula I-a wherein
X is H;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
$R^{4B}$ is F or —$OCF_3$; and
$R^2$ is

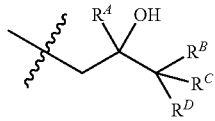

wherein
$R^A$ is H or $CH_3$; and
$R^B$, $R^C$, and $R^D$ are H; or
$R^B$, $R^C$, and $R^D$ are fluoro; or
$R^B$ and $R^C$ are H, and $R^D$ is $C_{1-4}$ alkoxy, —$OCH_2$-cyclopropyl, or —$OCH_2CF_3$.

In one embodiment, the invention is directed to compounds of Formula I-a wherein
X is H;
n is 0, 1, or 2;
$R^{4A}$ is H, F, $CH_3$, —$CH(CH_3)_2$, t-Bu, $CF_3$, —$OCH_3$, —O—$CH(CH_3)_2$, or —$OCF_3$;
each $R^{4B}$ is independently F or —$OCF_3$; and
$R^2$ is

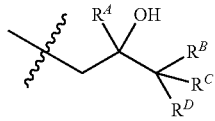

wherein
$R^A$ is H or $CH_3$; and
$R^B$, $R^C$, and $R^D$ are each independently H or fluoro; or
$R^B$ and $R^C$ are H, and $R^D$ is $C_{1-4}$ alkoxy, —$OCH_2$-cyclopropyl, or —$OCH_2CF_3$.

In one embodiment, the invention is directed to compounds of Formula I-a wherein
n is 0 or 1;
$R^{4A}$ is F, $CF_3$, or —$OCF_3$; and
$R^2$ is

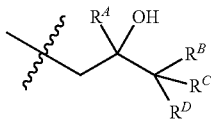

wherein
$R^A$ is H; and
$R^B$, $R^C$, and $R^D$ are fluoro; or
$R^B$ and $R^C$ are H, and $R^D$ is —$OCH_3$, —$OCH_2CH_3$, —$OCH(CH_3)_2$, —$OC(CH_3)_3$, —$OCH_2$-cyclopropyl, or —$OCH_2CF_3$.

In one embodiment, the invention is directed to compounds of Formula I-a wherein
X is H;
n is 0 or 1;
$R^{4A}$ is F, $CF_3$, or —$OCF_3$; and
$R^2$ is

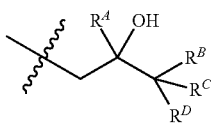

wherein
$R^A$ is H; and
$R^B$, $R^C$, and $R^D$ are fluoro; or
$R^B$ and $R^C$ are H, and $R^D$ is —$OCH_3$, —$OCH_2CH_3$, —$OCH(CH_3)_2$, —$OC(CH_3)_3$, —$OCH_2$-cyclopropyl, or —$OCH_2CF_3$.

In one embodiment, the invention is directed to compounds of Formula I-a wherein
X is H;
n is 0;
$R^{4A}$ is F; and
$R^2$ is

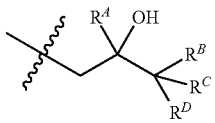

wherein
$R^A$ is H; and
$R^B$, $R^C$, and $R^D$ are fluoro; or
$R^B$ and $R^C$ are H, and $R^D$ is —$OCH_3$, —$OCH_2CH_3$, —$OCH(CH_3)_2$, —$OC(CH_3)_3$, —$OCH_2$-cyclopropyl, or —$OCH_2CF_3$.

Exemplary compounds of Formula I include, but are not limited to:
3-amino-N-(2-hydroxy-2-methylpropyl)-5-{[4-(trifluoromethoxy)phenyl]sulfonyl}pyridine-2-carboxamide;
3-amino-N-(3,3,3-trifluoro-2-hydroxy-2-methylpropyl)-5-{[4-(trifluoromethoxy)phenyl]sulfonyl}pyridine-2-carboxamide;
3-amino-N-(2-hydroxy-3-methoxypropyl)-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(3-hydroxypyrrolidin-1-yl)methanone;

3-amino-N-[(4-hydroxy-1-methylpiperidin-4-yl)methyl]-5-{[4-(trifluoromethoxy)phenyl]sulfonyl}pyridine-2-carboxamide;
3-amino-N-(3,3,3-trifluoro-2-hydroxypropyl)-5-{[4-(trifluoromethoxy)phenyl]sulfonyl}pyridine-2-carboxamide;
3-amino-N-(tetrahydrofuran-2-ylmethyl)-5-{[4-(trifluoromethoxy)phenyl]sulfonyl}pyridine-2-carboxamide;
3-amino-N-(1,4-dioxan-2-ylmethyl)-5-{[4-(trifluoromethoxy)phenyl]sulfonyl}pyridine-2-carboxamide;
3-amino-N-[2-(morpholin-4-yl)ethyl]-5-{[4-(trifluoromethoxy)phenyl]sulfonyl}pyridine-2-carboxamide;
3-amino-5-[(4-fluorophenyl)sulfonyl]-N-(2-hydroxy-2-methylpropyl)pyridine-2-carboxamide;
3-amino-N-(2-hydroxy-2-methylpropyl)-5-{[4-(trifluoromethyl)phenyl]sulfonyl}pyridine-2-carboxamide;
3-amino-N-(1-hydroxybutan-2-yl)-5-{[4-(trifluoromethoxy)phenyl]sulfonyl}pyridine-2-carboxamide;
3-amino-N-(1-hydroxy-3-methylbutan-2-yl)-5-{[4-(trifluoromethoxy)phenyl]sulfonyl}pyridine-2-carboxamide;
3-amino-N-(2-hydroxyethyl)-5-{[4-(trifluoromethoxy)phenyl]sulfonyl}pyridine-2-carboxamide;
3-amino-N-[(1-hydroxycyclopropyl)methyl]-5-{[4-(trifluoromethoxy)phenyl]sulfonyl}pyridine-2-carboxamide;
3-amino-N-(2-hydroxy-3,3-dimethylbutyl)-5-{[4-(trifluoromethoxy)phenyl]sulfonyl}pyridine-2-carboxamide;
rac-3-amino-N-[(1R,2R)-2-hydroxycyclohexyl]-5-{[4-(trifluoromethoxy)phenyl]sulfonyl}pyridine-2-carboxamide;
3-amino-N-(3-hydroxy-2,2-dimethylpropyl)-5-{[4-(trifluoromethoxy)phenyl]sulfonyl}pyridine-2-carboxamide;
3-amino-5-[(4-fluorophenyl)sulfonyl]-N-(3,3,3-trifluoro-2-hydroxy-2-methylpropyl)pyridine-2-carboxamide;
3-amino-N-[(2R)-2-hydroxypropyl]-5-{[4-(trifluoromethoxy)phenyl]sulfonyl}pyridine-2-carboxamide;
3-amino-N-[(2S)-2-hydroxypropyl]-5-{[4-(trifluoromethoxy)phenyl]sulfonyl}pyridine-2-carboxamide;
3-amino-N-{[1-(hydroxymethyl)cyclopropyl]methyl}-5-{[4-(trifluoromethoxy)phenyl]sulfonyl}pyridine-2-carboxamide;
3-amino-N-{[1-(hydroxymethyl)cyclobutyl]methyl}-5-{[4-(trifluoromethoxy)phenyl]sulfonyl}pyridine-2-carboxamide;
3-amino-N-(3-hydroxy-2-methylpropyl)-5-{[4-(trifluoromethoxy)phenyl]sulfonyl}pyridine-2-carboxamide;
3-amino-5-[(4-fluorophenyl)sulfonyl]-N-[(2S)-3,3,3-trifluoro-2-hydroxypropyl]pyridine-2-carboxamide;
3-amino-N-[(2S)-3,3,3-trifluoro-2-hydroxypropyl]-5-{[4-(trifluoromethoxy)phenyl]sulfonyl}pyridine-2-carboxamide;
3-amino-5-[(4-fluorophenyl)sulfonyl]-N-(3,3,3-trifluoro-2-hydroxypropyl)pyridine-2-carboxamide;
3-amino-N-[(3-hydroxytetrahydrofuran-3-yl)methyl]-5-{[4-(trifluoromethoxy)phenyl]sulfonyl}pyridine-2-carboxamide;
3-amino-N-[(4-hydroxytetrahydro-2H-pyran-4-yl)methyl]-5-{[4-(trifluoromethoxy)phenyl]sulfonyl}pyridine-2-carboxamide;
3-amino-5-[(4-fluorophenyl)sulfonyl]-N-[(1-hydroxycyclopropyl)methyl]pyridine-2-carboxamide;
3-amino-N-[3-(cyclopropylmethoxy)-2-hydroxypropyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(3-hydroxyazetidin-1-yl)methanone;
rac-3-amino-N-[(3R,4S)-4-hydroxytetrahydro-2H-pyran-3-yl]-5-{[4-(trifluoromethoxy)phenyl]sulfonyl}pyridine-2-carboxamide;
3-amino-N-(4-hydroxy-2,2-dimethylbutyl)-5-{[4-(trifluoromethoxy)phenyl]sulfonyl}pyridine-2-carboxamide;
3-amino-N-[2-hydroxy-2-(tetrahydro-2H-pyran-4-yl)ethyl]-5-{[4-(trifluoromethoxy)phenyl]sulfonyl}pyridine-2-carboxamide;
3-amino-5-[(4-fluorophenyl)sulfonyl]-N-[(2R)-3,3,3-trifluoro-2-hydroxypropyl]pyridine-2-carboxamide;
3-amino-N-[(2R)-3,3,3-trifluoro-2-hydroxypropyl]-5-{[4-(trifluoromethoxy)phenyl]sulfonyl}pyridine-2-carboxamide;
3-amino-N-[3-(2-ethoxyethoxy)-2-hydroxypropyl]-5-{[4-(trifluoromethoxy)phenyl]sulfonyl}pyridine-2-carboxamide;
3-amino-5-[(3-fluorophenyl)sulfonyl]-N-(2-hydroxy-2-methylpropyl)pyridine-2-carboxamide;
(3-amino-5-{[4-(trifluoromethoxy)phenyl]sulfonyl}pyridin-2-yl)(3,3-difluoroazetidin-1-yl)methanone;
3-amino-N-[2-hydroxy-1-(4-methylphenyl)ethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(3-methoxyazetidin-1-yl)methanone;
3-amino-N-[1-(ethylamino)-1-oxopropan-2-yl]-5-{[4-(trifluoromethoxy)phenyl]sulfonyl}pyridine-2-carboxamide;
3-amino-N-(1,3-dihydroxypropan-2-yl)-5-{[4-(trifluoromethoxy)phenyl]sulfonyl}pyridine-2-carboxamide;
3-amino-N-(4-hydroxybutyl)-5-{[4-(trifluoromethoxy)phenyl]sulfonyl}pyridine-2-carboxamide;
3-amino-N-[(2R)-1-hydroxy-4-methylpentan-2-yl]-5-{[4-(trifluoromethoxy)phenyl]sulfonyl}pyridine-2-carboxamide;
3-amino-N-[(2S)-3,3-dimethyl-1-(methylamino)-1-oxobutan-2-yl]-5-{[4-(trifluoromethoxy)phenyl]sulfonyl}pyridine-2-carboxamide;
3-amino-N-[2-(ethylamino)-2-oxoethyl]-5-{[4-(trifluoromethoxy)phenyl]sulfonyl}pyridine-2-carboxamide;
3-amino-N-[(2S)-1-amino-3-methyl-1-oxobutan-2-yl]-5-{[4-(trifluoromethoxy)phenyl]sulfonyl}pyridine-2-carboxamide;
3-amino-N-[(2R)-2,3-dihydroxypropyl]-5-{[4-(trifluoromethoxy)phenyl]sulfonyl}pyridine-2-carboxamide;
3-amino-N-(3-hydroxy-3-methylbutyl)-5-{[4-(trifluoromethoxy)phenyl]sulfonyl}pyridine-2-carboxamide;
3-amino-N-(4,4,4-trifluoro-3-hydroxybutyl)-5-{[4-(trifluoromethoxy)phenyl]sulfonyl}pyridine-2-carboxamide;
3-amino-N-[(3S)-3-hydroxybutyl]-5-{[4-(trifluoromethoxy)phenyl]sulfonyl}pyridine-2-carboxamide;
3-amino-N-(3-hydroxy-4-methoxybutyl)-5-{[4-(trifluoromethoxy)phenyl]sulfonyl}pyridine-2-carboxamide;
3-amino-N-(4-amino-4-oxobutan-2-yl)-5-{[4-(trifluoromethoxy)phenyl]sulfonyl}pyridine-2-carboxamide;
$N^2$-[(3-amino-5-{[4-(trifluoromethoxy)phenyl]sulfonyl}pyridin-2-yl)carbonyl]-L-leucinamide;
3-amino-N-[2-oxo-2-(propan-2-ylamino)ethyl]-5-{[4-(trifluoromethoxy)phenyl]sulfonyl}pyridine-2-carboxamide;
3-amino-N-[2-(cyclopropylamino)-2-oxoethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(3,3-dimethylazetidin-1-yl)methanone;
(3-amino-5-{[4-(trifluoromethoxy)phenyl]sulfonyl}pyridin-2-yl)[3-(morpholin-4-yl)azetidin-1-yl]methanone;
1-[(3-amino-5-{[4-(trifluoromethoxy)phenyl]sulfonyl}pyridin-2-yl)carbonyl]azetidine-3-carbonitrile;

1-[(3-amino-5-{[4-(trifluoromethoxy)phenyl]
sulfonyl}pyridin-2-yl)carbonyl]-N,N-dimethylazetidine-3-carboxamide;
3-amino-N-[(2R)-3,3,3-trifluoro-2-hydroxypropyl]-5-{[4-(trifluoromethyl)phenyl]sulfonyl}pyridine-2-carboxamide;
3-amino-N-[(2S)-3,3,3-trifluoro-2-hydroxypropyl]-5-{[4-(trifluoromethyl)phenyl]sulfonyl}pyridine-2-carboxamide;
(3-amino-5-{[4-(trifluoromethoxy)phenyl]
sulfonyl}pyridin-2-yl)(azetidin-1-yl)methanone;
(3-amino-5-{[4-(trifluoromethoxy)phenyl]
sulfonyl}pyridin-2-yl)[3-(hydroxymethyl)azetidin-1-yl]
methanone;
(3-amino-5-{[4-(trifluoromethoxy)phenyl]
sulfonyl}pyridin-2-yl)(3-fluoroazetidin-1-yl)methanone;
(3-amino-5-{[4-(trifluoromethoxy)phenyl]
sulfonyl}pyridin-2-yl)(2-oxa-6-azaspiro[3.3]hept-6-yl)
methanone;
3-amino-N-[(2R)-2-hydroxy-3-methoxypropyl]-5-{[4-(trifluoromethoxy)phenyl]sulfonyl}pyridine-2-carboxamide;
3-amino-N-[(2R)-2-hydroxy-3-methoxypropyl]-5-{[4-(trifluoromethyl)phenyl]sulfonyl}pyridine-2-carboxamide;
3-amino-5-{[2-fluoro-4-(trifluoromethoxy)phenyl]sulfonyl}-N-(2-hydroxy-3-methoxypropyl)pyridine-2-carboxamide;
3-amino-5-[(4-fluorophenyl)sulfonyl]-N-(4,4,4-trifluoro-3-hydroxybutyl)pyridine-2-carboxamide;
3-amino-N-[2-hydroxy-2-(tetrahydrofuran-3-yl)ethyl]-5-{[4-(trifluoromethoxy)phenyl]sulfonyl}pyridine-2-carboxamide;
rac-3-amino-N-[(3R,4S)-4-hydroxytetrahydrofuran-3-yl]-5-{[4-(trifluoromethoxy)phenyl]sulfonyl}pyridine-2-carboxamide;
3-amino-N-(2-hydroxyethyl)-5-{[2-(trifluoromethoxy)phenyl]sulfonyl}pyridine-2-carboxamide;
(3-amino-5-{[2-(trifluoromethoxy)phenyl]
sulfonyl}pyridin-2-yl)(3-hydroxyazetidin-1-yl)methanone;
(3-amino-5-{[2-fluoro-4-(trifluoromethoxy)phenyl]
sulfonyl}pyridin-2-yl)(3-hydroxyazetidin-1-yl)methanone;
(3-amino-5-{[2-(trifluoromethoxy)phenyl]
sulfonyl}pyridin-2-yl)(3,3-difluoroazetidin-1-yl)methanone;
(3-amino-5-{[4-(trifluoromethoxy)phenyl]
sulfonyl}pyridin-2-yl)[3-hydroxy-3-(trifluoromethyl)
azetidin-1-yl]methanone;
3-amino-N-(2-hydroxy-3-methoxypropyl)-5-{[2-(trifluoromethoxy)phenyl]sulfonyl}pyridine-2-carboxamide;
3-amino-N-[(2R)-3,3,3-trifluoro-2-hydroxypropyl]-5-{[2-(trifluoromethoxy)phenyl]sulfonyl}pyridine-2-carboxamide;
3-amino-N-[(2S)-2-hydroxypropyl]-5-{[2-(trifluoromethoxy)phenyl]sulfonyl}pyridine-2-carboxamide;
rac-3-amino-N-[(3R,4S)-4-hydroxytetrahydro-2H-pyran-3-yl]-5-{[2-(trifluoromethoxy)phenyl]sulfonyl}pyridine-2-carboxamide;
3-amino-5-[(4,4-difluoropiperidin-1-yl)sulfonyl]-N-(3,3,3-trifluoro-2-hydroxypropyl)pyridine-2-carboxamide;
(3-amino-5-{[2-(trifluoromethoxy)phenyl]
sulfonyl}pyridin-2-yl)[3-hydroxy-3-(trifluoromethyl)
azetidin-1-yl]methanone;
(3-amino-5-{[4-(trifluoromethoxy)phenyl]
sulfonyl}pyridin-2-yl)(3-cyclopropyl-3-hydroxyazetidin-1-yl)methanone;
3-amino-N-(2-hydroxy-4-methylpentyl)-5-{[4-(trifluoromethoxy)phenyl]sulfonyl}pyridine-2-carboxamide;
3-amino-N-(3-ethoxy-2-hydroxypropyl)-5-{[4-(trifluoromethoxy)phenyl]sulfonyl}pyridine-2-carboxamide;
(3-amino-5-{[4-(trifluoromethoxy)phenyl]
sulfonyl}pyridin-2-yl)(3-hydroxy-3-methylazetidin-1-yl)
methanone;
3-amino-N-[2-hydroxy-3-(propan-2-yloxy)propyl]-5-{[4-(trifluoromethoxy)phenyl]sulfonyl}pyridine-2-carboxamide;
(3-amino-5-{[4-(trifluoromethyl)phenyl]sulfonyl}pyridin-2-yl)(3-hydroxy-3-methylazetidin-1-yl)methanone;
3-amino-N-[2-hydroxy-3-(propan-2-yloxy)propyl]-5-{[4-(trifluoromethyl)phenyl]sulfonyl}pyridine-2-carboxamide;
3-amino-N-[(2S)-1-amino-1-oxobutan-2-yl]-5-{[4-(trifluoromethoxy)phenyl]sulfonyl}pyridine-2-carboxamide;
3-amino-5-[cyclopropyl(methyl)sulfamoyl]-N-(3,3,3-trifluoro-2-hydroxypropyl)pyridine-2-carboxamide;
3-amino-N-(3,3,3-trifluoro-2-hydroxypropyl)-5-{[4-(trifluoromethyl)piperidin-1-yl]sulfonyl}pyridine-2-carboxamide;
3-amino-N-[2-hydroxy-1-(4-methoxyphenyl)ethyl]-5-{[4-(trifluoromethoxy)phenyl]sulfonyl}pyridine-2-carboxamide;
3-amino-5-[(3,3-difluoroazetidin-1-yl)sulfonyl]-N-(3,3,3-trifluoro-2-hydroxypropyl)pyridine-2-carboxamide;
3-amino-5-{[2-fluoro-4-(trifluoromethyl)phenyl]sulfonyl}-N-[(2S)-2-hydroxypropyl]pyridine-2-carboxamide;
3-amino-5-{[2-fluoro-4-(trifluoromethyl)phenyl]sulfonyl}-N-[(2R)-2-hydroxy-3-methoxypropyl]pyridine-2-carboxamide;
3-amino-N-[(2S)-2-hydroxypropyl]-5-{[4-(trifluoromethyl)phenyl]sulfonyl}pyridine-2-carboxamide;
3-amino-N-[(3R)-tetrahydrofuran-3-ylmethyl]-5-{[4-(trifluoromethyl)phenyl]sulfonyl}pyridine-2-carboxamide;
3-amino-N-[(3S)-tetrahydrofuran-3-ylmethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)(3,3-difluoroazetidin-1-yl)methanone;
3-amino-N-[2-oxo-2-(propan-2-ylamino)ethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3R)-tetrahydrofuran-3-ylmethyl]pyridine-2-carboxamide;
3-amino-5-{[2-fluoro-4-(trifluoromethyl)phenyl]sulfonyl}-N-[(2R)-3,3,3-trifluoro-2-hydroxypropyl]pyridine-2-carboxamide;
3-amino-5-[cyclopropyl(2-methoxyethyl)sulfamoyl]-N-(3,3,3-trifluoro-2-hydroxypropyl)pyridine-2-carboxamide;
3-amino-5-(2,3-dihydro-4H-1,4-benzoxazin-4-ylsulfonyl)-N-(3,3,3-trifluoro-2-hydroxypropyl)pyridine-2-carboxamide;
(3-amino-5-{[4-(trifluoromethyl)phenyl]sulfonyl}pyridin-2-yl)(3,3-dimethylazetidin-1-yl)methanone;
(3-amino-5-{[2-fluoro-4-(trifluoromethyl)phenyl]
sulfonyl}pyridin-2-yl)(3,3-dimethylazetidin-1-yl)methanone;
(3-amino-5-{[2-fluoro-4-(trifluoromethyl)phenyl]
sulfonyl}pyridin-2-yl)[3-hydroxy-3-(trifluoromethyl)
azetidin-1-yl]methanone;
3-amino-5-{[2-fluoro-4-(trifluoromethyl)phenyl]sulfonyl}-N-[2-oxo-2-(propan-2-ylamino)ethyl]pyridine-2-carboxamide;

3-amino-5-{[2-fluoro-4-(trifluoromethyl)phenyl]sulfonyl}-N-[(3S)-tetrahydrofuran-3-ylmethyl]pyridine-2-carboxamide;

3-amino-5-{[2-fluoro-4-(trifluoromethoxy)phenyl]sulfonyl}-N-[(3R)-tetrahydrofuran-3-ylmethyl]pyridine-2-carboxamide;

3-amino-5-{[2-fluoro-4-(trifluoromethoxy)phenyl]sulfonyl}-N-[(3S)-tetrahydrofuran-3-ylmethyl]pyridine-2-carboxamide;

3-amino-5-{[2-fluoro-4-(trifluoromethoxy)phenyl]sulfonyl}-N-[(2R)-3,3,3-trifluoro-2-hydroxypropyl]pyridine-2-carboxamide;

3-amino-N-{[1-(ethoxymethyl)cyclobutyl]methyl}-5-{[4-(trifluoromethoxy)phenyl]sulfonyl}pyridine-2-carboxamide;

(3-amino-5-{[4-(trifluoromethoxy)phenyl]sulfonyl}pyridin-2-yl)[3-(2,2-difluoroethoxy)azetidin-1-yl]methanone;

3-amino-N-(trans-3-methoxycyclobutyl)-5-{[4-(trifluoromethoxy)phenyl]sulfonyl}pyridine-2-carboxamide;

(3-amino-5-{[4-(trifluoromethoxy)phenyl]sulfonyl}pyridin-2-yl)(6-oxa-2-azaspiro[3.5]non-2-yl)methanone;

3-amino-N-(3,3-difluorocyclobutyl)-5-{[4-(trifluoromethoxy)phenyl]sulfonyl}pyridine-2-carboxamide;

3-amino-N-(3-methoxypropyl)-5-{[4-(trifluoromethoxy)phenyl]sulfonyl}pyridine-2-carboxamide;

3-amino-N-[2-(1-methylcyclopropyl)ethyl]-5-{[4-(trifluoromethoxy)phenyl]sulfonyl}pyridine-2-carboxamide;

(3-amino-5-{[4-(trifluoromethoxy)phenyl]sulfonyl}pyridin-2-yl)(6-oxa-2-azaspiro[3.4]oct-2-yl)methanone;

(3-amino-5-{[4-(trifluoromethoxy)phenyl]sulfonyl}pyridin-2-yl)(3-methylazetidin-1-yl)methanone;

3-amino-N-(tetrahydrofuran-3-yl)-5-{[4-(trifluoromethoxy)phenyl]sulfonyl}pyridine-2-carboxamide;

3-amino-N-[(3R)-tetrahydrofuran-3-yl]-5-{[4-(trifluoromethoxy)phenyl]sulfonyl}pyridine-2-carboxamide;

3-amino-N-(tetrahydro-2H-pyran-4-ylmethyl)-5-{[4-(trifluoromethoxy)phenyl]sulfonyl}pyridine-2-carboxamide;

(3-amino-5-{[4-(trifluoromethoxy)phenyl]sulfonyl}pyridin-2-yl)(3-ethyl-3-fluoroazetidin-1-yl)methanone;

3-amino-N-[3-(cyclopropylmethoxy)-2-hydroxypropyl]-5-{[4-(trifluoromethyl)phenyl]sulfonyl}pyridine-2-carboxamide;

3-amino-N-[3-(cyclopropylmethoxy)-2-hydroxypropyl]-5-{[2-fluoro-4-(trifluoromethyl)phenyl]sulfonyl}pyridine-2-carboxamide;

3-amino-5-{[2-fluoro-4-(trifluoromethyl)phenyl]sulfonyl}-N-[2-hydroxy-3-(propan-2-yloxy)propyl]pyridine-2-carboxamide;

(3-amino-5-{[2-fluoro-4-(trifluoromethoxy)phenyl]sulfonyl}pyridin-2-yl)(3,3-dimethylazetidin-1-yl)methanone;

3-amino-5-{[2-fluoro-4-(trifluoromethoxy)phenyl]sulfonyl}-N-[2-oxo-2-(propan-2-ylamino)ethyl]pyridine-2-carboxamide;

3-amino-5-[(3,4-difluorobenzyl)(methyl)sulfamoyl]-N-(3,3,3-trifluoro-2-hydroxypropyl)pyridine-2-carboxamide;

3-amino-5-[(2,4-difluorobenzyl)(methyl)sulfamoyl]-N-(3,3,3-trifluoro-2-hydroxypropyl)pyridine-2-carboxamide;

3-amino-5-[(4-methoxybenzyl)(methyl)sulfamoyl]-N-(3,3,3-trifluoro-2-hydroxypropyl)pyridine-2-carboxamide;

3-amino-5-(morpholin-4-yl sulfonyl)-N-(3,3,3-trifluoro-2-hydroxypropyl)pyridine-2-carboxamide;

3-amino-N-[(3R)-tetrahydro-2H-pyran-3-yl]-5-{[4-(trifluoromethoxy)phenyl]sulfonyl}pyridine-2-carboxamide;

3-amino-N-[2-(furan-2-yl)ethyl]-5-{[4-(trifluoromethoxy)phenyl]sulfonyl}pyridine-2-carboxamide;

3-amino-N-[(2S)-1-hydroxybutan-2-yl]-5-{[4-(trifluoromethoxy)phenyl]sulfonyl}pyridine-2-carboxamide;

3-amino-N-(tetrahydro-2H-pyran-3-ylmethyl)-5-{[4-(trifluoromethoxy)phenyl]sulfonyl}pyridine-2-carboxamide;

3-amino-N-[(3S)-tetrahydrofuran-3-yl]-5-{[4-(trifluoromethoxy)phenyl]sulfonyl}pyridine-2-carboxamide;

3-amino-N-[(4R)-3,4-dihydro-2H-chromen-4-yl]-5-{[4-(trifluoromethoxy)phenyl]sulfonyl}pyridine-2-carboxamide;

3-amino-N-(tetrahydro-2H-pyran-4-yl)-5-{[4-(trifluoromethoxy)phenyl]sulfonyl}pyridine-2-carboxamide;

3-amino-N-[2-(1,3-dioxolan-2-yl)ethyl]-5-{[4-(trifluoromethoxy)phenyl]sulfonyl}pyridine-2-carboxamide;

3-amino-N-[(2S)-1-hydroxy-3-methylbutan-2-yl]-5-{[4-(trifluoromethoxy)phenyl]sulfonyl}pyridine-2-carboxamide;

3-amino-N-(1-oxaspiro[4.5]dec-3-yl)-5-{[4-(trifluoromethoxy)phenyl]sulfonyl}pyridine-2-carboxamide;

3-amino-N-(1-oxaspiro[4.4]non-3-yl)-5-{[4-(trifluoromethoxy)phenyl]sulfonyl}pyridine-2-carboxamide;

3-amino-N-(oxetan-3-yl)-5-{[4-(trifluoromethoxy)phenyl]sulfonyl}pyridine-2-carboxamide;

3-amino-N-(2-cyclopropylethyl)-5-{[4-(trifluoromethoxy)phenyl]sulfonyl}pyridine-2-carboxamide;

3-amino-N-[(3,3-difluorocyclobutyl)methyl]-5-{[4-(trifluoromethoxy)phenyl]sulfonyl}pyridine-2-carboxamide;

(3-amino-5-{[4-(trifluoromethoxy)phenyl]sulfonyl}pyridin-2-yl)[3-(methoxymethyl)-3-methylazetidin-1-yl]methanone;

3-amino-N-(cyclopropylmethyl)-5-{[4-(trifluoromethoxy)phenyl]sulfonyl}pyridine-2-carboxamide;

3-amino-N-[(4-methyltetrahydro-2H-pyran-3-yl)methyl]-5-{[4-(trifluoromethoxy)phenyl]sulfonyl}pyridine-2-carboxamide;

(3-amino-5-{[4-(trifluoromethyl)phenyl]sulfonyl}pyridin-2-yl)[3-(trifluoromethyl)azetidin-1-yl]methanone;

(3-amino-5-{[4-(trifluoromethyl)phenyl]sulfonyl}pyridin-2-yl)[3-(difluoromethoxy)azetidin-1-yl]methanone;

(3-amino-5-{[4-(trifluoromethyl)phenyl]sulfonyl}pyridin-2-yl)[3-hydroxy-3-(propan-2-yl)azetidin-1-yl]methanone;

(3-amino-5-{[2-fluoro-4-(trifluoromethyl)phenyl]sulfonyl}pyridin-2-yl)[3-(trifluoromethyl)azetidin-1-yl]methanone;

(3-amino-5-{[2-fluoro-4-(trifluoromethyl)phenyl]sulfonyl}pyridin-2-yl)[3-(difluoromethoxy)azetidin-1-yl]methanone;

(3-amino-5-{[2-fluoro-4-(trifluoromethyl)phenyl]sulfonyl}pyridin-2-yl)[3-hydroxy-3-(propan-2-yl)azetidin-1-yl]methanone;

3-amino-5-{[2-fluoro-4-(trifluoromethyl)phenyl]sulfonyl}-N-(2-hydroxy-4-methoxy-2-methylbutyl)pyridine-2-carboxamide;

(3-amino-5-{[2-fluoro-4-(trifluoromethyl)phenyl]sulfonyl}pyridin-2-yl)(3,3-difluoroazetidin-1-yl)methanone;

(3-amino-5-{[4-(trifluoromethyl)phenyl]sulfonyl}pyridin-2-yl)[3-(2-hydroxypropan-2-yl)azetidin-1-yl]methanone;

3-amino-N-[2-hydroxy-3-(2-methylpropoxy)propyl]-5-{[4-(trifluoromethyl)phenyl]sulfonyl}pyridine-2-carboxamide;

3-amino-N-(2-hydroxy-4-methoxy-2-methylbutyl)-5-{[4-(trifluoromethyl)phenyl]sulfonyl}pyridine-2-carboxamide;

3-amino-5-{[2-fluoro-4-(trifluoromethoxy)phenyl]sulfonyl}-N-[2-hydroxy-3-(propan-2-yloxy)propyl]pyridine-2-carboxamide;
3-amino-N-[3-(cyclopropylmethoxy)-2-hydroxypropyl]-5-{[2-fluoro-4-(trifluoromethoxy)phenyl]sulfonyl}pyridine-2-carboxamide;
3-amino-5-{[2-fluoro-4-(trifluoromethyl)phenyl]sulfonyl}-N-[2-hydroxy-3-(2-methylpropoxy)propyl]pyridine-2-carboxamide;
3-amino-5-{[2-fluoro-4-(trifluoromethoxy)phenyl]sulfonyl}-N-[2-hydroxy-3-(2-methylpropoxy)propyl]pyridine-2-carboxamide;
(3-amino-5-{[2-fluoro-4-(trifluoromethoxy)phenyl]sulfonyl}pyridin-2-yl)(3,3-difluoroazetidin-1-yl)methanone;
(3-amino-5-{[2-fluoro-4-(trifluoromethoxy)phenyl]sulfonyl}pyridin-2-yl)[3-hydroxy-3-(trifluoromethyl)azetidin-1-yl]methanone;
(3-amino-5-{[2-fluoro-4-(trifluoromethoxy)phenyl]sulfonyl}pyridin-2-yl)[3-(2-hydroxypropan-2-yl)azetidin-1-yl]methanone;
(3-amino-5-{[2-fluoro-4-(trifluoromethoxy)phenyl]sulfonyl}pyridin-2-yl)[3-hydroxy-3-(propan-2-yl)azetidin-1-yl]methanone;
{3-amino-5-[(4-fluorophenyl)sulfonyl]pyridin-2-yl}[3-hydroxy-3-(trifluoromethyl)azetidin-1-yl]methanone;
3-amino-N-[(2R)-2-hydroxy-3-methoxypropyl]-5-{[2-(trifluoromethoxy)phenyl]sulfonyl}pyridine-2-carboxamide;
(3-amino-5-{[2-fluoro-4-(trifluoromethyl)phenyl]sulfonyl}pyridin-2-yl)[3-(2-hydroxypropan-2-yl)azetidin-1-yl]methanone;
3-amino-5-{[(2R)-2-methylpyrrolidin-1-yl]sulfonyl}-N-(3,3,3-trifluoro-2-hydroxypropyl)pyridine-2-carboxamide;
3-amino-5-{[(3S)-3-fluoropyrrolidin-1-yl]sulfonyl}-N-(3,3,3-trifluoro-2-hydroxypropyl)pyridine-2-carboxamide;
3-amino-5-{[(2S)-2-methylpyrrolidin-1-yl]sulfonyl}-N-(3,3,3-trifluoro-2-hydroxypropyl)pyridine-2-carboxamide;
3-amino-5-[(3-methylpiperidin-1-yl)sulfonyl]-N-(3,3,3-trifluoro-2-hydroxypropyl)pyridine-2-carboxamide;
3-amino-5-[(3,3-difluoropiperidin-1-yl)sulfonyl]-N-(3,3,3-trifluoro-2-hydroxypropyl)pyridine-2-carboxamide;
3-amino-5-[(4-methylpiperidin-1-yl)sulfonyl]-N-(3,3,3-trifluoro-2-hydroxypropyl)pyridine-2-carboxamide;
3-amino-5-[(3,5-dimethylpiperidin-1-yl)sulfonyl]-N-(3,3,3-trifluoro-2-hydroxypropyl)pyridine-2-carboxamide;
3-amino-5-[(3,3-difluoropyrrolidin-1-yl)sulfonyl]-N-(3,3,3-trifluoro-2-hydroxypropyl)pyridine-2-carboxamide;
3-amino-5-[(4-fluorobenzyl)(methyl)sulfamoyl]-N-(3,3,3-trifluoro-2-hydroxypropyl)pyridine-2-carboxamide;
3-amino-N-(3-methylbutan-2-yl)-5-{[4-(trifluoromethyl)phenyl]sulfonyl}pyridine-2-carboxamide;
3-amino-N-(2-methylpropyl)-5-{[4-(trifluoromethyl)phenyl]sulfonyl}pyridine-2-carboxamide;
3-amino-N-[2-(tetrahydrofuran-2-ylmethoxy)ethyl]-5-{[4-(trifluoromethyl)phenyl]sulfonyl}pyridine-2-carboxamide;
3-amino-N-(2,2-dimethylpropyl)-5-{[4-(trifluoromethyl)phenyl]sulfonyl}pyridine-2-carboxamide;
3-amino-N-[2-(propan-2-yloxy)ethyl]-5-{[4-(trifluoromethyl)phenyl]sulfonyl}pyridine-2-carboxamide;
3-amino-5-{[4-(trifluoromethoxy)phenyl]sulfonyl}-N-[4-(trifluoromethyl)tetrahydro-2H-pyran-4-yl]pyridine-2-carboxamide;
3-amino-5-[(3-fluoropiperidin-1-yl)sulfonyl]-N-(3,3,3-trifluoro-2-hydroxypropyl)pyridine-2-carboxamide;
3-amino-5-[(4-fluoropiperidin-1-yl)sulfonyl]-N-(3,3,3-trifluoro-2-hydroxypropyl)pyridine-2-carboxamide;
3-amino-5-[(4-methoxypiperidin-1-yl)sulfonyl]-N-(3,3,3-trifluoro-2-hydroxypropyl)pyridine-2-carboxamide;
3-amino-5-[(4-tert-butylpiperidin-1-yl)sulfonyl]-N-(3,3,3-trifluoro-2-hydroxypropyl)pyridine-2-carboxamide;
3-amino-N-(3,3,3-trifluoro-2-hydroxypropyl)-5-{[4-(trifluoromethyl)piperidin-1-yl]sulfonyl}pyridine-2-carboxamide;
3-amino-5-[(3,3-dimethylazetidin-1-yl)sulfonyl]-N-(3,3,3-trifluoro-2-hydroxypropyl)pyridine-2-carboxamide;
3-amino-5-{[(3R)-tetrahydrofuran-3-ylmethyl]sulfamoyl}-N-(3,3,3-trifluoro-2-hydroxypropyl)pyridine-2-carboxamide;
3-amino-N-[2-hydroxy-3-(2,2,2-trifluoroethoxy)propyl]-5-{[4-(trifluoromethyl)phenyl]sulfonyl}pyridine-2-carboxamide;
3-amino-N-(2-methoxyethyl)-5-{[4-(trifluoromethyl)phenyl]sulfonyl}pyridine-2-carboxamide;
(3-amino-5-{[4-(trifluoromethoxy)phenyl]sulfonyl}pyridin-2-yl)(3,3-difluoropyrrolidin-1-yl)methanone;
(3-amino-5-{[4-(trifluoromethoxy)phenyl]sulfonyl}pyridin-2-yl)[(3R)-3-fluoropyrrolidin-1-yl]methanone;
3-amino-N-[(1R,2S)-2-hydroxycyclopentyl]-5-{[4-(trifluoromethyl)phenyl]sulfonyl}pyridine-2-carboxamide;
(3-amino-5-{[4-(trifluoromethoxy)phenyl]sulfonyl}pyridin-2-yl)[(3S)-3-fluoropyrrolidin-1-yl]methanone;
3-amino-N-[(3S)-1-methylpyrrolidin-3-yl]-5-{[4-(trifluoromethoxy)phenyl]sulfonyl}pyridine-2-carboxamide;
3-amino-N-[(3R)-1-methylpyrrolidin-3-yl]-5-{[4-(trifluoromethoxy)phenyl]sulfonyl}pyridine-2-carboxamide;
3-amino-N-(2,2,2-trifluoroethyl)-5-{[4-(trifluoromethyl)phenyl]sulfonyl}pyridine-2-carboxamide;
3-amino-N-(1-methylazetidin-3-yl)-5-{[4-(trifluoromethoxy)phenyl]sulfonyl}pyridine-2-carboxamide;
3-amino-5-{methyl[4-(trifluoromethyl)benzyl]sulfamoyl}-N-(3,3,3-trifluoro-2-hydroxypropyl)pyridine-2-carboxamide;
3-amino-5-{[4-(trifluoromethyl)phenyl]sulfonyl}-N-(3,3,3-trifluoropropyl)pyridine-2-carboxamide;
3-amino-5-{[2-fluoro-4-(trifluoromethyl)phenyl]sulfonyl}-N-[2-hydroxy-3-(2,2,2-trifluoroethoxy)propyl]pyridine-2-carboxamide;
3-amino-5-{[4-(trifluoromethoxy)phenyl]sulfonyl}-N-[3-(trifluoromethyl)oxetan-3-yl]pyridine-2-carboxamide;
3-amino-N-[(1S,2S)-2-hydroxycyclopentyl]-5-{[4-(trifluoromethyl)phenyl]sulfonyl}pyridine-2-carboxamide;
rac-3-amino-N-[(3R,4S)-4-hydroxytetrahydro-2H-pyran-3-yl]-5-{[4-(trifluoromethyl)phenyl]sulfonyl}pyridine-2-carboxamide;
3-amino-N-(2-hydroxyethyl)-5-{[4-(trifluoromethyl)phenyl]sulfonyl}pyridine-2-carboxamide;
rac-3-amino-5-{[2-fluoro-4-(trifluoromethyl)phenyl]sulfonyl}-N-[(3R,4S)-4-hydroxytetrahydro-2H-pyran-3-yl]pyridine-2-carboxamide;
3-amino-5-{[2-fluoro-4-(trifluoromethyl)phenyl]sulfonyl}-N-(2-hydroxyethyl)pyridine-2-carboxamide;
3-amino-5-[(4-methoxyphenyl)sulfonyl]-N-(3,3,3-trifluoro-2-hydroxypropyl)pyridine-2-carboxamide;
3-amino-N-[2-hydroxy-3-(2-methoxyethoxy)propyl]-5-{[4-(trifluoromethyl)phenyl]sulfonyl}pyridine-2-carboxamide;
3-amino-N-(3-methoxypropyl)-5-{[4-(trifluoromethyl)phenyl]sulfonyl}pyridine-2-carboxamide;
3-amino-N-(cyclopropylmethyl)-5-{[4-(trifluoromethyl)phenyl]sulfonyl}pyridine-2-carboxamide;

3-amino-N-(3-tert-butoxy-2-hydroxypropyl)-5-{[2-fluoro-4-(trifluoromethyl)phenyl]sulfonyl}pyridine-2-carboxamide;

3-amino-5-[methyl(3,3,3-trifluoropropyl)sulfamoyl]-N-(3,3,3-trifluoro-2-hydroxypropyl)pyridine-2-carboxamide;

(3-amino-5-{[4-(trifluoromethyl)phenyl]sulfonyl}pyridin-2-yl)[(2S)-2-(hydroxymethyl)pyrrolidin-1-yl]methanone;

3-amino-N-(1-hydroxy-2-methylpropan-2-yl)-5-{[4-(trifluoromethyl)phenyl]sulfonyl}pyridine-2-carboxamide;

3-amino-N-[(1-hydroxycyclopropyl)methyl]-5-{[4-(trifluoromethyl)phenyl]sulfonyl}pyridine-2-carboxamide;

(3-amino-5-{[4-(trifluoromethyl)phenyl]sulfonyl}pyridin-2-yl) [(3R,4R)-3,4-dihydroxypyrrolidin-1-yl]methanone;

3-amino-N-[(4-hydroxy-1-methylpiperidin-4-yl)methyl]-5-{[4-(trifluoromethyl)phenyl]sulfonyl}pyridine-2-carboxamide;

(3-amino-5-{[4-(trifluoromethyl)phenyl]sulfonyl}pyridin-2-yl)[3-(2,2-difluoroethoxy)azetidin-1-yl]methanone;

(3-amino-5-{[4-(trifluoromethyl)phenyl]sulfonyl}pyridin-2-yl)[3-(methoxymethyl)-3-methylazetidin-1-yl]methanone;

(3-amino-5-{[4-(trifluoromethyl)phenyl]sulfonyl}pyridin-2-yl) [(2R)-2-(hydroxymethyl)pyrrolidin-1-yl]methanone;

3-amino-N-[(2S)-1-hydroxybutan-2-yl]-5-{[4-(trifluoromethyl)phenyl]sulfonyl}pyridine-2-carboxamide;

3-amino-N-[(3R,4S)-4-hydroxytetrahydro-2H-pyran-3-yl]-5-{[4-(trifluoromethyl)phenyl]sulfonyl}pyridine-2-carboxamide;

3-amino-N-(3,3,3-trifluoro-2-hydroxypropyl)-5-{[3-(trifluoromethoxy)phenyl]sulfonyl}pyridine-2-carboxamide;

3-amino-5-{[4-(propan-2-yloxy)phenyl]sulfonyl}-N-(3,3,3-trifluoro-2-hydroxypropyl)pyridine-2-carboxamide;

3-amino-5-[(tetrahydrofuran-2-ylmethyl)sulfonyl]-N-(3,3,3-trifluoro-2-hydroxypropyl)pyridine-2-carboxamide;

3-amino-N-(2-hydroxy-3-methoxypropyl)-5-{[4-(trifluoromethyl)phenyl]sulfonyl}pyridine-2-carboxamide;

3-amino-N-[2-(trifluoromethoxy)ethyl]-5-{[4-(trifluoromethyl)phenyl]sulfonyl}pyridine-2-carboxamide;

3-amino-N-(2,2-difluoro-3-hydroxypropyl)-5-{[4-(trifluoromethyl)phenyl]sulfonyl}pyridine-2-carboxamide;

3-amino-N-[(2S)-3-(cyclopropylmethoxy)-2-hydroxypropyl]-5-{[4-(trifluoromethoxy)phenyl]sulfonyl}pyridine-2-carboxamide;

3-amino-N-[(2S)-2-hydroxy-3-(propan-2-yloxy)propyl]-5-{[4-(trifluoromethyl)phenyl]sulfonyl}pyridine-2-carboxamide;

3-amino-5-(phenyl sulfonyl)-N-(3,3,3-trifluoro-2-hydroxypropyl)pyridine-2-carboxamide;

3-amino-5-[(4-methylphenyl)sulfonyl]-N-(3,3,3-trifluoro-2-hydroxypropyl)pyridine-2-carboxamide;

3-amino-5-{[4-(propan-2-yl)phenyl]sulfonyl}-N-(3,3,3-trifluoro-2-hydroxypropyl)pyridine-2-carboxamide;

3-amino-5-[(4-tert-butylphenyl)sulfonyl]-N-(3,3,3-trifluoro-2-hydroxypropyl)pyridine-2-carboxamide;

3-amino-N-[(2R)-2-hydroxy-3-(2,2,2-trifluoroethoxy)propyl]-5-{[4-(trifluoromethyl)phenyl]sulfonyl}pyridine-2-carboxamide;

3-amino-N-[(2S)-2-hydroxy-3-(2,2,2-trifluoroethoxy)propyl]-5-{[4-(trifluoromethyl)phenyl]sulfonyl}pyridine-2-carboxamide;

3-amino-6-bromo-5-[(4-fluorophenyl)sulfonyl]-N-[(2R)-3,3,3-trifluoro-2-hydroxypropyl]pyridine-2-carboxamide;

3-amino-N-[(2R)-3-(cyclopropylmethoxy)-2-hydroxypropyl]-5-{[4-(trifluoromethoxy)phenyl]sulfonyl}pyridine-2-carboxamide;

3-amino-N-[(2R)-2-hydroxy-3-(propan-2-yloxy)propyl]-5-{[4-(trifluoromethyl)phenyl]sulfonyl}pyridine-2-carboxamide;

3-amino-5-(phenylsulfonyl)-N-[(2R)-3,3,3-trifluoro-2-hydroxypropyl]pyridine-2-carboxamide;

3-amino-5-[(3-fluorophenyl)sulfonyl]-N-[(2R)-3,3,3-trifluoro-2-hydroxypropyl]pyridine-2-carboxamide;

[3-amino-5-(phenylsulfonyl)pyridin-2-yl][3-hydroxy-3-(trifluoromethyl)azetidin-1-yl]methanone;

{3-amino-5-[(3-fluorophenyl)sulfonyl]pyridin-2-yl}[3-hydroxy-3-(trifluoromethyl)azetidin-1-yl]methanone;

3-amino-N-[(3S,4R)-4-hydroxytetrahydro-2H-pyran-3-yl]-5-{[4-(trifluoromethyl)phenyl]sulfonyl}pyridine-2-carboxamide;

3-amino-6-cyclopropyl-N-(2-hydroxyethyl)-5-{[4-(trifluoromethyl)phenyl]sulfonyl}pyridine-2-carboxamide;

3-amino-6-(4-fluorophenyl)-5-[(4-fluorophenyl)sulfonyl]-N-[(2R)-3,3,3-trifluoro-2-hydroxypropyl]pyridine-2-carboxamide;

3-amino-6-cyclopropyl-N-(2-hydroxyethyl)-5-(phenyl sulfonyl)pyridine-2-carboxamide;

3-amino-5-(cyclopentylsulfonyl)-6-(4-fluorophenyl)-N-[(2S)-2-hydroxypropyl]pyridine-2-carboxamide;

3-amino-6-(4-fluorophenyl)-5-[(2-hydroxyethyl)sulfonyl]-N-[(2S)-2-hydroxypropyl]pyridine-2-carboxamide;

3-amino-5-(ethyl sulfonyl)-6-(4-fluorophenyl)-N-[(2S)-2-hydroxypropyl]pyridine-2-carboxamide;

3-amino-6-(4-fluorophenyl)-N-[(2S)-2-hydroxypropyl]-5-(propan-2-ylsulfonyl)pyridine-2-carboxamide;

3-amino-6-(4-fluorophenyl)-N-[(2S)-2-hydroxypropyl]-5-[(2-methoxyethyl)sulfonyl]pyridine-2-carboxamide;

3-amino-N-[(2S)-2-hydroxypropyl]-5-{[(2S)-2-methylpyrrolidin-1-yl]sulfonyl}pyridine-2-carboxamide;

3-amino-5-[(4-fluorobenzyl)sulfamoyl]-N-[(2S)-2-hydroxypropyl]pyridine-2-carboxamide;

3-amino-5-{[2-(hydroxymethyl)pyrrolidin-1-yl]sulfonyl}-N-[(2S)-2-hydroxypropyl]pyridine-2-carboxamide;

3-amino-5-[(4-fluorobenzyl)(methyl)sulfamoyl]-N-[(2S)-2-hydroxypropyl]pyridine-2carboxamide;

3-amino-5-{[(2S)-2-methylpyrrolidin-1-yl]sulfonyl}-N-[2-oxo-2-(propan-2-ylamino)ethyl]pyridine-2-carboxamide;

1-[(3-amino-5-{[(2S)-2-methylpyrrolidin-1-yl]sulfonyl}pyridin-2-yl)carbonyl]azetidine-3-carboxamide;

(3-amino-5-{[(2S)-2-methylpyrrolidin-1-yl]sulfonyl}pyridin-2-yl)(3-hydroxyazetidin-1-yl)methanone;

3-amino-N-(3-fluoro-2-hydroxypropyl)-5-{[4-(trifluoromethoxy)phenyl]sulfonyl}pyridine-2-carboxamide;

3-amino-6-cyclopropyl-5-[(4-fluorophenyl)sulfonyl]-N-[(2S)-2-hydroxypropyl]pyridine-2-carboxamide;

3-amino-6-cyclopropyl-5-(ethyl sulfonyl)-N-[(2S)-2-hydroxypropyl]pyridine-2-carboxamide;

3-amino-N-(2-hydroxy-3-methoxypropyl)-5-{[(2S)-2-methylpyrrolidin-1-yl]sulfonyl}pyridine-2-carboxamide;

3-amino-N-[(2S)-2-hydroxypropyl]-5-[(2-methoxyethyl)(methyl)sulfamoyl]pyridine-2-carboxamide;

3-amino-5-[cyclobutyl(methyl)sulfamoyl]-N-[(2S)-2-hydroxypropyl]pyridine-2-carboxamide;

3-amino-N-(3,3-difluoro-2-hydroxypropyl)-5-{[4-(trifluoromethoxy)phenyl]sulfonyl}pyridine-2-carboxamide;

3-amino-N-[(2S)-2-hydroxypropyl]-6-methoxy-5-{[4-(trifluoromethoxy)phenyl]sulfonyl}pyridine-2-carboxamide;

3-amino-N-[(4-methoxypyrimidin-2-yl)methyl]-5-{[(2S)-2-methylpyrrolidin-1-yl]sulfonyl}pyridine-2-carboxamide;

3-amino-5-{[(2S)-2-methylpyrrolidin-1-yl]sulfonyl}-N-[(6-oxo-1,6-dihydropyrimidin-2-yl)methyl]pyridine-2-carboxamide;

3-amino-6-(dimethylamino)-N-[(2S)-2-hydroxypropyl]-5-{[4-(trifluoromethoxy)phenyl]sulfonyl}pyridine-2-carboxamide;
3-amino-6-(3-fluorophenoxy)-N-[(2S)-2-hydroxypropyl]-5-{[4-(trifluoromethoxy)phenyl]sulfonyl}pyridine-2-carboxamide;
3-amino-6-(cyclopropylamino)-N-[(2S)-2-hydroxypropyl]-5-{[4-(trifluoromethoxy)phenyl]sulfonyl}pyridine-2-carboxamide;
3-amino-N'-(methoxyacetyl)-5-{[4-(trifluoromethoxy)phenyl]sulfonyl}pyridine-2-carbohydrazide;
3-amino-N'-(hydroxyacetyl)-5-{[4-(trifluoromethoxy)phenyl]sulfonyl}pyridine-2-carbohydrazide;
3-amino-N-[(2S)-2-hydroxypropyl]-6-(2-methoxyethoxy)-5-{[4-(trifluoromethoxy)phenyl]sulfonyl}pyridine-2-carboxamide;
3-amino-6-[2-(dimethylamino)ethoxy]-N-[(2S)-2-hydroxypropyl]-5-{[4-(trifluoromethoxy)phenyl]sulfonyl}pyridine-2-carboxamide;
3-amino-6-cyclopropyl-N-[(2S)-2-hydroxypropyl]-5-{[4-(trifluoromethoxy)phenyl]sulfonyl}pyridine-2-carboxamide;
3-amino-N-(1H-pyrazol-3-yl)-5-{[4-(trifluoromethoxy)phenyl]sulfonyl}pyridine-2-carboxamide;
3-amino-N-[1-(hydroxymethyl)cyclopropyl]-5-{[4-(trifluoromethyl)phenyl]sulfonyl}pyridine-2-carboxamide;
3-amino-N-[(1S,2S)-2-methoxycyclopentyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)(3-fluoro-3-methylazetidin-1-yl)methanone;
(3-amino-5-{[4-(trifluoromethyl)phenyl]sulfonyl}pyridin-2-yl)(6-oxa-2-azaspiro[3.5]non-2-yl)methanone;
3-amino-N-[(2R)-2-hydroxy-3-methoxypropyl]-5-(phenylsulfonyl)pyridine-2-carboxamide;
3-amino-5-{[4-(trifluoromethoxy)phenyl]sulfonyl}pyridine-2-carboxamide;
3-amino-6-bromo-5-[(4-fluorophenyl)sulfonyl]pyridine-2-carboxamide;
and pharmaceutically acceptable salts thereof.

Compounds of the invention are named by using Name 2014 naming algorithm by Advanced Chemical Development or Struct=Name naming algorithm as part of CHEMDRAW® ULTRA v. 12.0.2.1076 or Professional Version 15.0.0.106.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of Formula I and I-a wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula I and I-a, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula I and I-a may generally be prepared by conventional techniques known to those skilled in the art or by processes analogous to those described in the accompanying Examples using an appropriate isotopically-labeled reagents in place of the non-labeled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of Formula I and I-a may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of Formula I and I-a may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid, and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, refers to derivatives of the compounds of the invention which have cleavable groups. Such derivatives become, by solvolysis or under physiological conditions, the compounds of the invention which are pharmaceutically active in vivo. Prodrugs of the compounds of the invention are, within the scope of sound medical judgement, suitable for use in contact with the tissues of humans and lower animals without undue toxicity, irritation, allergic response, and the like, commensurate with a reasonable benefit/risk ratio, and effective for their intended use.

The invention contemplates compounds of Formula I and I-a formed by synthetic means or formed by in vivo biotransformation of a prodrug.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

When employed as a pharmaceutical, a compound of the invention is typically administered in the form of a pharmaceutical composition. Such compositions can be prepared in a manner well known in the pharmaceutical art and comprise a therapeutically effective amount of a compound of Formula I or I-a, or a pharmaceutically acceptable salt thereof together with a pharmaceutically acceptable carrier. The phrase "pharmaceutical composition" refers to a composition suitable for administration in medical or veterinary use.

The pharmaceutical compositions that comprise a compound of Formula I or I-a, alone or in combination with further therapeutically active ingredient, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous diluents, solvents, or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it may be desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In certain embodiments, solid dosage forms may contain from 1% to 95% (w/w) of a compound of Formula I or I-a. In certain embodiments, the compound of Formula I or I-a, or pharmaceutically acceptable salts thereof, may be present in the solid dosage form in a range of from 5% to 70% (w/w). In such solid dosage forms, the active compound may be mixed with at least one inert, pharmaceutically acceptable carrier, such as sodium citrate or dicalcium phosphate and/or a), fillers or extenders such as starches, lactose, sucrose, glucose, mannitol, and silicic acid; b) binders such as carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form may be a capsule, tablet, cachet, or lozenge itself, or it may be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition may, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the $LD_{50}$ of the compound, the pharmacokinetic profile of the compound, contraindicated drugs, and the side-effects of the compound at various concentrations, as applied to the mass and overall health of the subject. Administration may be accomplished via single or divided doses.

The compounds utilized in the pharmaceutical method of the invention may be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

A compound of the invention may also be administered in sustained release forms or from sustained release drug delivery systems.

Methods of Use

The compounds and compositions using any amount and any route of administration may be administered to a subject for the treatment or prevention of cystic fibrosis, pancreatic insufficiency, Sjögren's Syndrome (SS), chronic obstructive lung disease (COLD), or chronic obstructive airway disease (COAD).

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, via implantation, transdermally, topically, and via implantation. In certain embodiments, the compounds and compositions thereof may be delivered orally. The compounds may also be delivered rectally, bucally, intravaginally, ocularly, or by insufflation. CFTR-modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as modulators of CFTR. Thus, the compounds and compositions are particularly useful for treating or lessening the severity, or progression of a disease, disorder, or a condition where hyperactivity or inactivity of CFTR is involved. Accordingly, the invention provides a method for treating cystic fibrosis, pancreatic insufficiency, Sjögren's Syndrome (SS), chronic obstructive lung disease (COLD), or chronic obstructive airway disease (COAD) in a subject, wherein the method comprises the step of administering to said subject a therapeutically effective amount of a compound of Formula I or I-a or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, and/or VI mutation.

In another embodiment, the present invention provides compounds of the invention, or pharmaceutical compositions comprising a compound of the invention for use in medicine. In a particular embodiment, the present invention provides compounds of the invention, or a pharmaceutically acceptable salt thereof, or a pharmaceutical composition comprising a compound of the invention, for use in medicine. In a particular embodiment, the present invention provides compounds of the invention or pharmaceutical compositions comprising a compound of the invention, for use in the treatment of cystic fibrosis, pancreatic insufficiency, Sjögren's Syndrome (SS), chronic obstructive lung disease (COLD) or chronic obstructive airway disease (COAD). In a more particular embodiment, the present invention provides compounds of the invention or pharmaceutical compositions comprising a compound of the invention, for use in the treatment of cystic fibrosis. In a more particular embodiment, the cystic fibrosis is caused by a Class I, II, III, IV and/or VI mutation.

One embodiment is directed to the use of a compound according to Formula I or I-a or a pharmaceutically acceptable salt thereof in the preparation of a medicament. The medicament optionally can comprise one or more additional therapeutic agents. In some embodiments, the medicament is for use in the treatment of cystic fibrosis, pancreatic insufficiency, Sjögren's Syndrome (SS), chronic obstructive lung disease (COLD) or chronic obstructive airway disease (COAD). In a particular embodiment, the medicament is for use in the treatment of cystic fibrosis. In a more particular embodiment, the cystic fibrosis is caused by a Class I, II, III, IV and/or VI mutation.

This invention also is directed to the use of a compound according to Formula I or I-a or a pharmaceutically acceptable salt thereof in the manufacture of a medicament for the treatment of cystic fibrosis, Sjögren's syndrome, pancreatic insufficiency, chronic obstructive lung disease, and chronic obstructive airway disease. The medicament optionally can comprise one or more additional therapeutic agents. In a particular embodiment, the invention is directed to the use of a compound according to Formula I or a pharmaceutically acceptable salt thereof in the manufacture of a medicament for the treatment of cystic fibrosis. In a more particular embodiment, the cystic fibrosis is caused by a Class I, II, III, IV and/or VI mutation.

In one embodiment, the present invention provides pharmaceutical compositions comprising a compound of the invention, or a pharmaceutically acceptable salt thereof, and one or more additional therapeutic agents. In another embodiment, the present invention provides pharmaceutical compositions comprising a compound of the invention, or a pharmaceutically acceptable salt thereof, and one or more additional therapeutic agents wherein the additional therapeutic agents are selected from the group consisting of CFTR modulators and CFTR amplifiers. In another embodiment, the present invention provides pharmaceutical compositions comprising a compound of the invention, or a pharmaceutically acceptable salt thereof, and one or more additional therapeutic agents wherein the additional therapeutic agents are CFTR modulators.

In one embodiment, the present invention provides pharmaceutical compositions comprising a compound of the invention, or a pharmaceutically acceptable salt thereof, and one or more additional therapeutic agents. In one embodiment, the present invention provides pharmaceutical compositions comprising a compound of the invention, or a pharmaceutically acceptable salt thereof, and one or more correctors. In one embodiment, the present invention provides pharmaceutical compositions comprising a compound of the invention, and another therapeutic agent. In a particular embodiment, the other therapeutic agent is a cystic fibrosis treatment agent. In one embodiment, the present invention provides a method for treating cystic fibrosis in a subject comprising administering a compound of the invention, or a pharmaceutically acceptable salt thereof, and one or more additional therapeutic agents. In another embodiment, the present invention provides a method for treating cystic fibrosis in a subject comprising administering a compound of the invention, or a pharmaceutically acceptable salt thereof, and one or more additional therapeutic agents wherein the additional therapeutic agents are selected from the group consisting of CFTR modulators and CFTR amplifiers. In one embodiment, the present invention provides a method for treating cystic fibrosis in a subject comprising administering a compound of the invention, or a pharmaceutically acceptable salt thereof, and one or more additional therapeutic agents wherein the additional therapeutic agents are CFTR modulators. In one embodiment, the present invention provides a method for treating cystic fibrosis in a subject comprising administering a compound of the invention, or a pharmaceutically acceptable salt thereof, and, and another therapeutic agent. In a particular embodiment, the other therapeutic agent is a cystic fibrosis treatment agent. In one embodiment, the present invention provides a method for treating cystic fibrosis in a subject comprising administering a therapeutically effective amount of a compound of the invention, or a pharmaceutically acceptable salt thereof. In a particular embodiment, the additional therapeutic agent(s) are one or more correctors. In another embodiment, the additional therapeutic agent(s) is selected from the group consisting of CFTR modulators and CFTR amplifiers. In another embodiment, the other therapeutic agent(s) is a CFTR modulator. In a more particular embodiment, the cystic fibrosis is caused by a Class I, II, III, IV and/or VI mutation.

The present compounds or pharmaceutically acceptable salts thereof may be administered as the sole active agent or it may be co-administered with other therapeutic agents, including other compounds or a pharmaceutically acceptable salt thereof that demonstrate the same or a similar therapeutic activity and that are determined to be safe and efficacious for such combined administration. The present compounds may be co-administered to a subject. The term "co-administered" means the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or pharmaceutically acceptable salts thereof may be co-administered with a therapeutically effective amount of one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers. In one embodiment, the CFTR mediated disease is cystic fibrosis, chronic obstructive pulmonary disease (COPD), dry eye disease, pancreatic insufficiency, or Sjogren's Syndrome. In one embodiment, the CFTR mediated disease is cystic fibrosis. In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulators. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of CFTR potentiators include, but are not limited to, Ivacaftor (VX-770), CTP-656, NVS-QBW251, FD1860293, and N-(3-carbamoyl-5,5,7,7-tetramethyl-5,7-dihydro-4H-thieno[2,3-c]pyran-2-yl)-1H-pyrazole-5-carboxamide. Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014180562 and WO2015018823.

In one embodiment, the potentiator can be selected from the group consisting of
Ivacaftor (VX-770, N-(2,4-di-tert-butyl-5-hydroxyphenyl)-4-oxo-1,4-dihydroquinoline-3-carboxamide);
CTP-656;
NVS-QBW251:
FD1860293;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide
2-(1-hydroxycyclopropanecarboxamido)-5,5,7,7-tetramethyl-5,7-dihydro-4H-thieno[2,3-c]pyran-3-carboxamide;
5,5,7,7-tetrametramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;
N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;
N-(3-carbamoyl-5,5,7,7-tetramethyl-5,7-dihydro-4H-thieno[2,3-c]pyran-2-yl)-5-(trifluoromethyl)-1H-pyrazole-3-carboxamide;
5-tert-butyl-N-(3-carbamoyl-5, 5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-5-ethyl-1H-pyrazole-3-carboxamide;
N-(3-carbamoyl-5,5,7,7-tetramethyl-5,7-dihydro-4H-thieno[2,3-c]pyran-2-yl)-3-ethyl-4-methyl-1H-pyrazole-5-carboxamide;
2-(2-hydroxypropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-4-chloro-1H-pyrazole-3-carboxamide;
N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;
4-bromo-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-4-chloro-5-methyl-1H-pyrazole-3-carboxamide;
N-(3-carbamoyl-5,5,7,7-tetramethyl-5,7-dihydro-4H-thieno[2,3-c]pyran-2-yl)-4-methyl-1H-pyrazole-3-carboxamide;
2-(2-hydroxy-3,3-dimethylbutanamido)-5,5,7,7-tetramethyl-5,7-dihydro-4H-thieno[2,3-c]pyran-3-carboxamide;
2-[(2-hydroxy-4-methyl-pentanoyl)amino]-5,5,7,7-tetramethyl-4H-thieno[2,3-c]pyran-3-carboxamide;
5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;
N-(3-carbamoyl-5,5,7,7-tetramethyl-4H-thieno[2,3-c]pyran-2-yl)-4-(3-methoxypropyl)-1H-pyrazole-3-carboxamide;
N-(3-carbamoyl-5,5,7,7-tetramethyl-4H-thieno[2,3-c]pyran-2-yl)-4-(2-ethoxyethyl)-1H-pyrazole-3-carboxamide;
2-[[(2S)-2-hydroxy-3,3-dimethyl-butanoyl]amino]-5,5,7,7-tetramethyl-4H-thieno[2,3-c]pyran-3-carboxamide;
2-[[(2R)-2-hydroxy-3,3-dimethyl-butanoyl]amino]-5,7,7-tetramethyl-4H-thieno[2,3-c]pyran-3-carboxamide;
2-[(2-hydroxy-2,3,3-trimethyl-butanoyl)amino]-5,5,7,7-tetramethyl-4H-thieno[2,3-c]pyran-3-carboxamide;
[5-[(3-carbamoyl-5,5,7,7-tetramethyl-4H-thieno[2,3-c]pyran-2-yl)carbamoyl]pyrazol-1-yl]methyl dihydrogen phosphate;
[3-[(3-carbamoyl-5,5,7,7-tetramethyl-4H-thieno[2,3-c]pyran-2-yl)carbamoyl]pyrazol-1-yl]methyl dihydrogen phosphate;
N-(3-carbamoyl-5,5,7,7-tetramethyl-4H-thieno[2,3-c]pyran-2-yl)-4-(1,4-dioxan-2-yl)-1H-pyrazole-3-carboxamide;
5,5,7,7-tetramethyl-2-[[(2S)-3,3,3-trifluoro-2-hydroxy-2-methyl-propanoyl]amino]-4H-thieno[2,3-c]pyran-3-carboxamide; and
2-[[(2S)-2-hydroxypropanoyl]amino]-5,5,7,7-tetramethyl-4H-thieno[2,3-c]pyran-3-carboxamide.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2851, GLPG2222, GLPG2665, GLPG2737, VX-152, VX-440, FDL169, FDL304, FD2052160, and FD2035659. Examples of correctors are also disclosed in U.S. application Ser. No. 14/925,649, 62/073,573, 14/926,727, and 62/073,586.

In one embodiment, the corrector(s) can be selected from the group consisting of
Lumacaftor (VX-809);
1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);
VX-983;
GLPG2665;
GLPG2851;
GLPG2222;
GLPG2737;
VX-152;
VX-440;
FDL169
FDL304;
FD2052160;
FD2035659;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;
3-[(2R,4R)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;

3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;

3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;

3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid; and 4-[(2R,4S)-4-({[1-(2,2-difluoro-1,3-benzodioxol-5-yl)cyclopropyl]carbonyl}amino)tetrahydro-2H-pyran-2-yl]benzoic acid.

In one embodiment, the additional therapeutic agent is a CFTR amplifier. CFTR amplifiers enhance the effect of known CFTR modulators, such as potentiators and correctors. Examples of CFTR amplifier include PTI130 and PTI-428. Examples of amplifiers are also disclosed in publications: WO2015138909 and WO2015138934.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in PCT Publication No. WO2009074575 and WO2013043720; and U.S. Pat. No. 8,999,976.

In one embodiment, the ENaC inhibitor is VX-371.

In one embodiment, the ENaC inhibitor is SPX-101 (S18).

This invention also is directed to kits that comprise one or more compounds and/or salts of the invention, and, optionally, one or more additional therapeutic agents.

This invention also is directed to methods of use of the compounds, salts, compositions, and/or kits of the invention to, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

Chemical Synthetic Procedures

General

The compounds of the invention can be prepared from readily available starting materials using the following general methods and procedures. It will be appreciated that where typical or preferred process conditions (i.e. reaction temperatures, times, mole ratios of reactants, solvents, pressures, etc.) were given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (*Protective Groups in Organic Synthesis Third Edition*; Greene, T W and Wuts, P G M, Eds.; Wiley-Interscience: New York, 1991).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 µm). Thin layer chromatography was carried out using pre-coated silica gel F-254 plates (thickness 0.25 mm). $^1$H NMR spectra were recorded on a Bruker Advance 300 NMR spectrometer (300 MHz), an Agilent 400 MHz NMR spectrometer or a 500 MHz spectrometer. Chemical shifts (δ) for $^1$H NMR spectra were reported in parts per million (ppm) relative to tetramethylsilane (δ 0.00) or the appropriate residual solvent peak, i.e. CHCl$_3$ (δ 7.27), as internal reference. Multiplicities were given as singlet (s), doublet (d), doublet of doublets (ddd), doublet of doublets of doublets of doublets (dddd), doublet of doublets of quartets (ddq), doublet of doublets of triplets (ddt), doublet of quartets (dq), doublet of triplets of doublets (dtd), heptet (hept), triplet (t), triplet of doublets of doublets (tdd), triplet of quartets (tq), quartet (q), quartet of doublets (qd), quartet of triplets (qt), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 µm, 2.1 mm ID×50 mm L, Waters Acquity UPLC BEH C18 1.7 µm, 2.1 mm ID×30 mm L, or Waters Xterra® MS 5 m C18, 100×4.6 mm. The methods were using either MeCN/H$_2$O gradients (H$_2$O contains either 0.1% TFA or 0.1% NH$_3$) or MeOH/H$_2$O gradients (H$_2$O contains 0.05% TFA). Microwave heating was performed with a Biotage® Initiator.

For the compounds purified by preparative chromatography, an XSelect™ CSH Prep Guard Column, C18 19×10 mm 5 m (Waters) with an XSelect™ CSH Prep OBD Column, C18 19×100 mm 5 µm (Waters) and a gradient of 0.1% formic acid in water (A) and acetonitrile (B) at a flow rate of 20 mL/minute is used. Alternatively, an XBridge™ Prep Guard Column, C18 19×10 mm 5 m (Waters) with a XBridge™ Prep OBD Column, C18 19×100 mm 5 m (Waters) and a gradient of 0.5% NH$_3$ in water (A) and acetonitrile (B) at a flow rate of 20 mL/minute is used. After elution, the solvent was removed under vacuum to provide the product.

All the compounds prepared using flow chemistry were purified by automated reversed phase HPLC, using a Phenomenex® Luna® C8(2), 5 µm, 100 Å, 50×30 mm, with a SecurityGuard™ 15×30 mm guard column, and a gradient of acetonitrile (A) and 0.1% trifluoroacetic acid in water (B), at a flow rate of 40 mL/min (0-1.0 minute 10% A, 1.0-9.0 minutes linear gradient 10-100% A, 9.0-9.5 minutes 100% A, 9.5-10.0 minutes linear gradient 100-10% A). After elution, solvent was removed under vacuum to provide the pure product.

Racemic mixtures were separated on an Agilent HP1100 system with UV detection. Column used: Chiralpak® IA (10×250 mm, 5 µm). Solvents used: iPrOH and tBME. Enantiomeric purity was determined on an Agilent HP1100 system with UV detection. Column used: Chiralpak IA (4.6×250 mm, 5 µm). Solvents used: iPrOH and tBME.

List of abbreviations used in the experimental section:

| Abbreviation | Definition |
|---|---|
| DCM | dichloromethane |
| MeCN | acetonitrile |
| DMF | N,N-dimethylformamide |
| AcOH or HOAc | acetic acid |
| eq | equivalents |
| TFA | trifluoroacetic acid |
| THF | tetrahydrofuran |
| NMR | nuclear magnetic resonance |
| DMSO | dimethyl sulfoxide |
| LC/MS or LCMS | liquid chromatography- mass spectrometry |
| EtOAc | ethyl acetate |
| EtOH | ethanol |
| MeOH | methanol |
| tBME | tert-butyl methyl ether |
| s | singlet |
| br s | broad singlet |
| d | duplet or doublet |
| dd | double duplet or doublet of doublets |
| m | multiplet |
| min | minute |
| mL | milliliter |
| µL | microliter |
| g | gram |
| mg | milligram |
| atm | atmosphere |
| rcf | relative centrifugal force |
| rpm | revolutions per minute |
| NEt$_3$ | triethylamine |
| DIEA | diisopropylethylamine |
| mmol | millimoles |
| HPLC | high pressure liquid chromatography |
| NMP | N-methylpyrrolidinone |
| NBS | N-bromosuccinimide |
| NCS | N-chlorosuccinimide |
| NIS | N-iodosuccinimide |
| ppm | parts per million |
| Pd$_2$(dba)$_3$ | tris(dibenzylideneacetone)dipalladium(0) |
| Pd(OAc)$_2$ | palladium(II) acetate |
| Xantphos | 4,5-bis(diphenylphosphino)-9,9-dimethylxanthene |
| SM | starting material |
| Cpd | compound |
| Int | intermediate |
| MW | molecular weight |
| Mes | molecular weight measured |
| NA | not active |
| Pd(dppf)Cl$_2$ | [1,1'-bis(diphenylphosphino)ferrocene]dichloropalladium(II) |
| Pd(dppf)Cl$_2$•CH$_2$Cl$_2$ or Pd(dppf)Cl$_2$•DCM | [1,1'-bis(diphenylphosphino)ferrocene]dichloropalladium(II) complex with dichloromethane |
| µm | micrometer |
| iPrOH | iso-propanol |
| DMA | dimethylacetamide |
| DBU | 1,8-diazabicycloundec-7-ene |
| DiPPF | 1,1'-bis(di-isopropylphosphino)ferrocene |
| HATU | 1-[bis(dimethylamino)methylene]-1H-1,2,3-triazolo[4,5-d]pyridinium 3-oxid hexafluorophosphate |
| mCPBA | meta-chloroperoxybenzoic acid |
| EDC or EDCI | N-(3-dimethylaminopropyl)-N'-ethylcarbodiimide |
| HOBt | 1-hydroxybenzotriazole |

Synthetic Preparation of the Compounds of the Invention

EXAMPLE 1

General Synthetic Methods

The compounds of the invention and the comparative examples can be produced according to the following schemes.

Scheme 1: Synthesis of sulfones by $S_N$—Ar and oxidation

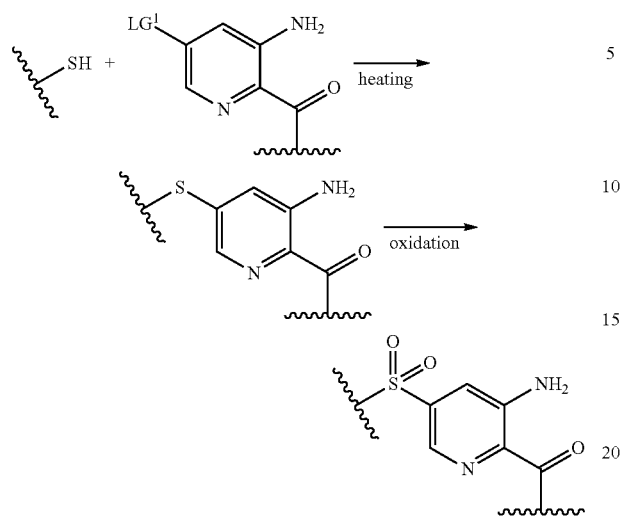

LG$^1$ is fluorine, chlorine, bromine, iodine or a sulfonate.

Scheme 2: Synthesis of sulfones by metal catalyzed chemistry

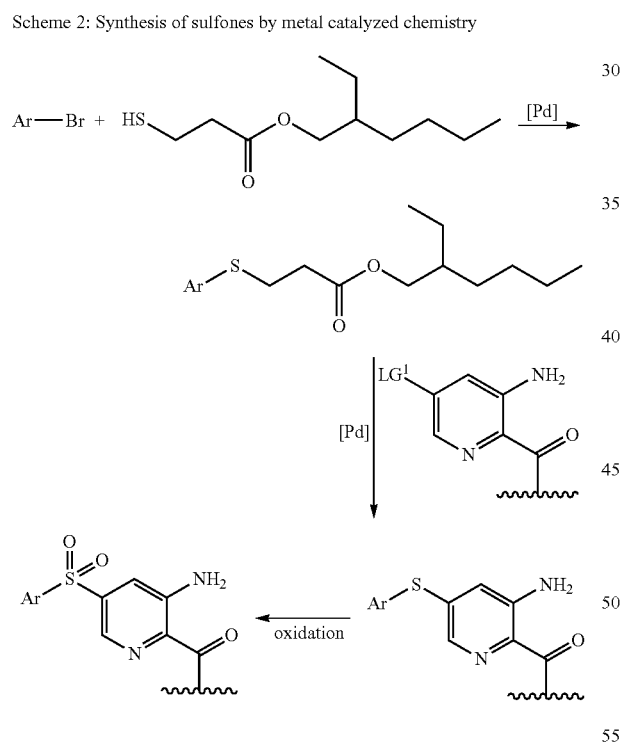

LG$^1$ is fluorine, chlorine, bromine, iodine or a sulfonate.

Scheme 3: Synthesis of sulfonamides

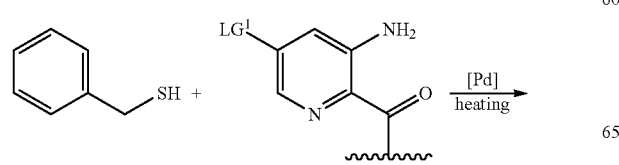

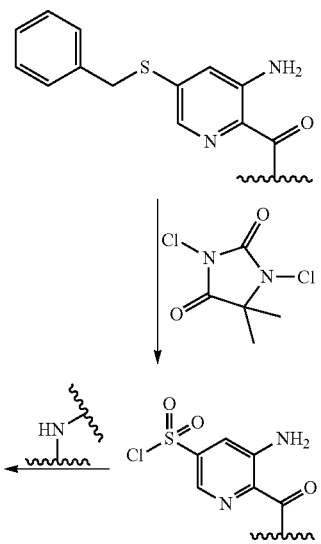

LG$^1$ is fluorine, chlorine, bromine, iodine or a sulfonate.

Scheme 4: Synthesis of amides

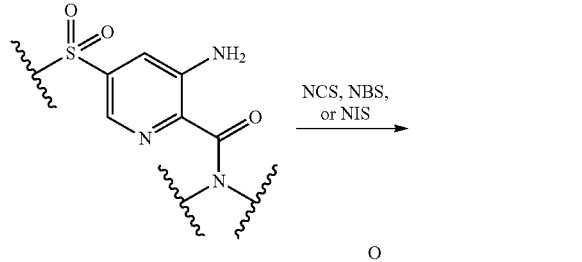

Scheme 5: Derivatization of pyridine ring

LG$^2$ is chlorine, bromine or iodine.

Scheme 6: Synthesis of tetra-substituted pyridine rings

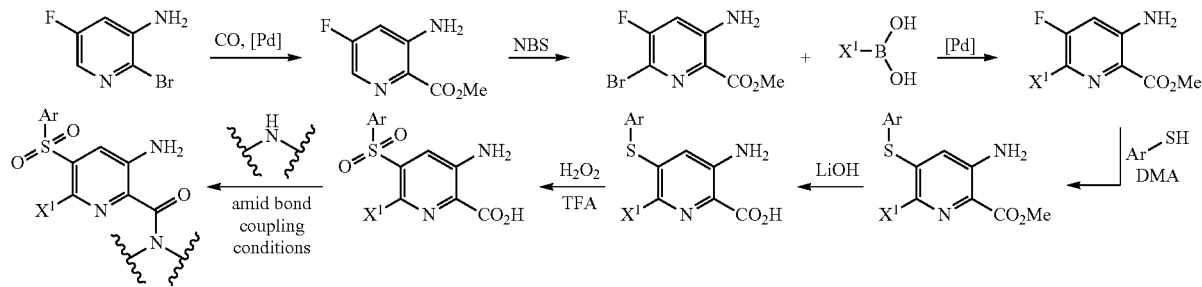

$X^1$ is $C_{1-4}$ alkyl optionally substituted with one or more independently selected halo; or cyclopropyl or phenyl each optionally substituted with one or more independently selected $R^5$ groups.

Alternatively, the $S_NAr$ step with the ArSH can be conducted before the Suzuki step. Then the following scheme was applied:

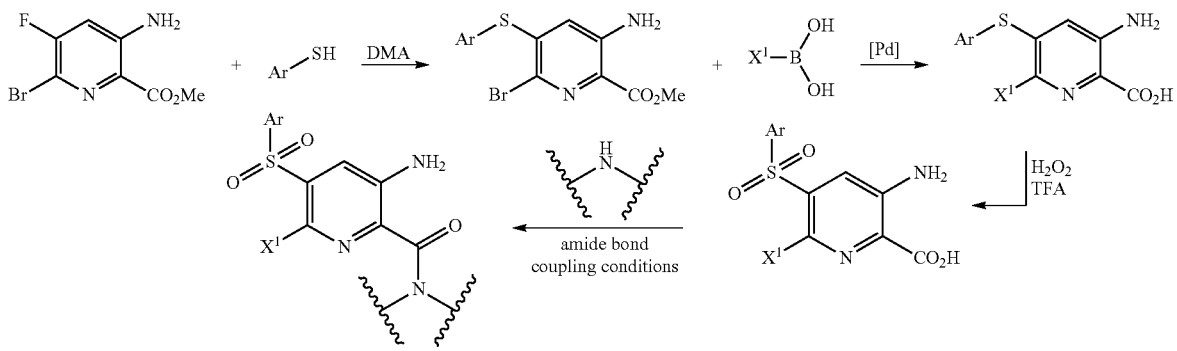

$X^1$ is $C_{1-4}$ alkyl optionally substituted with one or more independently selected halo; or cyclopropyl or phenyl each optionally substituted with one or more independently selected $R^5$ groups.

EXAMPLE 2

Synthesis of Intermediates

Intermediate 3: 3-Amino-5-benzylsulfanyl-pyridine-2-carboxylic acid (3,3,3-trifluoro-2-hydroxy-propyl)-amide

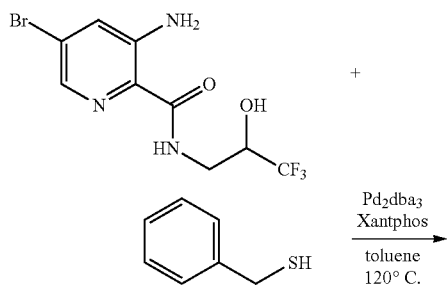

-continued

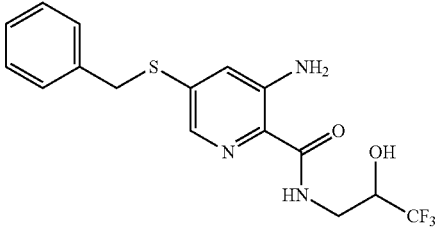

A mixture of 3-amino-5-bromo-pyridine-2-carboxylic acid (3,3,3-trifluoro-2-hydroxy-propyl)-amide (Int 8, 2.9 g, 8.87 mmol), benzyl mercaptan (CAS: 100-53-8, 1.25 mL, 10.6 mmol), $Pd_2(dba)_3$ (247 mg, 0.27 mmol), Xantphos (311 mg, 0.54 mmol) and N,N-diisopropylethylamine (3.1 mL, 17.7 mmol) was dissolved in toluene (50 mL). The mixture was flushed with $N_2$ and stirred at 120° C. overnight. After concentration, the titled compound was obtained that was either used as such or purified using column chromatography with a gradient from 0% EtOAc in petroleum ether to 100% EtOAc to yield the titled compound.

Intermediate 4: 3-Amino-5-(4-trifluoromethoxy-benzenesulfonyl)-pyridine-2-carboxylic acid

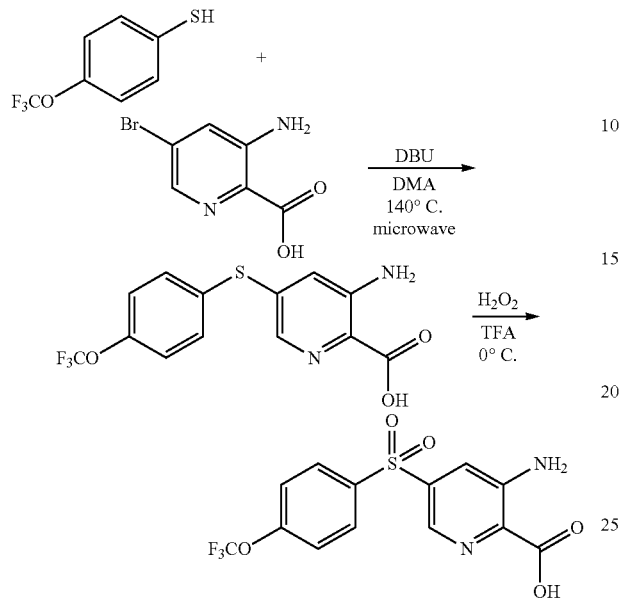

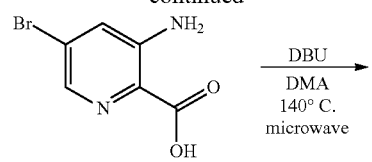

Step 1: 3-Amino-5-(4-trifluoromethoxy-phenylsulfanyl)-pyridine-2-carboxylic acid:

A solution of 3-amino-5-bromo-pyridine-2-carboxylic acid (Int 1, 3.26 g, 15 mmol), 4-trifluoromethoxy-benzenethiol (CAS: 169685-29-4, 3.5 g, 18 mmol) and DBU (2.22 mL, 15 mmol) was prepared in DMA (15 mL). This mixture was heated at 140° C. for 45 minutes in a microwave reactor. Next, the mixture was diluted with a mixture of 1% AcOH in water. A suspension was obtained that was subsequently filtered. This collected solid was washed with a 1% AcOH/water mixture followed by washing with petroleum ether. After drying in a vacuum oven, the titled compound was obtained.

Step 2: 3-Amino-5-(4-trifluoromethoxy-benzenesulfonyl)-pyridine-2-carboxylic acid:

3-Amino-5-(4-trifluoromethoxy-phenylsulfanyl)-pyridine-2-carboxylic acid (12.5 g, 40 mmol) was dissolved in TFA (80 mL), and the resulting mixture was cooled to 0° C. with an ice bath. Next, $H_2O_2$ (14 mL, 160 mmol) was added, and the mixture was stirred at 0° C. until the reaction was finished. For workup, the mixture was diluted with a mixture of 1% AcOH in water. A suspension was obtained that was subsequently filtered. The collected solid was washed with a 1% AcOH/water mixture followed by washing with petroleum ether. After drying in a vacuum oven, the titled compound was obtained.

Intermediate 5: 3-Amino-5-(4-trifluoromethyl-benzenesulfonyl)-pyridine-2-carboxylic acid

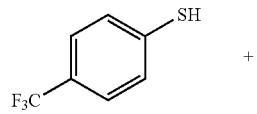

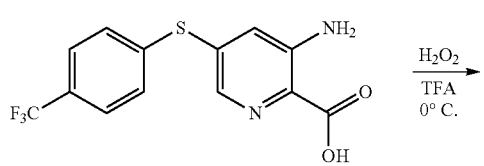

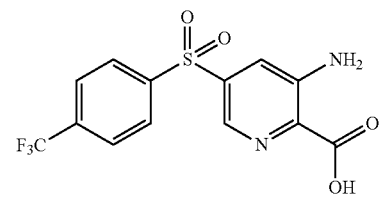

Step 1: 3-Amino-5-(4-trifluoromethyl-phenyl sulfanyl)-pyridine-2-carboxylic acid:

A solution of 3-amino-5-bromopyridine-2-carboxylic acid (Int 1, 3.78 g, 17.4 mmol), 4-trifluoromethyl-benzenethiol (CAS: 825-83-2, 4.1 g, 21 mmol) and DBU (2.60 mL, 17.4 mmol) was prepared in DMA (15 mL). This mixture was heated at 140° C. for 45 minutes in a microwave reactor. Next, the mixture was diluted with a mixture of 1% AcOH in water. A suspension was obtained that was subsequently filtered. The collected solid was washed with a 1% AcOH/water mixture followed by washing with petroleum ether. After drying in a vacuum oven, a powder was obtained that was used without additional purification.

Step 2: 3-Amino-5-(4-trifluoromethyl-benzenesulfonyl)-pyridine-2-carboxylic acid:

3-Amino-5-(4-trifluoromethyl-phenylsulfanyl)-pyridine-2-carboxylic acid (5.5 g, 17.5 mmol) was dissolved in TFA (35 mL), and the resulting mixture was cooled at 0° C. with an ice bath. Next, $H_2O_2$ (6.0 mL, 70 mmol) was added, and the mixture was stirred at 0° C. until the reaction was finished. For the workup, the mixture was diluted with a mixture of 1% AcOH in water. A suspension was obtained that was subsequently filtered. This collected solid was washed with a 1% AcOH/water mixture followed by washing with petroleum ether. After drying in a vacuum oven, the titled compound was obtained.

Intermediate 6: 3-Amino-5-(2-fluoro-4-trifluoromethoxy-benzenesulfonyl)-pyridine-2-carboxylic acid

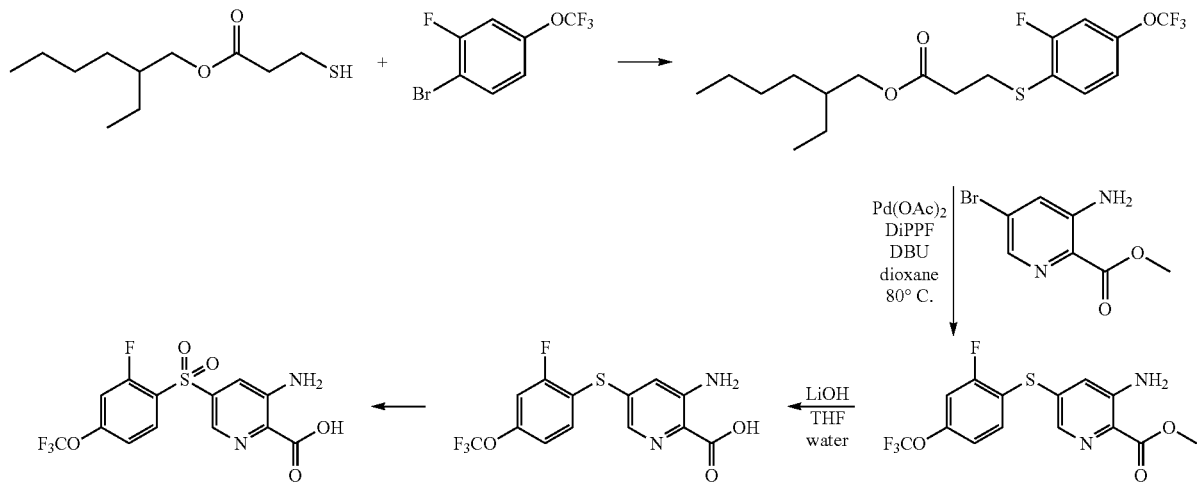

Step 1: 3-(2-Fluoro-4-trifluoromethoxy-phenylsulfanyl)-propionic acid 2-ethyl-hexyl ester:

1-Bromo-2-fluoro-4-(trifluoromethoxy)benzene (CAS: 168971-68-4, 20 g, 77 mmol) was mixed with N,N-diisopropylethylamine (27 mL, 144 mmol) in toluene (260 mL). The mixture was flushed with $N_2$. Next, $Pd_2(dba)_3$ (2.12 g, 2.32 mmol), Xantphos (2.68 g, 4.64 mmol) and 3-mercaptopropionic acid 2-ethylhexylester (CAS: 50448-95-8, 20 g, 77 mmol) were added. The mixture was flushed again with $N_2$ and heated at 110° C. overnight. The mixture was then filtered through a plug of silica and eluted with EtOAc. The combined organic fractions were concentrated, and the obtained residue was purified by column chromatography (a gradient from 100% petroleum ether to 5% EtOAc in petroleum ether was applied) to give the titled compound.

Step 2: 3-Amino-5-(2-fluoro-4-trifluoromethoxy-phenylsulfanyl)-pyridine-2-carboxylic acid methyl ester:

3-Amino-5-bromo-pyridine-2-carboxylic acid methyl ester (Int 13, 3.45 g, 14.9 mmol) was mixed with 3-(2-fluoro-4-trifluoromethoxy-phenylsulfanyl)-propionic acid 2-ethyl-hexyl ester (5.91 g, 14.9 mmol), DBU (4.46 mL, 29.9 mmol), $Pd(OAc)_2$ (168 mg, 0.75 mmol) and DiPPF (624 mg, 0.149 mmol) in dioxane (75 mL). The mixture was degassed and put under a $N_2$ atmosphere. The mixture was then heated at 105° C. overnight after which it was diluted with EtOAc and extracted with water. The organic phase was separated, dried and concentrated. Next, the residue was purified by chromatography (a gradient from 100% petroleum ether to 20% EtOAc in petroleum ether was applied) to give the titled compound.

Step 3: 3-Amino-5-(2-fluoro-4-trifluoromethoxy-phenylsulfanyl)-pyridine-2-carboxylic acid:

3-Amino-5-(2-fluoro-4-trifluoromethoxy-phenyl sulfanyl)-pyridine-2-carboxylic acid methyl ester (4.18 g, 11.5 mmol) was mixed with LiOH (332 mg, 13.8 mmol) in a mixture of water (10 mL) and THF (50 mL). The mixture was stirred at 40° C. overnight after which it was concentrated and acidified to pH=4. The obtained suspension was filtered to give the titled compound.

Step 4: 3-Amino-5-(2-fluoro-4-trifluoromethoxy-benzenesulfonyl)-pyridine-2-carboxylic acid:

3-Amino-5-(2-fluoro-4-trifluoromethoxy-phenyl sulfanyl)-pyridine-2-carboxylic acid (3.2 g, 9.2 mmol) was dissolved in TFA (30 mL). The mixture was cooled at 0° C. and $H_2O_2$ (3.17 mL, 36.8 mmol) was added dropwise. After overnight stirring at ambient temperature, the mixture was diluted with water. The resulting suspension was filtered to give a solid that was washed with water and dried to give the titled compound.

Intermediate 7: 3-Amino-5-(2-fluoro-4-trifluoromethyl-benzenesulfonyl)-pyridine-2-carboxylic acid

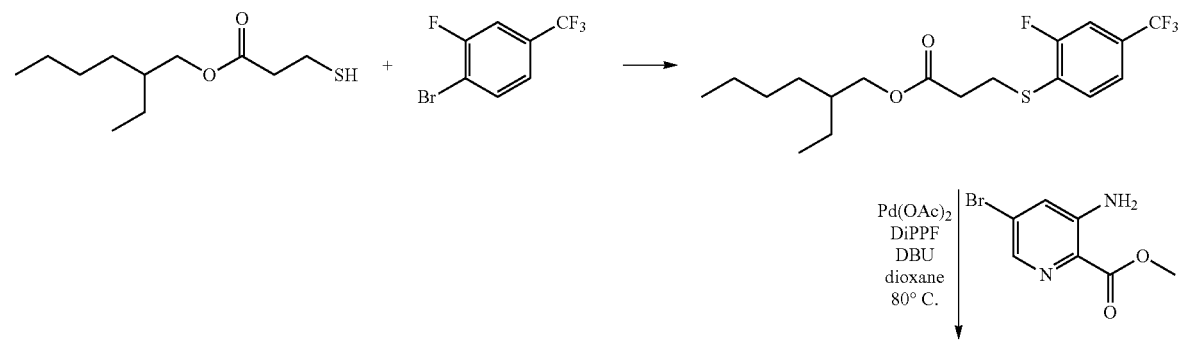

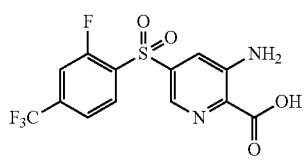 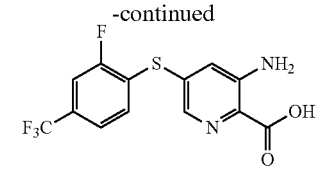 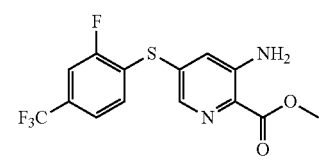

Step 1: 3-(2-Fluoro-4-trifluoromethyl-phenylsulfanyl)-propionic acid 2-ethyl-hexyl ester:

1-Bromo-2-fluoro-4-(trifluoromethyl)benzene (CAS: 40161-54-4, 9.4 g, 39 mmol) was mixed with N,N-diisopropylethylamine (13.5 mL, 78 mmol) in toluene (130 mL). The mixture was flushed with $N_2$. Next, $Pd_2(dba)_3$ (1.43 g, 1.56 mmol), Xantphos (1.80 g, 3.12 mmol) and 3-mercaptopropionic acid 2-ethylhexylester (CAS: 50448-95-8, 11 mL, 48 mmol) were added. The mixture was flushed again with $N_2$ and heated at 110° C. overnight. The mixture was then filtered over a plug of silica and eluted with EtOAc. The combined organic fractions were concentrated and the obtained residue was purified by column chromatography (a gradient from 100% petroleum ether to 5% EtOAc in petroleum ether was applied) to give the titled compound.

Step 2: 3-Amino-5-(2-fluoro-4-trifluoromethyl-phenyl sulfanyl)-pyridine-2-carboxylic acid methyl ester:

3-(2-Fluoro-4-trifluoromethyl-phenylsulfanyl)-propionic acid 2-ethyl-hexyl ester (5.67 g, 14.9 mmol) was mixed with 3-amino-5-bromo-pyridine-2-carboxylic acid methyl ester (Int 13, 3.45 g, 14.9 mmol), $Pd(OAc)_2$ (168 mg, 0.75 mmol), DiPPF (624 mg, 0.15 mmol) and DBU (4.46 mL, 29.9 mmol) in dioxane (75 mL). The mixture was degassed and put under a $N_2$ atmosphere. The mixture was then heated at 105° C. overnight after which it was diluted with EtOAc and extracted with water. The organic phase was separated, dried and concentrated. Next, the residue was purified by chromatography (a gradient from 100% petroleum ether to 20% EtOAc in petroleum ether was applied) to give the titled compound.

Step 3: 3-Amino-5-(2-fluoro-4-trifluoromethyl-phenyl sulfanyl)-pyridine-2-carboxylic acid:

3-Amino-5-(2-fluoro-4-trifluoromethyl-phenyl sulfanyl)-pyridine-2-carboxylic acid methyl ester (3.25 g, 9.36 mmol) was dissolved in a mixture of THF (50 mL) and water (10 mL). LiOH (270 mg, 11.2 mmol) was added after which the mixture was stirred at 40° C. overnight. The mixture was concentrated, and the resulting aqueous phase was acidified to pH=4. The obtained suspension was collected by filtration and dried to give the titled compound.

Step 4: 3-Amino-5-(2-fluoro-4-trifluoromethyl-benzenesulfonyl)-pyridine-2-carboxylic acid:

3-Amino-5-(2-fluoro-4-trifluoromethyl-phenyl sulfanyl)-pyridine-2-carboxylic acid (2.89 g, 8.7 mmol) was dissolved in TFA (30 mL). The mixture was cooled at 0° C. and $H_2O_2$ (3.0 mL, 34.8 mmol) was added dropwise. After overnight stirring at ambient temperature, the mixture was diluted with water. The resulting suspension was filtered to give a solid that was washed with water and dried to give the titled compound.

Intermediate 8: 3-Amino-5-bromo-pyridine-2-carboxylic acid (3,3,3-trifluoro-2-hydroxy-propyl)-amide

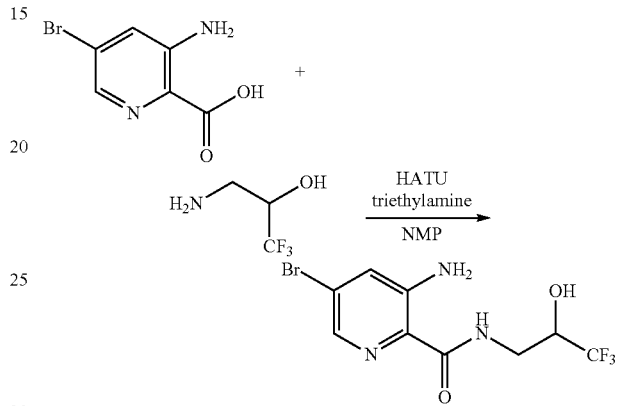

3-Amino-5-bromopyridine-2-carboxylic acid (Int 1, 5.1 g, 23.5 mmol) was dissolved in NMP (170 mL). After the addition of HATU (CAS: 148893-10-1, 13.4 g, 35.3 mmol), triethylamine (9.8 mL, 71 mmol) and 3-amino-1,1,1-trifluoro-propan-2-ol (HCl salt, CAS: 431-38-9, 5.82 g, 35.3 mmol), the resulting mixture was stirred at room temperature. When the reaction was finished, the mixture was diluted with water and extracted with EtOAc. The combined organic fractions were washed with water, dried over $Na_2SO_4$, filtered and concentrated to give the titled compound.

Intermediate 9: 5-Amino-6-(3,3,3-trifluoro-2-hydroxy-propylcarbamoyl)-pyridine-3-sulfonyl chloride

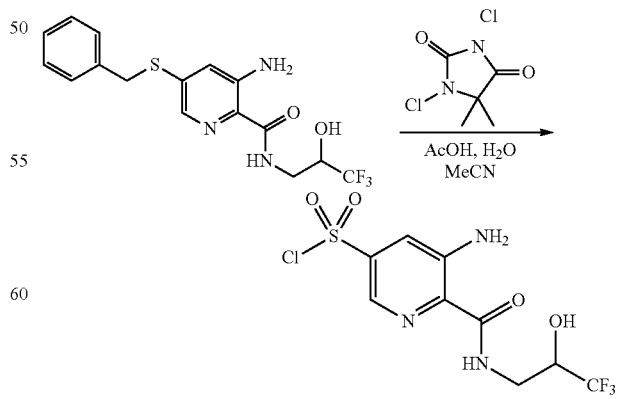

3-Amino-5-benzylsulfanyl-pyridine-2-carboxylic acid (3,3,3-trifluoro-2-hydroxy-propyl)-amide (Int 3, 371 mg, 1 mmol) was suspended in a mixture of AcOH (0.15 mL), H₂O (0.25 mL) and CH₃CN (3.5 mL). The resulting mixture was cooled at 0° C. Next, 1,3-dichloro-5,5-dimethylhydantoin (CAS: 118-52-5, 394 mg, 2 mmol) was added portion wise. After 10 minutes, the reaction mixture was used as such in subsequent sulfonamide formations.

Intermediate 10: 3-Amino-5-(4-fluoro-benzenesulfonyl)-pyridine-2-carboxylic acid

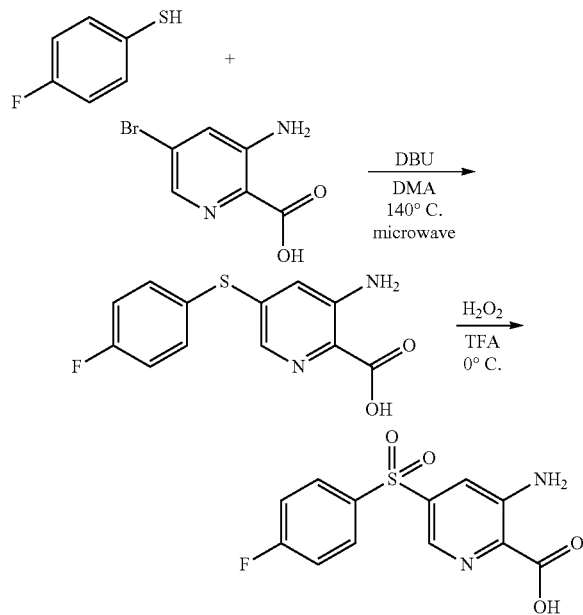

Step 1: 3-Amino-5-(4-fluoro-phenyl sulfanyl)-pyridine-2-carboxylic acid:

A solution of 3-amino-5-bromopyridine-2-carboxylic acid (Int 1, 13 g, 60 mmol), 4-fluoro-benzenethiol (CAS: 371-42-6, 7.68 g, 60 mmol) and DBU (0.89 mL, 6 mmol) was prepared in DMA (90 mL). This mixture was heated at 140° C. for 50 minutes in the microwave reactor. Next, the mixture was diluted with a mixture of 1% AcOH in water. A suspension was obtained that was subsequently filtered. The collected solid was washed with 1% AcOH in water followed by washing with petroleum ether. After drying in a vacuum oven, the titled compound was obtained.

Step 2: 3-Amino-5-(4-fluoro-benzenesulfonyl)-pyridine-2-carboxylic acid:

3-Amino-5-(4-fluoro-phenyl sulfanyl)-pyridine-2-carboxylic acid (25.5 g, 96.4 mmol) was dissolved in TFA (260 mL), and the resulting mixture was cooled at 0° C. with an ice bath. Next, H₂O₂ (33.3 mL, 386 mmol) was added, and the mixture was stirred at 0° C. for 30 minutes after which the reaction was allowed to reach ambient temperature. After reaction completion, the mixture was diluted with water and cooled to 0° C. while stirring. The obtained precipitate was collected by filtration. The obtained solid was washed with water and dried in the vacuum oven to give the titled compound.

Intermediate 11: 3-Amino-5-(2-trifluoromethoxy-benzenesulfonyl)-pyridine-2-carboxylic acid

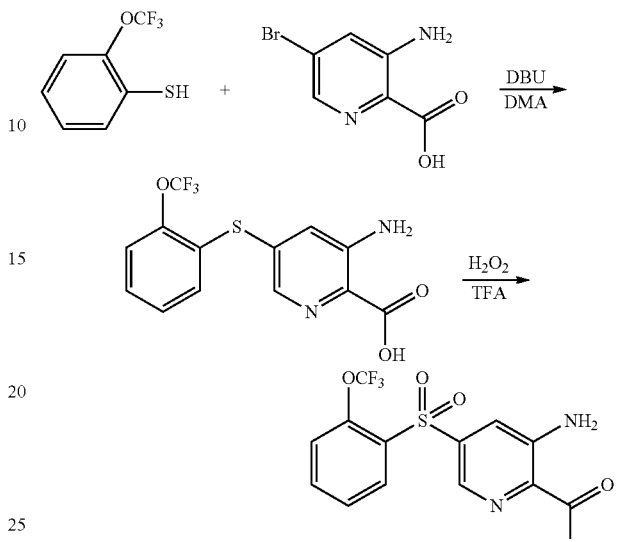

Step 1: 3-Amino-5-(2-trifluoromethoxy-phenylsulfanyl)-pyridine-2-carboxylic acid:

3-Amino-5-bromopyridine-2-carboxylic acid (Int 1, 868 mg, 4 mmol) was dissolved in DMA (15 mL) together with 2-trifluoromethoxy-thiophenol (CAS: 175278-01-0, 776 mg, 4 mmol) and DBU (600 µL, 4 mmol). The resulting mixture was heated in the microwave reactor at 140° C. for 60 minutes. Next, the mixture was diluted with water, acidified with AcOH to pH=4 and cooled at 0° C. The resulting precipitate was collected by filtration, subsequently washed with water and petroleum ether to give a solid. After drying the solid in the vacuum oven, the titled compound was obtained.

Step 2: 3-Amino-5-(2-trifluoromethoxy-benzenesulfonyl)-pyridine-2-carboxylic acid:

3-Amino-5-(2-trifluoromethoxy-phenylsulfanyl)-pyridine-2-carboxylic acid (830 mg, 2.5 mmol) was dissolved in TFA (5 mL), and the resulting mixture was cooled at 0° C. Next, H₂O₂ (0.86 mL, 10 mmol) was added. After stirring at ambient temperature overnight, the mixture was poured into water. The mixture was acidified to pH=4, and the resulting suspension was filtered to give a cake that was washed with water. After drying, the titled compound was obtained.

Intermediate 12:
3-Amino-5-benzenesulfonyl-pyridine-2-carboxylic acid

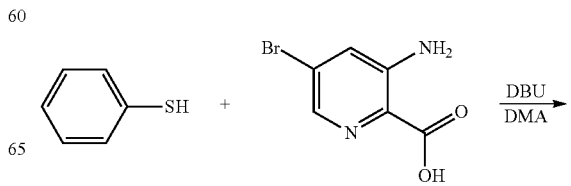

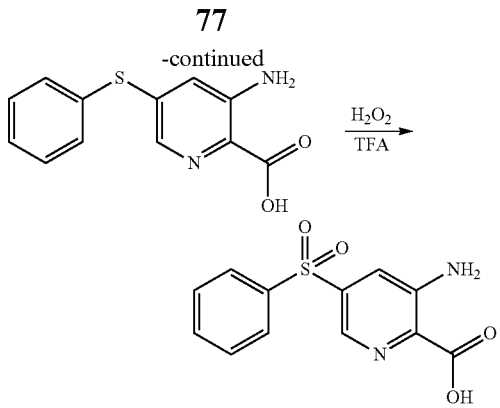

Step 1: 3-Amino-5-phenyl sulfanyl-pyridine-2-carboxylic acid:

3-Amino-5-bromopyridine-2-carboxylic acid (Int 1, CAS: 870997-85-6, 1.00 g, 4.61 mmol) was dissolved in DMA (10 mL) together with thiophenol (CAS: 108-98-5, 495 µL, 4.84 mmol) and DBU (688 µL, 4.61 mmol). The resulting mixture was heated in a microwave reactor at 140° C. for 45 minutes. If the reaction was not complete, the mixture was reheated at 140° C. for 45 minutes in the microwave reactor. Next, the mixture was diluted with water and extracted with EtOAc. The obtained organic phases were combined, dried and concentrated to give the titled compound that was used as such.

Step 2: 3-Amino-5-benzenesulfonyl-pyridine-2-carboxylic acid:

3-Amino-5-phenylsulfanyl-pyridine-2-carboxylic acid (1.13 g, 4.61 mmol) was dissolved in TFA (20 mL), and the resulting mixture was cooled at 0° C. Next, $H_2O_2$ (1.59 mL, 18.4 mmol) was added. After stirring at ambient temperature overnight, the mixture was poured into water. The resulting suspension was filtered to give a cake that was washed with water. After drying, the titled compound was obtained.

Intermediate 13:
3-Amino-5-bromo-pyridine-2-carboxylic acid methyl ester

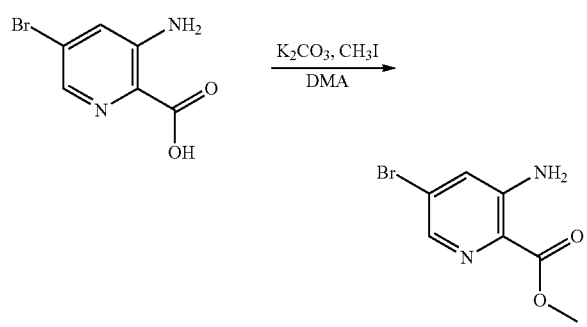

3-Amino-5-bromopyridine-2-carboxylic acid (Int 1, 2.17 g, 10 mmol) was mixed with $K_2CO_3$ (1.38 g, 10 mmol) and $CH_3I$ (CAS: 74-88-4, 620 µL, 10 mmol) in DMA (40 mL). The resulting mixture was stirred at ambient temperature overnight. Next, the mixture was diluted with water which gives rise to a suspension. Filtration, followed by washing with water and subsequent drying yielded the titled compound that was used as such.

Intermediate 14:
(R)-1-Amino-3-methoxy-propan-2-ol

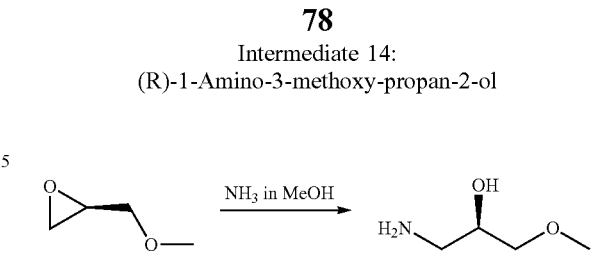

The epoxide (CAS: 64491-70-9, 2.20 g, 25 mmol) was dissolved in a mixture of $NH_3$ in MeOH (7 M, 140 mL), and the resulting mixture was stirred at room temperature overnight under a $N_2$ atmosphere. Next, the mixture was concentrated to give the titled compound.

Intermediate 15:
1-Amino-3-(2,2,2-trifluoro-ethoxy)-propan-2-ol

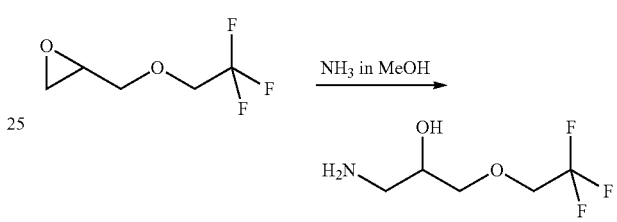

The epoxide (CAS: 407-12-5, 77 µL, 0.64 mmol) was dissolved in a mixture of $NH_3$ in MeOH (7 M, 1 mL), and the resulting mixture was stirred at room temperature overnight under a $N_2$ atmosphere. Next, the mixture was concentrated to give the titled compound.

Intermediate 16:
1-Amino-3-(2-methoxy-ethoxy)-propan-2-ol

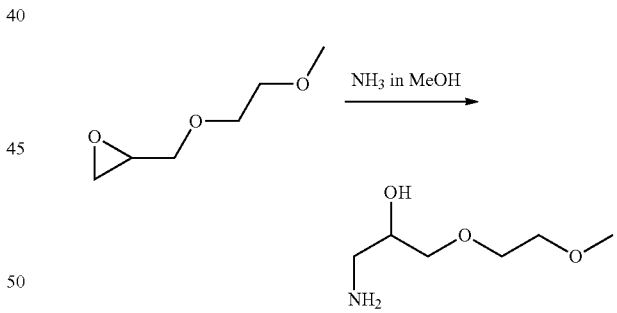

The epoxide (CAS: 13483-49-3, 100 mg, 0.75 mmol) was dissolved in a mixture of $NH_3$ in MeOH (7 M, 4 mL), and the resulting mixture was stirred at room temperature overnight under a $N_2$ atmosphere. Next, the mixture was concentrated to give the titled compound.

Intermediate 17: 1-Amino-3-tert-butoxy-propan-2-ol

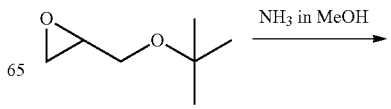

-continued

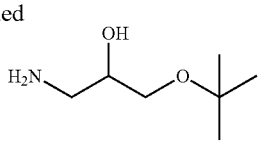

The epoxide (CAS: 7665-72-7, 218 µL, 1.54 mmol) was dissolved in a mixture of NH₃ in MeOH (7 M, 2 mL), and the resulting mixture was stirred at room temperature overnight under a N₂ atmosphere. Next, the mixture was concentrated to give the titled compound.

Intermediate 18: 3-Amino-5-(3-fluoro-benzenesulfonyl)-pyridine-2-carboxylic acid

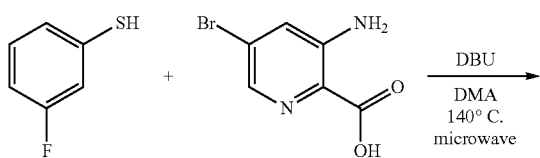

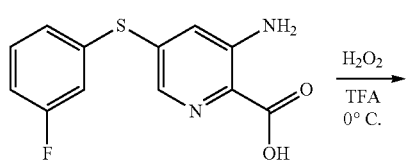

Step 1: 3-Amino-5-(3-fluoro-phenyl sulfanyl)-pyridine-2-carboxylic acid:

A solution of 3-amino-5-bromopyridine-2-carboxylic acid (Int 1, 1.0 g, 4.63 mmol), 3-fluoro-benzenethiol (CAS: 2557-77-9, 400 µL, 4.63 mmol) and DBU (70 µL, 0.46 mmol) was prepared in DMA (7 mL). This mixture was heated at 140° C. overnight. Next, the mixture was diluted with a mixture of 1% AcOH in water. A suspension was obtained that was subsequently filtered. The solid was washed with a 1% AcOH/water mixture followed by washing with petroleum ether. After drying in a vacuum oven, the titled compound was obtained.

Step 2: 3-Amino-5-(3-fluoro-benzenesulfonyl)-pyridine-2-carboxylic acid:

3-Amino-5-(3-fluoro-phenylsulfanyl)-pyridine-2-carboxylic acid (1.2 g, 4.6 mmol) was dissolved in TFA (13 mL), and the resulting mixture was cooled at 0° C. with an ice bath. Next, H₂O₂ (1.6 mL, 18.4 mmol) was added, and the mixture was stirred at 0° C. for 30 minutes, after which the reaction was allowed to reach ambient temperature. After completion, the reaction was diluted with water and cooled to 0° C. while stirring. The obtained precipitate was collected by filtration. The resulting solid was washed with water and dried in the vacuum oven to give the titled compound.

Intermediate 19: (2R)-3-Amino-1,1,1-trifluoropropan-2-ol

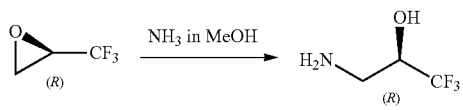

The epoxide (CAS: 143142-90-9, 7 g, 62.5 mmol) was dissolved in a mixture of NH₃ in MeOH (7 M, 300 mL), and the resulting mixture was stirred at room temperature overnight under a N₂ atmosphere. Next, the mixture was concentrated to give the titled compound.

Intermediate 20: rac-(3R,4S)-3-aminotetrahydro-2H-pyran-4-ol

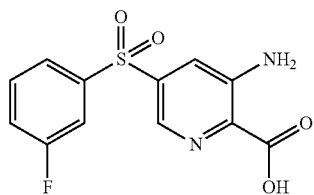

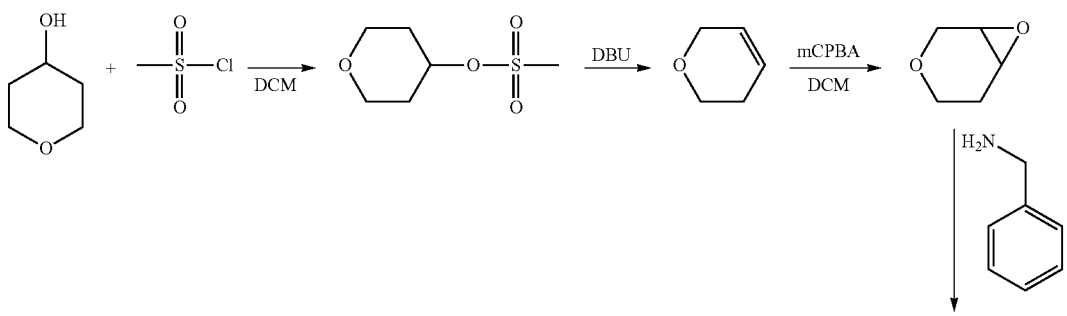

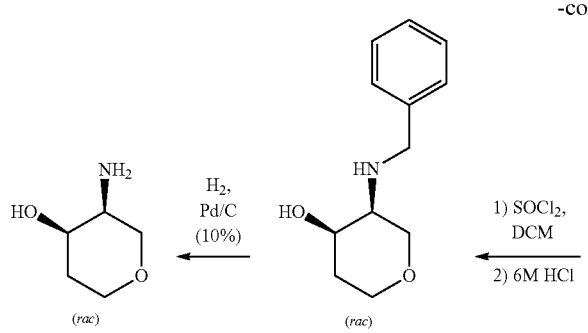
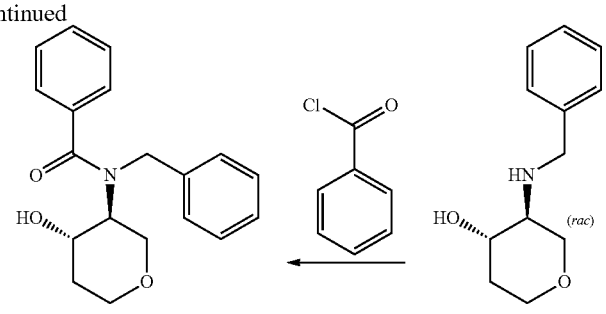

Step 1: methanesulfonic-acid-tetrahydro-pyran-4-yl ester:

N,N'-Diisopropylethylamine (25.6 mL, 147.0 mmol) was added to a solution of tetrahydro-2H-pyran-4-ol (CAS: 2081-44-9, 10.0 g, 98.0 mmol) in dry DCM (160 mL) cooled at 0° C. The resulting mixture was stirred for 10 minutes under argon at 0° C. Then methanesulfonyl chloride (CAS: 124-63-0, 8.72 mL, 112.7 mmol) was added, and the mixture was stirred at 0° C. for 2 h. The reaction mixture was extracted with DCM and 0.5 M HCl. The organic fraction was washed with water, brine and saturated NaHCO$_3$. The combined organic layers were dried over Na$_2$SO$_4$, filtered and concentrated in vacuo to give the titled compound.

Step 2: 3,6-dihydro-2H-pyran:

DBU (16.4 mL) was added to methanesulfonic-acid-tetrahydro-pyran-4-yl ester (16.4 g, 90.9 mmol), and the mixture was heated from 90° C. to 150° C. over 1 h and then 5 h at 150° C. $^1$H NMR showed that the starting material was consumed and desired compound was formed. The titled compound was collected from the reaction mixture using distillation at 70-75° C., 5.7 g.

Step 3: 3,7-dioxa-bicyclo[4.1.0]heptane:

To a solution of mCPBA (23.5 g, 136.2 mmol) in DCM (15 mL) was added a solution of 3,6-dihydro-2H-pyran (5.7 g, 68.1 mmol) in DCM (10 mL), and this mixture was stirred at ambient temperature for 6 h. The reaction was monitored by $^1$H NMR, and when incomplete, additional mCPBA (11.8 g, 68.1 mmol) was added followed by stirring at room temperature overnight. Next, the reaction mixture was filtered, and the filtrate was washed with saturated aqueous Na$_2$SO$_3$, NaHCO$_3$, and water. The organic fraction was dried over Na$_2$SO$_4$, filtered and concentrated in vacuo to afford the titled compound, 4.7 g.

Step 4: rac-(3R,4R)-3-(benzylamino)tetrahydro-2H-pyran-4-ol:

A mixture of 3,7-dioxa-bicyclo[4.1.0]heptane (3.0 g, 30 mmol) and benzylamine (CAS: 100-46-9, 3.2 mL, 30 mmol) in EtOH (50 mL) was stirred at reflux temperature overnight. The reaction mixture was concentrated. The crude residue was thoroughly re-suspended by sonication and stirring in diethyl ether (20 mL). The precipitate was filtered off and washed with diethyl ether to give the titled compound, 2.9 g.

Step 5: rac-N-benzyl-N-[(3R,4R)-4-hydroxytetrahydro-2H-pyran-3-yl]benzamide:

Benzoyl chloride (CAS: 98-88-4, 1.60 mL, 13.8 mmol) was added dropwise to a cooled solution (ice bath) of rac-(3R,4R)-3-(benzylamino)tetrahydro-2H-pyran-4-ol (2.85 g, 13.8 mmol) and triethylamine (5.74 mL, 41.4 mmol) in dry DCM (30 mL). The reaction mixture was stirred at room temperature for 2 h. The mixture was then washed twice with 2 M HCl. The aqueous washings were extracted with DCM, then the combined organic extracts were dried over Na$_2$SO$_4$, filtered and concentrated affording the titled compound, 4.3 g.

Step 6: rac-(3R,4S)-3-(benzylamino)tetrahydro-2H-pyran-4-ol:

A solution of rac-N-benzyl-N-[(3R,4R)-4-hydroxytetrahydro-2H-pyran-3-yl]benzamide (4.3 g, 13.8 mmol) in dry DCM (20 mL) was added dropwise to thionyl chloride (CAS: 7719-09-7, 3.8 mL, 52.4 mmol) at 0° C. After stirring the reaction mixture for 4 h at room temperature, volatiles were removed under reduced pressure and the residue was treated with 6 M HCl (40 mL) and under vigorous stirring heated at reflux overnight. The suspension was then cooled, the precipitated benzoic acid was filtered off, and the acidic aqueous phase was extracted 3× with EtOAc. Next, 5 M NaOH was added carefully to the acidic aqueous phase until pH>10. The aqueous layer was extracted with a double volume of diethyl ether. After separation, the aqueous phase was extracted additionally 3× with diethyl ether. The combined organic phases were dried over Na$_2$SO$_4$, filtered and concentrated to yield the titled compound, 3.0 g.

Step 7: rac-(3R,4S)-3-aminotetrahydro-2H-pyran-4-ol

A solution of rac-(3R,4S)-3-(benzylamino)tetrahydro-2H-pyran-4-ol (3.0 g, 14.5 mmol) in dry MeOH (90 mL) was hydrogenated over 10% Pd/C (1.15 g) for 1 h at room temperature and at 1 atm H$_2$. After completion, the catalyst was removed by filtration through diatomaceous earth rinsing with MeOH, and the filtrate was concentrated to give the titled compound, 1.5 g.

Intermediate 21:
3-Amino-6-bromo-5-fluoro-pyridine-2-carboxylic acid methyl ester

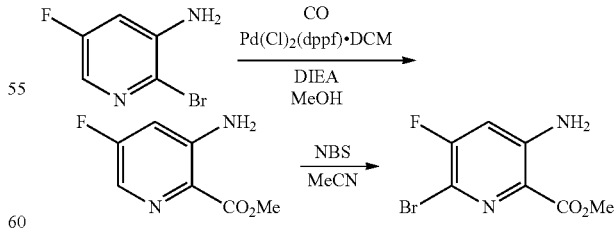

Step 1: 3-Amino-5-fluoro-pyridine-2-carboxylic acid methyl ester:

A solution of 3-amino-2-bromo-5-fluoropyridine (CAS: 884495-03-8, 955 mg, 5 mmol) and Pd(dppf)Cl$_2$·CH$_2$Cl$_2$ (204 mg, 25 mmol) in dry MeOH (15 mL) and DIEA (1.74 mL, 10 mmol) was flushed with N$_2$ after which a pressure of 8 atm CO was applied. The reaction was heated at 70° C. After completion, the mixture was diluted with water and extracted with EtOAc. The combined organic fractions were washed with NH₄Cl solution, dried over Na₂SO₄, filtered and concentrated. The obtained residue was purified by column chromatography eluted using a mixture of EtOAc and petroleum ether (25:75). The obtained titled compound was used as such.

Step 2: 3-Amino-6-bromo-5-fluoro-pyridine-2-carboxylic acid methyl ester:

3-Amino-5-fluoro-pyridine-2-carboxylic acid methyl ester (550 mg, 3.23 mmol) was mixed with NBS (690 mg, 3.88 mmol) in MeCN. The resulting suspension was stirred at ambient temperature. After overnight stirring, the mixture was diluted with water, and the resulting precipitate was filtered off and washed with water and petroleum ether. After drying in a vacuum oven at 50° C., the titled compound was obtained.

Intermediate 22: 3-Amino-6-cyclopropyl-5-fluoro-pyridine-2-carboxylic acid

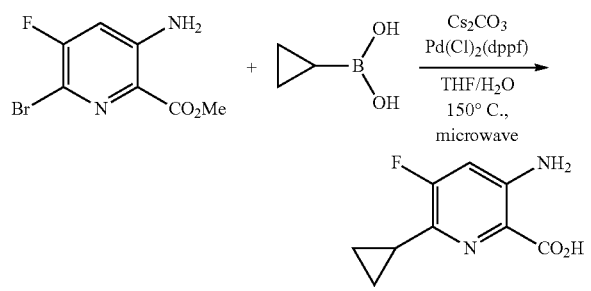

A mixture of 3-amino-6-bromo-5-fluoro-pyridine-2-carboxylic acid methyl ester (Intermediate 21, 640 mg, 2.5 mmol), cyclopropyl boronic acid (CAS: 411235-57-9, 893 mg, 10.3 mmol), Pd(Cl)₂(dppf) (209 mg, 0.256 mmol) and Cs₂CO₃ (640 mg, 2.5 mmol) in THF (10 mL) and water (100 µL) was heated at 150° C. in the microwave reactor for 20 minutes. The reaction mixture was filtered over a plug of silica. Concentration gave the titled compound that was used as such.

Intermediate 23: 3-amino-5-(benzylsulfanyl)-N-[(2S)-2-hydroxypropyl]pyridine-2-carboxamide

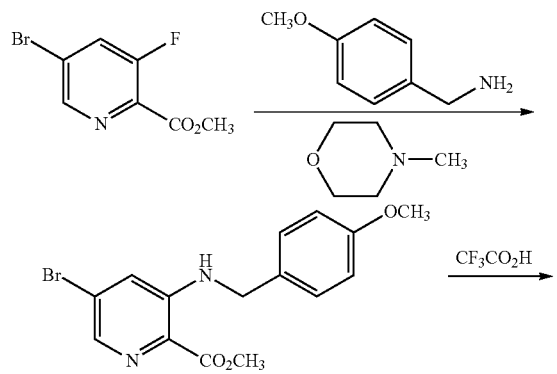

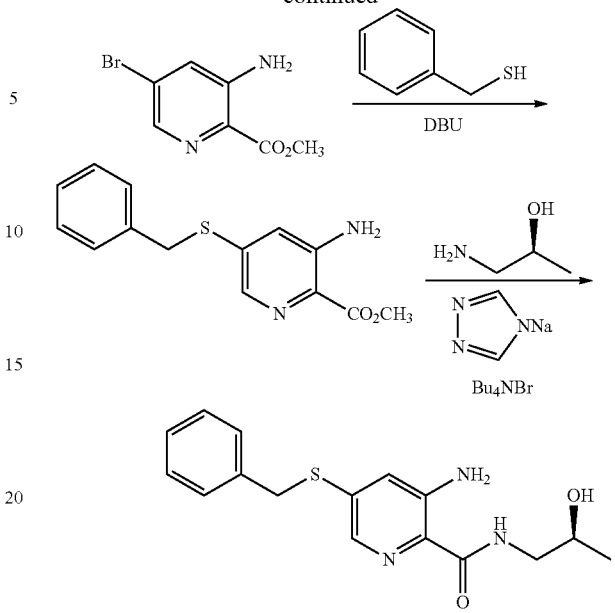

Step 1: methyl 5-bromo-3-[(4-methoxybenzyl)amino]pyridine-2-carboxylate:

A mixture of methyl 5-bromo-3-fluoropyridine-2-carboxylate (936 mg, 4.00 mmol) and p-methoxybenzylamine (780 µL, 6.0 mmol) was heated in N-methylmorpholine (8.0 mL) at 110° C. for two hours with microwave irradiation (Biotage® Initiator). The reaction mixture was brought to room temperature and concentrated. The residue was diluted with 1:2 tert-butyl methyl ether/heptane and filtered through basic alumina with a 2:1 tert-butyl methyl ether/heptane rinse to give the titled compound (1.365 g) used as is without additional purification. MS (DCI) m/z 351/353 (M+H)⁺.

Step 2: methyl 3-amino-5-bromopyridine-2-carboxylate:

Methyl 5-bromo-3-[(4-methoxybenzyl)amino]pyridine-2-carboxylate (1.36 g, <3.8 mmol, Step 1) was dissolved into anhydrous CH₂Cl₂ (6 mL) and trifluoroacetic acid (2 mL) and heated at 40° C. for 18 hours. The reaction mixture was concentrated, diluted with CH₂Cl₂/heptane, filtered through silica with 1:1 ethyl acetate/heptane, and concentrated. The residue was chromatographed on silica (5 to 15% ethyl acetate in 1:1 CH₂Cl₂/heptane) to give the titled compound (905 mg). ¹H NMR (400 MHz, CDCl₃) δ ppm 3.95 (s, 3H), 6.90 (br s, 2H), 7.34 (d, J=1.9 Hz, 1H), 8.11 (d, J=1.9 Hz, 1H); MS (ESI) m/z 231/233 (M+H)⁺.

Step 3: methyl 3-amino-5-(benzyl sulfanyl)pyridine-2-carboxylate:

A flask containing methyl 3-amino-5-bromopyridine-2-carboxylate (826 mg, 3.57 mmol, Step 2), benzylthiol (630 µL, 5.37 mmol) and DBU (1.6 mL, 10.7 mmol) mixed with N-methylmorpholine (8 mL) was flushed with nitrogen, and the reaction mixture heated at reflux for 40 minutes, with brisk stirring as a second phase forms, then brought to room temperature. The mixture was partially concentrated, treated with 1 M aqueous citric acid (7 mL) and extracted four times with 1:1 CH₂Cl₂/heptane. The combined organic phases were washed with 1:1 1 M aqueous citric acid/brine, and the separated aqueous phase was extracted once with 1:1 CH₂Cl₂/heptane. The organic phases were dried (Na₂SO₄), combined and filtered with a thorough CH₂Cl₂ rinse of the solids. The filtrate was concentrated and chromatographed on silica (0 to 10% ethyl acetate in 1:1 CH₂Cl₂/heptanes) to give the titled compound (518 mg). ¹H NMR (500 MHz, DMSO-d₆) δ ppm 3.77 (s, 3H), 4.30 (s, 2H), 6.70 (s, 2H), 7.14 (d, J=2.0 Hz, 1H), 7.24-7.28 (m, 1H), 7.31-7.35 (m, 2H), 7.40-7.43 (m, 2H), 7.73 (d, J=2.0 Hz, 1H); MS (DCI) m/z 275 (M+H)⁺.

Step 4: 3-amino-5-(benzylsulfanyl)-N-[(2S)-2-hydroxypropyl]pyridine-2-carboxamide:

Methyl 3-amino-5-(benzyl sulfanyl)pyridine-2-carboxylate (429 mg, 1.56 mmol), (S)-1-aminopropan-2-ol (250 µL, 3.2 mmol), sodium 1,2,4-triazolide (158 mg, 1.56 mmol Hz, 1H), 3.47 (ddd, J=14.0, 6.5, 3.2 Hz, 1H), 3.91-3.99 (m, 1H), 4.16 (s, 2H), 5.94 (br s, 2H), 6.85 (d, J=2.0 Hz, 1H), 7.24-7.36 (m, 5H), 7.72 (d, J=2.0 Hz, 1H), 8.19-8.28 (m, 1H); MS (ESI) m/z 318 (M+H)⁺.

Intermediate 24: ethyl 3-amino-5-{[(2S)-2-methyl-pyrrolidin-1-yl]sulfonyl}pyridine-2-carboxylate

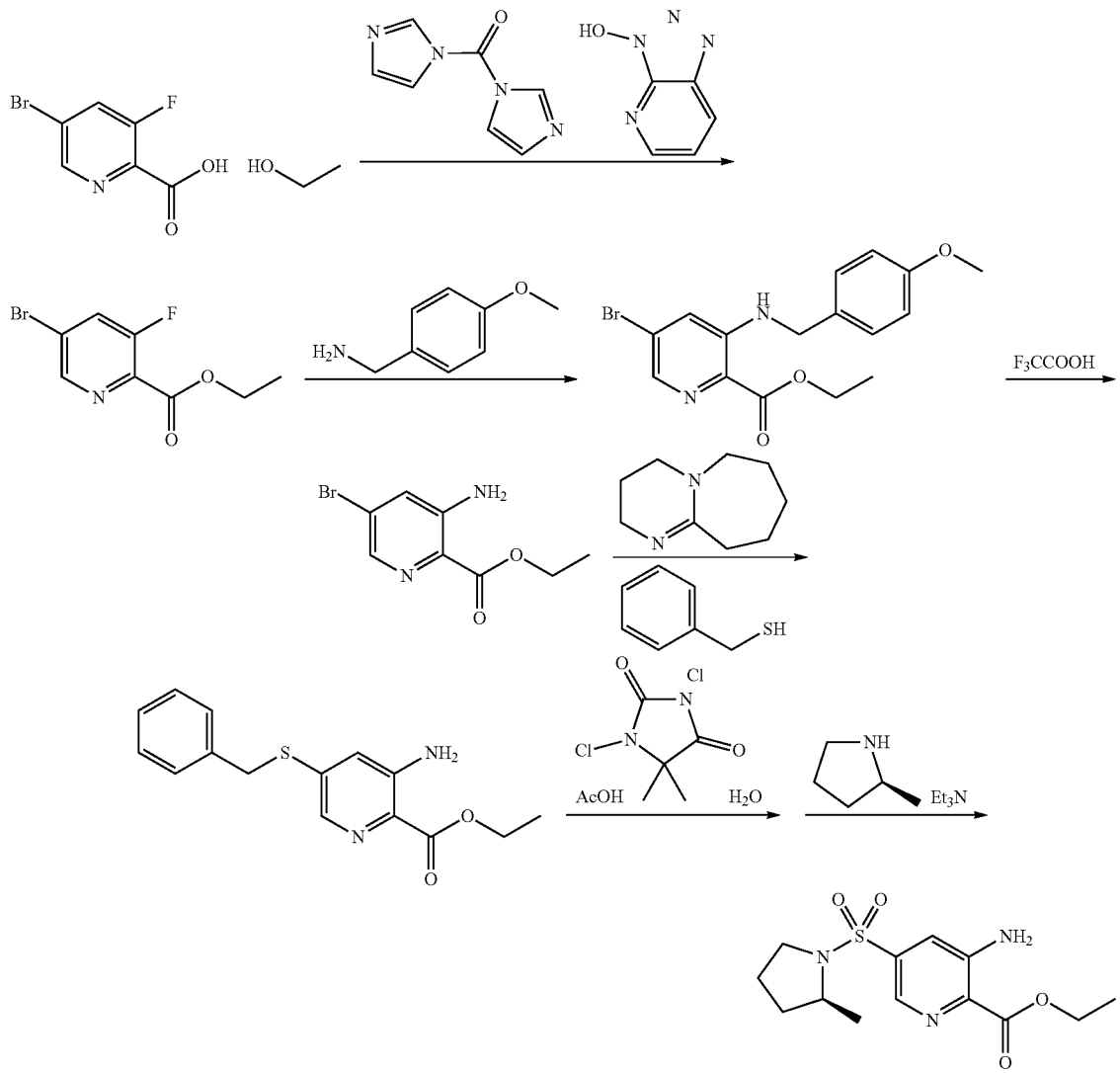

[90% technical grade]) and tetrabutylammonium bromide (251 mg, 0.78 mmol) were heated at 90° C. in anhydrous dioxane (5 mL) overnight. The suspension was brought to room temperature, dissolved in methanol and concentrated. The residue was diluted with acetonitrile (~15 mL) and stirred for 20 minutes, then diluted further with tert-butyl methyl ether (7 mL) and stirred another ten minutes. The solid titled compound was collected by filtration with a 1:1 acetonitrile/tert-butyl methyl ether rinse (0.25 g). The filtrate was chromatographed on silica (5 to 40% tert-butyl methyl ether/CH₂Cl₂) to give a second crop of the titled compound (367 mg). ¹H NMR (400 MHz, CD₂Cl₂) δ ppm 1.19 (d, J=6.3 Hz, 3H), 2.80 (br s, 1H), 3.27 (ddd, J=14.0, 7.4, 5.9

Step 1: ethyl 5-bromo-3-fluoropyridine-2-carboxylate:

A solution of 5-bromo-3-fluoropyridine-2-carboxylic acid (10.23 g, 46.5 mmol) in anhydrous acetonitrile (40 mL) and anhydrous N,N-dimethylformamide (10 mL) was added dropwise over twelve minutes to a suspension of carbonyl diimidazole (7.94 g, 49.0 mmol) in anhydrous acetonitrile (80 mL), cooled with a water ice bath. After a few more minutes the thick suspension was removed from the bath and stirred another hour. Then a solution of 1-hydroxy-7-azabenzotriazole (127 mg, 0.93 mmol, HOAT) in ethanol (11 mL, 188 mmol) was added, and the mixture was stirred overnight. The reaction mixture was filtered with a thorough CH₃CN rinse, and the filtrate was concentrated and chromatographed on silica (50 to 80% CH₂Cl₂/heptane) to give the titled compound (7.707 g). ¹H NMR (400 MHz, CDCl₃) δ ppm 1.44 (t, J=7.1 Hz, 3H), 4.49 (q, J=7.1 Hz, 2H), 7.76 (dd, J=9.3, 1.8 Hz, 1H), 8.60-8.63 (m, 1H); MS (ESI) m/z 265/267 (M+NH₄)⁺.

Step 2: ethyl 5-bromo-3-[(4-methoxybenzyl)amino]pyridine-2-carboxylate:

A mixture of ethyl 5-bromo-3-fluoropyridine-2-carboxylate (2.477 g, 10.0 mmol, Step 1) and p-methoxybenzylamine (1.95 mL, 15.0 mmol) was heated in N-methylmorpholine (20 mL) at 110° C. for an hour. The reaction mixture was brought to room temperature and concentrated. The residue was diluted with 2:1 tert-butyl methyl ether/heptane and filtered through basic alumina with more 2:1 tert-butyl methyl ether/heptane to give the titled compound as a solid used without further purification (3.40 g). ¹H NMR (501 MHz, CDCl₃) δ ppm 1.43 (t, J=7.1 Hz, 3H), 3.81 (s, 3H), 4.34 (d, J=5.4 Hz, 2H), 4.43 (q, J=7.1 Hz, 2H), 6.88-6.91 (m, 2H), 7.20 (d, J=1.9 Hz, 1H), 7.24-7.27 (m, 2H), 8.02 (d, J=1.9 Hz, 1H), 8.12-8.18 (m, 1H); MS (ESI) m/z 365/367 (M+H)⁺.

Step 3: ethyl 3-amino-5-bromopyridine-2-carboxylate:

The ethyl 5-bromo-3-[(4-methoxybenzyl)amino]pyridine-2-carboxylate (3.40 g, 9.3 mmol, Step 2) was dissolved into anhydrous CH₂Cl₂ (15 mL) and trifluoroacetic acid (5 mL), and the mixture was stirred at room temperature three days. The reaction mixture was concentrated. The residue was diluted with CH₂Cl₂/heptane and chromatographed on silica (5 to 15% ethyl acetate in 1:1 CH₂Cl₂/heptane) to give the titled compound (2.317 g). ¹H NMR (400 MHz, CDCl₃) δ ppm 1.42 (t, J=7.1 Hz, 3H), 4.41 (q, J=7.1 Hz, 2H), 7.37 (d, J=1.9 Hz, 1H), 7.67 (br s, 2H), 8.14 (d, J=1.9 Hz, 1H); MS (ESI) m/z 245/247 (M+H)⁺.

Step 4: ethyl 3-amino-5-(benzyl sulfanyl)pyridine-2-carboxylate:

A mixture of ethyl 3-amino-5-bromopyridine-2-carboxylate (4.90 g, 20.0 mmol, Step 3), benzylthiol (2.82 mL, 24.0 mmol) and DBU (9.0 mL, 60 mmol) in N-methylmorpholine (40 mL) was flushed with nitrogen and heated at 80° C. for two hours. The mixture was concentrated under vacuum, treated with 3 M aqueous citric acid (15 mL) and extracted first with tert-butyl methyl ether and then with 20% acetonitrile/tert-butyl methyl ether. The combined organic phases were washed with brine, dried (Na₂SO₄) and concentrated to a solid. This was slurried in tert-butyl methyl ether, collected by filtration with a tert-butyl methyl ether rinse and dried under vacuum to give the titled compound (3.986 g). ¹H NMR (501 MHz, CD₂Cl₂) δ ppm 1.38 (t, J=7.1 Hz, 3H), 4.19 (s, 2H), 4.34 (q, J=7.1 Hz, 2H), 5.74 (br s, 2H), 6.86 (d, J=2.0 Hz, 1H), 7.25-7.29 (m, 1H), 7.30-7.34 (m, 2H), 7.34-7.37 (m, 2H), 7.86 (d, J=2.0 Hz, 1H); MS (ESI) m/z 289 (M+H)⁺.

Step 5: ethyl 3-amino-5-{[(2S)-2-methylpyrrolidin-1-yl]sulfonyl}pyridine-2-carboxylate:

Ethyl 3-amino-5-(benzylsulfanyl)pyridine-2-carboxylate (289 mg, 1.0 mmol, Step 4), water (250 μL) and acetic acid (150 μL) were dissolved into acetonitrile (8.0 mL) and dichloromethane (2.0 mL), cooled with a water ice bath, and treated slowly with solid 1,3-dichloro-1,5-dimethylhydantoin (395 mg, 2.0 mmol) to give a yellow solution which was stirred fifteen minutes to give the intermediate sulfonyl chloride. This cold mixture was added to a solution of (S)-2-methylpyrrolidine (305 μL, 3.0 mmol) and triethylamine (560 μL, 4.0 mmol) in acetonitrile (4.0 mL), also cooled in the ice bath, with an acetonitrile (1.0 mL) rinse. Then the reaction mixture was removed from the bath and stirred at room temperature for 30 minutes before being concentrated and chromatographed on silica (5 to 15% ethyl acetate in 1:1 CH₂Cl₂/heptane) to give the title compound (287 mg). ¹H NMR (400 MHz, CD₂Cl₂) δ ppm 1.30 (d, J=6.4 Hz, 3H), 1.41 (t, J=7.1 Hz, 3H), 1.49-1.65 (m, 2H), 1.70-1.93 (m, 2H), 3.14-3.22 (m, 1H), 3.41-3.48 (m, 1H), 3.68-3.77 (m, 1H), 4.42 (q, J=7.1 Hz, 2H), 6.02 (br s, 2H), 7.47 (d, J=1.9 Hz, 1H), 8.31 (d, J=1.9 Hz, 1H); MS (ESI) m/z 314 (M+H)⁺.

Intermediate 25: 3-amino-5-(benzylsulfanyl)-N-[(4-methoxypyrimidin-2-yl)methyl]pyridine-2-carboxamide

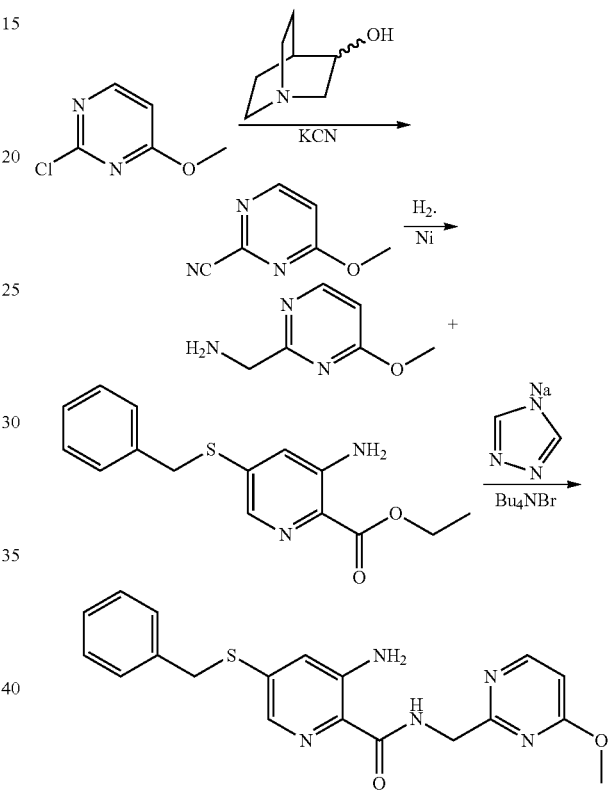

Step 1: 4-methoxypyrimidine-2-carbonitrile:

To a solution of potassium cyanide (2.70 g, 41.5 mmol) in water (5 mL) was added 2-chloro-4-methoxypyrimidine (4.99 g, 34.5 mmol), 3-quinuclidinol (1.10 g, 8.65 mmol) and acetonitrile (70 mL). The mixture was heated at 50° C. for two hours, brought to room temperature and filtered with an acetonitrile rinse. The filtrate was concentrated, and the residue extracted first with tert-butyl methyl ether and then with 1:1 ethyl acetate/tert-butyl methyl ether. Extracts were sequentially filtered through a short plug of silica (10 g) to give the titled compound (4.361 g). ¹H NMR (400 MHz, CDCl₃) δ ppm 4.05 (s, 3H), 6.92 (d, J=5.8 Hz, 1H), 8.49 (d, J=5.8 Hz, 1H); 13C NMR (101 MHz, CDCl₃) δ ppm 54.9, 111.8, 115.6, 144.2, 157.7, 169.8; MS (DCI) m/z 153 (M+NH₄)⁺.

Step 2: 1-(4-methoxypyrimidin-2-yl)methanamine:

4-Methoxypyrimidine-2-carbonitrile (908 mg, 6.72 mmol) and acetic acid (25 mL) were added to nickel (2.7 g, 46.0 mmol) in a 50 mL pressure bottle and shaken under a 50 psi hydrogen atmosphere at room temperature for 100 minutes. The reaction mixture was then filtered, partially concentrated and chromatographed on silica (0 to 15% concentrated aqueous ammonium hydroxide/acetonitrile). Mixed fractions were rechromatographed as before and material from both chromatographies was combined to give the titled compound (979 mg). $^1$H NMR (400 MHz, DMSO-$d_6$) δ ppm 3.79 (s, 2H), 3.93 (s, 3H), 6.78 (d, J=5.8 Hz, 1H), 8.46 (d, J=5.8 Hz, 1H); MS (DCI) m/z 140 (M+H)$^+$.

Step 3: 3-amino-5-(benzyl sulfanyl)-N-[(4-methoxypyrimidin-2-yl)methyl]pyridine-2-carboxamide:

Ethyl 3-amino-5-(benzylsulfanyl)pyridine-2-carboxylate (159 mg, 0.55 mmol, Intermediate 24-Step 4), 1-(4-methoxypyrimidin-2-yl)methanamine (98 mg, 0.70 mmol, Step 2), 1,2,4-triazolylsodium (46 mg, 0.5 mmol) and tetrabutylammonium bromide (32 mg, 0.1 mmol) were heated at 75° C. under nitrogen in anhydrous dioxane (1.5 mL) overnight. More 1-(4-methoxypyrimidin-2-yl)methanamine (55 mg, 0.4 mmol) was added, and the mixture was heated at 90° C. another day before being chromatographed on silica (30 to 50% ethyl acetate in 1:1 dichloromethane/heptane) to give the titled compound (109 mg). $^1$H NMR (501 MHz, CD$_2$Cl$_2$) δ ppm 3.98 (s, 3H), 4.18 (s, 2H), 4.66 (dd, J=5.4, 0.7 Hz, 2H), 5.98 (br s, 2H), 6.62 (dt, J=5.8, 0.7 Hz, 1H), 6.88 (d, J=2.0 Hz, 1H), 7.25-7.29 (m, 1H), 7.30-7.36 (m, 4H), 7.78 (d, J=2.0 Hz, 1H), 8.40 (d, J=5.8 Hz, 1H), 8.83-8.88 (m, 1H); MS (ESI) m/z 382 (M+H)$^+$.

Intermediate 26: methyl 3-amino-5-fluoro-6-(4-fluorophenyl)pyridine-2-carboxylate

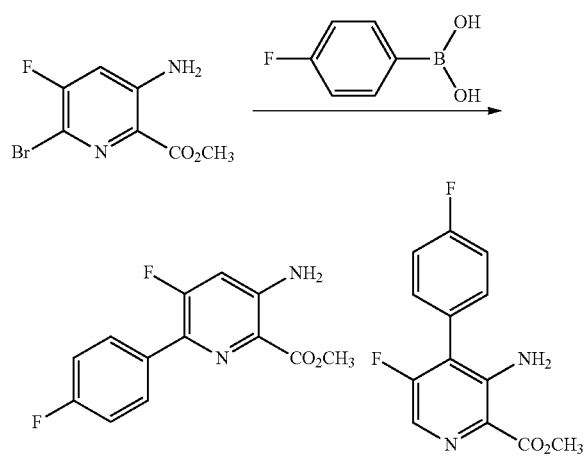

A mixture of 3-amino-6-bromo-5-fluoro-pyridine-2-carboxylic acid methyl ester (Int 21, 125 mg, 0.5 mmol), 4-fluorophenylboronic acid (84 mg, 0.600 mmol), K$_2$CO$_3$ (83 mg, 0.600 mmol) and [1,1'-bis(diphenylphosphino)ferrocene]palladium(II) dichloride (18.29 mg, 0.025 mmol) in H$_2$O (0.5 mL) and dioxane (2 mL) was flushed with N$_2$ and heated to 95° C. for 30 minutes. The mixture was partitioned between ethyl acetate and saturated aqueous NaHCO$_3$ solution. The ethyl acetate layer was washed with brine, dried (MgSO$_4$), filtered and concentrated. Chromatography on silica gel eluting with a gradient of 15 to 100% ethyl acetate in heptanes provided the titled compound (110 mg, 0.416 mmol, 83% yield) as the first compound to elute. $^1$H NMR (400 MHz, CDCl$_3$) δ ppm 7.91-7.85 (m, 1H), 7.16-7.09 (m, 1H), 6.81 (d, J=12.0 Hz, 0H), 5.91 (br s, 1H), 3.97 (s, 1H).

Intermediate 27: methyl 3-amino-6-cyclopropyl-5-fluoropyridine-2-carboxylate

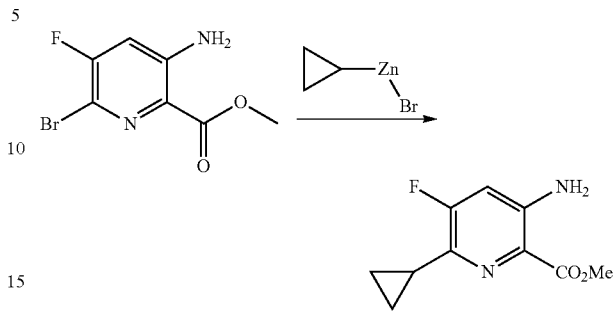

A solution of 3-amino-6-bromo-5-fluoro-pyridine-2-carboxylic acid methyl ester (Int 21, 160 mg, 0.642 mmol) and [1,3-bis(2,6-diisopropylphenyl)imidazol-2-ylidene](3-chloropyridyl)palladium(II) dichloride (43.8 mg, 0.064 mmol) in tetrahydrofuran (1 mL) was stirred under N$_2$ for 20 minutes. The mixture was treated slowly with a 0.5 M solution of cyclopropylzinc bromide in tetrahydrofuran (7710 μL, 3.85 mmol) over 10 minutes and then stirred at room temperature for 15 minutes. The mixture was quenched with 1 M HCl (2 mL) and extracted with ethyl acetate (30 mL). The ethyl acetate layer was washed with brine, dried (MgSO$_4$), filtered, and concentrated. The residue was chromatographed on silica gel eluting with a gradient of 15-30% ethyl acetate in heptanes to provide the titled compound (123 mg, 0.585 mmol, 91% yield). $^1$H NMR (501 MHz, CDCl$_3$) δ ppm 6.66 (d, J=10.8 Hz, 1H), 5.67 (br s, 2H), 3.90 (s, 3H), 2.18-2.12 (m, 1H), 1.05-1.01 (m, 2H), 0.93-0.89 (m, 2H).

Intermediate 28: methyl 6-bromo-3-nitro-5-{[4-(trifluoromethoxy)phenyl]sulfonyl}pyridine-2-carboxylate

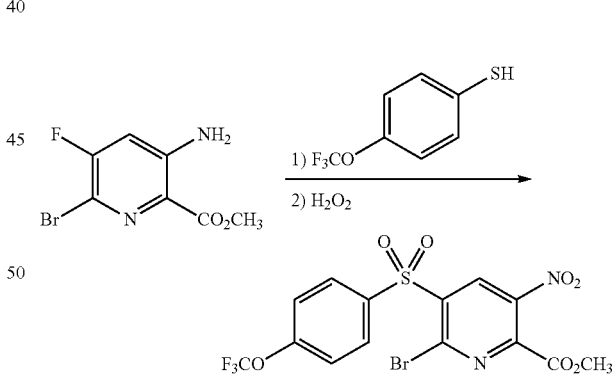

Step 1: methyl 3-amino-6-bromo-5-{[4-(trifluoromethoxy)phenyl]sulfanyl}pyridine-2-carboxylate:

A mixture of 3-amino-6-bromo-5-fluoro-pyridine-2-carboxylic acid methyl ester (Int 21, 0.036 g, 0.145 mmol), 4-(trifluoromethoxy)thiophenol (0.028 g, 0.145 mmol) and K$_2$CO$_3$ (0.060 g, 0.434 mmol) in N,N-dimethylformamide (1 mL) was warmed from 40° C. to 70° C. over 30 minutes, increasing the temperature ~5° C. every ~5 minutes. The mixture was cooled and partitioned between tert-butyl methyl ether (~30 mL) and water (~15 mL). The organic layer was washed with brine, dried (MgSO$_4$), filtered, and concentrated. The residue was chromatographed on silica gel eluting with a gradient of 15 to 30% ethyl acetate in heptanes to provide the titled compound (54 mg, 0.128 mmol, 88% yield). $^1$H NMR (500 MHz, CDCl$_3$) δ ppm 7.62-7.59 (m, 2H), 7.35-7.32 (m, 2H), 6.18 (s, 1H), 5.68 (br s, 2H), 3.93 (s, 3H); MS (ESI+) m/z 423,425 (M+H)$^+$; MS (ESI−) m/z 421,423 (M−H)$^−$.

Step 2: methyl 6-bromo-3-nitro-5-{[4-(trifluoromethoxy)phenyl]sulfonyl}pyridine-2-carboxylate:

A solution of methyl 3-amino-6-bromo-5-{[4-(trifluoromethoxy)phenyl]sulfanyl}pyridine-2-carboxylate (53 mg, 0.125 mmol, Step 1) in trifluoroacetic acid (2 mL) was treated with hydrogen peroxide (102 µL, 1.002 mmol), stirred at room temperature for 15 minutes and then heated to 55° C. for 6 hours. The mixture was cooled and partitioned between ethyl acetate (~50 mL) and water (~25 mL). The ethyl acetate layer was washed with saturated aqueous NaHCO$_3$ solution, washed with brine, dried (MgSO$_4$), filtered, and concentrated. The residue was chromatographed on silica gel eluting with 10% ethyl acetate in heptanes to provide the titled compound (33 mg, 0.068 mmol, 54.3% yield). $^1$H NMR (400 MHz, CDCl$_3$) δ ppm 9.28 (s, 1H), 8.11-8.07 (m, 2H), 7.42 (d, J=8.4 Hz, 2H), 4.04 (s, 3H).

Intermediate 29: 1-amino-3-fluoropropan-2-ol

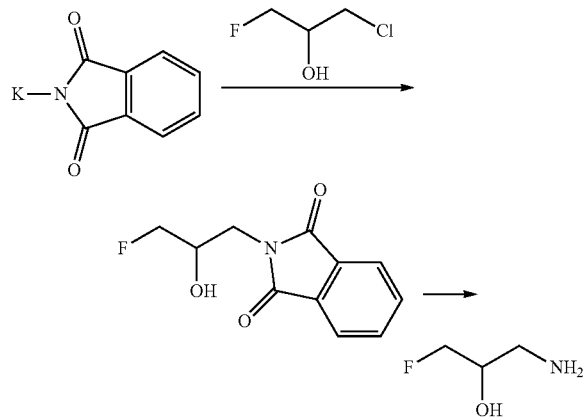

Step 1: 2-(3-fluoro-2-hydroxypropyl)-1H-isoindole-1,3 (2H)-dione

A solution of 1-chloro-3-fluoroisopropanol (4.13 g, 36.7 mmol) in N,N-dimethylformamide (80 mL) was treated all at once with potassium phthalimide (8.16 g, 44.0 mmol) and heated to 80° C. for 8 hours and then allowed to stir at room temperature over the weekend (~50 hours). The mixture was concentrated to remove most of the N,N-dimethylformamide. The residue was partitioned between 1H HCl (50 mL) and tert-butyl methyl ether (50 mL). The layers were separated, and the aqueous was extracted twice with tert-butyl methyl ether (2×50 mL). The combined tert-butyl methyl ether layers were washed with brine, dried (MgSO$_4$), filtered, and concentrated. The residue was treated with ~1:1 heptanes:CH$_2$Cl$_2$ (~100 mL), cooled to 0° C., and the resulting solid was collected by filtration and discarded. The filtrate was concentrated, and the residue was chromatographed on silica gel eluted with 15-100% ethyl acetate in heptanes to provide the titled compound (4.66 g, 20.88 mmol, 56.9% yield). $^1$H NMR (400 MHz, CDCl$_3$) δ ppm 7.92-7.82 (m, 2H), 7.79-7.70 (m, 2H), 4.54 (qd, J=9.8, 4.4 Hz, 1H), 4.42 (qd, J=9.8, 4.4 Hz, 1H), 4.23-4.10 (m, 1H), 3.97-3.86 (m, 2H), 2.80 (d, J=6.3 Hz, 1H); MS (ESI+) m/z 256 (M+CH$_3$OH+H)$^+$.

Step 2: 1-amino-3-fluoropropan-2-ol

A mixture of 2-(3-fluoro-2-hydroxypropyl)-1H-isoindole-1,3(2H)-dione (2 g, 8.96 mmol) and 13% HCl (20 mL) was heated to 105° C. overnight. The mixture was cooled to room temperature. The mixture was partitioned between ethyl acetate (~75 mL, discarded) and H$_2$O (30 mL). A solid was present which was removed by filtration and discarded. The layers of the filtrate were separated, and the aqueous layer was washed twice with ethyl acetate (2×50 mL). The aqueous layer was concentrated to an oil and dried under vacuum with heating (70° C.) to provide the titled compound as a hydrochloride salt (1.08 g, 8.34 mmol, 93% yield). $^1$H NMR (501 MHz, DMSO-d$_6$) δ ppm 8.17 (s, 3H), 5.82 (d, J=5.0 Hz, 1H), 4.47-4.41 (m, 1H), 4.38-4.31 (m, 1H), 4.03-3.93 (m, 1H), 2.92 (dd, J=12.9, 3.6 Hz, 1H), 2.73 (dd, J=12.9, 8.8 Hz, 1H).

Intermediate 30:
3-amino-5-bromopyridine-2-carboxamide

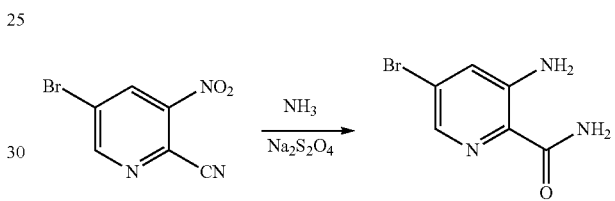

To a suspension of 5-bromo-3-nitropicolinonitrile (10 g, 43.9 mmol) in water (90 ml) was added 28% aqueous ammonia solution (15.59 ml, 202 mmol), and the mixture was stirred at room temperature for 30 minutes. Sodium hydrosulfite (43.8 g, 216 mmol) was added to the reaction mixture portionwise (exotherm observed from 21° C. to 32° C. and 32° C. to 41° C. with the first two portions). The reaction flask was transferred to cold water bath, and the remainder of the sodium hydrosulfite was added to the reaction mixture at a rate keeping the reaction temperature at 24-26° C. The reaction mixture was stirred at room temperature for 2 hours. The resultant precipitate was collected by filtration, washed with water and dried in vacuum oven overnight to give a solid (2.388 g). The solid was partitioned between ethyl acetate and water. The organic fraction was dried over anhydrous sodium sulfate, filtered, and concentrated to give the titled compound that was used without additional purification. $^1$H NMR (400 MHz, DMSO-d$_6$) δ ppm 6.92 7.08 (m, 2H), 7.37 (d, J=2.1 Hz, 2H), 7.78 (d, J=2.0 Hz, 1H), 7.82-7.92 (m, 1H); MS (ESI) m/z 215.9 (M+H)$^+$.

Intermediate 31: 3-amino-5-[(4-fluorophenyl)sulfonyl]pyridine-2-carboxamide

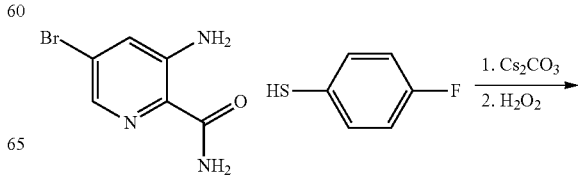

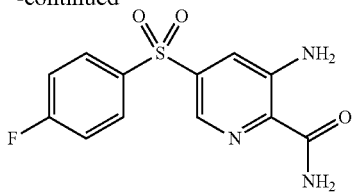

Step 1: 3-amino-5-[(4-fluorophenyl)sulfanyl]pyridine-2-carboxamide

To a solution of 3-amino-5-bromopyridine-2-carboxamide (Int 30, 2.38 g, 11.02 mmol) in 1-methyl-2-pyrrolidinone (10 mL) was added cesium carbonate (4.49 g, 13.77 mmol) and 4-fluorothiophenol (1.174 ml, 11.02 mmol). The reaction mixture was stirred at 65° C. for 2.5 hours, and then was stirred at 80° C. for 6.5 hours. The reaction mixture was cooled to room temperature and water (10 mL) was added. The resultant precipitate was collected by filtration, washed with water, and dried in vacuum oven to give a solid (2.8284 g). The solid was sonicated with a 7:3 mixture of heptanes: tert-butyl methyl ether. The solid was collected by filtration and then sonicated with 1:1 mixture of heptanes: tert-butyl methyl ether. The solid was collected by filtration and again sonicated with 1:1 mixture of heptanes: tert-butyl methyl ether. The solid was collected by filtration to give the titled compound, which was used without further purification. $^1$H NMR (500 MHz, DMSO-$d_6$) δ ppm 6.82 (p, J=2.1 Hz, 1H), 6.92 (s, 2H), 7.27 (s, 1H), 7.32 (ddt, J=9.2, 7.1, 2.3 Hz, 2H), 7.56 (tq, J=5.8, 3.2 Hz, 3H), 7.82 (s, 1H); MS (ESI+) m/z 264 (M+H)$^+$.

Step 2: 3-amino-5-[(4-fluorophenyl)sulfonyl]pyridine-2-carboxamide

To a cold (0° C.) solution of 3-amino-5-[(4-fluorophenyl)sulfanyl]pyridine-2-carboxamide (3.2 g, 12.15 mmol, step 1) in trifluoroacetic acid (20 ml) was added 30% hydrogen peroxide in water (4.97 ml, 48.6 mmol) in dropwise manner over 25 minutes. The reaction mixture was stirred for 6 hours at a temperature increasing from 0 to 15° C. 1% Acetic acid in water (100 mL) was added to the reaction mixture, and the resultant precipitate was collected by filtration and air dried overnight. The solid was triturated with dichloromethane and methanol. The filtrate was concentrated, and the residue was purified by flash chromatography using a 120 g silica cartridge eluted with 0-3.5% $CH_3OH/CH_2Cl_2$. Both materials were combined and used without further purification. $^1$H NMR (400 MHz, DMSO-$d_6$) δ ppm 7.24 (s, 2H), 7.45-7.53 (m, 2H), 7.54-7.61 (m, 1H), 7.67 (d, J=2.1 Hz, 1H), 7.99-8.09 (m, 3H), 8.15 (d, J=2.0 Hz, 1H).

TABLE I

Illustrative intermediates

| Int | Structure | Name | SM | MW | Mes |
|---|---|---|---|---|---|
| 1 | 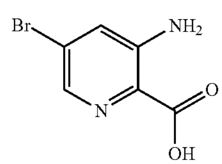 [SMILES: Nc1cc(Cl)cnc1C(=O)O] | 3-Amino-5-bromopyridine-2-carboxylic acid CAS: 870997-85-6 | Commercial | 217 | 217-219 |
| 2 | 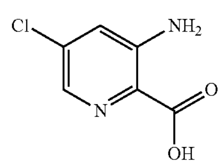 | 3-Amino-5-chloropyridine-2-carboxylic acid CAS: 53636-68-3 | Commercial | 173 | 174 |
| 3 | 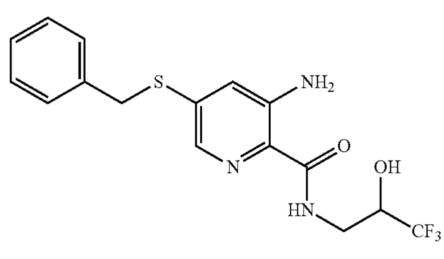 [SMILES: Nc1cc(SCc2ccccc2)cnc1C(=O)NCC(O)C(F)(F)F] | 3-Amino-5-benzylsulfanyl-pyridine-2-carboxylic acid (3,3,3-trifluoro-2-hydroxy-propyl)-amide | Int 8 | 371 | 372 |
| 4 | 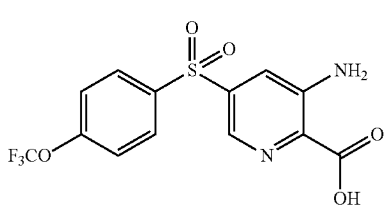 [SMILES: Nc1cc(S(=O)(=O)c2ccc(OC(F)(F)F)cc2)cnc1C(=O)O] | 3-Amino-5-(4-trifluoromethoxy-benzenesulfonyl)-pyridine-2-carboxylic acid | Int 1 | 362 | 363 |

TABLE I-continued

Illustrative intermediates

| Int | Structure | Name | SM | MW | Mes |
|---|---|---|---|---|---|
| 5 | 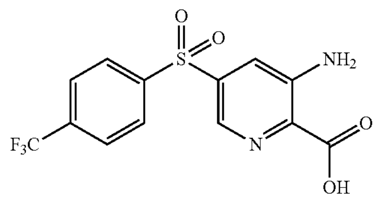 [SMILES: Nc1cc(S(=O)(=O)c2ccc(C(F)(F)F)cc2)cnc1C(=O)O] | 3-Amino-5-(4-trifluoromethyl-benzenesulfonyl)-pyridine-2-carboxylic acid | Int 1 | 346 | 347 |
| 6 | 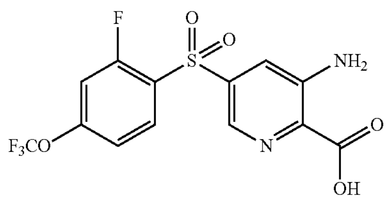 [SMILES: Nc1cc(S(=O)(=O)c2ccc(OC(F)(F)F)cc2F)cnc1C(=O)O] | 3-Amino-5-(2-fluoro-4-trifluoromethoxy-benzenesulfonyl)-pyridine-2-carboxylic acid | Int 1 | 380 | 381 |
| 7 | 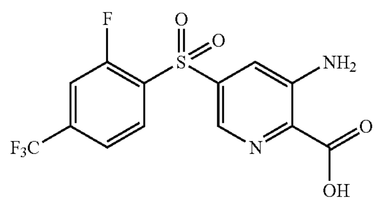 [SMILES: Nc1cc(S(=O)(=O)c2ccc(C(F)(F)F)cc2F)cnc1C(=O)O] | 3-Amino-5-(2-fluoro-4-trifluoromethyl-benzenesulfonyl)-pyridine-2-carboxylic acid | Int 1 | 364 | 365 |
| 8 | 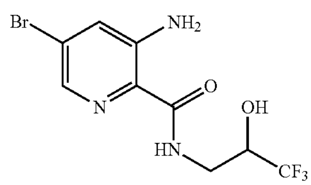 | 3-Amino-5-bromo-pyridine-2-carboxylic acid (3,3,3-trifluoro-2-hydroxy-propyl)-amide | Int 1 | 328 | 328-330 |
| 9 | 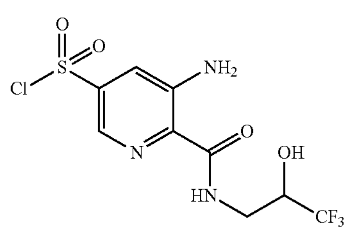 [SMILES: Nc1cc(S(=O)(=O)Cl)cnc1C(=O)NCC(O)C(F)(F)F] | 5-Amino-6-(3,3,3-trifluoro-2-hydroxy-propylcarbamoyl)-pyridine-3-sulfonyl chloride | Int 3 | 348 | 399 (*) |
| 10 | 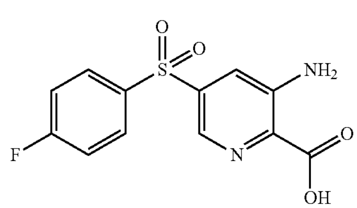 [SMILES: Nc1cc(S(=O)(=O)c2ccc(F)cc2)cnc1C(=O)O] | 3-Amino-5-(4-fluorobenzenesulfonyl)-pyridine-2-carboxylic acid | Int 1 | 296 | 297 |
| 11 | 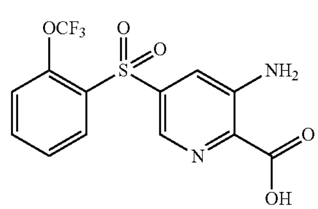 [SMILES: Nc1cc(S(=O)(=O)c2ccccc2OC(F)(F)F)cnc1C(=O)O] | 3-Amino-5-(2-trifluoromethoxy-benzenesulfonyl)-pyridine-2-carboxylic acid | Int 1 | 362 | 363 |

TABLE I-continued

Illustrative intermediates

| Int | Structure | Name | SM | MW | Mes |
|---|---|---|---|---|---|
| 12 | 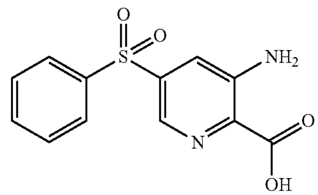 [SMILES: Nc1cc(S(=O)(=O)c2ccccc2)cnc1C(=O)O] | 3-Amino-5-benzenesulfonyl-pyridine-2-carboxylic acid | Int 1 | 278 | 279 |
| 13 | 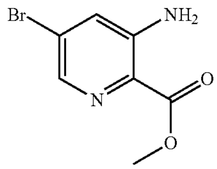 | 3-Amino-5-bromo-pyridine-2-carboxylic acid methyl ester | Int 1 | 231 | 232 |
| 14 | 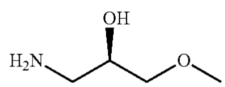 | (R)-1-Amino-3-methoxy-propan-2-ol | CAS: 64491-70-9 | 105 | 106 |
| 15 | 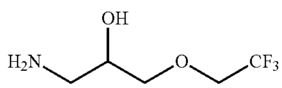 [SMILES: NCC(O)COCC(F)(F)F] | 1-Amino-3-(2,2,2-trifluoro-ethoxy)-propan-2-ol | CAS: 407-12-5 | 173 | 174 |
| 16 | 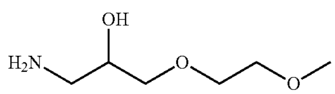 | 1-Amino-3-(2-methoxy-ethoxy)-propan-2-ol | CAS: 13483-49-3 | 149 | 150 |
| 17 | 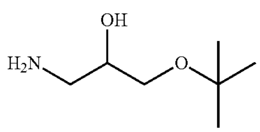 | 1-Amino-3-tert-butoxy-propan-2-ol | CAS: 7665-72-7 | 147 | 148 |
| 18 | 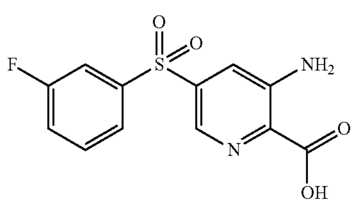 [SMILES: Nc1cc(S(=O)(=O)c2cccc(F)c2)cnc1C(=O)O] | 3-Amino-5-(3-fluoro-benzenesulfonyl)-pyridine-2-carboxylic acid | Int 1 | 296 | 297 |
| 19 | 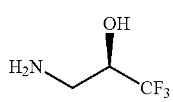 | (2R)-3-amino-1,1,1-trifluoropropan-2-ol | Commercial or from CAS: 143142-90-9 | 129 | 130 |
| 20 | 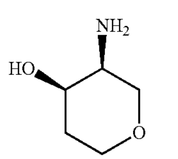 | rac-(3R,4S)-3-aminotetrahydro-2H-pyran-4-ol | Tetrahydro-2H-pyran-4-ol CAS: 2081-44-9 | 117 | 118 |
| 21 | 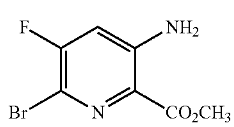 | 3-Amino-6-bromo-5-fluoro-pyridine-2-carboxylic acid methyl ester | 3-Amino-2-bromo-5-fluoropyridine CAS: 884495-03-8 | 248 | 249-251 |
| 22 | 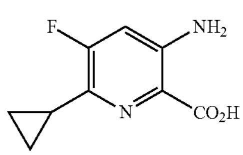 [SMILES: Nc1cc(F)c(C2CC2)nc1C(=O)O] | 3-Amino-6-cyclopropyl-5-fluoro-pyridine-2-carboxylic acid | Int 21 | 196 | 197 |

TABLE I-continued

Illustrative intermediates

| Int | Structure | Name | SM | MW | Mes |
|---|---|---|---|---|---|
| 23 | 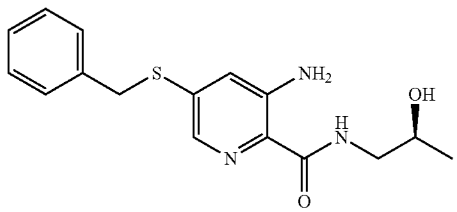 [SMILES: C[C@H](O)CNC(=O)c1ncc(SCc2ccccc2)cc1N] | 3-Amino-5-(benzylsulfanyl)-N-[(2S)-2-hydroxypropyl]pyridine-2-carboxamide | CAS: 1211538-72-5 | 317 | 318 |
| 24 | 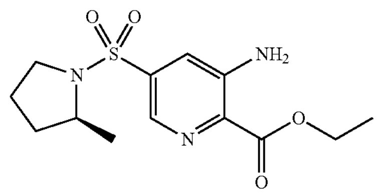 [SMILES: CCOC(=O)c1ncc(S(=O)(=O)N2CCC[C@@H]2C)cc1N] | ethyl 3-amino-5-{[(2S)-2-methylpyrrolidin-1-yl]sulfonyl}pyridine-2-carboxylate | CAS: 1214377-71-5 | 313 | 314 |
| 25 | 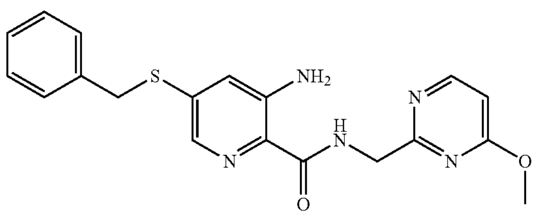 [SMILES: COc1ccnc(CNC(=O)c2ncc(SCc3ccccc3)cc2N)n1] | 3-amino-5-(benzylsulfanyl)-N-[(4-methoxypyrimidin-2-yl)methyl]pyridine-2-carboxamide | CAS: 22536-63-6 | 381 | 382 |
| 26 | 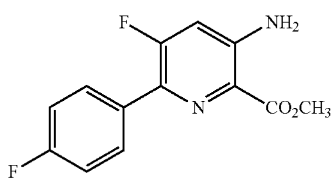 [SMILES: COC(=O)c1nc(-c2ccc(F)cc2)c(F)cc1N] | methyl 3-amino-5-fluoro-6-(4-fluorophenyl)pyridine-2-carboxylate | Int 21 | 264 | 265 |
| 27 | 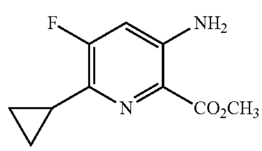 [SMILES: COC(=O)c1nc(C2CC2)c(F)cc1N] | methyl 3-amino-6-cyclopropyl-5-fluoropyridine-2-carboxylate | Int 21 | 210 | 211 |
| 28 | 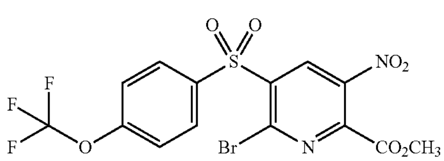 [SMILES: COC(=O)c1nc(Br)c(S(=O)(=O)c2ccc(OC(F)(F)F)cc2)cc1[N+](=O)[O-]] | methyl 6-bromo-3-nitro-5-{[4-(trifluoromethoxy)phenyl]sulfonyl}pyridine-2-carboxylate | Int 21 | 485 | |
| 29 | 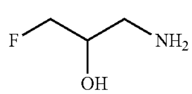 | 1-amino-3-fluoropropan-2-ol hydrochloride | CAS: 453-11-2 | 93 | 94 |
| 30 | 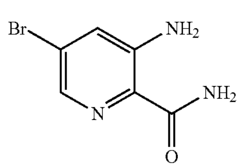 [SMILES: NC(=O)c1ncc(Br)cc1N] | 3-amino-5-bromopyridine-2-carboxamide | CAS: 573675-25-9 | 214 | 215 |

TABLE I-continued

Illustrative intermediates

| Int | Structure | Name | SM | MW | Mes |
|---|---|---|---|---|---|
| 31 | ![structure] | 3-amino-5-[(4-fluorophenyl)sulfonyl]pyridine-2-carboxamide | Int 30 | 295 | 296 |

* Intermediate 9 was quenched with morpholine for mass spectrometry analysis.

EXAMPLE 3

General Synthetic Methods for Preparation of the Compounds of Invention

Method A1: HATU or 2,4,6-tripropyl-1,3,5,2,4,6-trioxatriphosphinane 2,4,6-trioxide coupling

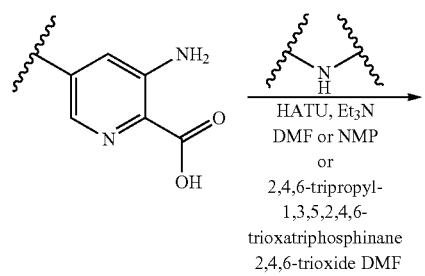

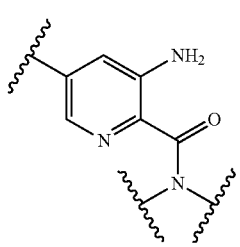

To a NMP solution containing the amine (1-2 eq), HATU (1-1.5 eq) and Et₃N (2-5 eq), the acid (1 eq) is added. The resulting mixtures are stirred at room temperature until the reaction is finished. The desired product is obtained after chromatographic separation or by precipitation in water. Alternatively, a DMF solution containing the acid (1 eq), amine (2 eq), and triethylamine (5 eq) is stirred at ambient temperature. Extractive work up and chromatographic purification give the amide product.

Method A2: HATU Coupling Using Flow Chemistry

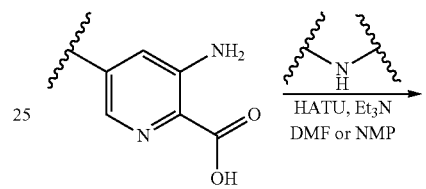

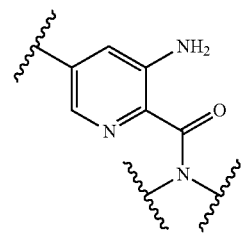

The reaction is run in a flow chemistry reactor. First, a stock solution is prepared in dimethylacetamide containing the acid at a concentration of 0.17 Molar, and triethylamine at a concentration of 0.50 Molar. Next, the following reactants are combined and mixed in a 0.2 mm inner diameter mixing tube and loaded into an injection loop: (a) 0.25 mL of the stock solution (0.043 mmol, 1.0 equivalent the acid and 0.125 mmol of triethylamine in dimethylacetamide, (b) 0.250 mL of a solution of 0.063 mmol (1.5 equivalents) of HATU (1-[bis(dimethylamino)methylene]-1H-1,2,3-triazolo[4,5-b]pyridinium 3-oxid hexafluorophosphate) (CAS 148893-10-1) and 0.13 mmol (3.0 equivalents) of diisopropylethylamine in 0.25 mL of dimethylacetamide, and (c) 0.253 mL of a solution of the amine (0.05 mmol, 1.2 equivalents) in dimethylacetamide. The reactants are injected into a flow reactor (containing a Hastelloy coil, 0.75 mm inner diameter, 1.8 mL internal volume) heated at 100° C. at a flow rate of 0.18 mL/minute (a 10 minute residence time at 100° C.). On exiting the flow reactor, the reaction is purified by liquid chromatography to give the target product, and product-containing fractions are concentrated to dryness under vacuum.

Method A3: Coupling for Acyl Hydrazide Formation

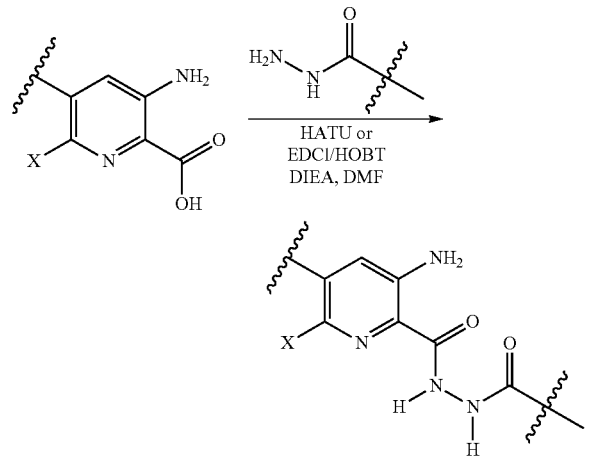

The acid (1 eq) and HATU (1.1 eq) are combined in DMF and stirred at ambient temperature for 30 minutes. The mixture is then added to a solution of the hydrazide (1.3 eq) in DMF and Hunig's base (2 eq) is added. The resulting mixtures are stirred at room temperature until the reaction is finished. The desired product is obtained after extractive workup or chromatographic separation.

Alternatively, the acid (1 eq), hydrazide (1.1 eq), Hunig's base, EDCI (1.5 eq), and HOBt (1.5 eq) are combined in DMF and stirred at room temperature until the reaction is finished. The desired product is obtained after extractive workup or chromatographic separation.

Method A4: Amide Formation from Ester

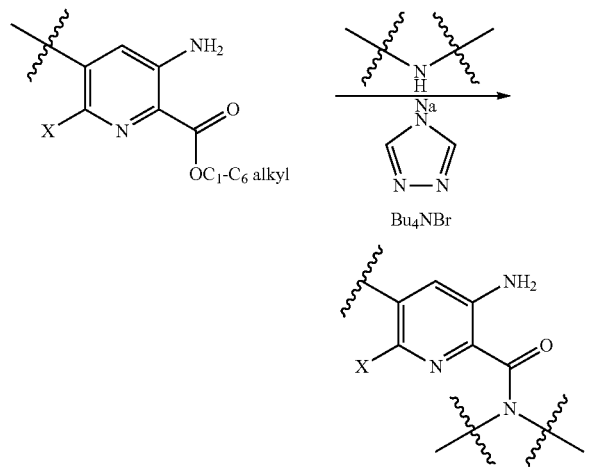

The ester (1 eq), amine (1.6-4 eq), sodium 1,2,4-triazolide (1 eq) and optional tetrabutylammonium bromide (0.5 eq) are combined in dioxane and heated overnight at 80-105° C. The desired product is obtained after chromatographic purification.

Method B1: $S_NAr$ to Introduce Thioether

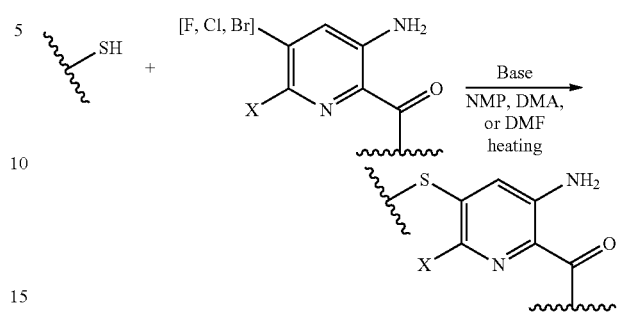

A solution of the amino pyridine (1 eq), the thiol (1.2-2 eq) and the base DBU (1-2 eq) is prepared in NMP, DMA or DMF. This mixture is heated at 140° C. for 45 minutes in a microwave reactor. Alternatively, $K_2CO_3$ in DMA can be used at 100° C. The reaction can also be heated under thermal conditions. The reaction is worked up by either precipitation in 1% AcOH in water or by extraction with EtOAc or tert-butyl methyl ether. In both cases, a crude residue is obtained that was used as such or that is purified by column chromatography to give the desired product.

Method B2: $S_NAr$ to Introduce Ether

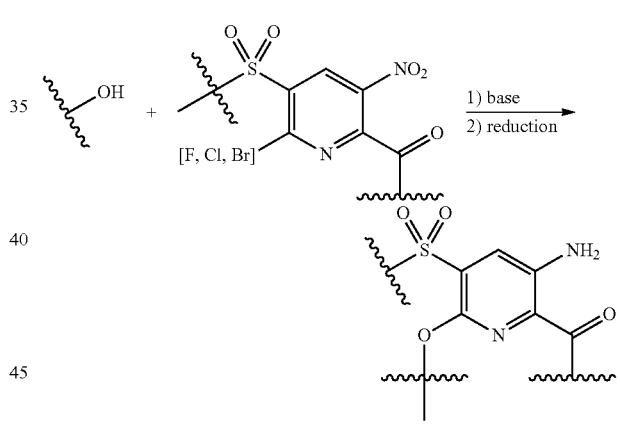

A solution of the halopyridine in an alcohol is treated with potassium carbonate at 45-60° C. The reaction mixture is worked up extractively and the product of the substitution reaction purified chromatographically. Alternatively, the halopyridine (1 eq) in an alcohol (1.5 eq) is treated with potassium tert-butoxide (1.1 eq) in tert-butanol at ambient temperature. The reaction mixture is worked up extractively and the product of the substitution reaction purified chromatographically. In another alternative, the halopyridine (1 eq) is treated with a higher molecular weight alcohol or phenol (2 eq) and potassium carbonate in N,N-dimethylformamide at ambient temperature. The reaction is worked up extractively to provide the substitution reaction product. The nitro group is subsequently reduced with hydrogen in the presence of 10% palladium on carbon in tetrahydrofuran at 55° C. or with trifluoroacetic acid at ambient temperature. Alternatively, the reduction is achieved with hydrogen in the presence of Raney® nickel in tetrahydrofuran. Chromatographic purification gives the amino-ether-pyridine.

Method B3: S$_N$Ar to Introduce Amine

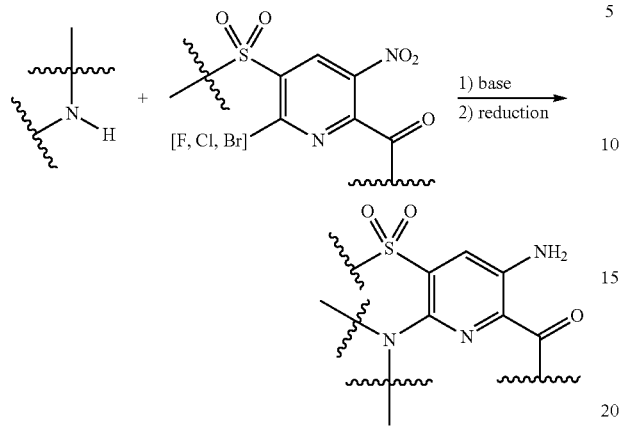

A solution of the halopyridine in tetrahydrofuran is treated with excess amine. The reaction mixture is worked up extractively. The nitro group is subsequently reduced with hydrogen in the presence of 10% palladium on carbon in tetrahydrofuran at 55° C. Chromatographic purification gives the bis-amino-pyridine.

Method C1: Oxidation of Thioether to Sulfone with H$_2$O$_2$

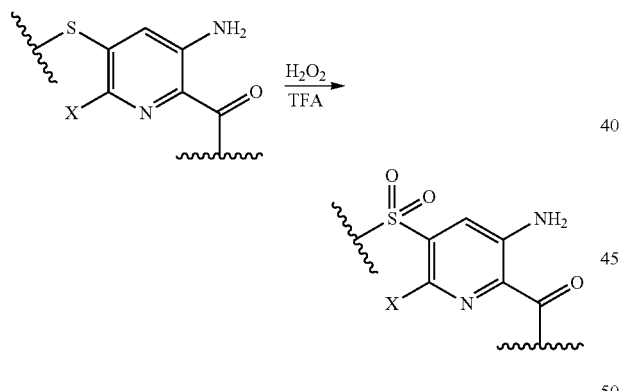

The thioether (1 eq) is dissolved in TFA, and the resulting mixture is cooled at 0° C. Next, H$_2$O$_2$ (4 eq) is added, and the mixture is stirred at 0° C. until the reaction is finished. For the workup, the mixture is diluted with a mixture of 1% AcOH in water. A suspension is obtained that is subsequently filtered to give a solid. This solid is washed with a 1% AcOH/water mixture followed by washing with petroleum ether. After drying in a vacuum oven, a powder is obtained that was used as such. Alternatively, the solid from the reaction can be collected by filtration, washed with water, and dried. Additional purification is achieved chromatographically. In some instances, the primary amine is oxidized to the corresponding nitro moiety. The nitro group can be transformed back the amine using the reduction procedures described in Method B2 or Method B3.

Method C2: Oxidation of Thioether to Sulfone with mCPBA or Hydrogen Peroxide

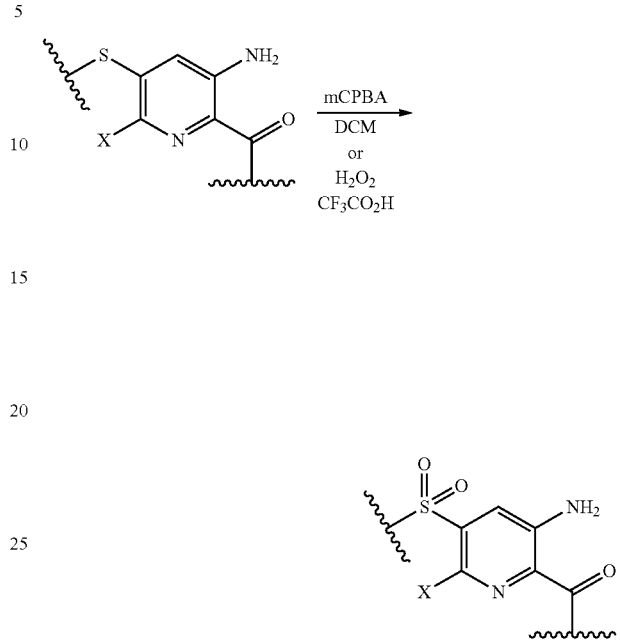

The thioether (1 eq) is mixed with mCPBA (2 eq) in DCM at 0° C. After 1 h, additional mCPBA (2 eq) is added to drive the reaction to completion. Next, the mixture is concentrated, and the obtained crude residue is purified by preparative chromatography to give the desired product.

Alternatively, the thioether is dissolved in trifluoroacetic acid and treated with 30% hydrogen peroxide between 0° C. and ambient temperature until complete oxidation is achieved. Extractive workup gives the sulfone.

Method D1: Sulfonamide Formation

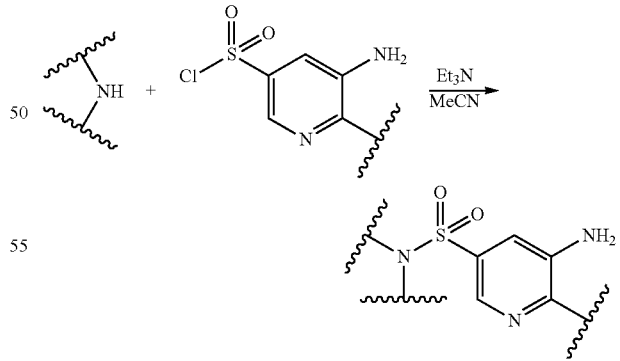

To a mixture of the amine (1.5 eq) and Et$_3$N (4 eq) in acetonitrile, the sulfonyl chloride (1 eq) is added. The resulting mixture is stirred at room temperature until the reaction is finished. The desired product is obtained after chromatographic purification using a gradient from 100% petroleum ether to 100% EtOAc.

Method D2: Sulfonamide Formation

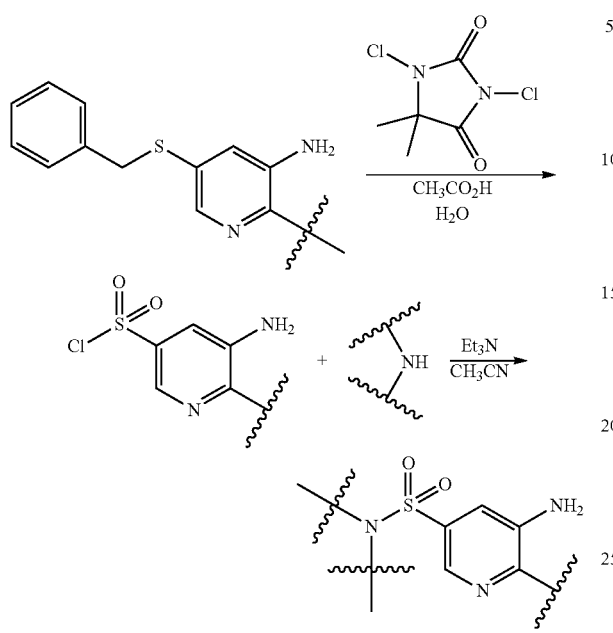

A mixture of the benzylsulfide (1 eq), water, and acetic acid in acetonitrile is treated with 1,3-dichloro-1,5-dimethylhydantoin (2 eq) at or below 0° C. over 15-30 minutes. Then, amine (3 eq) and triethylamine (4 eq) are added as a solution in acetonitrile at or below 0° C. The reaction mixture is allowed to warm to ambient temperature with continued stirring over 0.5-1 hour. Following concentration, purification is achieved chromatographically by normal phase flash chromatography or reverse-phase HPLC.

Method E1: Reducing Oxidized Side Product with Iron

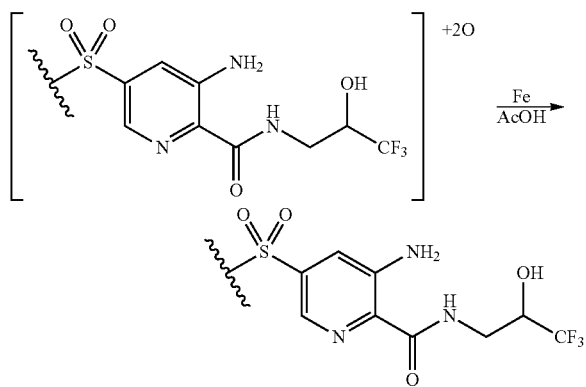

In certain cases, it is observed that during oxidation method C1, an oxidized side product is formed. Therefore, the crude obtained after method C1, is dissolved in AcOH and iron (4 eq) is added. The mixture is then heated at 50° C. overnight. Next, the mixture is diluted with NaHCO$_3$ solution and extracted with EtOAc. Combined organic fractions are concentrated, and the resulting crude residue is purified by preparative chromatography to give the desired product.

Method F1: Bromination of Pyridine Ring with NBS

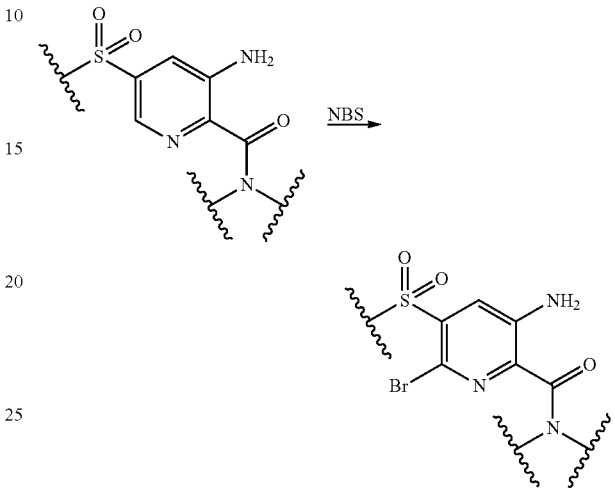

To a solution of the 3-aminopyridine (1 eq) in MeCN or N,N-dimethylformamide, NBS (1 eq) is added. The resulting mixture is stirred at a temperature between room temperature and 45° C. overnight. Next, the mixture is added to water or brine and diluted with EtOAc or dichloromethane. Combined organic fractions after extraction are dried over Na$_2$SO$_4$, filtered and concentrated. The obtained crude residue is purified by preparative chromatography or flash chromatography to give the desired product.

Method G1: Suzuki Coupling

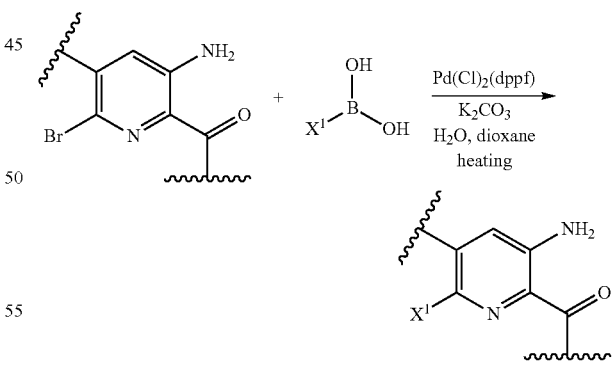

$X^1$ is $C_{1-4}$ alkyl optionally substituted with one or more independently selected halo; or cyclopropyl or phenyl each optionally substituted with one or more independently selected $R^5$ groups.

To a solution of the 3-amino-6-bromopyridine (1 eq) in a dioxane/water mixture (4/1) or tetrahydrofuran/water mixture (10:0.1), K$_2$CO$_3$ (1.2 eq), Pd(Cl)$_2$(dppf) (0.05 eq) and boronic acid (1.2 eq) are added. The mixture is heated at 95° C. Extraction with EtOAc gives an organic fraction that is concentrated to give a crude residue that is used as such. Alternatively, Cs$_2$CO$_3$ can be used instead of K$_2$CO$_3$. Heating can be achieved conventionally or with microwave irradiation.

Method H1: Acid Formation from Ester Hydrolysis

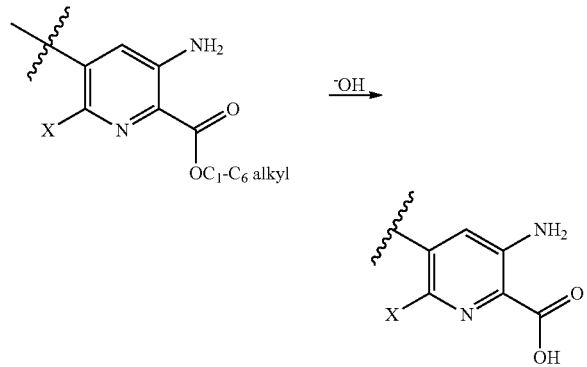

The ester is treated with a base such as but not limited to aqueous lithium hydroxide, sodium hydroxide, or potassium hydroxide in tetrahydrofuran, methanol, or a mixture thereof at ambient to the reflux temperature. The reaction mixture can be acidified and then extracted with ethyl acetate. Concentration of the organic fraction gives the carboxylic acid.

Compound 21: 3-amino-N-[(2S)-2-hydroxypropyl]-5-{[4-(trifluoromethoxy)phenyl]sulfonyl}pyridine-2-carboxamide 3-Amino-5-(4-trifluoromethoxy-benzenesulfonyl)-pyridine-2-carboxylic acid (Int 4, 500 mg, 1.38 mmol) was dissolved in NMP (10 mL) together with HATU (580 mg, 1.52 mmol), triethylamine (580 µL, 4.14 mmol) and (S)-(+)-1-amino-2-propanol (CAS: 2799-17-9, 114 mg, 1.52 mmol). The mixture was stirred overnight at room temperature. The reaction mixture was poured into water and extracted with EtOAc. The organic fractions were combined and concentrated. The obtained residue was purified by column chromatography (eluent system: EtOAc/petroleum ether 45/55) to give the titled compound.

Compound 36: 3-amino-5-[(4-fluorophenyl)sulfonyl]-N-[(2R)-3,3,3-trifluoro-2-hydroxypropyl]pyridine-2-carboxamide To a solution of 3-amino-5-(4-fluorobenzenesulfonyl)-pyridine-2-carboxylic acid (Int 10, 17.4 g, 58.7 mmol) in NMP (130 mL), triethylamine (16.3 mL, 117 mmol) and (2R)-3-amino-1,1,1-trifluoropropan-2-ol (Int 19, 7.58 g, 58.7 mmol) were added. The resulting mixture was stirred at room temperature for a few minutes, before adding HATU (portionwise, 22.32 g, 58.7 mmol). The resulting mixture was stirred at room temperature. Next, the mixture was added to water, and the obtained suspension was stirred vigorously for 30 minutes. The resulting solid was collected by filtration and washed with water and diisopropyl ether. In this way, a solid was obtained that was subsequently purified via precipitation from chloroform/MeOH (for about 10 g of crude, 300 mL of chloroform and 10 mL of MeOH was used), yielding the titled compound.

Compound 39: 3-amino-5-[(3-fluorophenyl)sulfonyl]-N-(2-hydroxy-2-methylpropyl)pyridine-2-carboxamide 3-Amino-5-chloropyridine-2-carboxylic acid (Int 2, 2 g, 11.6 mmol) was dissolved in NMP (100 mL) together with 1-amino-2-methyl-propan-2-ol (CAS: 2854-16-2, 1.14 g, 12.8 mmol), triethylamine (3.56 mL, 25.6 mmol) and HATU (4.87 g, 12.8 mmol). The resulting mixture was stirred at room temperature overnight. Next, the mixture was diluted with water and extracted with EtOAc. The organic fractions were combined, concentrated and the resulting crude residue was purified by column chromatography (petroleum ether/EtOAc 95/5 to 50/50) to give 3-amino-5-chloro-pyridine-2-carboxylic acid (2-hydroxy-2-methyl-propyl)-amide.

3-Amino-5-chloro-pyridine-2-carboxylic acid (2-hydroxy-2-methyl-propyl)-amide (150 mg, 0.62 mmol) was mixed with 3-fluorobenzenethiol (CAS: 2557-77-9, 156 µL, 1.85 mmol) and DBU (280 µL, 1.85 mmol) in DMA (2 mL). The resulting mixture was stirred for 72 h at 65° C. Next, the mixture was diluted with water and extracted with EtOAc. Concentration of the combined organic fractions gives crude 3-amino-5-(3-fluoro-phenyl sulfanyl)-pyridine-2-carboxylic acid (2-hydroxy-2-methyl-propyl)-amide that was used as such.

3-Amino-5-(3-fluoro-phenyl sulfanyl)-pyridine-2-carboxylic acid (2-hydroxy-2-methyl-propyl)-amide (0.62 mmol) was mixed with mCPBA (210 mg, 1.24 mmol) in dichloromethane at 0° C. and subsequently stirred at 0° C. for 1 h. The mixture was concentrated to dryness. The compound was purified by preparative chromatography to give the titled compound.

Compound 70: 3-amino-N-[(2R)-2-hydroxy-3-methoxypropyl]-5-{[4-(trifluoromethyl)phenyl]sulfonyl}pyridine-2-carboxamide 3-Amino-5-(4-trifluoromethyl-benzenesulfonyl)-pyridine-2-carboxylic acid (Int 5, 26.6 g, 76.9 mmol) was dissolved in NMP (530 mL) together with HATU (32.2 g, 84.6 mmol), triethylamine (21.4 mL, 154 mmol) and (R)-1-amino-3-methoxy-propan-2-ol (Int 14, 11.9 g, 84.6 mmol). The mixture was stirred at room temperature for 30 minutes. The reaction mixture was poured into water to give a suspension. The precipitate was collected by filtration. The remaining aqueous phase was extracted with EtOAc. The EtOAc fractions were concentrated, and the resulting crude residue was purified together with the precipitate obtained from filtration. The purification was done by column chromatography using petroleum ether/EtOAc (60/40 to 40/60) to give the titled compound.

Compound 77: (3-amino-5-{[2-fluoro-4-(trifluoromethoxy)phenyl]sulfonyl}pyridin-2-yl) (3-hydroxyazetidin-1-yl)methanone To a solution of azetidin-3-ol (CAS: 45347-82-8, 11 mg, 0.1 mmol) in NMP (0.5 mL) and triethylamine (0.28 µL, 0.2 mmol), 3-amino-5-(2-fluoro-4-trifluoromethoxy-benzenesulfonyl)-pyridine-2-carboxylic acid (Int 6, 38 mg, 0.1 mmol) and HATU (38 mg, 0.1 mmol) were added. The mixture was stirred at room temperature for 3 h. The mixture was added to water, washed with water, petroleum ether and diisopropyl ether. The solid was taken up in water/diisopropyl ether and sonicated, filtered, and washed once again with diisopropyl ether and petroleum ether. The solid was dried in vacuum oven at 50° C. to give the titled compound.

Compound 84: 3-amino-5-[(4,4-difluoropiperidin-1-yl)sulfonyl]-N-(3,3,3-trifluoro-2-hydroxypropyl) pyridine-2-carboxamide 4,4-Difluoropiperidine (CAS: 21987-29-1, 47 µL, 0.54 mmol) and triethylamine (150 µL, 1.08 mmol) were mixed in acetonitrile (1 mL). 5-Amino-6-(3,3,3-trifluoro-2-hydroxy-propylcarbamoyl)-pyridine-3-sulfonyl chloride (Int 9, 0.18 mmol) was added. The mixture was stirred at room temperature for 2 h. Ethyl acetate and water were added, and the layers were separated. The combined organic layers were concentrated to dryness. The residue was purified by chromatography (eluent gradient from 100% petroleum ether to 100% EtOAc) to give the titled compound.

Compound 85: (3-amino-5-{[2-(trifluoromethoxy) phenyl]sulfonyl}pyridin-2-yl)[3-hydroxy-3-(trifluoromethyl)azetidin-1-yl]methanone To a solution of 3-(trifluoromethyl)-azetidine-3-ol (HCl salt, CAS: 848192-96-1, 23 mg, 0.13 mmol) in NMP (1 mL) and triethylamine (0.35 µL, 0.26 mmol), 3-amino-5-(2-trifluoromethoxy-benzenesulfonyl)-pyridine-2-carboxylic acid (Int 11, 45 mg, 0.13 mmol) and HATU (47 mg, 0.13 mmol) were added. The mixture was stirred at room temperature for 30 minutes. The reaction mixture was added to water, sonicated and filtered. The solid was taken up again in water, sonicated and filtered, and washed with water and petroleum ether. Both the filtrate and solid were extracted with ethyl acetate. The combined organic fractions were washed with water and brine, dried over sodium sulfate, filtered and concentrated to dryness. The compound was purified by preparative chromatography to give the titled compound.

Compound 91: (3-amino-5-{[4-(trifluoromethyl) phenyl]sulfonyl}pyridin-2-yl) (3-hydroxy-3-methyl-azetidin-1-yl)methanone 3-Amino-5-(4-trifluoromethyl-benzenesulfonyl)-pyridine-2-carboxylic acid (Int 5, 300 mg, 0.867 mmol) was dissolved in NMP (5 mL) together with HATU (362 mg, 0.953 mmol), triethylamine (266 µL, 1.906 mmol) and 3-hydroxy-3-methylazetidine (HCl salt, CAS: 124668-46-8, 119 mg, 0.953 mmol). The mixture was stirred overnight under nitrogen at room temperature. The reaction mixture was poured into water to give a suspension. The precipitate was collected by filtration and dried in a vacuum oven at 50° C. The compound was purified on silica using petroleum ether/EtOAc (50/50 to 0/100) to give the titled compound.

Compound 98: 3-amino-5-{[2-fluoro-4-(trifluoromethyl)phenyl]sulfonyl}-N-[(2S)-2-hydroxypropyl] pyridine-2-carboxamide 3-Amino-5-(2-fluoro-4-trifluoromethyl-benzenesulfonyl)-pyridine-2-carboxylic acid (Int 7, 400 mg, 1.10 mmol) was dissolved in NMP (4 mL) together with HATU (460 mg, 1.21 mmol), triethylamine (337 µL, 2.42 mmol) and (S)-(+)-1-amino-2-propanol (CAS: 2799-17-9, 91 mg, 1.21 mmol). The mixture was stirred overnight at room temperature. The reaction mixture was poured into water to give a suspension. The precipitate was collected by filtration. The obtained precipitate was purified by column chromatography using petroleum ether/EtOAc (100/0 to 40/60) to give the titled compound.

Compound 201: 3-amino-N-[2-hydroxy-3-(2,2,2-trifluoroethoxy)propyl]-5-{[4-(trifluoromethyl)phenyl]sulfonyl}pyridine-2-carboxamide 3-Amino-5-(4-trifluoromethyl-benzenesulfonyl)-pyridine-2-carboxylic acid (Int 5, 500 mg, 1.46 mmol) was dissolved in NMP (5 mL) together with HATU (1-[bis (dimethylamino)methylene]-1H-1,2,3-triazolo[4,5-b]pyridinium 3-oxid hexafluorophosphate) (609 mg, 1.60 mmol), triethylamine (446 µL, 3.20 mmol) and 1-amino-3-(2,2,2-trifluoro-ethoxy)-propan-2-ol (Int 15, 277 mg, 1.10 mmol). After stirring at room temperature for 5 minutes, the mixture was diluted with water and extracted with EtOAc. Combined organic fractions were concentrated, and the obtained crude residue was purified by column chromatography using petroleum ether/EtOAc (100/0 to 0/100) to give the titled compound.

Compound 211: 3-amino-5-{methyl[4-(trifluoromethyl)benzyl]sulfamoyl}-N-(3,3,3-trifluoro-2-hydroxypropyl)pyridine-2-carboxamide 5-Amino-6-(3,3,3-trifluoro-2-hydroxy-propylcarbamoyl)-pyridine-3-sulfonyl chloride (Int 9, 0.27 mmol, in a solution of AcOH, water and acetonitrile) was diluted in a mixture acetonitrile (0.17 mL) and triethylamine (0.48 mmol, 67 µL). Next, N-methyl-1-(4-trifluoromethyl)phenyl) methanamine (CAS: 90390-11-7, 0.81 mmol, 154 mg) was added. After stirring at room temperature for 1 hour, the reaction mixture was evaporated and the crude was purified by preparative chromatography to give the titled compound.

Compound 224: 3-amino-N-(3-tert-butoxy-2-hydroxypropyl)-5-{[2-fluoro-4-(trifluoromethyl)phenyl]sulfonyl}pyridine-2-carboxamide 3-Amino-5-(2-fluoro-4-trifluoromethyl-benzenesulfonyl)-pyridine-2-carboxylic acid (Int 7, 150 mg, 0.395 mmol) was dissolved in NMP (2 mL) together with HATU (1-[bis (dimethylamino)methylene]-1H-1,2,3-triazolo[4,5-b]pyridinium 3-oxid hexafluorophosphate) (330 mg, 0.434 mmol), triethylamine (141 µL, 0.878 mmol) and 1-amino-3-tert-butoxy-propan-2-ol (Int 17, 64 mg, 0.434 mmol). After overnight stirring at room temperature, the mixture was diluted with water and extracted with EtOAc. Combined organic fractions were concentrated, and the obtained crude residue was purified by preparative chromatography to give the titled compound.

Compound 236: 3-amino-N-(3,3,3-trifluoro-2-hydroxypropyl)-5-{[3-(trifluoromethoxy)phenyl] sulfonyl}pyridine-2-carboxamide 3-Amino-5-bromo-pyridine-2-carboxylic acid (3,3,3-trifluoro-2-hydroxy-propyl)-amide (Int 8, 200 mg, 0.61 mmol) was dissolved in DMA (1.20 mL) and DBU (273 µL, 0.18 mmol) and 3-(trifluoromethoxy)thiophenol (CAS: 220239-66-7, 196 mg, 1 mmol) were added. The mixture was heated at 105° C. for 72 h. The mixture was diluted with water and extracted with EtOAc. The combined organic fractions were concentrated to give 3-amino-5-(3-trifluoromethoxy-phenylsulfanyl)-pyridine-2-carboxylic acid (3,3,3-trifluoro-2-hydroxy-propyl)-amide that was used as such in the next step.

TFA (1.7 mL) was added drop wise to 3-amino-5-(3-trifluoromethoxy-phenylsulfanyl)-pyridine-2-carboxylic acid (3,3,3-trifluoro-2-hydroxy-propyl)-amide (0.61 mmol) at 0° C. The mixture was stirred for 10 minutes before adding $H_2O_2$ (230 μL, 4.2 eq). The reaction mixture was warmed up to room temperature and was stirred overnight. The mixture was diluted with $NaHCO_3$ solution till pH=8 was reached. Subsequently, the mixture was extracted with ethyl acetate. The combined organic fractions were washed with water and brine, dried over sodium sulfate and concentrated to dryness. The obtained crude residue was purified by preparative chromatography to give the titled compound.

Compound 244: 3-amino-5-(phenylsulfonyl)-N-(3,3,3-trifluoro-2-hydroxypropyl)pyridine-2-carboxamide 3-Amino-5-bromo-pyridine-2-carboxylic acid (3,3,3-trifluoro-2-hydroxy-propyl)-amide (Int 8, 200 mg, 0.61 mmol) was dissolved in DMA (1.20 mL), and then DBU (273 μL, 0.18 mmol) and thiophenol (CAS108-98-5, 76 μL, 0.73 mmol) were added. The mixture was heated at 105° C. for 72 h. The mixture was diluted with water and extracted with EtOAc. Combined organic fractions were concentrated to give 3-amino-5-phenylsulfanyl-pyridine-2-carboxylic acid (3,3,3-trifluoro-2-hydroxy-propyl)-amide that was used as such in the next step.

TFA (1.7 mL) was added drop wise 3-amino-5-phenylsulfanyl-pyridine-2-carboxylic acid (3,3,3-trifluoro-2-hydroxy-propyl)-amide (0.61 mmol) at 0° C. The mixture was stirred for 10 minutes before adding $H_2O_2$ (230 μL, 4.2 eq). The reaction mixture was warmed up to room temperature and was stirred overnight. The mixture was diluted with $NaHCO_3$ solution to pH=8 was reached. Subsequently, the mixture was extracted with ethyl acetate. Combined organic fractions were washed with water and brine, dried over sodium sulfate, filtered and concentrated to dryness. The obtained crude material was used as such in the next step.

Iron metal (22 mg, 0.4 mmol) was added to the crude material in AcOH (1 mL). The mixture was stirred overnight at 50° C. in a sealed tube. The mixture was diluted with $NaHCO_3$ solution to pH=8 was reached. Subsequently, the mixture was extracted with ethyl acetate. Combined organic fractions were washed with water and brine, dried over sodium sulfate, filtered and concentrated to dryness. The obtained crude residue was purified by preparative chromatography to give the titled compound.

Compound 255: [3-amino-5-(phenyl sulfonyl)pyridin-2-yl][3-hydroxy-3-(trifluoromethyl)azetidin-1-yl]methanone 3-Amino-5-benzenesulfonyl-pyridine-2-carboxylic acid (Int 12, 200 mg, 0.72 mmol) was dissolved in NMP (4 mL) together with HATU (1-[bis(dimethylamino)methylene]-1H-1,2,3-triazolo[4,5-b]pyridinium 3-oxid hexafluorophosphate) (301 mg, 0.79 mmol), triethylamine (221 μL, 1.58 mmol) and 3-(trifluoromethyl)azetidin-3-ol (HCl salt, CAS: 848192-96-1, 141 mg, 0.791 mmol). After overnight stirring at room temperature, the mixture was diluted with water to give a suspension. This suspension was filtered, and the obtained solid was purified using column chromatography (eluent gradient from 100% petroleum ether to 100% EtOAc) to give the titled compound.

Compound 256: {3-amino-5-[(3-fluorophenyl)sulfonyl]pyridin-2-yl}[3-hydroxy-3-(trifluoromethyl)azetidin-1-yl]methanone To a solution of 3-(trifluoromethyl)-azetidine-3-ol (HCl salt, CAS: 848192-96-1, 172 mg, 0.97 mmol) in NMP (6 mL) and triethylamine (0.25 mL, 1.76 mmol), 3-amino-5-(3-fluoro-benzenesulfonyl)-pyridine-2-carboxylic acid (Int 18, 260 mg, 0.88 mmol) and HATU (369 mg, 0.97 mmol) were added. The mixture was stirred at room temperature for 30 minutes. The mixture was added to water, and the precipitate was collected by filtration. The residue was triturated with water and diisopropyl ether. Water was added to obtain a suspension. The suspension was dried overnight on a freeze dryer to give the titled compound.

Compound 259: 3-amino-6-(4-fluorophenyl)-5-[(4-fluorophenyl) sulfonyl]-N-[(2R)-3,3,3-trifluoro-2-hydroxypropyl]pyridine-2-carboxamide A mixture of 3-amino-6-bromo-5-fluoro-pyridine-2-carboxylic acid methyl ester (Intermediate 21, 249 mg, 1 mmol), $Pd(dppf)Cl_2$ (41 mg, 0.05 mmol), 4-fluorophenylboronic acid (CAS: 1765-93-1, 168 mg, 1.2 mmol) and $K_2CO_3$ (166 mg, 1.2 mmol) in dioxane/$H_2O$ (4 mL/1 mL) was heated at 95° C. in a closed vial (flushed with $N_2$). Next, the mixture was added into water and extracted with EtOAc. Combined organic fractions were dried over $Na_2SO_4$, filtered and concentrated in vacuo to give 3-amino-5-fluoro-6-(4-fluoro-phenyl)-pyridine-2-carboxylic acid methyl ester.

3-Amino-5-fluoro-6-(4-fluoro-phenyl)-pyridine-2-carboxylic acid methyl ester (211 mg, 0.8 mmol) was mixed in DMA with 4-fluorobenzenethiol (CAS: 371-42-6, 102 mg, 0.8 mmol) and DBU (122 μL, 0.8 mmol). The mixture was heated in a microwave reactor at 145° C. for 45 minutes. Dilution with water and extraction with EtOAc gives 3-amino-6-(4-fluoro-phenyl)-5-(4-fluoro-phenylsulfanyl)-pyridine-2-carboxylic acid methyl ester.

3-Amino-6-(4-fluoro-phenyl)-5-(4-fluoro-phenylsulfanyl)-pyridine-2-carboxylic acid methyl ester (0.1 mmol) was hydrolyzed in a THF/$H_2O$ mixture (1 mL/0.2 mL) using LiOH at 45° C. After overnight stirring, 3-amino-6-(4-fluoro-phenyl)-5-(4-fluoro-phenylsulfanyl)-pyridine-2-carboxylic acid was obtained by acidifying the mixture to pH=3 and extraction with EtOAc. Concentration gave the crude product that was used as such.

3-Amino-6-(4-fluoro-phenyl)-5-(4-fluoro-phenylsulfanyl)-pyridine-2-carboxylic acid (0.1 mmol) was dissolved in TFA (1 mL) together with $H_2O_2$ (34 μL, 0.4 mmol) at 0° C. When the reaction was complete, the mixture was added to water and the resulting precipitate was collected to give crude 3-amino-5-(4-fluoro-benzenesulfonyl)-6-(4-fluorophenyl)-pyridine-2-carboxylic acid that was used as such.

3-Amino-5-(4-fluoro-benzenesulfonyl)-6-(4-fluoro-phenyl)-pyridine-2-carboxylic acid (0.1 mmol) was dissolved in NMP together with HATU (38 mg, 0.1 mmol), $Et_3N$ (28 μL, 0.2 mmol) and (2R)-3-amino-1,1,1-trifluoropropan-2-ol (Intermediate 19, 17 mg). The mixture was stirred at ambient temperature after which it was purified by preparative chromatography to give the titled compound.

Compound 260: 3-amino-6-cyclopropyl-N-(2-hydroxyethyl)-5-(phenylsulfonyl)pyridine-2-carboxamide A mixture of 3-amino-6-bromo-5-fluoro-pyridine-2-carboxylic acid methyl ester (Intermediate 21, 200 mg, 0.8 mmol), thiophenol (CAS: 108-98-5, 88 mg, 0.8 mmol) and $K_2CO_3$ (332 mg, 2.4 mmol) in 3 mL of DMA was heated at 100° C. for 2.5 h. The mixture was poured into 10 mL of water, extracted with EtOAc, dried and concentrated to afford. After the addition of water, a precipitate was formed. Collection by filtration gave 3-amino-6-bromo-5-phenylsulfanyl-pyridine-2-carboxylic acid methyl ester that was used as such.

To a mixture of THF and water (7 mL, 10:0.1) was added 3-amino-6-bromo-5-phenylsulfanyl-pyridine-2-carboxylic acid methyl ester (235 mg, 0.69 mmol), cyclopropylboronic acid (301 mg, 3.46 mmol), $Cs_2CO_3$ (674 mg, 2.07 mmol) and $Pd(dppf)Cl_2$ (56 mg, 0.069 mmol) was heated in microwave reactor at 150° C. for 15 minutes. The reaction mixture was filtered over a plug of silica (DCM, then EtOAc) and concentrated in vacuo to afford 100 mg of crude 3-amino-6-cyclopropyl-5-phenylsulfanyl-pyridine-2-carboxylic acid that was used in a next step.

3-Amino-6-cyclopropyl-5-phenylsulfanyl-pyridine-2-carboxylic acid (125 mg, 0.35 mmol) was dissolved in 2 mL of TFA at 0° C. $H_2O_2$ (0.14 mL, 1.4 mmol; 30% in $H_2O$) was added, and the reaction mixture was stirred at room temperature for 2 hours. The mixture was poured into 5 mL of water, extracted with EtOAc, dried and concentrated to afford 3-amino-5-benzenesulfonyl-6-cyclopropyl-pyridine-2-carboxylic acid that was used in the next step as such.

3-Amino-5-benzenesulfonyl-6-cyclopropyl-pyridine-2-carboxylic acid (50 mg, 0.13 mmol), 2-aminoethanol (CAS: 141-43-5, 8 mg, 0.13 mmol) and HATU (49 mg, 0.13 mmol) were dissolved in 1 mL of DMF and stirred at room temperature for 2 minutes. 4-Methylmorpholine (43 µL, 0.39 mmol) was added and stirring was continued at ambient temperature for 2 h. The reaction mixture was poured into water (10 mL) and extracted with EtOAc (25 mL). The organic extract was washed with saturated $NH_4Cl$ solution (5 mL), dried and concentrated in vacuo to give the titled compound that was further purified by preparative chromatography.

Compound 261: 3-amino-5-(cyclopentanesulfonyl)-6-(4-fluorophenyl)-N-[(2S)-2-hydroxypropyl]pyridine-2-carboxamide A mixture of methyl 3-amino-5-fluoro-6-(4-fluorophenyl)pyridine-2-carboxylate (20 mg, 0.076 mmol, Intermediate 26), cyclopentanethiol (11.60 mg, 0.114 mmol) and $K_2CO_3$ (20.92 mg, 0.151 mmol) in N,N-dimethylacetamide (0.5 mL) was heated to 100° C. for 90 minutes and allowed to stand at room temperature over the weekend. The mixture was diluted with tert-butyl methyl ether (30 mL) and washed with saturated aqueous $NaHCO_3$ solution (10 mL), water (15 mL), and brine. The organic fraction was dried ($MgSO_4$), filtered and concentrated to provide methyl 3-amino-5-(cyclopentylsulfanyl)-6-(4-fluorophenyl)pyridine-2-carboxylate. LC/MS (ESI+) m/z 347 (M+H)$^+$.

A solution of methyl 3-amino-5-(cyclopentylsulfanyl)-6-(4-fluorophenyl)pyridine-2-carboxylate (26.3 mg, 0.076 mmol) in tetrahydrofuran (1.5 mL) was diluted with methanol (1.5 mL), treated with 1 M NaOH (0.5 mL) and stirred at 55° C. for 1 hour. The mixture was cooled, treated with 2% citric acid solution (10 mL) and extracted with ethyl acetate (twice, 25 mL and 25 mL). The combined ethyl acetate layers were washed with brine, dried ($MgSO_4$), filtered and concentrated to provide 3-amino-5-(cyclopentylsulfanyl)-6-(4-fluorophenyl)pyridine-2-carboxylic acid (45 mg, 0.135 mmol, 178% yield) which contained some cyclopentanethiol from the previous step. $^1$H NMR (501 MHz, $CDCl_3$) δ ppm 7.54 (ddd, J=8.3, 5.2, 2.5 Hz, 2H), 7.15-7.09 (m, 2H), 6.95 (s, 1H), 5.83 (s, 2H), 3.55-3.50 (m, 1H), 2.13 (dt, J=10.5, 5.0 Hz, 2H), 1.82-1.56 (m, 6H); MS (ESI+) m/z 333 (M+H)$^+$; MS (ESI−) m/z 331 (M−H)$^-$.

A solution of 3-amino-5-(cyclopentyl sulfanyl)-6-(4-fluorophenyl)pyridine-2-carboxylic acid (45 mg, 0.135 mmol) in trifluoroacetic acid (1 mL) was cooled to 0° C., treated with 30% hydrogen peroxide (55.3 µL, 0.542 mmol), stirred for 30 minutes, treated with more 30% hydrogen peroxide (55.3 µL, 0.542 mmol), stirred at room temperature for 2 hours, treated with more 30% hydrogen peroxide (55.3 µL, 0.542 mmol) and stirred overnight. The mixture was diluted with ethyl acetate (30 mL), washed with 10% aqueous $NaHSO_3$ solution, washed with brine, dried ($MgSO_4$), filtered and concentrated. The residue was dissolved in ethyl acetate (30 mL), and washed with a 5:1 mixture of 10% $NaHSO_4$ solution: 10% $Na_2SO_3$ solution. The ethyl acetate layer was washed with brine, dried ($MgSO_4$), filtered and concentrated to provide 3-amino-5-(cyclopentanesulfonyl)-6-(4-fluorophenyl)pyridine-2-carboxylic acid (31 mg, 0.085 mmol, 62.8% yield). $^1$H NMR (400 MHz, $CDCl_3$) δ ppm 7.98 (s, 1H), 7.61 (dd, J=8.5, 5.4 Hz, 2H), 7.17 (t, J=8.6 Hz, 2H), 6.15 (br s, 2H), 2.92-2.83 (m, 1H), 1.90-1.45 (m, 8H); MS (ESI+) m/z 365 (M+H)$^+$.

A solution of 3-amino-5-(cyclopentanesulfonyl)-6-(4-fluorophenyl)pyridine-2-carboxylic acid (31 mg, 0.085 mmol), 1-[bis(dimethylamino)methylene]-1H-1,2,3-triazolo[4,5-b]pyridinium 3-oxid hexafluorophosphate (48.5 mg, 0.128 mmol) and (S)-(+)-1-amino-2-propanol (12.78 mg, 0.170 mmol) in N,N-dimethylformamide (1 mL) was treated with triethylamine (35.6 µL, 0.255 mmol) and stirred overnight. The mixture was diluted with tert-butyl methyl ether (30 mL) and washed with $H_2O$ (15 mL). The layers were separated, and the aqueous layer was extracted with tert-butyl methyl ether (15 mL). The combined tert-butyl methyl ether layers were washed with brine, dried ($MgSO_4$), filtered, and concentrated. The residue was chromatographed on silica gel eluting with a gradient of 25 to 100% ethyl acetate in heptanes to provide the titled compound, 3-amino-5-(cyclopentanesulfonyl)-6-(4-fluorophenyl)-N-[(2S)-2-hydroxypropyl]pyridine-2-carboxamide (18 mg, 0.043 mmol, 50.2% yield).

Compound 262: 3-amino-6-(4-fluorophenyl)-5-[(2-hydroxyethyl)sulfonyl]-N-[(2S)-2-hydroxypropyl]pyridine-2-carboxamide A mixture of methyl 3-amino-5-fluoro-6-(4-fluorophenyl)pyridine-2-carboxylate (20 mg, 0.076 mmol, Intermediate 26), 2-mercaptoethanol (11.83 mg, 0.151 mmol) and $K_2CO_3$ (20.92 mg, 0.151 mmol) in N,N-dimethylacetamide (0.5 mL) was heated to 100° C. for 15 minutes and then cooled. The mixture was diluted with tert-butyl methyl ether (30 mL) and washed sequentially with saturated aqueous $NaHCO_3$ solution (10 mL), water (15 mL), and brine, dried ($MgSO_4$), filtered and concentrated to provide methyl 3-amino-6-(4-fluorophenyl)-5-[(2-hydroxyethyl)sulfanyl]pyridine-2-carboxylate. $^1$H NMR (400 MHz, $CDCl_3$) δ ppm 7.63-7.52 (m, 2H), 7.15-7.04 (m, 2H), 6.99 (s, 1H), 5.81 (br s, 2H), 3.93 (s, 3H), 3.80 (q, J=5.9 Hz, 2H), 3.04 (t, J=6.1 Hz, 2H); MS (ESI+) m/z 323 (M+H)$^+$.

A solution of methyl 3-amino-6-(4-fluorophenyl)-5-[(2-hydroxyethyl)sulfanyl]pyridine-2-carboxylate (24.50 mg, 0.076 mmol) in trifluoroacetic acid (2 mL) was cooled to 0° C., treated with 30% hydrogen peroxide (31.1 µL, 0.304 mmol), stirred at room temperature for 1 hour, treated with more 30% hydrogen peroxide (31.1 µL, 0.304 mmol), stirred for 1 hour, treated with 30% hydrogen peroxide (31.1 µL, 0.304 mmol) and stirred overnight. The mixture was diluted with ethyl acetate (30 mL), washed sequentially with saturated aqueous NaHCO$_3$ solution, 10% aqueous Na$_2$SO$_3$ solution, and brine, dried (MgSO$_4$), filtered and concentrated to provide the titled compound as a mixture of methyl 3-amino-6-(4-fluorophenyl)-5-[(2-hydroxyethyl)sulfonyl]pyridine-2-carboxylate and the corresponding trifluoroacetic acid ester, methyl 3-amino-6-(4-fluorophenyl)-5-({2-[(trifluoroacetyl)oxy]ethyl}sulfonyl)pyridine-2-carboxylate. MS (ESI+) m/z 355 (M+H)$^+$.

A solution of methyl 3-amino-6-(4-fluorophenyl)-5-[(2-hydroxyethyl)sulfonyl]pyridine-2-carboxylate and methyl 3-amino-6-(4-fluorophenyl)-5-({2-[(trifluoroacetyl)oxy]ethyl}sulfonyl)pyridine-2-carboxylate in tetrahydrofuran (1.5 mL) was diluted with methanol (1.5 mL), treated with 1 M NaOH solution (0.5 mL), stirred at 55° C. for 45 minutes, treated with ethanol (1 mL) and more 1 M NaOH (1 mL) and heated to 100° C. for 10 minutes. The mixture was cooled to room temperature and made acidic (pH<1) by the dropwise addition of concentrated H$_2$SO$_4$, heated to 60° C. for 30 minutes and heated to 105° C. overnight. The mixture was cooled to room temperature, and the pH was adjusted to ~3 with the addition of 0.2 M NaOH and extracted with ethyl acetate (three times). The combined ethyl acetate layers were washed with brine, dried (MgSO$_4$), filtered and concentrated to provide 3-amino-6-(4-fluorophenyl)-5-[(2-hydroxyethyl)sulfonyl]pyridine-2-carboxylic acid. MS (ESI+) m/z 341 (M+H)$^+$; MS (ESI−) m/z 339 (M−H)$^−$.

A solution of 3-amino-6-(4-fluorophenyl)-5-[(2-hydroxyethyl)sulfonyl]pyridine-2-carboxylic acid (15 mg, 0.044 mmol), 1-[bis(dimethylamino)methylene]-1H-1,2,3-triazolo[4,5-b]pyridinium 3-oxid hexafluorophosphate (25.1 mg, 0.066 mmol) and (S)-(+)-1-amino-2-propanol (6.62 mg, 0.088 mmol) in N,N-dimethylformamide (1 mL) was treated with triethylamine (18.43 µl, 0.132 mmol) and stirred overnight. The mixture was diluted with tert-butyl methyl ether (30 mL) and washed with H$_2$O (15 mL). The layers were separated, and the aqueous layer was extracted twice with tert-butyl methyl ether (2×15 mL). The combined tert-butyl methyl ether layers were washed with brine, dried (MgSO$_4$), filtered, and concentrated. The residue was chromatographed on silica gel eluting with a gradient of 50 to 100% [9:1 ethyl acetate:ethanol] in ethyl acetate. The product was then dried under vacuum at 70° C. for 2 hours to provide the titled compound, 3-amino-6-(4-fluorophenyl)-5-[(2-hydroxyethyl)sulfonyl]-N-[(2S)-2-hydroxypropyl]pyridine-2-carboxamide (8.5 mg, 0.021 mmol, 48.5% yield).

Compound 263: 3-amino-5-(ethylsulfonyl)-6-(4-fluorophenyl)-N-[(2S)-2-hydroxypropyl]pyridine-2-carboxamide A mixture of methyl 3-amino-5-fluoro-6-(4-fluorophenyl)pyridine-2-carboxylate (22 mg, 0.083 mmol, Intermediate 26), ethanethiol (30.8 µL, 0.416 mmol) and K$_2$CO$_3$ (23.01 mg, 0.167 mmol) in N,N-dimethylacetamide (0.5 mL) was heated to 100° C. for 90 minutes and was allowed to stand at room temperature over the weekend. The mixture was diluted with tert-butyl methyl ether (30 mL) and washed sequentially with saturated aqueous NaHCO$_3$ solution (10 mL), water (15 mL), and brine, dried (MgSO$_4$), filtered and concentrated to give methyl 3-amino-5-(ethylsulfanyl)-6-(4-fluorophenyl)pyridine-2-carboxylate. $^1$H NMR (400 MHz, CDCl$_3$) δ ppm 7.60-7.55 (m, 2H), 7.12-7.06 (m, 2H), 6.84 (s, 1H), 5.79 (s, 2H), 3.93 (s, 3H), 2.86 (q, J=7.4 Hz, 2H), 1.33 (t, J=7.4 Hz, 3H); MS (ESI+) m/z 307 (M+H)$^+$; MS (ESI−) m/z 305 (M−H)$^−$.

A solution of methyl 3-amino-5-(ethyl sulfanyl)-6-(4-fluorophenyl)pyridine-2-carboxylate (25.4 mg, 0.083 mmol) in tetrahydrofuran (1.5 mL) was diluted with methanol (1.5 mL), treated with 1 M NaOH (0.5 mL), heated to 55° C. for 1 hour, cooled, treated with 10% citric acid (5 mL) and extracted with ethyl acetate (30 mL). The ethyl acetate layer was isolated, washed with brine, dried (MgSO$_4$), filtered and concentrated to provide 3-amino-5-(ethylsulfanyl)-6-(4-fluorophenyl)pyridine-2-carboxylic acid (25 mg, 0.086 mmol, 103% yield). $^1$H NMR (400 MHz, DMSO-d$_6$) δ ppm 7.58-7.52 (m, 2H), 7.26-7.19 (m, 2H), 7.18 (s, 1H), 2.90 (q, J=7.3 Hz, 2H), 1.24 (t, J=7.3 Hz, 3H); MS (ESI+) m/z 293 (M+H)$^+$; MS (ESI−) m/z 291 (M−H)$^−$.

A solution of 3-amino-5-(ethyl sulfanyl)-6-(4-fluorophenyl)pyridine-2-carboxylic acid (25 mg, 0.086 mmol) in trifluoroacetic acid (1 mL) was cooled to 0° C., treated with 30% hydrogen peroxide (34.9 µL, 0.342 mmol), stirred for 30 minutes, treated with more 30% hydrogen peroxide (34.9 µL, 0.342 mmol), and stirred at room temperature overnight. The mixture was partitioned between ethyl acetate (~30 mL) and water (~15 mL). The ethyl acetate layer was washed with 10% aqueous NaHSO$_3$ solution (~15 mL) and brine, dried (MgSO$_4$), filtered and concentrated to provide 3-amino-5-(ethyl sulfonyl)-6-(4-fluorophenyl)pyridine-2-carboxylic acid as a trifluoroacetic acid salt (40 mg, 0.091 mmol, 107% yield). $^1$H NMR (400 MHz, DMSO-d$_6$) δ ppm 7.96 (s, 1H), 7.57-7.51 (m, 2H), 7.30-7.23 (m, 2H), 2.82 (q, J=7.4 Hz, 2H), 0.95 (t, J=7.4 Hz, 3H); MS (ESI+) m/z 325 (M+H)$^+$.

A solution of 3-amino-5-(ethyl sulfonyl)-6-(4-fluorophenyl)pyridine-2-carboxylic acid (27.9 mg, 0.086 mmol), 1-[bis(dimethylamino)methylene]-1H-1,2,3-triazolo[4,5-b]pyridinium 3-oxid hexafluorophosphate (98 mg, 0.258 mmol) and (S)-(+)-1-amino-2-propanol (19.38 mg, 0.258 mmol) in N,N-dimethylformamide (1 mL) was treated with triethylamine (59.9 µL, 0.430 mmol) and stirred at room temperature for 4 hours. The mixture was partitioned between tert-butyl methyl ether (30 mL) and water (~15 mL). The layers were separated, and the aqueous layer was extracted with tert-butyl methyl ether (15 mL). The combined tert-butyl methyl ether layers were washed with brine, dried (MgSO$_4$), filtered, and concentrated. The residue was chromatographed on silica gel eluting with a gradient of 25 to 100% ethyl acetate in heptane, then rechromatographed on silica gel eluting with a gradient of 0 to 100% [1:1 CH$_2$Cl$_2$: ethyl acetate] in [9:1 CH$_2$Cl$_2$:ethyl acetate] to provide the titled compound, 3-amino-5-(ethylsulfonyl)-6-(4-fluorophenyl)-N-[(2S)-2-hydroxypropyl]pyridine-2-carboxamide (10.5 mg, 0.028 mmol, 32.0% yield).

Compound 264: 3-amino-6-(4-fluorophenyl)-N-[(2S)-2-hydroxypropyl]-5-(propan-2-ylsulfonyl)pyridine-2-carboxamide A mixture of methyl 3-amino-5-fluoro-6-(4-fluorophenyl)pyridine-2-carboxylate (20 mg, 0.076 mmol, Intermediate 26), 2-propanethiol (28.8 mg, 0.378 mmol) and K$_2$CO$_3$ (31.4 mg, 0.227 mmol) in N,N-dimethylacetamide (0.5 mL) was heated to 100° C. for 20 minutes. The mixture was cooled, diluted with tert-butyl methyl ether (30 mL) and washed sequentially with saturated aqueous NaHCO$_3$ solution (10 mL), water (15 mL), and brine, dried (MgSO$_4$), filtered and concentrated to provide methyl 3-amino-6-(4-fluorophenyl)-5-(propan-2-ylsulfanyl)pyridine-2-carboxylate. $^1$H NMR (400 MHz, CDCl$_3$) δ ppm 7.61-7.55 (m, 2H), 7.11-7.04 (m, 2H), 6.94 (s, 1H), 5.77 (s, 2H), 3.93 (s, 3H), 3.32 (hept, J=6.7 Hz, 1H), 1.30 (d, J=6.7 Hz, 6H); MS (ESI+) m/z 321 (M+H)$^+$; MS (ESI−) m/z 319 (M−H)$^−$.

A solution of methyl 3-amino-6-(4-fluorophenyl)-5-(propan-2-ylsulfanyl)pyridine-2-carboxylate (0.024 g, 0.076 mmol) in tetrahydrofuran (1.5 mL) was diluted with methanol (1.5 mL), treated with 1 M NaOH (0.5 mL), heated to 55° C. for 15 minutes, cooled, diluted with water (15 mL), acidified with 1 M HCl (2 mL) and extracted with ethyl acetate (30 mL). The ethyl acetate layer was washed with brine, dried (MgSO$_4$), filtered, and concentrated to provide 3-amino-6-(4-fluorophenyl)-5-(propan-2-ylsulfanyl)pyridine-2-carboxylic acid. MS (ESI+) m/z 307 (M+H)$^+$; MS (ESI−) m/z 305 (M−H)$^−$.

A solution of 3-amino-6-(4-fluorophenyl)-5-(propan-2-ylsulfanyl)pyridine-2-carboxylic acid (0.023 g, 0.076 mmol) in trifluoroacetic acid (1 mL) was cooled to 0° C., treated with 30% hydrogen peroxide solution (0.031 mL, 0.304 mmol), stirred for 1 hour, treated with more 30% hydrogen peroxide solution (0.031 mL, 0.304 mmol), and stirred for 4 hours. The mixture was partitioned between ethyl acetate (~30 mL) and water (~15 mL). The ethyl acetate layer was washed with brine, dried (MgSO$_4$), filtered and concentrated to provide 3-amino-6-(4-fluorophenyl)-5-(propan-2-yl sulfonyl)pyridine-2-carboxylic acid as a trifluoroacetic acid salt. $^1$H NMR (400 MHz, CDCl$_3$) δ ppm 7.98 (s, 1H), 7.59 (ddt, J=8.3, 5.2, 2.9 Hz, 2H), 7.21-7.12 (m, 2H), 5.49 (br s, 4H), 2.62 (hept, J=6.7 Hz, 1H), 1.10 (d, J=6.8 Hz, 6H); MS (ESI+) m/z 339 (M+H)$^+$; MS (ESI−) m/z 337 (M−H)$^−$.

A solution of 3-amino-6-(4-fluorophenyl)-5-(propan-2-ylsulfonyl)pyridine-2-carboxylic acid (29.1 mg, 0.086 mmol), 1-[bis(dimethylamino)methylene]-1H-1,2,3-triazolo[4,5-b]pyridinium 3-oxid hexafluorophosphate (98 mg, 0.258 mmol) and (S)-(+)-1-amino-2-propanol (19.38 mg, 0.258 mmol) in N,N-dimethylformamide (1 mL) was treated with triethylamine (59.9 µL, 0.430 mmol) and stirred at room temperature overnight. The mixture was partitioned between tert-butyl methyl ether (30 mL) and water (~15 mL). The layers were separated and the aqueous fraction was extracted with tert-butyl methyl ether (15 mL). The combined tert-butyl methyl ether layers were washed with brine, dried (MgSO$_4$), filtered, and concentrated. The residue was chromatographed on silica gel eluting with a gradient of 25 to 100% ethyl acetate in heptanes to provide the titled compound, 3-amino-6-(4-fluorophenyl)-N-[(2S)-2-hydroxypropyl]-5-(propan-2-ylsulfonyl)pyridine-2-carboxamide (16 mg, 0.040 mmol, 47.0% yield).

Compound 265: 3-amino-6-(4-fluorophenyl)-N-[(2S)-2-hydroxypropyl]-5-[(2-methoxyethyl)sulfonyl]pyridine-2-carboxamide A mixture of methyl 3-amino-5-fluoro-6-(4-fluorophenyl)pyridine-2-carboxylate (20 mg, 0.076 mmol, Intermediate 26), 2-methoxyethanethiol (34.9 mg, 0.378 mmol) and K$_2$CO$_3$ (31.4 mg, 0.227 mmol) in N,N-dimethylacetamide (0.5 mL) was heated to 100° C. for 15 minutes. The mixture was cooled, diluted with tert-butyl methyl ether (30 mL) and washed sequentially with saturated aqueous NaHCO$_3$ solution (10 mL), water (15 mL), and brine, dried (MgSO$_4$), filtered and concentrated to provide 3-amino-6-(4-fluorophenyl)-5-(propan-2-ylsulfonyl)pyridine-2-carboxylic acid. $^1$H NMR (400 MHz, CDCl$_3$) δ ppm 7.60-7.55 (m, 2H), 7.09 (t, J=8.8 Hz, 2H), 6.94 (s, 1H), 5.80 (br s, 2H), 3.93 (s, 3H), 3.59 (t, J=6.5 Hz, 2H), 3.36 (s, 3H), 3.03 (t, J=6.5 Hz, 2H); MS (ESI+) m/z 337 (M+H)$^+$; MS (ESI−) m/z 335 (M−H)$^−$.

A solution of 3-amino-6-(4-fluorophenyl)-5-(propan-2-ylsulfonyl)pyridine-2-carboxylic acid (0.026 g, 0.076 mmol) in tetrahydrofuran (1.5 mL) was diluted with methanol (1.5 mL), treated with 1 M NaOH (~0.5 mL), heated to 50° C. for 10 minutes, heated to 55° C. for 25 minutes, cooled, diluted with water (15 mL), acidified with 1 M HCl (~2 mL) and extracted with ethyl acetate (30 mL). The ethyl acetate layer was washed with brine, dried (MgSO$_4$), filtered, and concentrated to provide 3-amino-6-(4-fluorophenyl)-5-[(2-methoxyethyl)sulfanyl]pyridine-2-carboxylic acid. MS (ESI+) m/z 321 (M+H)$^+$; MS (ESI−) m/z 319 (M−H)$^−$.

A solution of 3-amino-6-(4-fluorophenyl)-5-[(2-methoxyethyl)sulfanyl]pyridine-2-carboxylic acid (0.024 g, 0.076 mmol) in trifluoroacetic acid (1 mL) was cooled to 0° C., treated with 30% hydrogen peroxide solution (0.031 mL, 0.304 mmol), stirred for 1 hour, treated with more 30% hydrogen peroxide solution (0.031 mL, 0.304 mmol), stirred for 4 hours, treated with more 30% hydrogen peroxide solution (0.062 mL, 0.608 mmol) and stirred overnight. The mixture was partitioned between ethyl acetate (~30 mL) and water (~15 mL). The ethyl acetate layer was washed with brine, dried (MgSO$_4$), filtered and concentrated to 3-amino-6-(4-fluorophenyl)-5-[(2-methoxyethyl)sulfonyl]pyridine-2-carboxylic acid as a trifluoroacetic acid salt. $^1$H NMR (501 MHz, DMSO-d$_6$) δ ppm 7.95 (s, 1H), 7.55-7.49 (m, 2H), 7.30-7.24 (m, 2H), 3.49-3.45 (m, 2H), 3.13 (t, J=5.8 Hz, 2H), 3.02 (s, 3H); MS (ESI+) m/z 355 (M+H)$^+$; MS (ESI−) m/z 353 (M−H)$^−$.

A solution of 3-amino-6-(4-fluorophenyl)-5-[(2-methoxyethyl)sulfonyl]pyridine-2-carboxylic acid (30.5 mg, 0.086 mmol), 1-[bis(dimethylamino)methylene]-1H-1,2,3-triazolo[4, 5-b]pyridinium 3-oxid hexafluorophosphate (98 mg, 0.258 mmol) and (S)-(+)-1-amino-2-propanol (19.38 mg, 0.258 mmol) in N,N-dimethylformamide (1 mL) was treated with triethylamine (59.9 µL, 0.430 mmol) and stirred at room temperature for 2 hours. The mixture was partitioned between tert-butyl methyl ether (30 mL) and water (~15 mL). The layers were separated, and the aqueous fraction was extracted with tert-butyl methyl ether (15 mL). The combined tert-butyl methyl ether layers were washed with brine, dried (MgSO$_4$), filtered, and concentrated. The residue was chromatographed on silica gel eluting with a gradient of 25 to 100% ethyl acetate in heptanes to provide the titled compound, 3-amino-6-(4-fluorophenyl)-N-[(2S)-2-hydroxypropyl]-5-[(2-methoxyethyl)sulfonyl]pyridine-2-carboxamide (9.2 mg, 0.022 mmol, 26.0% yield).

Compound 266: 3-amino-N-[(2S)-2-hydroxypropyl]-5-{[(2S)-2-methylpyrrolidin-1-yl]sulfonyl}pyridine-2-carboxamide 3-Amino-5-(benzyl sulfanyl)-N-[(2S)-2-hydroxypropyl]pyridine-2-carboxamide (64 mg, 0.20 mmol, Intermediate 23), water (50 µL) and acetic acid (30 µL) were dissolved into acetonitrile (1.0 mL), cooled below −10° C. and treated slowly with solid 1,3-dichloro-1,5-dimethylhydantoin (79 mg, 0.40 mmol) to give a yellow suspension which was stirred for fifteen minutes to give the intermediate sulfonyl chloride. This cold mixture was added to a solution of (S)-2-methylpyrrolidine (61 µL, 0.60 mmol) and triethylamine (112 µL, 0.80 mmol) in acetonitrile (700 µL), also cooled in the −10° C. bath, with an acetonitrile (300 µL) rinse. Then the reaction mixture was removed from the bath and stirred at room temperature for an hour before being concentrated and chromatographed on silica (50 to 80% tert-butyl methyl ether in 1:1 CH₂Cl₂/heptane) to give the titled compound (44 mg).

Compound 267: 3-amino-5-[(4-fluorobenzyl)sulfamoyl]-N-[(2S)-2-hydroxypropyl]pyridine-2-carboxamide 3-Amino-5-(benzyl sulfanyl)-N-[(2S)-2-hydroxypropyl]pyridine-2-carboxamide (64 mg, 0.20 mmol, Intermediate 23), water (50 μL) and acetic acid (30 μL) were dissolved into acetonitrile (1.0 mL), cooled below −10° C. and treated slowly with solid 1,3-dichloro-1,5-dimethylhydantoin (79 mg, 0.40 mmol) to give a yellow suspension which was stirred fifteen minutes to give the intermediate sulfonyl chloride. This cold mixture was added to a solution of 4-fluorobenzylamine (69 μL, 0.60 mmol) and triethylamine (112 μL, 0.80 mmol) in acetonitrile (700 μL), also cooled in the −10° C. bath, with an acetonitrile (300 μL) rinse. Then the reaction mixture was removed from the bath and stirred at room temperature for 30 minutes before being concentrated and chromatographed on silica (30 to 40% ethyl acetate in 1:3 CH₂Cl₂/heptane) to give impure material, which was repurified by preparative HPLC on a Waters Sunfire™ C8 column (30×150 mm) with a 20 to 50% gradient of acetonitrile in 0.1% aqueous trifluoroacetic acid to give the titled compound (28 mg).

Compound 268: 3-amino-5-{[2-(hydroxymethyl)pyrrolidin-1-yl]sulfonyl}-N-[(2S)-2-hydroxypropyl]pyridine-2-carboxamide 3-Amino-5-(benzyl sulfanyl)-N-[(2S)-2-hydroxypropyl]pyridine-2-carboxamide (64 mg, 0.20 mmol, Intermediate 23), water (50 μL) and acetic acid (30 μL) were dissolved into acetonitrile (1.0 mL), cooled below −10° C. and treated slowly with solid 1,3-dichloro-1,5-dimethylhydantoin (79 mg, 0.40 mmol) to give a yellow suspension which was stirred fifteen minutes to give the intermediate sulfonyl chloride. This cold mixture was added to a solution of racemic pyrrolidin-2-ylmethanol (62 μL, 0.60 mmol) and triethylamine (112 μL, 0.80 mmol) in acetonitrile (700 μL), also cooled in the −10° C. bath, with an acetonitrile (300 μL) rinse. Then the reaction mixture was removed from the bath and stirred at room temperature for 30 minutes before being concentrated and filtered through silica with ethyl acetate. The filtrate was concentrated and purified by preparative HPLC on a Waters Sunfire™ C8 column (30×150 mm) with a 20 to 50% gradient of acetonitrile in 0.1% aqueous trifluoroacetic acid to give a residue which was rechromatographed on silica (2:1 ethyl acetate/heptane then 100% ethyl acetate) to give the titled compound (10 mg).

Compound 269: 3-amino-5-[(4-fluorobenzyl)(methyl)sulfamoyl]-N-[(2S)-2-hydroxypropyl]pyridine-2-carboxamide 3-Amino-5-(benzyl sulfanyl)-N-[(2S)-2-hydroxypropyl]pyridine-2-carboxamide (64 mg, 0.20 mmol, Intermediate 23), water (50 μL) and acetic acid (30 μL) were dissolved into acetonitrile (1.0 mL), cooled near −10° C., and treated slowly with solid 1,3-dichloro-1,5-dimethylhydantoin (79 mg, 0.40 mmol) to give a yellow suspension which was stirred more than fifteen minutes to give the intermediate sulfonyl chloride. This cold mixture was added to a solution of 4-fluorobenzyl(methyl)amine (79 μL, 0.60 mmol) and triethylamine (112 μL, 0.80 mmol) in acetonitrile (700 μL), also cooled in the −10° C. bath, with an acetonitrile (300 μL) rinse. Then the reaction mixture was removed from the bath and stirred at room temperature for 30 minutes before being concentrated and filtered through silica with ethyl acetate. The filtrate was purified by preparative HPLC on a Waters Sunfire™ C8 column (30×150 mm) with a 40 to 70% gradient of acetonitrile in 0.1% aqueous trifluoroacetic acid to give the titled compound (30 mg).

Compound 270: 3-amino-5-{[(2S)-2-methylpyrrolidin-1-yl]sulfonyl}-N-[2-oxo-2-(propan-2-ylamino)ethyl]pyridine-2-carboxamide Ethyl 3-amino-5-{[(2S)-2-methylpyrrolidin-1-yl]sulfonyl}pyridine-2-carboxylate (63 mg, 0.20 mmol, Intermediate 24), 2-amino-N-isopropylacetamide (37 mg, 0.32 mmol), sodium 1,2,4-triazolide (20 mg, 0.20 mmol [90% tech. grade]) and tetrabutylammonium bromide (32 mg, 0.1 mmol) were heated at 90° C. in anhydrous dioxane (500 μL) overnight. The suspension was brought to room temperature and concentrated. The residue was placed on silica for chromatography (5 to 25% ethyl acetate/dichloromethane); mixed fractions were rechromatographed similarly to before to give the titled compound (52 mg).

Compound 271: 1-[(3-amino-5-{[(2S)-2-methylpyrrolidin-1-yl]sulfonyl}pyridin-2-yl)carbonyl]azetidine-3-carboxamide Ethyl 3-amino-5-{[(2S)-2-methylpyrrolidin-1-yl]sulfonyl}pyridine-2-carboxylate (47 mg, 0.15 mmol, Intermediate 24), azetidine-3-carboxamide (23 mg, 0.23 mmol), sodium 1,2,4-triazolide (15 mg, 0.15 mmol [90% technical grade]) and tetrabutylammonium bromide (24 mg, 0.074 mmol) were heated at 90° C. in anhydrous dioxane (400 μL) overnight. The suspension was brought to room temperature and placed on silica for chromatography (2:1 ethyl acetate/heptane then 0 to 40% acetonitrile/ethyl acetate) to give the titled compound (27 mg).

Compound 272: (3-amino-5-{[(2S)-2-methylpyrrolidin-1-yl]sulfonyl}pyridin-2-yl) (3-hydroxyazetidin-1-yl)methanone Ethyl 3-amino-5-{[(2S)-2-methylpyrrolidin-1-yl]sulfonyl}pyridine-2-carboxylate (47 mg, 0.15 mmol, Intermediate 24), 3-azetidinol hydrochloride (17 mg, 0.16 mmol), sodium 1,2,4-triazolide (15 mg, 0.15 mmol [90% technical grade]) and tetrabutylammonium bromide (24 mg, 0.074 mmol) were heated at 90° C. in anhydrous dioxane (400 μL) overnight. DBU (23.5 μL, 0.16 mmol) was added and heating was recommenced for another day. The suspension was brought to room temperature and concentrated. The residue was placed on silica for chromatography (2:1 ethyl acetate/heptane, then ethyl acetate) to give a very impure material which was repurified by preparative HPLC on a Waters Sunfire™ C8 column (30×150 mm) with a 20 to 50% gradient of acetonitrile in 0.1% aqueous trifluoroacetic acid to give the titled compound (2 mg).

Compound 273: 3-amino-N-(3-fluoro-2-hydroxypropyl)-5-{[4-(trifluoromethoxy)phenyl]sulfonyl}pyridine-2-carboxamide A solution of 3-amino-5-(4-trifluoromethoxy-benzenesulfonyl)-pyridine-2-carboxylic acid (Int 4, 100 mg, 0.276 mmol) and 1-[bis(dimethylamino)methylene]-1H-1,2,3-triazolo[4,5-b]pyridinium 3-oxid hexafluorophosphate (210 mg, 0.552 mmol) in N,N-dimethylformamide (1.3 mL) was treated with triethylamine (192 µL, 1.380 mmol), stirred for 30 minutes, treated with a solution of 1-amino-3-fluoropropan-2-ol hydrochloride (53.6 mg, 0.414 mmol, Intermediate 29) in N,N-dimethylformamide (0.5 mL) and stirred overnight at room temperature. The mixture was partitioned between tert-butyl methyl ether (50 mL) and water (~30 mL). The layers were separated, and the tert-butyl methyl ether layer was washed sequentially with water (30 mL) and brine, dried (MgSO$_4$), filtered, and concentrated. The residue was chromatographed on silica gel eluting with a gradient of 25 to 100% ethyl acetate in heptanes and then chromatographed again on silica gel eluting with a gradient of 0 to 100% [1:1 CH$_2$Cl$_2$:ethyl acetate] in [9:1 CH$_2$Cl$_2$: ethyl acetate] to provide the titled compound (87 mg, 0.199 mmol, 72.1% yield).

Compound 274: 3-amino-6-cyclopropyl-5-[(4-fluorophenyl)sulfonyl]-N-[(2S)-2-hydroxypropyl]pyridine-2-carboxamide A mixture of methyl 3-amino-6-cyclopropyl-5-fluoropyridine-2-carboxylate (46 mg, 0.219 mmol, Intermediate 27), 4-fluorothiophenol (28.0 mg, 0.219 mmol) and K$_2$CO$_3$ (60.5 mg, 0.438 mmol) in N,N-dimethylacetamide (0.5 mL) was heated to 90° C. for 30 minutes. The mixture was cooled, diluted with tert-butyl methyl ether (30 mL) and washed sequentially with 1 M HCl solution (10 mL) water (15 mL) and brine, dried (MgSO$_4$), filtered and concentrated. The residue was dissolved in tetrahydrofuran (1 mL), diluted with methanol (1 mL), treated with 1 M NaOH (0.5 mL) and heated to 55° C. for 30 minutes. The mixture was cooled to room temperature, treated with 1 M HCl and extracted with ethyl acetate (30 mL). The ethyl acetate layer was washed with brine, dried (MgSO4), filtered and concentrated to provide 3-amino-6-cyclopropyl-5-[(4-fluorophenyl)sulfanyl]pyridine-2-carboxylic acid. $^1$H NMR (400 MHz, CDCl$_3$) δ ppm 10.78 (br s, 1H), 7.55-7.49 (m, 2H), 7.21-7.14 (m, 2H), 6.33 (s, 1H), 5.50 (br s, 2H), 2.22-2.15 (m, 1H), 1.03-0.92 (m, 4H); MS (ESI+) m/z 305 (M+H)$^+$; MS (ESI−) m/z 303 (M−H)$^−$.

A solution of 3-amino-6-cyclopropyl-5-[(4-fluorophenyl)sulfanyl]pyridine-2-carboxylic acid (38.9 mg, 0.128 mmol) in trifluoroacetic acid (0.8 mL) was cooled to 0° C., treated with 30% hydrogen peroxide (52.2 µL, 0.511 mmol), and allowed to stir at room temperature for 7 hours. The mixture was diluted with water (5 mL), made basic with 1 M NaOH, and then brought to pH ~3 with dropwise addition of 10% citric acid solution. The mixture was extracted with ethyl acetate (30 mL). The ethyl acetate layer was washed with brine, dried (MgSO$_4$), filtered and concentrated to provide 3-amino-6-cyclopropyl-5-[(4-fluorophenyl)sulfonyl]pyridine-2-carboxylic acid. $^1$H NMR (400 MHz, CDCl$_3$) δ ppm 7.95 (s, 1H), 7.94-7.89 (m, 2H), 7.27-7.20 (m, 2H), 5.22 (br s, 2H), 2.60 (tt, J=7.7, 5.3 Hz, 1H), 0.87-0.82 (m, 4H); MS (ESI+) m/z 386 (M+H)$^+$.

A solution of 3-amino-6-cyclopropyl-5-[(4-fluorophenyl)sulfonyl]pyridine-2-carboxylic acid (43.1 mg, 0.128 mmol), 1-[bis(dimethylamino)methylene]-1H-1,2,3-triazolo[4,5-b]pyridinium 3-oxid hexafluorophosphate (146 mg, 0.384 mmol) and (S)-(+)-1-amino-2-propanol (28.8 mg, 0.384 mmol) in N,N-dimethylformamide (1 mL) was treated with triethylamine (89 µL, 0.640 mmol) and stirred at room temperature overnight. The mixture was partitioned between tert-butyl methyl ether (30 mL) and water (~15 mL). The tert-butyl methyl ether layer was washed with water and brine, dried (MgSO$_4$), filtered, and concentrated. The residue was chromatographed on silica gel eluting with a gradient of ethyl acetate in heptanes and then chromatographed again on silica gel eluting with a gradient of 50 to 100% diethyl ether in heptanes and then choromatographed again on silica gel eluting with a gradient of 0 to 100% ethyl acetate in [9:1 CH$_2$Cl$_2$:ethyl acetate] to provide the titled compound, 3-amino-6-cyclopropyl-5-[(4-fluorophenyl)sulfonyl]-N-[(2S)-2-hydroxypropyl]pyridine-2-carboxamide (18 mg, 0.046 mmol, 35.7% yield).

Compound 275: 3-amino-6-cyclopropyl-5-(ethylsulfonyl)-N-[(2S)-2-hydroxypropyl]pyridine-2-carboxamide A mixture of methyl 3-amino-6-cyclopropyl-5-fluoropyridine-2-carboxylate (22 mg, 0.105 mmol, Intermediate 27), ethanethiol (13 mg, 0.21 mmol) and K$_2$CO$_3$ (28.9 mg, 0.209 mmol) in N,N-dimethylacetamide (0.5 mL) was heated to 90° C. for 30 minutes. The mixture was cooled, diluted with tert-butyl methyl ether (30 mL), washed sequentially with saturated aqueous NaHCO$_3$ solution (10 mL), water (15 mL) and brine, dried (MgSO$_4$), filtered and concentrated to provide methyl 3-amino-6-cyclopropyl-5-(ethyl sulfanyl)pyridine-2-carboxylate. $^1$H NMR (400 MHz, CDCl$_3$) δ ppm 6.73 (s, 1H), 5.58 (br s, 2H), 3.90 (s, 3H), 2.95 (q, J=7.4 Hz, 2H), 2.08 (tt, J=8.1, 5.0 Hz, 1H), 1.41 (t, J=7.4 Hz, 3H), 1.00-0.87 (m, 4H); MS (ESI+) m/z 253 (M+H)$^+$.

A solution of methyl 3-amino-6-cyclopropyl-5-(ethylsulfanyl)pyridine-2-carboxylate (0.105 mmol) in tetrahydrofuran (1 mL) was diluted with methanol (1 mL), treated with 1 M NaOH (0.5 mL) and heated to 55° C. for 30 minutes. The mixture was cooled to room temperature, treated with 1 M HCl and extracted with ethyl acetate (30 mL). The ethyl acetate layer was washed with brine, dried (MgSO$_4$), filtered, concentrated and to provide 3-amino-6-cyclopropyl-5-(ethylsulfanyl)pyridine-2-carboxylic acid. $^1$H NMR (400 MHz, CDCl$_3$) δ ppm 6.78 (s, 1H), 5.64 (br s, 2H), 2.97 (q, J=7.4 Hz, 2H), 2.18-2.12 (m, 1H), 1.42 (t, J=7.4 Hz, 3H), 1.01-0.87 (m, 4H); MS (ESI+) m/z 239 (M+H)$^+$; MS (ESI−) m/z 237 (M−H)$^−$.

A solution of 3-amino-6-cyclopropyl-5-(ethylsulfanyl) pyridine-2-carboxylic acid (14.5 mg, 0.061 mmol) in trifluoroacetic acid (0.4 mL) was cooled to 0° C., treated with 30% hydrogen peroxide (24.86 µL, 0.243 mmol) and stirred at room temperature for 7 hours. More 30% hydrogen peroxide solution (0.012 mL) was added, and the reaction mixture was stirred overnight. The mixture was diluted with water (5 mL), and the resulting mixture was made basic with 1 M NaOH, and then brought to pH ~3 with the dropwise addition of 10% aqueous citric acid solution. The mixture was extracted twice with ethyl acetate (2×25 mL). The combined ethyl acetate layers were washed with brine, dried (MgSO$_4$), filtered, and concentrated. The residue was chromatographed on silica gel eluting with a gradient of 50-100% [200:1:1 ethyl acetate:HCOOH:H$_2$O] in heptanes to provide 3-amino-6-cyclopropyl-5-(ethylsulfonyl)pyridine-2-carboxylic acid (3 mg, 0.011 mmol, 18.24% yield).

A solution of 3-amino-6-cyclopropyl-5-(ethylsulfonyl) pyridine-2-carboxylic acid (4.7 mg, 0.017 mmol), 1-[bis (dimethylamino)methylene]-1H-1,2,3-triazolo[4,5-b]pyridinium 3-oxid hexafluorophosphate (19.83 mg, 0.052 mmol) and (S)-(+)-1-amino-2-propanol (3.92 mg, 0.052 mmol) in N,N-dimethylformamide (0.5 mL) was treated with triethylamine (12.12 µL, 0.087 mmol) and stirred at room temperature for 2 hours. The mixture was partitioned between tert-butyl methyl ether (30 mL) and water (~15 mL). The tert-butyl methyl ether layer was washed with water and brine, dried (MgSO$_4$), filtered, and concentrated. The residue was chromatographed on silica gel eluting with a gradient of 50 to 100% ethyl acetate in heptanes to provide the titled compound, 3-amino-6-cyclopropyl-5-(ethylsulfonyl)-N-[(2S)-2-hydroxypropyl]pyridine-2-carboxamide (2 mg, 6.11 mol, 35.1% yield). $^1$H NMR (400 MHz, CDCl$_3$) δ ppm 8.19 (br s, 1H), 7.63 (s, 1H), 5.99 (br s, 2H), 4.07-4.00 (m, 1H), 3.58 (ddd, J=13.8, 6.7, 3.2 Hz, 1H), 3.36-3.28 (m, 3H), 2.84-2.75 (m, 1H), 2.37 (d, J=4.1 Hz, 1H), 1.30 (t, J=7.4 Hz, 3H), 1.26 (d, J=6.2 Hz, 3H), 1.09-1.02 (m, 4H); MS (ESI+) m/z 328 (M+H)$^+$; MS (ESI−) m/z 326 (M−H)$^−$.

Compound 276: 3-amino-N-(2-hydroxy-3-methoxypropyl)-5-{[(2S)-2-methylpyrrolidin-1-yl]sulfonyl}pyridine-2-carboxamide Ethyl 3-amino-5-{[(2S)-2-methylpyrrolidin-1-yl]sulfonyl}pyridine-2-carboxylate (47 mg, 0.15 mmol, Intermediate 24), 1-amino-3-methoxypropan-2-ol (24 mg, 0.23 mmol), 1,2,4-triazolylsodium (15 mg, 0.17 mmol) and tetrabutylammonium bromide (16 mg, 0.05 mmol) were heated at 90° C. under nitrogen in anhydrous dioxane (400 μL) overnight. The suspension was brought to room temperature and placed on silica for chromatography (50 to 75% ethyl acetate/heptane) to give the titled compound (38 mg).

Compound 277: 3-amino-N-[(2S)-2-hydroxypropyl]-5-[(2-methoxyethyl)(methyl)sulfamoyl]pyridine-2-carboxamide 3-Amino-5-(benzyl sulfanyl)-N-[(2S)-2-hydroxypropyl]pyridine-2-carboxamide (64 mg, 0.20 mmol, Intermediate 23), water (50 μL) and acetic acid (30 μL) were dissolved into acetonitrile (400 μL), cooled below −10° C., and treated slowly with solid 1,3-dichloro-1,5-dimethylhydantoin (79 mg, 0.40 mmol) to give a yellow suspension which was stirred fifteen minutes to give the intermediate sulfonyl chloride. This cold mixture was added to a solution of (2-methoxyethyl)methylamine (65 μL, 0.60 mmol) and triethylamine (112 μL, 0.80 mmol) in acetonitrile (700 μL), also cooled in the −10° C. bath, with an acetonitrile (300 μL) rinse. Then the reaction mixture was removed from the bath and stirred at room temperature for 30 minutes before being concentrated and chromatographed on silica (0 to 2% acetonitrile/tert-butyl methyl ether) to give an impure product which was rechromatographed on silica (10 to 40% acetonitrile/dichloromethane) to give the titled compound (29 mg).

Compound 278: 3-amino-5-[cyclobutyl(methyl)sulfamoyl]-N-[(2S)-2-hydroxypropyl]pyridine-2-carboxamide 3-Amino-5-(benzyl sulfanyl)-N-[(2S)-2-hydroxypropyl]pyridine-2-carboxamide (64 mg, 0.20 mmol, Intermediate 23), water (50 μL) and acetic acid (30 μL) were dissolved into acetonitrile (1.0 mL), cooled below −10° C., and treated slowly with solid 1,3-dichloro-1,5-dimethylhydantoin (79 mg, 0.40 mmol) to give a yellow suspension which was stirred twenty minutes to give the intermediate sulfonyl chloride. This cold mixture was added to a solution of N-methylcyclobutanamine (51 mg, 0.60 mmol) and triethylamine (112 μL, 0.80 mmol) in acetonitrile (700 μL), also cooled in the −10° C. bath, with an acetonitrile (300 μL) rinse. Then the reaction mixture was removed from the bath and stirred at room temperature for 30 minutes before being concentrated, redissolved into CH$_2$Cl$_2$, washed with water and chromatographed on silica (30 to 50% ethyl acetate/dichloromethane) to give an impure product which was rechromatographed on silica (30 to 50% ethyl acetate in 1:1 dichloromethane/heptane) to give the titled compound (55 mg, 80% pure).

Compound 279: 3-amino-N-(3, 3-difluoro-2-hydroxypropyl)-5-{[4-(trifluoromethoxy)phenyl]sulfonyl}pyridine-2-carboxamide A solution of 3-amino-5-(4-trifluoromethoxy-benzenesulfonyl)-pyridine-2-carboxylic acid (Int 4, 50 mg, 0.138 mmol) and 1-[bis(dimethylamino)methylene]-1H-1,2,3-triazolo[4,5-b]pyridinium 3-oxid hexafluorophosphate (79 mg, 0.207 mmol) in N,N-dimethylformamide (1 mL) was treated with triethylamine (77 μL, 0.552 mmol), stirred for 30 minutes, treated with a solution of 3-amino-1,1-difluoropropan-2-ol hydrochloride (CAS #1785058-84-5, 30.5 mg, 0.207 mmol) in N,N-dimethylformamide (0.5 mL) and stirred at room temperature for 2 hours. The mixture was partitioned between tert-butyl methyl ether (50 mL) and water (~30 mL). The layers were separated, and the tert-butyl methyl ether layer was washed sequentially with water (30 mL) and brine, dried (MgSO$_4$), filtered, and concentrated. The residue was chromatographed on silica gel eluting with a gradient of ethyl acetate in heptanes to provide the titled compound (11.5 mg, 0.025 mmol, 18.30% yield).

Compound 280: 3-amino-N-[(2S)-2-hydroxypropyl]-6-methoxy-5-{[4-(trifluoromethoxy)phenyl]sulfonyl}pyridine-2-carboxamide A mixture of methyl 6-bromo-3-nitro-5-{[4-(trifluoromethoxy)phenyl]sulfonyl}pyridine-2-carboxylate (32 mg, 0.066 mmol, Intermediate 28) and methanol (1 mL) was treated with K$_2$CO$_3$ (~10 mg) and stirred at 55° C. for 15 minutes. The mixture was partitioned between ethyl acetate (~30 mL) and 1 M HCl (~10 mL). The ethyl acetate layer was washed with brine, dried (MgSO$_4$), filtered, and concentrated. The residue was chromatographed on silica gel eluting with a gradient of 10 to 30% ethyl acetate in heptanes to provide methyl 6-methoxy-3-nitro-5-{[4-(trifluoromethoxy)phenyl]sulfonyl}pyridine-2-carboxylate (16 mg, 0.037 mmol, 55.6% yield). $^1$H NMR (400 MHz, CDCl$_3$) δ ppm 9.16 (s, 1H), 8.11-8.03 (m, 2H), 7.39 (d, J=8.4 Hz, 2H), 4.11 (s, 3H), 4.02 (s, 3H).

A mixture of methyl 6-methoxy-3-nitro-5-{[4-(trifluoromethoxy)phenyl]sulfonyl}pyridine-2-carboxylate (13 mg, 0.030 mmol) and 10% Pd/C (~1.5 mg) in tetrahydrofuran (~0.25 mL) was stirred under an atmosphere of H$_2$ (balloon) at room temperature for 1 hour. More 10% Pd/C (~3 mg) was added, and the mixture was stirred at 55° C. for 30 minutes. The mixture was cooled and concentrated with a stream of N$_2$. The residue was chromatographed on silica gel eluting with a gradient of 50 to 100% [9:1 CH$_2$Cl$_2$:ethyl acetate] in heptanes to provide methyl 3-amino-6-methoxy-5-{[4-(trifluoromethoxy)phenyl]sulfonyl}pyridine-2-carboxylate (9 mg, 0.022 mmol, 74.3% yield). $^1$H NMR (501 MHz, CDCl$_3$) δ ppm 8.06-8.03 (m, 2H), 7.89 (s, 1H), 7.33 (dd, J=8.9, 0.8 Hz, 2H), 5.62 (br s, 2H), 3.91 (s, 3H), 3.88 (s, 3H); MS (ESI+) m/z 407 (M+H)$^+$; MS (ESI−) m/z 405 (M−H)$^−$.

A mixture of methyl 3-amino-6-methoxy-5-{[4-(trifluoromethoxy)phenyl]sulfonyl}pyridine-2-carboxylate (8.6 mg, 0.021 mmol), (S)-(+)-1-amino-2-propanol (3.18 mg, 0.042 mmol), 1,2,4-triazolylsodium (1.927 mg, 0.021 mmol) and tetrabutylammonium bromide (3.41 mg, 10.58 mol) in dioxane (0.3 mL) was heated to 90° C. for 15 minutes, and then heated to 100° C. for 2 hours. More (S)-(+)-1-amino-2-propanol (~10 eq, 32 mg) was added, and the mixture was heated to 105° C. for 30 minutes. The mixture was cooled and partitioned between tert-butyl methyl ether (~30 mL) and water (~15 mL). The layers were separated, and the aqueous layer was extracted with tert-butyl methyl ether (~15 mL). The combined tert-butyl methyl ether layers were washed with brine, dried ($MgSO_4$), filtered, and concentrated. The residue was chromatographed on silica gel eluting with a gradient of 50 to 100% ethyl acetate in heptanes to provide the titled compound, 3-amino-N-[(2S)-2-hydroxypropyl]-6-methoxy-5-{[4-(trifluoromethoxy)phenyl]sulfonyl}pyridine-2-carboxamide (8 mg, 0.018 mmol, 84% yield).

Compound 281: 3-amino-N-[(4-methoxypyrimidin-2-yl)methyl]-5-{[(2S)-2-methylpyrrolidin-1-yl]sulfonyl}pyridine-2-carboxamide 3-Amino-5-(benzylsulfanyl)-N-[(4-methoxypyrimidin-2-yl)methyl]pyridine-2-carboxamide (103 mg, 0.27 mmol, Intermediate 25), water (70 µL) and acetic acid (40 µL) were dissolved into acetonitrile (1.5 mL) and dichloromethane (0.5 mL), cooled with a water ice bath (precipitate formed), and treated slowly with solid 1,3-dichloro-1,5-dimethylhydantoin (108 mg, 0.55 mmol) to give a yellow solution which was stirred fifteen minutes to give the intermediate sulfonyl chloride. This cold mixture was added to a solution of (S)-2-methylpyrrolidine (83 µL, 0.81 mmol) and triethylamine (151 µL, 1.08 mmol) in acetonitrile (1 mL), also cooled in the ice bath, with an acetonitrile (0.5 mL) rinse. Then the reaction mixture was removed from the bath and stirred at room temperature for 30 minutes before being concentrated and chromatographed on silica (30 to 50% ethyl acetate in 1:1 dichloromethane/heptane). Mixed fractions were rechromatographed as before. Better fractions from both columns were combined to give the titled compound (71 mg, 85% pure).

Compound 282: 3-amino-5-{[(2S)-2-methylpyrrolidin-1-yl]sulfonyl}-N-[(6-oxo-1,6-dihydropyrimidin-2-yl)methyl]pyridine-2-carboxamide 3-Amino-N-[(4-methoxypyrimidin-2-yl)methyl]-5-{[(2S)-2-methylpyrrolidin-1-yl]sulfonyl}pyridine-2-carboxamide (63 mg, 0.15 mmol, Compound 281) and a small quantity of $Na_2S_2O_5$ were dissolved into a mixture of n-propanol (1.0 mL) and concentrated aqueous hydroiodic acid (400 µL, stabilized with $H_3PO_2$). The reaction vessel was flushed with nitrogen, heated at 80° C. with an oil bath for two hours, brought to room temperature and added slowly to a mixture of 3 M aqueous $Na_2CO_3$ (400 µL) and a micro spatula full of $Na_2S_2O_5$ cooled with a water ice bath. Additional dry $Na_2CO_3$ was added to the mixture, and after the resultant mixture was stirred cold in an ice bath, it was diluted with ethyl acetate/heptane. The organic phase was added directly to silica for chromatography (50% ethyl acetate/heptane then 100% ethyl acetate) to the titled compound (21 mg).

Compound 283: 3-amino-6-(dimethylamino)-N-[(2S)-2-hydroxypropyl]-5-{[4-(trifluoromethoxy)phenyl]sulfonyl}pyridine-2-carboxamide A solution of methyl 6-bromo-3-nitro-5-{[4-(trifluoromethoxy)phenyl]sulfonyl}pyridine-2-carboxylate (40 mg, 0.082 mmol, Intermediate 28) in tetrahydrofuran (~1 mL) was treated with excess 40% dimethylamine in water (10 drops) and stirred for 15 minutes. The mixture was partitioned between tert-butyl methyl ether (~30 mL) and water (15 mL). The tert-butyl methyl ether layer was washed with brine, dried ($MgSO_4$), filtered and concentrated to provide methyl 6-(dimethylamino)-3-nitro-5-{[4-(trifluoromethoxy)phenyl]sulfonyl}pyridine-2-carboxylate (37 mg, 0.082 mmol, 100% yield). $^1$H NMR (400 MHz, $CDCl_3$) δ ppm 8.44 (s, 1H), 7.98-7.94 (m, 2H), 7.42 (d, J=8.1 Hz, 2H), 4.00 (s, 3H), 3.35 (s, 6H); MS (ESI+) m/z 450 (M+H)$^+$.

In a vial, a mixture of methyl 6-(dimethylamino)-3-nitro-5-{[4-(trifluoromethoxy)phenyl]sulfonyl}pyridine-2-carboxylate (36 mg, 0.080 mmol) and 10% Pd/C (~5 mg) in tetrahydrofuran (~0.5 mL) was stirred under an atmosphere of $H_2$ (balloon) at room temperature for 20 minutes, then heated to 55° C. until the reaction was complete. The mixture was concentrated with a stream of $N_2$. The residue was chromatographed on silica gel eluting with a gradient of 15 to 30% ethyl acetate in heptanes to provide methyl 3-amino-6-(dimethylamino)-5-{[4-(trifluoromethoxy)phenyl]sulfonyl}pyridine-2-carboxylate (22 mg, 0.052 mmol, 65.5% yield). $^1$H NMR (400 MHz, $CDCl_3$) δ ppm 7.97-7.93 (m, 2H), 7.93 (s, 1H), 7.29 (d, J=8.1 Hz, 2H), 5.81 (br s, 2H), 3.91 (s, 3H), 2.51 (s, 6H).

A mixture of methyl 3-amino-6-(dimethylamino)-5-{[4-(trifluoromethoxy)phenyl]sulfonyl}pyridine-2-carboxylate (21 mg, 0.050 mmol), (S)-(+)-1-amino-2-propanol (15.04 mg, 0.200 mmol) and 1,2,4-triazolylsodium (4.56 mg, 0.050 mmol) in dioxane (0.3 mL) was heated to 105° C. for 1 hour. The mixture was cooled and partitioned between tert-butyl methyl ether (~30 mL) and water (~15 mL). The layers were separated and the aqueous layer was extracted with tert-butyl methyl ether (~15 mL). The combined tert-butyl methyl ether layers were washed with brine, dried ($MgSO_4$), filtered, and concentrated. The residue was chromatographed on silica gel eluting with a gradient of 30 to 100% ethyl acetate in heptanes to provide the titled compound, 3-amino-6-(dimethylamino)-N-[(2S)-2-hydroxypropyl]-5-{[4-(trifluoromethoxy)phenyl]sulfonyl}pyridine-2-carboxamide (18 mg, 0.039 mmol, 78% yield).

Compound 284: 3-amino-6-(3-fluorophenoxy)-N-[(2S)-2-hydroxypropyl]-5-{[4-(trifluoromethoxy)phenyl]sulfonyl}pyridine-2-carboxamide A mixture of methyl 6-bromo-3-nitro-5-{[4-(trifluoromethoxy)phenyl]sulfonyl}pyridine-2-carboxylate (40 mg, 0.082 mmol, Intermediate 28), 3-fluorophenol (18.48 mg, 0.165 mmol) and $K_2CO_3$ (30 mg) in N,N-dimethylformamide (~0.5 mL) was stirred at room temperature overnight. The mixture was partitioned between tert-butyl methyl ether (~30 mL) and water (15 mL). The tert-butyl methyl ether layer was washed with brine, dried ($MgSO_4$), filtered and concentrated to provide methyl 6-(3-fluorophenoxy)-3-nitro-5-{[4-(trifluoromethoxy)phenyl]sulfonyl}pyridine-2-carboxylate (30.4 mg). $^1$H NMR (400 MHz, $CDCl_3$) δ ppm 9.27 (s, 1H), 8.15-8.11 (m, 2H), 7.41 (d, J=8.6 Hz, 2H), 7.38-7.33 (m, 1H), 7.03 (td, J=8.6, 8.1, 1.7 Hz, 1H), 6.72-6.66 (m, 2H), 3.93 (s, 3H).

A mixture of methyl 6-(3-fluorophenoxy)-3-nitro-5-{[4-(trifluoromethoxy)phenyl]sulfonyl}pyridine-2-carboxylate (30.4 mg, 0.059 mmol) and 10% Pd/C (12 mg, 0.011 mmol) in tetrahydrofuran (1 mL) under $H_2$ was stirred at room temperature for 30 minutes and heated to 55° C. overnight. The mixture was concentrated with a stream of $N_2$. The residue was chromatographed on silica gel eluting with a gradient of 15 to 50% ethyl acetate in heptanes to provide methyl 3-amino-6-(3-fluorophenoxy)-5-{[4-(trifluoromethoxy)phenyl]sulfonyl}pyridine-2-carboxylate (3.8 mg, 7.81 mol, 13.27% yield). $^1$H NMR (400 MHz, CDCl$_3$) δ ppm 8.05-8.02 (m, 2H), 7.99 (s, 1H), 7.30 (d, J=8.1 Hz, 2H), 7.26-7.22 (m, 1H), 6.87-6.81 (m, 1H), 6.70-6.65 (m, 2H), 5.86 (br s, 2H), 3.82 (s, 3H); MS (ESI+) m/z 487 (M+H)$^+$; MS (ESI−) m/z 485 (M−H)$^−$.

A mixture of methyl 3-amino-6-(3-fluorophenoxy)-5-{[4-(trifluoromethoxy)phenyl]sulfonyl}pyridine-2-carboxylate (3.8 mg, 7.81 mol), 1,2,4-triazolylsodium (0.711 mg, 7.81 mol) and (S)-(+)-1-amino-2-propanol (1.174 mg, 0.016 mmol) in dioxane (0.2 mL) was heated to 110° C. for 1 hour. The mixture was cooled and partitioned between ethyl acetate and saturated aqueous NaHCO$_3$ solution. The ethyl acetate layer was washed with brine, dried (MgSO$_4$), filtered, and concentrated. The residue was chromatographed on silica gel eluting with a gradient of 50 to 100% ethyl acetate in heptanes to provide the titled compound, 3-amino-6-(3-fluorophenoxy)-N-[(2S)-2-hydroxypropyl]-5-{[4-(trifluoromethoxy)phenyl]sulfonyl}pyridine-2-carboxamide (2.5 mg, 4.72 mol, 60.4% yield).

Compound 285: 3-amino-6-(cyclopropylamino)-N-[(2S)-2-hydroxypropyl]-5-{[4-(trifluoromethoxy)phenyl]sulfonyl}pyridine-2-carboxamide A solution of methyl 6-bromo-3-nitro-5-{[4-(trifluoromethoxy)phenyl]sulfonyl}pyridine-2-carboxylate (40 mg, 0.082 mmol, Intermediate 28) in tetrahydrofuran (~1 mL) was treated with excess cyclopropylamine (47.1 mg, 0.824 mmol), and the mixture was stirred at room temperature for 15 minutes. The mixture was partitioned between tert-butyl methyl ether (~30 mL) and water (15 mL). The tert-butyl methyl ether layer was washed with brine, dried (MgSO$_4$), filtered and concentrated to provide methyl 6-(cyclopropylamino)-3-nitro-5-{[4-(trifluoromethoxy)phenyl]sulfonyl}pyridine-2-carboxylate (34.9 mg, 0.076 mmol, 92% yield). $^1$H NMR (400 MHz, CDCl$_3$) δ ppm 8.78 (s, 1H), 7.95-7.90 (m, 2H), 7.66 (d, J=2.4 Hz, 1H), 7.40 (d, J=8.5 Hz, 2H), 4.01 (s, 3H), 3.11-3.04 (m, 1H), 0.98-0.92 (m, 2H), 0.62-0.57 (m, 2H); MS (ESI+) m/z 462 (M+H)$^+$; MS (ESI−) m/z 460 (M−H)$^−$.

A mixture of methyl 6-(cyclopropylamino)-3-nitro-5-{[4-(trifluoromethoxy)phenyl]sulfonyl}pyridine-2-carboxylate (34.9 mg, 0.076 mmol) and 10% Pd/C (12 mg, 0.011 mmol) in tetrahydrofuran (1 mL) under H$_2$ was stirred at room temperature for 30 minutes and heated to 55° C. overnight. The mixture was concentrated with a stream of N$_2$. The residue was chromatographed on silica gel eluting with a gradient of 10 to 30% ethyl acetate in heptanes provided methyl 3-amino-6-(cyclopropylamino)-5-{[4-(trifluoromethoxy)phenyl]sulfonyl}pyridine-2-carboxylate (7 mg, 0.016 mmol, 21.45% yield). $^1$H NMR (400 MHz, CDCl$_3$) δ ppm 7.93-7.89 (m, 2H), 7.64 (s, 1H), 7.31 (d, J=8.2 Hz, 2H), 6.20 (br s, 1H), 5.28 (br s, 2H), 3.91 (s, 3H), 2.88-2.82 (m, 1H), 0.81-0.75 (m, 2H), 0.40-0.36 (m, 2H); MS (ESI+) m/z 432 (M+H)$^+$; MS (ESI−) m/z 430 (M−H)$^−$.

A mixture of methyl 3-amino-6-(cyclopropylamino)-5-{[4-(trifluoromethoxy)phenyl]sulfonyl}pyridine-2-carboxylate (7 mg, 0.016 mmol), 1,2,4-triazolylsodium (1.477 mg, 0.016 mmol) and (S)-(+)-1-amino-2-propanol (2.438 mg, 0.032 mmol) in dioxane (0.2 mL) was heated to 110° C. for 1 hour. The mixture was cooled and partitioned between ethyl acetate and saturated aqueous NaHCO$_3$ solution. The ethyl acetate layer was washed with brine, dried (MgSO$_4$), filtered, and concentrated. The residue was chromatographed on silica gel eluting with a gradient of 50 to 100% ethyl acetate in heptanes to provide the titled compound, 3-amino-6-(cyclopropylamino)-N-[(2S)-2-hydroxypropyl]-5-{[4-(trifluoromethoxy)phenyl]sulfonyl}pyridine-2-carboxamide (6.5 mg, 0.014 mmol, 84% yield).

Compound 286: 3-amino-N'-(methoxyacetyl)-5-{[4-(trifluoromethoxy)phenyl]sulfonyl}pyridine-2-carbohydrazide To a solution of 3-amino-5-(4-trifluoromethoxy-benzenesulfonyl)-pyridine-2-carboxylic acid (0.3018 g, 0.833 mmol, Int 4) and 2-methoxyacetohydrazide (0.095 g, 0.916 mmol) in DMF (3.00 ml) and Hunig's Base (0.291 ml, 1.666 mmol) were added EDCI (0.240 g, 1.250 mmol) and HOBt (0.191 g, 1.250 mmol) in one portion as neat solids. The reaction mixture was stirred at room temperature for 16 hours. The reaction mixture was then partitioned between tert-butyl methyl ether and a saturated aqueous solution of NH$_4$Cl. The combined organic extracts were dried over anhydrous sodium sulfate, filtered, and concentrated. The residue was purified via reverse phase chromatography using a Phenomenex® Luna® C8(2) 5 m 100 Å AXIA™ column (30 mm×75 mm) with a gradient of 5-100% acetonitrile (A) and 10 mM ammonium acetate in water (B) at a flow rate of 1.5 mL/minute (0-0.05 minute 5% A, 0.05-1.2 minutes 5-100% A, 1.2-1.4 minutes 100% A, 1.4-1.5 minutes 100-5% A. 0.25 minutes post-run delay) to give 180 mg of the titled compound.

Compound 287: 3-amino-N'-(hydroxyacetyl)-5-{[4-(trifluoromethoxy)phenyl]sulfonyl}pyridine-2-carbohydrazide To a solution of 3-amino-5-(4-trifluoromethoxy-benzenesulfonyl)-pyridine-2-carboxylic acid (Int 4, 0.050 g, 0.138 mmol) and 2-hydroxyacetohydrazide (0.016 g, 0.173 mmol) in N,N-dimethylformamide (0.5 mL) and N,N-diisopropylethylamine (0.048 mL, 0.276 mmol) was added N-(3-dimethylaminopropyl)-N'-ethylcarbodiimide hydrochloride (0.040 g, 0.207 mmol) and hydroxybenzotriazole (0.032 g, 0.207 mmol). The reaction mixture was stirred at room temperature for 19 hours. The reaction mixture was directly purified by preparative HPLC as described for Compound 286 to provide the titled compound (0.0412 g, 68.7%).

Compound 288: 3-amino-N-[(2S)-2-hydroxypropyl]-6-(2-methoxyethoxy)-5-{[4-(trifluoromethoxy)phenyl]sulfonyl}pyridine-2-carboxamide A solution of methyl 6-bromo-3-nitro-5-{[4-(trifluoromethoxy)phenyl]sulfonyl}pyridine-2-carboxylate (43 mg, 0.089 mmol, Intermediate 28) in 2-methoxyethanol (1 mL, 12.68 mmol) was treated with excess K$_2$CO$_3$ (40 mg), stirred at room temperature for 10 minutes, heated to 60° C. for 10 minutes, and cooled to room temperature. The mixture was partitioned between tert-butyl methyl ether (~30 mL) and 1 M HCl (~10 mL). The tert-butyl methyl ether layer was washed with brine, dried (MgSO$_4$), filtered, and concentrated. The residue was chromatographed on silica gel eluting with a gradient of 25 to 100% ethyl acetate in heptanes to provide 2-methoxyethyl 6-(2-methoxyethoxy)-3-nitro-5-{[4-(trifluoromethoxy)phenyl]sulfonyl}pyridine-2-carboxylate (23 mg, 0.044 mmol, 49.5% yield). $^1$H NMR (501 MHz, CDCl$_3$) δ ppm 9.17 (s, 1H), 8.15-8.12 (m, 2H), 7.36 (d, J=8.1 Hz, 2H), 4.65-4.63 (m, 2H), 4.57-4.55 (m, 2H), 3.71-3.68 (m, 4H), 3.39 (s, 3H), 3.38 (s, 3H); MS (ESI+) m/z 525 (M+H)⁺.

A suspension of Raney® nickel in water (approximately 0.1 mL of suspension) was transferred to a 4 mL vial and washed with tetrahydrofuran several times to remove the water. The Raney® nickel was treated with a solution of 2-methoxyethyl 6-(2-methoxyethoxy)-3-nitro-5-{[4-(trifluoromethoxy)phenyl]sulfonyl}pyridine-2-carboxylate (23 mg, 0.044 mmol) in tetrahydrofuran (~1 mL). The mixture was stirred under $H_2$ (balloon) until the reaction was complete. The atmosphere was exchanged with $N_2$, and the mixture was decanted from the Raney® nickel. The Raney® nickel was triturated several times with ethyl acetate. The tetrahydrofuran and the ethyl acetate from the decantation and triturations were combined and concentrated. The residue was chromatographed on silica gel eluting with a gradient of 15 to 50% ethyl acetate in heptanes to provide 2-methoxyethyl 3-amino-6-(2-methoxyethoxy)-5-{[4-(trifluoromethoxy)phenyl]sulfonyl}pyridine-2-carboxylate (6.5 mg, 0.013 mmol, 30.0% yield). ¹H NMR (400 MHz, CDCl₃) δ ppm 8.13-8.09 (m, 2H), 7.88 (s, 1H), 7.35-7.28 (m, 2H), 5.55 (br s, 2H), 4.46-4.41 (m, 4H), 3.72-3.69 (m, 2H), 3.66-3.63 (m, 2H), 3.40 (s, 3H), 3.38 (s, 3H); MS (ESI+) m/z 495 (M+H)⁺; MS (ESI−) m/z 493 (M−H)⁻.

A mixture of 2-methoxyethyl 3-amino-6-(2-methoxyethoxy)-5-{[4-(trifluoromethoxy)phenyl]sulfonyl}pyridine-2-carboxylate (6.2 mg, 0.013 mmol), 1,2,4-triazolylsodium (1.142 mg, 0.013 mmol) and (S)-(+)-1-amino-2-propanol (1.884 mg, 0.025 mmol) in dioxane (0.2 mL) was heated to 110° C. for 1 hour. The mixture was cooled and partitioned between ethyl acetate and saturated aqueous NaHCO₃ solution. The ethyl acetate layer was washed with brine, dried (MgSO₄), filtered, and concentrated. The residue was chromatographed on silica gel eluting with a gradient of 50 to 100% ethyl acetate in heptanes to provide the titled compound, 3-amino-N-[(2S)-2-hydroxypropyl]-6-(2-methoxyethoxy)-5-{[4-(trifluoromethoxy)phenyl]sulfonyl}pyridine-2-carboxamide (4 mg, 8.11 mol, 64.6% yield). ¹H NMR (400 MHz, CDCl₃) δ ppm 8.12-8.08 (m, 2H), 7.97 (t, J=6.0 Hz, 1H), 7.88 (s, 1H), 7.32 (d, J=8.6 Hz, 2H), 5.84 (br s, 2H), 4.37-4.34 (m, 2H), 4.03-3.95 (m, 1H), 3.69-3.65 (m, 2H), 3.56 (ddd, J=13.9, 6.6, 3.1 Hz, 1H), 3.39 (s, 3H), 3.27 (ddd, J=13.6, 7.3, 5.7 Hz, 1H), 2.31 (d, J=4.2 Hz, 1H), 1.23 (d, J=6.3 Hz, 3H); MS (ESI+) m/z 494 (M+H)⁺; MS (ESI−) m/z 492 (M−H)⁻.

Compound 289: 3-amino-6-[2-(dimethylamino)ethoxy]-N-[(2S)-2-hydroxypropyl]-5-{[4-(trifluoromethoxy)phenyl]sulfonyl}pyridine-2-carboxamide A solution of N,N-dimethylethanolamine (10.58 µL, 0.105 mmol) in tetrahydrofuran (0.5 mL) was treated with 1 M potassium tert-butoxide in tert-butanol (77 µL, 0.077 mmol) and stirred at room temperature for 15 minutes. This solution was transferred dropwise to a solution methyl 6-bromo-3-nitro-5-{[4-(trifluoromethoxy)phenyl]sulfonyl}pyridine-2-carboxylate (34 mg, 0.070 mmol, Intermediate 28) in tetrahydrofuran (0.2 mL), and the resultant mixture was stirred at room temperature for 3 hours. The mixture was partitioned between ethyl acetate (25 mL) and saturated aqueous NaHCO₃ solution (10 mL). The layers were separated, and the aqueous fraction was extracted with ethyl acetate (~15 mL). The combined ethyl acetate layers were washed with brine, dried (MgSO₄), filtered, and concentrated. The residue was chromatographed on silica gel eluting with a gradient of 50 to 100% [9:1 tert-butyl methyl ether:methanol] in tert-butyl methyl ether to provide methyl 6-[2-(dimethylamino)ethoxy]-3-nitro-5-{[4-(trifluoromethoxy)phenyl]sulfonyl}pyridine-2-carboxylate (21 mg, 0.043 mmol, 60.7% yield). ¹H NMR (400 MHz, CDCl₃) δ ppm 9.16 (s, 1H), 8.18 (d, J=8.8 Hz, 2H), 7.35 (d, J=8.4 Hz, 2H), 4.59 (t, J=5.6 Hz, 2H), 4.01 (s, 3H), 2.64 (t, J=5.6 Hz, 2H), 2.25 (s, 6H); MS (ESI+) m/z 494 (M+H)⁺.

A vial containing methyl 6-[2-(dimethylamino)ethoxy]-3-nitro-5-{[4-(trifluoromethoxy)phenyl]sulfonyl}pyridine-2-carboxylate (20 mg, 0.041 mmol) and 10% Pd/C (10 mg) was treated with acetic acid (0.5 mL), and the mixture stirred under $H_2$ (1 atmosphere) for 1 hour. The mixture was diluted with methanol and filtered through diatomaceous earth. The methanol filtrate was concentrated and then partitioned between ethyl acetate and saturated aqueous NaHCO₃ solution. The ethyl acetate layer was washed with brine, dried (MgSO₄), filtered, and concentrated. The residue was chromatographed on silica gel eluting with a gradient of 0 to 100% [3:1 ethyl acetate:ethanol] in heptanes to provide methyl 3-amino-6-[2-(dimethylamino)ethoxy]-5-{[4-(trifluoromethoxy)phenyl]sulfonyl}pyridine-2-carboxylate (15 mg, 0.032 mmol, 80% yield). ¹H NMR (400 MHz, CDCl₃) δ ppm 8.14-8.10 (m, 2H), 7.89 (s, 1H), 7.31 (d, J=8.1 Hz, 2H), 5.60 (br s, 2H), 4.37 (t, J=6.1 Hz, 2H), 3.89 (s, 3H), 2.57 (t, J=6.1 Hz, 2H), 2.27 (s, 6H); MS (ESI+) m/z 464 (M+H)⁺; MS (ESI−) m/z 462 (M−H)⁻.

A vial containing methyl 3-amino-6-[2-(dimethylamino)ethoxy]-5-{[4-(trifluoromethoxy)phenyl]sulfonyl}pyridine-2-carboxylate (14.6 mg, 0.032 mmol), (S)-(+)-1-amino-2-propanol (14.20 mg, 0.189 mmol) and 1,2,4-triazolylsodium (2.87 mg, 0.032 mmol) in dioxane (0.3 mL) was heated to 110° C. for 2 hours. The mixture was cooled and partitioned between tert-butyl methyl ether (25 mL) and saturated aqueous NaHCO₃ solution (~15 mL). The layers were separated, and the aqueous layer was extracted with tert-butyl methyl ether (15 mL). The combined tert-butyl methyl ether layers were washed with brine, dried (MgSO₄), filtered, and concentrated. The residue was chromatographed on silica gel eluting with a gradient of 20 to 100% [1:1 (9:1 ethanol: 37% aqueous NH₄OH):ethyl acetate] in ethyl acetate to provide the titled compound, 3-amino-6-[2-(dimethylamino)ethoxy]-N-[(2S)-2-hydroxypropyl]-5-{[4-(trifluoromethoxy)phenyl]sulfonyl}pyridine-2-carboxamide (13 mg, 0.026 mmol, 81% yield).

Compound 290: 3-amino-6-cyclopropyl-N-[(2S)-2-hydroxypropyl]-5-{[4-(trifluoromethoxy)phenyl]sulfonyl}pyridine-2-carboxamide A mixture of 4-(trifluoromethoxy)thiophenol (376 mg, 1.937 mmol), 3-amino-6-cyclopropyl-5-fluoro-pyridine-2-carboxylic acid (Int 22, 190 mg, 0.969 mmol) and 1,8-diazabicyclo[5.4.0]undec-7-ene (292 µL, 1.937 mmol) in N,N-dimethylformamide (1 mL) was heated to 140° C. for 45 minutes. The mixture was cooled and partitioned between tert-butyl methyl ether (30 mL) and 1 M HCl (10 mL). The tert-butyl methyl ether layer was washed with 0.1 M HCl (10 mL) and brine, dried (MgSO₄), filtered, and concentrated. The residue was chromatographed on silica gel eluting with a gradient of 15 to 100% ethyl acetate in heptanes to provide 3-amino-6-cyclopropyl-5-{[4-(trifluoromethoxy)phenyl]sulfanyl}pyridine-2-carboxylic acid (205 mg, 0.554 mmol, 57.2% yield). ¹H NMR (400 MHz, CDCl₃) δ ppm 7.53-7.49 (m, 2H), 7.29 (d, J=8.1 Hz, 2H), 6.50 (s, 1H), 5.55 (br s, 2H), 2.25-2.17 (m, 1H), 1.01-0.91 (m, 4H); MS (ESI+) m/z 371 (M+H)⁺; MS (ESI−) m/z 369 (M−H)⁻.

A solution of 3-amino-6-cyclopropyl-5-{[4-(trifluoromethoxy)phenyl]sulfanyl}pyridine-2-carboxylic acid (203 mg, 0.548 mmol) in trifluoroacetic acid (2 mL) was cooled to 0° C., treated with 30% aqueous hydrogen peroxide (224 µL, 2.193 mmol), stirred at 0° C. for 4 hours and stirred overnight at room temperature. The mixture was treated with water (30 mL) and stirred at room temperature for 1 hour. The solid was collected by filtration, washed with water and dried under vacuum with heating (50° C.) for 1 hour. The impure solid was chromatographed on silica gel eluting with a gradient of 25-100% [200:1:1 ethyl acetate:formic acid:water] in heptane to provide a product enriched in 6-cyclopropyl-3-nitro-5-[4-(trifluoromethoxy)benzene-1-sulfonyl]pyridine-2-carboxylic acid. This product was taken up in $CH_2Cl_2$ (~3 mL) and a solid precipitated. This solid was collected by filtration and dried under vacuum to provide 6-cyclopropyl-3-nitro-5-{[4-(trifluoromethoxy)phenyl]sulfonyl}pyridine-2-carboxylic acid. $^1$H NMR (400 MHz, DMSO-$d_6$) δ ppm 9.01 (s, 1H), 8.25-8.21 (m, 2H), 7.65 (d, J=8.3 Hz, 2H), 2.79 (tt, J=7.8, 4.7 Hz, 1H), 1.14-1.02 (m, 4H).

A mixture of 6-cyclopropyl-3-nitro-5-{[4-(trifluoromethoxy)phenyl]sulfonyl}pyridine-2-carboxylic acid (35 mg, 0.081 mmol) and 10% Pd/C (11 mg, 10.34 µmol) was treated with acetic acid (~0.5 mL) and stirred under $H_2$ for 1 hour. The mixture was diluted with methanol and filtered through diatomaceous earth. The methanol filtrate was concentrated, and the residue was partitioned between ethyl acetate and saturated aqueous $NaHCO_3$ solution. The ethyl acetate layer was washed with brine, dried ($MgSO_4$), filtered, and concentrated. The residue was chromatographed on silica gel eluting with a gradient of 50 to 100% ethyl acetate in heptanes to provide 3-amino-6-cyclopropyl-5-{[4-(trifluoromethoxy)phenyl]sulfonyl}pyridine-2-carboxylic acid (27 mg, 0.067 mmol, 83% yield). $^1$H NMR (400 MHz, CDCl$_3$) δ ppm 10.58 (s, 1H), 7.97-7.93 (m, 3H), 7.41-7.34 (m, 2H), 5.94 (br s, 2H), 2.59 (tt, J=7.1, 5.9 Hz, 1H), 0.87-0.82 (m, 4H); MS (ESI+) m/z 403 (M+H)$^+$; MS (ESI−) m/z 401 (M−H)$^−$.

A solution of 3-amino-6-cyclopropyl-5-{[4-(trifluoromethoxy)phenyl]sulfonyl}pyridine-2-carboxylic acid (26.2 mg, 0.065 mmol) and (S)-(+)-1-amino-2-propanol (9.78 mg, 0.130 mmol) in N,N-dimethylformamide (0.5 mL) was treated with triethylamine (45.4 µL, 0.326 mmol) and 50% 2,4,6-tripropyl-1,3,5,2,4,6-trioxatriphosphorinane 2,4,6-trioxide in N,N-dimethylformamide (124 mg, 0.195 mmol) and stirred at room temperature overnight. The mixture was partitioned between tert-butyl methyl ether (~30 mL) and 1 M HCl (~10 mL). The layers were separated, and the aqueous layer was extracted with tert-butyl methyl ether (15 mL). The combined tert-butyl methyl ether layers were washed with brine, dried ($MgSO_4$), filtered, and concentrated. The residue was chromatographed on silica gel eluting with a gradient of 15 to 50% ethyl acetate in heptanes to provide the titled compound, 3-amino-6-cyclopropyl-N-[(2S)-2-hydroxypropyl]-5-{[4-(trifluoromethoxy)phenyl]sulfonyl}pyridine-2-carboxamide (21 mg, 0.046 mmol, 70.2% yield).

Compound 297: 3-amino-5-{[4-(trifluoromethoxy)phenyl]sulfonyl}pyridine-2-carboxamide A solution of 3-amino-5-(4-trifluoromethoxy-benzenesulfonyl)-pyridine-2-carboxylic acid (Int 4, 140 mg, 0.386 mmol) and 1-[bis(dimethylamino)methylene]-1H-1,2,3-triazolo[4,5-b]pyridinium 3-oxid hexafluorophosphate (294 mg, 0.773 mmol, HATU) in N,N-dimethylformamide (1.4 mL) was treated with triethylamine (108 µL, 0.773 mmol), stirred at room temperature for 20 minutes, treated with an excess of 37% aqueous ammonium hydroxide solution (407 µL, 3.86 mmol), and stirred overnight. The mixture was diluted with water (20 mL) and stirred for 15 minutes. The solid that formed was collected by filtration, washed with water and dried under vacuum to provide the titled compound (129 mg, 0.357 mmol, 92% yield). MS (DCI+) m/z 362 [M+H]+, 379 [M+NH$_4$]+; $^1$H NMR (400 MHz, DMSO-$d_6$) δ ppm 8.17 (d, J=2.1 Hz, 1H), 8.13-8.09 (m, 2H), 8.02 (br s, 1H), 7.69 (d, J=2.1 Hz, 1H), 7.63 (d, J=8.1 Hz, 2H), 7.58 (br s, 1H), 7.25 (br s, 2H).

Compound 298: 3-amino-6-bromo-5-[(4-fluorophenyl)sulfonyl]pyridine-2-carboxamide To a solution of 3-amino-5-[(4-fluorophenyl)sulfonyl]pyridine-2-carboxamide (1.22 g, 4.14 mmol, Intermediate 31) in N,N-dimethylformamide (15 mL) was added N-bromosuccinimide (0.736 g, 4.14 mmol) in portionwise manner. The reaction mixture was stirred at room temperature overnight (19 hours). The reaction mixture was partitioned between dichloromethane and brine. The organic fraction was dried over anhydrous sodium sulfate, filtered, and concentrated. The residue was purified by flash chromatography using an 80 g silica cartridge eluted by 0-25% tert-butyl methyl ether/dichloromethane. A second flash chromatography using the same conditions gave the titled compound (0.486 g, 31.4%) as the first eluting isomer and then 3-amino-4-bromo-5-[(4-fluorophenyl)sulfonyl]pyridine-2-carboxamide eluted.

TABLE II

List of final compounds

| Cpd Number | Name | MW | Mes | Intermediate | Method |
|---|---|---|---|---|---|
| 1 | 3-amino-N-(2-hydroxy-2-methylpropyl)-5-{[4-(trifluoromethoxy)phenyl]sulfonyl}pyridine-2-carboxamide | 433 | 434 | 4 | A1 |
| 2 | 3-amino-N-(3,3,3-trifluoro-2-hydroxy-2-methylpropyl)-5-{[4-(trifluoromethoxy)phenyl]sulfonyl}pyridine-2-carboxamide | 487 | 488 | 4 | A1 |
| 3 | 3-amino-N-(2-hydroxy-3-methoxypropyl)-5-{[4-(trifluoromethoxy)phenyl]sulfonyl}pyridine-2-carboxamide | 449 | 450 | 4 | A1 |

TABLE II-continued

List of final compounds

| Cpd Number | Name | MW | Mes | Intermediate | Method |
|---|---|---|---|---|---|
| 4 | (3-amino-5-{[4-(trifluoromethoxy)phenyl]sulfonyl}pyridin-2-yl)(3-hydroxypyrrolidin-1-yl)methanone | 431 | 432 | 4 | A1 |
| 5 | 3-amino-N-[(4-hydroxy-1-methylpiperidin-4-yl)methyl]-5-{[4-(trifluoromethoxy)phenyl]sulfonyl}pyridine-2-carboxamide | 488 | 489 | 4 | A1 |
| 6 | 3-amino-N-(3,3,3-trifluoro-2-hydroxypropyl)-5-{[4-(trifluoromethoxy)phenyl]sulfonyl}pyridine-2-carboxamide | 473 | 474 | 4 | A1 |
| 7 | 3-amino-N-(tetrahydrofuran-2-ylmethyl)-5-{[4-(trifluoromethoxy)phenyl]sulfonyl}pyridine-2-carboxamide | 445 | 446 | 4 | A1 |
| 8 | 3-amino-N-(1,4-dioxan-2-ylmethyl)-5-{[4-(trifluoromethoxy)phenyl]sulfonyl}pyridine-2-carboxamide | 461 | 462 | 4 | A1 |
| 9 | 3-amino-N-[2-(morpholin-4-yl)ethyl]-5-{[4-(trifluoromethoxy)phenyl]sulfonyl}pyridine-2-carboxamide | 474 | 475 | 4 | A1 |
| 10 | 3-amino-5-[(4-fluorophenyl)sulfonyl]-N-(2-hydroxy-2-methylpropyl)pyridine-2-carboxamide | 367 | 368 | 10 | A1 |
| 11 | 3-amino-N-(2-hydroxy-2-methylpropyl)-5-{[4-(trifluoromethyl)phenyl]sulfonyl}pyridine-2-carboxamide | 417 | 418 | 5 | A1 |
| 12 | 3-amino-N-(1-hydroxybutan-2-yl)-5-{[4-(trifluoromethoxy)phenyl]sulfonyl}pyridine-2-carboxamide | 433 | 434 | 4 | A1 |
| 13 | 3-amino-N-(1-hydroxy-3-methylbutan-2-yl)-5-{[4-(trifluoromethoxy)phenyl]sulfonyl}pyridine-2-carboxamide | 447 | 448 | 4 | A1 |
| 14 | 3-amino-N-(2-hydroxyethyl)-5-{[4-(trifluoromethoxy)phenyl]sulfonyl}pyridine-2-carboxamide | 405 | 406 | 4 | A1 |
| 15 | 3-amino-N-[(1-hydroxycyclopropyl)methyl]-5-{[4-(trifluoromethoxy)phenyl]sulfonyl}pyridine-2-carboxamide | 431 | 432 | 4 | A1 |
| 16 | 3-amino-N-(2-hydroxy-3,3-dimethylbutyl)-5-{[4-(trifluoromethoxy)phenyl]sulfonyl}pyridine-2-carboxamide | 461 | 462 | 4 | A1 |
| 17 | rac-3-amino-N-[(1R,2R)-2-hydroxycyclohexyl]-5-{[4-(trifluoromethoxy)phenyl]sulfonyl}pyridine-2-carboxamide | 459 | 460 | 4 | A1 |
| 18 | 3-amino-N-(3-hydroxy-2,2-dimethylpropyl)-5-{[4-(trifluoromethoxy)phenyl]sulfonyl}pyridine-2-carboxamide | 447 | 448 | 4 | A1 |
| 19 | 3-amino-5-[(4-fluorophenyl)sulfonyl]-N-(3,3,3-trifluoro-2-hydroxy-2-methylpropyl)pyridine-2-carboxamide | 421 | 422 | 10 | A1 |
| 20 | 3-amino-N-[(2R)-2-hydroxypropyl]-5-{[4-(trifluoromethoxy)phenyl]sulfonyl}pyridine-2-carboxamide | 419 | 420 | 4 | A1 |
| 21 | 3-amino-N-[(2S)-2-hydroxypropyl]-5-{[4-(trifluoromethoxy)phenyl]sulfonyl}pyridine-2-carboxamide | 419 | 420 | 4 | A1 |
| 22 | 3-amino-N-{[1-(hydroxymethyl)cyclopropyl]methyl}-5-{[4-(trifluoromethoxy)phenyl]sulfonyl}pyridine-2-carboxamide | 445 | 446 | 4 | A1 |

TABLE II-continued

List of final compounds

| Cpd Number | Name | MW | Mes | Intermediate | Method |
|---|---|---|---|---|---|
| 23 | 3-amino-N-{[1-(hydroxymethyl)cyclobutyl]methyl}-5-{[4-(trifluoromethoxy)phenyl]sulfonyl}pyridine-2-carboxamide | 459 | 460 | 4 | A1 |
| 24 | 3-amino-N-(3-hydroxy-2-methylpropyl)-5-{[4-(trifluoromethoxy)phenyl]sulfonyl}pyridine-2-carboxamide | 433 | 434 | 4 | A1 |
| 25 | 3-amino-5-[(4-fluorophenyl)sulfonyl]-N-[(2S)-3,3,3-trifluoro-2-hydroxypropyl]pyridine-2-carboxamide | 407 | 408 | 10; 19 | A1 |
| 26 | 3-amino-N-[(2S)-3,3,3-trifluoro-2-hydroxypropyl]-5-{[4-(trifluoromethoxy)phenyl]sulfonyl}pyridine-2-carboxamide | 473 | 474 | 4; 19 | A1 |
| 27 | 3-amino-5-[(4-fluorophenyl)sulfonyl]-N-(3,3,3-trifluoro-2-hydroxypropyl)pyridine-2-carboxamide | 407 | 408 | 10 | A1 |
| 28 | 3-amino-N-[(3-hydroxytetrahydrofuran-3-yl)methyl]-5-{[4-(trifluoromethoxy)phenyl]sulfonyl}pyridine-2-carboxamide | 461 | 462 | 4 | A1 |
| 29 | 3-amino-N-[(4-hydroxytetrahydro-2H-pyran-4-yl)methyl]-5-{[4-(trifluoromethoxy)phenyl]sulfonyl}pyridine-2-carboxamide | 475 | 476 | 4 | A1 |
| 30 | 3-amino-5-[(4-fluorophenyl)sulfonyl]-N-[(1-hydroxycyclopropyl)methyl]pyridine-2-carboxamide | 365 | 366 | 10 | A1 |
| 31 | 3-amino-N-[3-(cyclopropylmethoxy)-2-hydroxypropyl]-5-{[4-(trifluoromethoxy)phenyl]sulfonyl}pyridine-2-carboxamide | 489 | 490 | 4 | A1 |
| 32 | (3-amino-5-{[4-(trifluoromethoxy)phenyl]sulfonyl}pyridin-2-yl)(3-hydroxyazetidin-1-yl)methanone | 417 | 418 | 4 | A1 |
| 33 | rac-3-amino-N-[(3R,4S)-4-hydroxytetrahydro-2H-pyran-3-yl]-5-{[4-(trifluoromethoxy)phenyl]sulfonyl}pyridine-2-carboxamide | 461 | 462 | 4; 20 | A1 |
| 34 | 3-amino-N-(4-hydroxy-2,2-dimethylbutyl)-5-{[4-(trifluoromethoxy)phenyl]sulfonyl}pyridine-2-carboxamide | 461 | 462 | 4 | A1 |
| 35 | 3-amino-N-[2-hydroxy-2-(tetrahydro-2H-pyran-4-yl)ethyl]-5-{[4-(trifluoromethoxy)phenyl]sulfonyl}pyridine-2-carboxamide | 489 | 490 | 4 | A1 |
| 36 | 3-amino-5-[(4-fluorophenyl)sulfonyl]-N-[(2R)-3,3,3-trifluoro-2-hydroxypropyl]pyridine-2-carboxamide | 407 | 408 | 10; 19 | A1 |
| 37 | 3-amino-N-[(2R)-3,3,3-trifluoro-2-hydroxypropyl]-5-{[4-(trifluoromethoxy)phenyl]sulfonyl}pyridine-2-carboxamide | 473 | 474 | 4; 19 | A1 |
| 38 | 3-amino-N-[3-(2-ethoxyethoxy)-2-hydroxypropyl]-5-{[4-(trifluoromethoxy)phenyl]sulfonyl}pyridine-2-carboxamide | 507 | 508 | 4 | A1 |
| 39 | 3-amino-5-[(3-fluorophenyl)sulfonyl]-N-(2-hydroxy-2-methylpropyl)pyridine-2-carboxamide | 367 | 368 | 2 | A1, B1, C2 |
| 40 | (3-amino-5-{[4-(trifluoromethoxy)phenyl]sulfonyl}pyridin-2-yl)(3,3-difluoroazetidin-1-yl)methanone | 437 | 438 | 4 | A1 |
| 41 | 3-amino-N-[2-hydroxy-1-(4-methylphenyl)ethyl]-5-{[4-(trifluoromethoxy)phenyl]sulfonyl}pyridine-2-carboxamide | 495 | 496 | 4 | A2 |

TABLE II-continued

List of final compounds

| Cpd Number | Name | MW | Mes | Intermediate | Method |
|---|---|---|---|---|---|
| 42 | (3-amino-5-{[4-(trifluoromethoxy)phenyl]sulfonyl}pyridin-2-yl)(3-methoxyazetidin-1-yl)methanone | 431 | 432 | 4 | A1 |
| 43 | 3-amino-N-[1-(ethylamino)-1-oxopropan-2-yl]-5-{[4-(trifluoromethoxy)phenyl]sulfonyl}pyridine-2-carboxamide | 460 | 461 | 4 | A2 |
| 44 | 3-amino-N-(1,3-dihydroxypropan-2-yl)-5-{[4-(trifluoromethoxy)phenyl]sulfonyl}pyridine-2-carboxamide | 435 | 436 | 4 | A2 |
| 45 | 3-amino-N-(4-hydroxybutyl)-5-{[4-(trifluoromethoxy)phenyl]sulfonyl}pyridine-2-carboxamide | 433 | 434 | 4 | A2 |
| 46 | 3-amino-N-[(2R)-1-hydroxy-4-methylpentan-2-yl]-5-{[4-(trifluoromethoxy)phenyl]sulfonyl}pyridine-2-carboxamide | 461 | 462 | 4 | A2 |
| 47 | 3-amino-N-[(2S)-3,3-dimethyl-1-(methylamino)-1-oxobutan-2-yl]-5-{[4-(trifluoromethoxy)phenyl]sulfonyl}pyridine-2-carboxamide | 488 | 489 | 4 | A2 |
| 48 | 3-amino-N-[2-(ethylamino)-2-oxoethyl]-5-{[4-(trifluoromethoxy)phenyl]sulfonyl}pyridine-2-carboxamide | 446 | 447 | 4 | A2 |
| 49 | 3-amino-N-[(2S)-1-amino-3-methyl-1-oxobutan-2-yl]-5-{[4-(trifluoromethoxy)phenyl]sulfonyl}pyridine-2-carboxamide | 460 | 461 | 4 | A2 |
| 50 | 3-amino-N-[(2R)-2,3-dihydroxypropyl]-5-{[4-(trifluoromethoxy)phenyl]sulfonyl}pyridine-2-carboxamide | 435 | 436 | 4 | A2 |
| 51 | 3-amino-N-(3-hydroxy-3-methylbutyl)-5-{[4-(trifluoromethoxy)phenyl]sulfonyl}pyridine-2-carboxamide | 447 | 448 | 4 | A1 |
| 52 | 3-amino-N-(4,4,4-trifluoro-3-hydroxybutyl)-5-{[4-(trifluoromethoxy)phenyl]sulfonyl}pyridine-2-carboxamide | 487 | 488 | 4 | A1 |
| 53 | 3-amino-N-[(3S)-3-hydroxybutyl]-5-{[4-(trifluoromethoxy)phenyl]sulfonyl}pyridine-2-carboxamide | 433 | 434 | 4 | A1 |
| 54 | 3-amino-N-(3-hydroxy-4-methoxybutyl)-5-{[4-(trifluoromethoxy)phenyl]sulfonyl}pyridine-2-carboxamide | 463 | 464 | 4 | A1 |
| 55 | 3-amino-N-(4-amino-4-oxobutan-2-yl)-5-{[4-(trifluoromethoxy)phenyl]sulfonyl}pyridine-2-carboxamide | 446 | 447 | 4 | A2 |
| 56 | $N^2$-[(3-amino-5-{[4-(trifluoromethoxy)phenyl]sulfonyl}pyridin-2-yl)carbonyl]-L-leucinamide | 474 | 475 | 4 | A2 |
| 57 | 3-amino-N-[2-oxo-2-(propan-2-ylamino)ethyl]-5-{[4-(trifluoromethoxy)phenyl]sulfonyl}pyridine-2-carboxamide | 460 | 461 | 4 | A2 |
| 58 | 3-amino-N-[2-(cyclopropylamino)-2-oxoethyl]-5-{[4-(trifluoromethoxy)phenyl]sulfonyl}pyridine-2-carboxamide | 458 | 459 | 4 | A2 |
| 59 | (3-amino-5-{[4-(trifluoromethoxy)phenyl]sulfonyl}pyridin-2-yl)(3,3-dimethylazetidin-1-yl)methanone | 429 | 430 | 4 | A1 |
| 60 | (3-amino-5-{[4-(trifluoromethoxy)phenyl]sulfonyl}pyridin-2-yl)[3-(morpholin-4-yl)azetidin-1-yl]methanone | 486 | 487 | 4 | A1 |

TABLE II-continued

List of final compounds

| Cpd Number | Name | MW | Mes | Intermediate | Method |
|---|---|---|---|---|---|
| 61 | 1-[(3-amino-5-{[4-(trifluoromethoxy)phenyl]sulfonyl}pyridin-2-yl)carbonyl]azetidine-3-carbonitrile | 426 | 427 | 4 | A1 |
| 62 | 1-[(3-amino-5-{[4-(trifluoromethoxy)phenyl]sulfonyl}pyridin-2-yl)carbonyl]-N,N-dimethylazetidine-3-carboxamide | 472 | 473 | 4 | A1 |
| 63 | 3-amino-N-[(2R)-3,3,3-trifluoro-2-hydroxypropyl]-5-{[4-(trifluoromethyl)phenyl]sulfonyl}pyridine-2-carboxamide | 457 | 458 | 5; 19 | A1 |
| 64 | 3-amino-N-[(2S)-3,3,3-trifluoro-2-hydroxypropyl]-5-{[4-(trifluoromethyl)phenyl]sulfonyl}pyridine-2-carboxamide | 457 | 458 | 5 | A1 |
| 65 | (3-amino-5-{[4-(trifluoromethoxy)phenyl]sulfonyl}pyridin-2-yl)(azetidin-1-yl)methanone | 401 | 402 | 4 | A1 |
| 66 | (3-amino-5-{[4-(trifluoromethoxy)phenyl]sulfonyl}pyridin-2-yl)[3-(hydroxymethyl)azetidin-1-yl]methanone | 431 | 432 | 4 | A1 |
| 67 | (3-amino-5-{[4-(trifluoromethoxy)phenyl]sulfonyl}pyridin-2-yl)(3-fluoroazetidin-1-yl)methanone | 419 | 420 | 4 | A1 |
| 68 | (3-amino-5-{[4-(trifluoromethoxy)phenyl]sulfonyl}pyridin-2-yl)(2-oxa-6-azaspiro[3.3]hept-6-yl)methanone | 443 | 444 | 4 | A1 |
| 69 | 3-amino-N-[(2R)-2-hydroxy-3-methoxypropyl]-5-{[4-(trifluoromethoxy)phenyl]sulfonyl}pyridine-2-carboxamide | 449 | 450 | 4; 14 | A1 |
| 70 | 3-amino-N-[(2R)-2-hydroxy-3-methoxypropyl]-5-{[4-(trifluoromethyl)phenyl]sulfonyl}pyridine-2-carboxamide | 433 | 434 | 5; 14 | A1 |
| 71 | 3-amino-5-{[2-fluoro-4-(trifluoromethoxy)phenyl]sulfonyl}-N-(2-hydroxy-3-methoxypropyl)pyridine-2-carboxamide | 467 | 468 | 6 | A1 |
| 72 | 3-amino-5-[(4-fluorophenyl)sulfonyl]-N-(4,4,4-trifluoro-3-hydroxybutyl)pyridine-2-carboxamide | 421 | 422 | 10 | A1 |
| 73 | 3-amino-N-[2-hydroxy-2-(tetrahydrofuran-3-yl)ethyl]-5-{[4-(trifluoromethoxy)phenyl]sulfonyl}pyridine-2-carboxamide | 475 | 476 | 4 | A1 |
| 74 | rac-3-amino-N-[(3R,4S)-4-hydroxytetrahydrofuran-3-yl]-5-{[4-(trifluoromethoxy)phenyl]sulfonyl}pyridine-2-carboxamide | 447 | 448 | 4 | A1 |
| 75 | 3-amino-N-(2-hydroxyethyl)-5-{[2-(trifluoromethoxy)phenyl]sulfonyl}pyridine-2-carboxamide | 405 | 406 | 11 | A1 |
| 76 | (3-amino-5-{[2-(trifluoromethoxy)phenyl]sulfonyl}pyridin-2-yl)(3-hydroxyazetidin-1-yl)methanone | 417 | 418 | 11 | A1 |
| 77 | (3-amino-5-{[2-fluoro-4-(trifluoromethoxy)phenyl]sulfonyl}pyridin-2-yl)(3-hydroxyazetidin-1-yl)methanone | 435 | 436 | 6 | A1 |
| 78 | (3-amino-5-{[2-(trifluoromethoxy)phenyl]sulfonyl}pyridin-2-yl)(3,3-difluoroazetidin-1-yl)methanone | 437 | 438 | 11 | A1 |
| 79 | (3-amino-5-{[4-(trifluoromethoxy)phenyl]sulfonyl}pyridin-2-yl)[3-hydroxy-3-(trifluoromethyl)azetidin-1-yl]methanone | 485 | 486 | 4 | A1 |

TABLE II-continued

List of final compounds

| Cpd Number | Name | MW | Mes | Intermediate | Method |
|---|---|---|---|---|---|
| 80 | 3-amino-N-(2-hydroxy-3-methoxypropyl)-5-{[2-(trifluoromethoxy)phenyl]sulfonyl}pyridine-2-carboxamide | 449 | 450 | 11 | A1 |
| 81 | 3-amino-N-[(2R)-3,3,3-trifluoro-2-hydroxypropyl]-5-{[2-(trifluoromethoxy)phenyl]sulfonyl}pyridine-2-carboxamide | 473 | 474 | 11; 19 | A1 |
| 82 | 3-amino-N-[(2S)-2-hydroxypropyl]-5-{[2-(trifluoromethoxy)phenyl]sulfonyl}pyridine-2-carboxamide | 419 | 420 | 11 | A1 |
| 83 | rac-3-amino-N-[(3R,4S)-4-hydroxytetrahydro-2H-pyran-3-yl]-5-{[2-(trifluoromethoxy)phenyl]sulfonyl}pyridine-2-carboxamide | 461 | 462 | 11; 20 | A1 |
| 84 | 3-amino-5-[(4,4-difluoropiperidin-1-yl)sulfonyl]-N-(3,3,3-trifluoro-2-hydroxypropyl)pyridine-2-carboxamide | 432 | 433 | 9 | D1 |
| 85 | (3-amino-5-{[2-(trifluoromethoxy)phenyl]sulfonyl}pyridin-2-yl)[3-hydroxy-3-(trifluoromethyl)azetidin-1-yl]methanone | 485 | 486 | 11 | A1 |
| 86 | (3-amino-5-{[4-(trifluoromethoxy)phenyl]sulfonyl}pyridin-2-yl)(3-cyclopropyl-3-hydroxyazetidin-1-yl)methanone | 457 | 458 | 4 | A1 |
| 87 | 3-amino-N-(2-hydroxy-4-methylpentyl)-5-{[4-(trifluoromethoxy)phenyl]sulfonyl}pyridine-2-carboxamide | 461 | 462 | 4 | A1 |
| 88 | 3-amino-N-(3-ethoxy-2-hydroxypropyl)-5-{[4-(trifluoromethoxy)phenyl]sulfonyl}pyridine-2-carboxamide | 463 | 464 | 4 | A1 |
| 89 | (3-amino-5-{[4-(trifluoromethoxy)phenyl]sulfonyl}pyridin-2-yl)(3-hydroxy-3-methylazetidin-1-yl)methanone | 431 | 432 | 4 | A1 |
| 90 | 3-amino-N-[2-hydroxy-3-(propan-2-yloxy)propyl]-5-{[4-(trifluoromethoxy)phenyl]sulfonyl}pyridine-2-carboxamide | 477 | 478 | 4 | A1 |
| 91 | (3-amino-5-{[4-(trifluoromethyl)phenyl]sulfonyl}pyridin-2-yl)(3-hydroxy-3-methylazetidin-1-yl)methanone | 415 | 416 | 5 | A1 |
| 92 | 3-amino-N-[2-hydroxy-3-(propan-2-yloxy)propyl]-5-{[4-(trifluoromethyl)phenyl]sulfonyl}pyridine-2-carboxamide | 461 | 462 | 5 | A1 |
| 93 | 3-amino-N-[(2S)-1-amino-1-oxobutan-2-yl]-5-{[4-(trifluoromethoxy)phenyl]sulfonyl}pyridine-2-carboxamide | 446 | 447 | 4 | A2 |
| 94 | 3-amino-5-[cyclopropyl(methyl)sulfamoyl]-N-(3,3,3-trifluoro-2-hydroxypropyl)pyridine-2-carboxamide | 382 | 383 | 9 | D1 |
| 95 | 3-amino-N-(3,3,3-trifluoro-2-hydroxypropyl)-5-{[4-(trifluoromethyl)piperidin-1-yl]sulfonyl}pyridine-2-carboxamide | 464 | 465 | 9 | D1 |
| 96 | 3-amino-N-[2-hydroxy-1-(4-methoxyphenyl)ethyl]-5-{[4-(trifluoromethoxy)phenyl]sulfonyl}pyridine-2-carboxamide | 511 | 462 | 4 | A2 |
| 97 | 3-amino-5-[(3,3-difluoroazetidin-1-yl)sulfonyl]-N-(3,3,3-trifluoro-2-hydroxypropyl)pyridine-2-carboxamide | 404 | 405 | 9 | D1 |
| 98 | 3-amino-5-{[2-fluoro-4-(trifluoromethyl)phenyl]sulfonyl}-N-[(2S)-2-hydroxypropyl]pyridine-2-carboxamide | 421 | 422 | 7 | A1 |

TABLE II-continued

List of final compounds

| Cpd Number | Name | MW | Mes | Intermediate | Method |
|---|---|---|---|---|---|
| 99 | 3-amino-5-{[2-fluoro-4-(trifluoromethyl)phenyl]sulfonyl}-N-[(2R)-2-hydroxy-3-methoxypropyl]pyridine-2-carboxamide | 451 | 452 | 7; 14 | A1 |
| 100 | 3-amino-N-[(2S)-2-hydroxypropyl]-5-{[4-(trifluoromethyl)phenyl]sulfonyl}pyridine-2-carboxamide | 403 | 404 | 5 | A1 |
| 101 | 3-amino-N-[(3R)-tetrahydrofuran-3-ylmethyl]-5-{[4-(trifluoromethyl)phenyl]sulfonyl}pyridine-2-carboxamide | 429 | 430 | 5 | A1 |
| 102 | 3-amino-N-[(3S)-tetrahydrofuran-3-ylmethyl]-5-{[4-(trifluoromethyl)phenyl]sulfonyl}pyridine-2-carboxamide | 429 | 430 | 5 | A1 |
| 103 | (3-amino-5-{[4-(trifluoromethyl)phenyl]sulfonyl}pyridin-2-yl)(3,3-difluoroazetidin-1-yl)methanone | 421 | 422 | 5 | A1 |
| 104 | 3-amino-N-[2-oxo-2-(propan-2-ylamino)ethyl]-5-{[4-(trifluoromethyl)phenyl]sulfonyl}pyridine-2-carboxamide | 444 | 445 | 5 | A1 |
| 105 | (3-amino-5-{[4-(trifluoromethyl)phenyl]sulfonyl}pyridin-2-yl)[3-hydroxy-3-(trifluoromethyl)azetidin-1-yl]methanone | 469 | 470 | 5 | A1 |
| 106 | 3-amino-5-{[2-fluoro-4-(trifluoromethyl)phenyl]sulfonyl}-N-[(3R)-tetrahydrofuran-3-ylmethyl]pyridine-2-carboxamide | 447 | 448 | 7 | A1 |
| 107 | 3-amino-5-{[2-fluoro-4-(trifluoromethyl)phenyl]sulfonyl}-N-[(2R)-3,3,3-trifluoro-2-hydroxypropyl]pyridine-2-carboxamide | 475 | 476 | 7; 19 | A1 |
| 108 | 3-amino-5-[cyclopropyl(2-methoxyethyl)sulfamoyl]-N-(3,3,3-trifluoro-2-hydroxypropyl)pyridine-2-carboxamide | 426 | 427 | 9 | D1 |
| 109 | 3-amino-5-(2,3-dihydro-4H-1,4-benzoxazin-4-ylsulfonyl)-N-(3,3,3-trifluoro-2-hydroxypropyl)pyridine-2-carboxamide | 446 | 447 | 9 | D1 |
| 110 | (3-amino-5-{[4-(trifluoromethyl)phenyl]sulfonyl}pyridin-2-yl)(3,3-dimethylazetidin-1-yl)methanone | 413 | 414 | 5 | A1 |
| 111 | (3-amino-5-{[2-fluoro-4-(trifluoromethyl)phenyl]sulfonyl}pyridin-2-yl)(3,3-dimethylazetidin-1-yl)methanone | 431 | 432 | 7 | A1 |
| 112 | (3-amino-5-{[2-fluoro-4-(trifluoromethyl)phenyl]sulfonyl}pyridin-2-yl)[3-hydroxy-3-(trifluoromethyl)azetidin-1-yl]methanone | 487 | 488 | 7 | A1 |
| 113 | 3-amino-5-{[2-fluoro-4-(trifluoromethyl)phenyl]sulfonyl}-N-[2-oxo-2-(propan-2-ylamino)ethyl]pyridine-2-carboxamide | 462 | 463 | 7 | A1 |
| 114 | 3-amino-5-{[2-fluoro-4-(trifluoromethyl)phenyl]sulfonyl}-N-[(3S)-tetrahydrofuran-3-ylmethyl]pyridine-2-carboxamide | 447 | 448 | 7 | A1 |
| 115 | 3-amino-5-{[2-fluoro-4-(trifluoromethoxy)phenyl]sulfonyl}-N-[(3R)-tetrahydrofuran-3-ylmethyl]pyridine-2-carboxamide | 463 | 464 | 6 | A1 |
| 116 | 3-amino-5-{[2-fluoro-4-(trifluoromethoxy)phenyl]sulfonyl}-N-[(3S)-tetrahydrofuran-3-ylmethyl]pyridine-2-carboxamide | 463 | 464 | 6 | A1 |

TABLE II-continued

List of final compounds

| Cpd Number | Name | MW | Mes | Intermediate | Method |
|---|---|---|---|---|---|
| 117 | 3-amino-5-{[2-fluoro-4-(trifluoromethoxy)phenyl]sulfonyl}-N-[(2R)-3,3,3-trifluoro-2-hydroxypropyl]pyridine-2-carboxamide | 491 | 492 | 6; 19 | A1 |
| 118 | 3-amino-N-{[1-(ethoxymethyl)cyclobutyl]methyl}-5-{[4-(trifluoromethoxy)phenyl]sulfonyl}pyridine-2-carboxamide | 488 | 488 | 4 | A2 |
| 119 | (3-amino-5-{[4-(trifluoromethoxy)phenyl]sulfonyl}pyridin-2-yl)[3-(2,2-difluoroethoxy)azetidin-1-yl]methanone | 481 | 482 | 4 | A2 |
| 120 | 3-amino-N-(trans-3-methoxycyclobutyl)-5-{[4-(trifluoromethoxy)phenyl]sulfonyl}pyridine-2-carboxamide | 445 | 446 | 4 | A2 |
| 121 | (3-amino-5-{[4-(trifluoromethoxy)phenyl]sulfonyl}pyridin-2-yl)(6-oxa-2-azaspiro[3.5]non-2-yl)methanone | 471 | 472 | 4 | A2 |
| 122 | 3-amino-N-(3,3-difluorocyclobutyl)-5-{[4-(trifluoromethoxy)phenyl]sulfonyl}pyridine-2-carboxamide | 451 | 452 | 4 | A2 |
| 123 | 3-amino-N-(3-methoxypropyl)-5-{[4-(trifluoromethoxy)phenyl]sulfonyl}pyridine-2-carboxamide | 433 | 434 | 4 | A2 |
| 124 | 3-amino-N-[2-(1-methylcyclopropyl)ethyl]-5-{[4-(trifluoromethoxy)phenyl]sulfonyl}pyridine-2-carboxamide | 443 | 444 | 4 | A2 |
| 125 | (3-amino-5-{[4-(trifluoromethoxy)phenyl]sulfonyl}pyridin-2-yl)(6-oxa-2-azaspiro[3.4]oct-2-yl)methanone | 457 | 458 | 4 | A2 |
| 126 | (3-amino-5-{[4-(trifluoromethoxy)phenyl]sulfonyl}pyridin-2-yl)(3-methylazetidin-1-yl)methanone | 415 | 416 | 4 | A2 |
| 127 | 3-amino-N-(tetrahydrofuran-3-yl)-5-{[4-(trifluoromethoxy)phenyl]sulfonyl}pyridine-2-carboxamide | 431 | 432 | 4 | A2 |
| 128 | 3-amino-N-[(3R)-tetrahydrofuran-3-yl]-5-{[4-(trifluoromethoxy)phenyl]sulfonyl}pyridine-2-carboxamide | 431 | 432 | 4 | A2 |
| 129 | 3-amino-N-(tetrahydro-2H-pyran-4-ylmethyl)-5-{[4-(trifluoromethoxy)phenyl]sulfonyl}pyridine-2-carboxamide | 459 | 460 | 4 | A2 |
| 130 | (3-amino-5-{[4-(trifluoromethoxy)phenyl]sulfonyl}pyridin-2-yl)(3-ethyl-3-fluoroazetidin-1-yl)methanone | 447 | 448 | 4 | A2 |
| 131 | 3-amino-N-[3-(cyclopropylmethoxy)-2-hydroxypropyl]-5-{[4-(trifluoromethyl)phenyl]sulfonyl}pyridine-2-carboxamide | 473 | 474 | 5 | A1 |
| 132 | 3-amino-N-[3-(cyclopropylmethoxy)-2-hydroxypropyl]-5-{[2-fluoro-4-(trifluoromethyl)phenyl]sulfonyl}pyridine-2-carboxamide | 491 | 492 | 7 | A1 |
| 133 | 3-amino-5-{[2-fluoro-4-(trifluoromethyl)phenyl]sulfonyl}-N-[2-hydroxy-3-(propan-2-yloxy)propyl]pyridine-2-carboxamide | 479 | 480 | 7 | A1 |
| 134 | (3-amino-5-{[2-fluoro-4-(trifluoromethoxy)phenyl]sulfonyl}pyridin-2-yl)(3,3-dimethylazetidin-1-yl)methanone | 447 | 448 | 6 | A1 |

TABLE II-continued

List of final compounds

| Cpd Number | Name | MW | Mes | Intermediate | Method |
|---|---|---|---|---|---|
| 135 | 3-amino-5-{[2-fluoro-4-(trifluoromethoxy)phenyl]sulfonyl}-N-[2-oxo-2-(propan-2-ylamino)ethyl]pyridine-2-carboxamide | 478 | 479 | 6 | A1 |
| 136 | 3-amino-5-[(3,4-difluorobenzyl)(methyl)sulfamoyl]-N-(3,3,3-trifluoro-2-hydroxypropyl)pyridine-2-carboxamide | 468 | 469 | 9 | D1 |
| 137 | 3-amino-5-[(2,4-difluorobenzyl)(methyl)sulfamoyl]-N-(3,3,3-trifluoro-2-hydroxypropyl)pyridine-2-carboxamide | 468 | 469 | 9 | D1 |
| 138 | 3-amino-5-[(4-methoxybenzyl)(methyl)sulfamoyl]-N-(3,3,3-trifluoro-2-hydroxypropyl)pyridine-2-carboxamide | 462 | 463 | 9 | D1 |
| 139 | 3-amino-5-(morpholin-4-ylsulfonyl)-N-(3,3,3-trifluoro-2-hydroxypropyl)pyridine-2-carboxamide | 398 | 399 | 9 | D1 |
| 140 | 3-amino-N-[(3R)-tetrahydro-2H-pyran-3-yl]-5-{[4-(trifluoromethoxy)phenyl]sulfonyl}pyridine-2-carboxamide | 445 | 446 | 4 | A2 |
| 141 | 3-amino-N-[2-(furan-2-yl)ethyl]-5-{[4-(trifluoromethoxy)phenyl]sulfonyl}pyridine-2-carboxamide | 455 | 456 | 4 | A2 |
| 142 | 3-amino-N-[(2S)-1-hydroxybutan-2-yl]-5-{[4-(trifluoromethoxy)phenyl]sulfonyl}pyridine-2-carboxamide | 433 | 434 | 4 | A2 |
| 143 | 3-amino-N-(tetrahydro-2H-pyran-3-ylmethyl)-5-{[4-(trifluoromethoxy)phenyl]sulfonyl}pyridine-2-carboxamide | 459 | 460 | 4 | A2 |
| 144 | 3-amino-N-[(3S)-tetrahydrofuran-3-yl]-5-{[4-(trifluoromethoxy)phenyl]sulfonyl}pyridine-2-carboxamide | 431 | 432 | 4 | A2 |
| 145 | 3-amino-N-[(4R)-3,4-dihydro-2H-chromen-4-yl]-5-{[4-(trifluoromethoxy)phenyl]sulfonyl}pyridine-2-carboxamide | 493 | 494 | 4 | A2 |
| 146 | 3-amino-N-(tetrahydro-2H-pyran-4-yl)-5-{[4-(trifluoromethoxy)phenyl]sulfonyl}pyridine-2-carboxamide | 445 | 446 | 4 | A2 |
| 147 | 3-amino-N-[2-(1,3-dioxolan-2-yl)ethyl]-5-{[4-(trifluoromethoxy)phenyl]sulfonyl}pyridine-2-carboxamide | 461 | 462 | 4 | A2 |
| 148 | 3-amino-N-[(2S)-1-hydroxy-3-methylbutan-2-yl]-5-{[4-(trifluoromethoxy)phenyl]sulfonyl}pyridine-2-carboxamide | 447 | 448 | 4 | A2 |
| 149 | 3-amino-N-(1-oxaspiro[4.5]dec-3-yl)-5-{[4-(trifluoromethoxy)phenyl]sulfonyl}pyridine-2-carboxamide | 500 | 500 | 4 | A2 |
| 150 | 3-amino-N-(1-oxaspiro[4.4]non-3-yl)-5-{[4-(trifluoromethoxy)phenyl]sulfonyl}pyridine-2-carboxamide | 485 | 486 | 4 | A2 |
| 151 | 3-amino-N-(oxetan-3-yl)-5-{[4-(trifluoromethoxy)phenyl]sulfonyl}pyridine-2-carboxamide | 417 | 418 | 4 | A2 |
| 152 | 3-amino-N-(2-cyclopropylethyl)-5-{[4-(trifluoromethoxy)phenyl]sulfonyl}pyridine-2-carboxamide | 429 | 430 | 4 | A2 |
| 153 | 3-amino-N-[(3,3-difluorocyclobutyl)methyl]-5-{[4-(trifluoromethoxy)phenyl]sulfonyl}pyridine-2-carboxamide | 465 | 466 | 4 | A2 |
| 154 | (3-amino-5-{[4-(trifluoromethoxy)phenyl]sulfonyl}pyridin-2-yl)[3-(methoxymethyl)-3-methylazetidin-1-yl]methanone | 459 | 460 | 4 | A2 |

TABLE II-continued

List of final compounds

| Cpd Number | Name | MW | Mes | Intermediate | Method |
|---|---|---|---|---|---|
| 155 | 3-amino-N-(cyclopropylmethyl)-5-{[4-(trifluoromethoxy)phenyl]sulfonyl}pyridine-2-carboxamide | 415 | 416 | 4 | A2 |
| 156 | 3-amino-N-[(4-methyltetrahydro-2H-pyran-3-yl)methyl]-5-{[4-(trifluoromethoxy)phenyl]sulfonyl}pyridine-2-carboxamide | 473 | 474 | 4 | A2 |
| 157 | (3-amino-5-{[4-(trifluoromethyl)phenyl]sulfonyl}pyridin-2-yl)[3-(trifluoromethyl)azetidin-1-yl]methanone | 453 | 454 | 5 | A1 |
| 158 | (3-amino-5-{[4-(trifluoromethyl)phenyl]sulfonyl}pyridin-2-yl)[3-(difluoromethoxy)azetidin-1-yl]methanone | 451 | 452 | 5 | A1 |
| 159 | (3-amino-5-{[4-(trifluoromethyl)phenyl]sulfonyl}pyridin-2-yl)[3-hydroxy-3-(propan-2-yl)azetidin-1-yl]methanone | 443 | 444 | 5 | A1 |
| 160 | (3-amino-5-{[2-fluoro-4-(trifluoromethyl)phenyl]sulfonyl}pyridin-2-yl)[3-(trifluoromethyl)azetidin-1-yl]methanone | 471 | 472 | 7 | A1 |
| 161 | (3-amino-5-{[2-fluoro-4-(trifluoromethyl)phenyl]sulfonyl}pyridin-2-yl)[3-(difluoromethoxy)azetidin-1-yl]methanone | 469 | 470 | 7 | A1 |
| 162 | (3-amino-5-{[2-fluoro-4-(trifluoromethyl)phenyl]sulfonyl}pyridin-2-yl)[3-hydroxy-3-(propan-2-yl)azetidin-1-yl]methanone | 461 | 462 | 7 | A1 |
| 163 | 3-amino-5-{[2-fluoro-4-(trifluoromethyl)phenyl]sulfonyl}-N-(2-hydroxy-4-methoxy-2-methylbutyl)pyridine-2-carboxamide | 479 | 480 | 7 | A1 |
| 164 | (3-amino-5-{[2-fluoro-4-(trifluoromethyl)phenyl]sulfonyl}pyridin-2-yl)(3,3-difluoroazetidin-1-yl)methanone | 439 | 440 | 7 | A1 |
| 165 | (3-amino-5-{[4-(trifluoromethyl)phenyl]sulfonyl}pyridin-2-yl)[3-(2-hydroxypropan-2-yl)azetidin-1-yl]methanone | 443 | 444 | 5 | A1 |
| 166 | 3-amino-N-[2-hydroxy-3-(2-methylpropoxy)propyl]-5-{[4-(trifluoromethyl)phenyl]sulfonyl}pyridine-2-carboxamide | 475 | 476 | 5 | A1 |
| 167 | 3-amino-N-(2-hydroxy-4-methoxy-2-methylbutyl)-5-{[4-(trifluoromethyl)phenyl]sulfonyl}pyridine-2-carboxamide | 461 | 462 | 5 | A1 |
| 168 | 3-amino-5-{[2-fluoro-4-(trifluoromethoxy)phenyl]sulfonyl}-N-[2-hydroxy-3-(propan-2-yloxy)propyl]pyridine-2-carboxamide | 495 | 496 | 6 | A1 |
| 169 | 3-amino-N-[3-(cyclopropylmethoxy)-2-hydroxypropyl]-5-{[2-fluoro-4-(trifluoromethoxy)phenyl]sulfonyl}pyridine-2-carboxamide | 507 | 508 | 6 | A1 |
| 170 | 3-amino-5-{[2-fluoro-4-(trifluoromethyl)phenyl]sulfonyl}-N-[2-hydroxy-3-(2-methylpropoxy)propyl]pyridine-2-carboxamide | 493 | 494 | 7 | A1 |
| 171 | 3-amino-5-{[2-fluoro-4-(trifluoromethoxy)phenyl]sulfonyl}-N-[2-hydroxy-3-(2-methylpropoxy)propyl]pyridine-2-carboxamide | 509 | 510 | 6 | A1 |
| 172 | (3-amino-5-{[2-fluoro-4-(trifluoromethoxy)phenyl]sulfonyl}pyridin-2-yl)(3,3-difluoroazetidin-1-yl)methanone | 455 | 456 | 6 | A1 |

TABLE II-continued

List of final compounds

| Cpd Number | Name | MW | Mes | Intermediate | Method |
|---|---|---|---|---|---|
| 173 | (3-amino-5-{[2-fluoro-4-(trifluoromethoxy)phenyl]sulfonyl}pyridin-2-yl)[3-hydroxy-3-(trifluoromethyl)azetidin-1-yl]methanone | 503 | 504 | 6 | A1 |
| 174 | (3-amino-5-{[2-fluoro-4-(trifluoromethoxy)phenyl]sulfonyl}pyridin-2-yl)[3-(2-hydroxypropan-2-yl)azetidin-1-yl]methanone | 477 | 478 | 6 | A1 |
| 175 | (3-amino-5-{[2-fluoro-4-(trifluoromethoxy)phenyl]sulfonyl}pyridin-2-yl)[3-hydroxy-3-(propan-2-yl)azetidin-1-yl]methanone | 477 | 478 | 6 | A1 |
| 176 | (3-amino-5-[(4-fluorophenyl)sulfonyl]pyridin-2-yl)[3-hydroxy-3-(trifluoromethyl)azetidin-1-yl]methanone | 419 | 420 | 10 | A1 |
| 177 | 3-amino-N-[(2R)-2-hydroxy-3-methoxypropyl]-5-{[2-(trifluoromethoxy)phenyl]sulfonyl}pyridine-2-carboxamide | 449 | 450 | 11; 14 | A1 |
| 178 | (3-amino-5-{[2-fluoro-4-(trifluoromethyl)phenyl]sulfonyl}pyridin-2-yl)[3-(2-hydroxypropan-2-yl)azetidin-1-yl]methanone | 461 | 462 | 7 | A1 |
| 179 | 3-amino-5-{[(2R)-2-methylpyrrolidin-1-yl]sulfonyl}-N-(3,3,3-trifluoro-2-hydroxypropyl)pyridine-2-carboxamide | 396 | 397 | 9 | D1 |
| 180 | 3-amino-5-{[(3S)-3-fluoropyrrolidin-1-yl]sulfonyl}-N-(3,3,3-trifluoro-2-hydroxypropyl)pyridine-2-carboxamide | 400 | 401 | 9 | D1 |
| 181 | 3-amino-5-{[(2S)-2-methylpyrrolidin-1-yl]sulfonyl}-N-(3,3,3-trifluoro-2-hydroxypropyl)pyridine-2-carboxamide | 396 | 397 | 9 | D1 |
| 182 | 3-amino-5-[(3-methylpiperidin-1-yl)sulfonyl]-N-(3,3,3-trifluoro-2-hydroxypropyl)pyridine-2-carboxamide | 410 | 411 | 9 | D1 |
| 183 | 3-amino-5-[(3,3-difluoropiperidin-1-yl)sulfonyl]-N-(3,3,3-trifluoro-2-hydroxypropyl)pyridine-2-carboxamide | 432 | 433 | 9 | D1 |
| 184 | 3-amino-5-[(4-methylpiperidin-1-yl)sulfonyl]-N-(3,3,3-trifluoro-2-hydroxypropyl)pyridine-2-carboxamide | 410 | 411 | 9 | D1 |
| 185 | 3-amino-5-[(3,5-dimethylpiperidin-1-yl)sulfonyl]-N-(3,3,3-trifluoro-2-hydroxypropyl)pyridine-2-carboxamide | 424 | 425 | 9 | D1 |
| 186 | 3-amino-5-[(3,3-difluoropyrrolidin-1-yl)sulfonyl]-N-(3,3,3-trifluoro-2-hydroxypropyl)pyridine-2-carboxamide | 418 | 419 | 9 | D1 |
| 187 | 3-amino-5-[(4-fluorobenzyl)(methyl)sulfamoyl]-N-(3,3,3-trifluoro-2-hydroxypropyl)pyridine-2-carboxamide | 450 | 451 | 9 | D1 |
| 188 | 3-amino-N-(3-methylbutan-2-yl)-5-{[4-(trifluoromethyl)phenyl]sulfonyl}pyridine-2-carboxamide | 415 | 416 | 5 | A1 |
| 189 | 3-amino-N-(2-methylpropyl)-5-{[4-(trifluoromethyl)phenyl]sulfonyl}pyridine-2-carboxamide | 401 | 402 | 5 | A1 |
| 190 | 3-amino-N-[2-(tetrahydrofuran-2-ylmethoxy)ethyl]-5-{[4-(trifluoromethyl)phenyl]sulfonyl}pyridine-2-carboxamide | 473 | 474 | 5 | A1 |
| 191 | 3-amino-N-(2,2-dimethylpropyl)-5-{[4-(trifluoromethyl)phenyl]sulfonyl}pyridine-2-carboxamide | 415 | 416 | 5 | A1 |
| 192 | 3-amino-N-[2-(propan-2-yloxy)ethyl]-5-{[4-(trifluoromethyl)phenyl]sulfonyl}pyridine-2-carboxamide | 431 | 432 | 5 | A1 |
| 193 | 3-amino-5-{[4-(trifluoromethoxy)phenyl]sulfonyl}-N-[4-(trifluoromethyl)tetrahydro-2H-pyran-4-yl]pyridine-2-carboxamide | 513 | 514 | 4 | A2 |

TABLE II-continued

List of final compounds

| Cpd Number | Name | MW | Mes | Intermediate | Method |
|---|---|---|---|---|---|
| 194 | 3-amino-5-[(3-fluoropiperidin-1-yl)sulfonyl]-N-(3,3,3-trifluoro-2-hydroxypropyl)pyridine-2-carboxamide | 414 | 415 | 9 | D1 |
| 195 | 3-amino-5-[(4-fluoropiperidin-1-yl)sulfonyl]-N-(3,3,3-trifluoro-2-hydroxypropyl)pyridine-2-carboxamide | 414 | 415 | 9 | D1 |
| 196 | 3-amino-5-[(4-methoxypiperidin-1-yl)sulfonyl]-N-(3,3,3-trifluoro-2-hydroxypropyl)pyridine-2-carboxamide | 426 | 427 | 9 | D1 |
| 197 | 3-amino-5-[(4-tert-butylpiperidin-1-yl)sulfonyl]-N-(3,3,3-trifluoro-2-hydroxypropyl)pyridine-2-carboxamide | 453 | 453 | 9 | D1 |
| 198 | 3-amino-N-(3,3,3-trifluoro-2-hydroxypropyl)-5-{[4-(trifluoromethoxy)piperidin-1-yl]sulfonyl}pyridine-2-carboxamide | 480 | 481 | 9 | D1 |
| 199 | 3-amino-5-[(3,3-dimethylazetidin-1-yl)sulfonyl]-N-(3,3,3-trifluoro-2-hydroxypropyl)pyridine-2-carboxamide | 396 | 397 | 9 | D1 |
| 200 | 3-amino-5-{[(3R)-tetrahydrofuran-3-ylmethyl]sulfamoyl}-N-(3,3,3-trifluoro-2-hydroxypropyl)pyridine-2-carboxamide | 412 | 413 | 9 | D1 |
| 201 | 3-amino-N-[2-hydroxy-3-(2,2,2-trifluoroethoxy)propyl]-5-{[4-(trifluoromethyl)phenyl]sulfonyl}pyridine-2-carboxamide | 501 | 502 | 5; 15 | A1 |
| 202 | 3-amino-N-(2-methoxyethyl)-5-{[4-(trifluoromethyl)phenyl]sulfonyl}pyridine-2-carboxamide | 403 | 404 | 5 | A1 |
| 203 | (3-amino-5-{[4-(trifluoromethoxy)phenyl]sulfonyl}pyridin-2-yl)(3,3-difluoropyrrolidin-1-yl)methanone | 451 | 452 | 4 | A2 |
| 204 | (3-amino-5-{[4-(trifluoromethoxy)phenyl]sulfonyl}pyridin-2-yl)[(3R)-3-fluoropyrrolidin-1-yl]methanone | 433 | 434 | 4 | A2 |
| 205 | 3-amino-N-[(1R,2S)-2-hydroxycyclopentyl]-5-{[4-(trifluoromethyl)phenyl]sulfonyl}pyridine-2-carboxamide | 429 | 430 | 5 | A1 |
| 206 | (3-amino-5-{[4-(trifluoromethoxy)phenyl]sulfonyl}pyridin-2-yl)[(3S)-3-fluoropyrrolidin-1-yl]methanone | 433 | 434 | 4 | A2 |
| 207 | 3-amino-N-[(3S)-1-methylpyrrolidin-3-yl]-5-{[4-(trifluoromethoxy)phenyl]sulfonyl}pyridine-2-carboxamide | 444 | 445 | 4 | A2 |
| 208 | 3-amino-N-[(3R)-1-methylpyrrolidin-3-yl]-5-{[4-(trifluoromethoxy)phenyl]sulfonyl}pyridine-2-carboxamide | 444 | 445 | 4 | A2 |
| 209 | 3-amino-N-(2,2,2-trifluoroethyl)-5-{[4-(trifluoromethyl)phenyl]sulfonyl}pyridine-2-carboxamide | 427 | 428 | 5 | A1 |
| 210 | 3-amino-N-(1-methylazetidin-3-yl)-5-{[4-(trifluoromethoxy)phenyl]sulfonyl}pyridine-2-carboxamide | 430 | 431 | 4 | A2 |
| 211 | 3-amino-5-{methyl[4-(trifluoromethyl)benzyl]sulfamoyl}-N-(3,3,3-trifluoro-2-hydroxypropyl)pyridine-2-carboxamide | 500 | 501 | 9 | D1 |
| 212 | 3-amino-5-{[4-(trifluoromethyl)phenyl]sulfonyl}-N-(3,3,3-trifluoropropyl)pyridine-2-carboxamide | 441 | 442 | 5 | A1 |
| 213 | 3-amino-5-{[2-fluoro-4-(trifluoromethyl)phenyl]sulfonyl}-N-[2-hydroxy-3-(2,2,2-trifluoroethoxy)propyl]pyridine-2-carboxamide | 519 | 520 | 7 | A1 |

TABLE II-continued

List of final compounds

| Cpd Number | Name | MW | Mes | Intermediate | Method |
|---|---|---|---|---|---|
| 214 | 3-amino-5-{[4-(trifluoromethoxy)phenyl]sulfonyl}-N-[3-(trifluoromethyl)oxetan-3-yl]pyridine-2-carboxamide | 485 | 486 | 4 | A2 |
| 215 | 3-amino-N-[(1S,2S)-2-hydroxycyclopentyl]-5-{[4-(trifluoromethyl)phenyl]sulfonyl}pyridine-2-carboxamide | 429 | 430 | 5 | A1 |
| 216 | rac-3-amino-N-[(3R,4S)-4-hydroxytetrahydro-2H-pyran-3-yl]-5-{[4-(trifluoromethyl)phenyl]sulfonyl}pyridine-2-carboxamide | 445 | 446 | 5; 20 | A1 |
| 217 | 3-amino-N-(2-hydroxyethyl)-5-{[4-(trifluoromethyl)phenyl]sulfonyl}pyridine-2-carboxamide | 389 | 390 | 5 | A1 |
| 218 | rac-3-amino-5-{[2-fluoro-4-(trifluoromethyl)phenyl]sulfonyl}-N-[(3R,4S)-4-hydroxytetrahydro-2H-pyran-3-yl]pyridine-2-carboxamide | 463 | 464 | 7; 20 | A1 |
| 219 | 3-amino-5-{[2-fluoro-4-(trifluoromethyl)phenyl]sulfonyl}-N-(2-hydroxyethyl)pyridine-2-carboxamide | 407 | 408 | 7 | A1 |
| 220 | 3-amino-5-[(4-methoxyphenyl)sulfonyl]-N-(3,3,3-trifluoro-2-hydroxypropyl)pyridine-2-carboxamide | 419 | 420 | 8 | B1, C1 |
| 221 | 3-amino-N-[2-hydroxy-3-(2-methoxyethoxy)propyl]-5-{[4-(trifluoromethyl)phenyl]sulfonyl}pyridine-2-carboxamide | 477 | 478 | 5; 16 | A1 |
| 222 | 3-amino-N-(3-methoxypropyl)-5-{[4-(trifluoromethyl)phenyl]sulfonyl}pyridine-2-carboxamide | 417 | 418 | 5 | A1 |
| 223 | 3-amino-N-(cyclopropylmethyl)-5-{[4-(trifluoromethyl)phenyl]sulfonyl}pyridine-2-carboxamide | 399 | 400 | 5 | A1 |
| 224 | 3-amino-N-(3-tert-butoxy-2-hydroxypropyl)-5-{[2-fluoro-4-(trifluoromethyl)phenyl]sulfonyl}pyridine-2-carboxamide | 493 | 494 | 7; 17 | A1 |
| 225 | 3-amino-5-[methyl(3,3,3-trifluoropropyl)sulfamoyl]-N-(3,3,3-trifluoro-2-hydroxypropyl)pyridine-2-carboxamide | 438 | 439 | 9 | D1 |
| 226 | (3-amino-5-{[4-(trifluoromethyl)phenyl]sulfonyl}pyridin-2-yl)[(2S)-2-(hydroxymethyl)pyrrolidin-1-yl]methanone | 429 | 430 | 5 | A1 |
| 227 | 3-amino-N-(1-hydroxy-2-methylpropan-2-yl)-5-{[4-(trifluoromethyl)phenyl]sulfonyl}pyridine-2-carboxamide | 417 | 418 | 5 | A1 |
| 228 | 3-amino-N-[(1-hydroxycyclopropyl)methyl]-5-{[4-(trifluoromethyl)phenyl]sulfonyl}pyridine-2-carboxamide | 415 | 416 | 5 | A1 |
| 229 | (3-amino-5-{[4-(trifluoromethyl)phenyl]sulfonyl}pyridin-2-yl)[(3R,4R)-3,4-dihydroxypyrrolidin-1-yl]methanone | 431 | 432 | 5 | A1 |
| 230 | 3-amino-N-[(4-hydroxy-1-methylpiperidin-4-yl)methyl]-5-{[4-(trifluoromethyl)phenyl]sulfonyl}pyridine-2-carboxamide | 472 | 473 | 5 | A1 |
| 231 | (3-amino-5-{[4-(trifluoromethyl)phenyl]sulfonyl}pyridin-2-yl)[3-(2,2-difluoroethoxy)azetidin-1-yl]methanone | 465 | 466 | 5 | A1 |
| 232 | (3-amino-5-{[4-(trifluoromethyl)phenyl]sulfonyl}pyridin-2-yl)[3-(methoxymethyl)-3-methylazetidin-1-yl]methanone | 443 | 444 | 5 | A1 |

TABLE II-continued

List of final compounds

| Cpd Number | Name | MW | Mes | Intermediate | Method |
|---|---|---|---|---|---|
| 233 | (3-amino-5-{[4-(trifluoromethyl)phenyl]sulfonyl}pyridin-2-yl)[(2R)-2-(hydroxymethyl)pyrrolidin-1-yl]methanone | 429 | 430 | 5 | A1 |
| 234 | 3-amino-N-[(2S)-1-hydroxybutan-2-yl]-5-{[4-(trifluoromethyl)phenyl]sulfonyl}pyridine-2-carboxamide | 417 | 418 | 5 | A1 |
| 235 | 3-amino-N-[(3R,4S)-4-hydroxytetrahydro-2H-pyran-3-yl]-5-{[4-(trifluoromethyl)phenyl]sulfonyl}pyridine-2-carboxamide | 445 | 446 | 5 | A1, Chiral separation, first eluting |
| 236 | 3-amino-N-(3,3,3-trifluoro-2-hydroxypropyl)-5-{[3-(trifluoromethoxy)phenyl]sulfonyl}pyridine-2-carboxamide | 473 | 474 | 8 | B1, C1 |
| 237 | 3-amino-5-{[4-(propan-2-yloxy)phenyl]sulfonyl}-N-(3,3,3-trifluoro-2-hydroxypropyl)pyridine-2-carboxamide | 447 | 448 | 8 | B1, C1 |
| 238 | 3-amino-5-[(tetrahydrofuran-2-ylmethyl)sulfonyl]-N-(3,3,3-trifluoro-2-hydroxypropyl)pyridine-2-carboxamide | 397 | 398 | 8 | B1, C1 |
| 239 | 3-amino-N-(2-hydroxy-3-methoxypropyl)-5-{[4-(trifluoromethyl)phenyl]sulfonyl}pyridine-2-carboxamide | 433 | 434 | 5 | A1 |
| 240 | 3-amino-N-[2-(trifluoromethoxy)ethyl]-5-{[4-(trifluoromethyl)phenyl]sulfonyl}pyridine-2-carboxamide | 457 | 458 | 5 | A1 |
| 241 | 3-amino-N-(2,2-difluoro-3-hydroxypropyl)-5-{[4-(trifluoromethyl)phenyl]sulfonyl}pyridine-2-carboxamide | 439 | 440 | 5 | A1 |
| 242 | 3-amino-N-[(2S)-3-(cyclopropylmethoxy)-2-hydroxypropyl]-5-{[4-(trifluoromethoxy)phenyl]sulfonyl}pyridine-2-carboxamide | 489 | 490 | 4 | A1, Chiral separation, first eluting |
| 243 | 3-amino-N-[(2S)-2-hydroxy-3-(propan-2-yloxy)propyl]-5-{[4-(trifluoromethyl)phenyl]sulfonyl}pyridine-2-carboxamide | 461 | 462 | 5 | A1, Chiral separation, first eluting |
| 244 | 3-amino-5-(phenylsulfonyl)-N-(3,3,3-trifluoro-2-hydroxypropyl)pyridine-2-carboxamide | 389 | 390 | 8 | B1, C1, E1 |
| 245 | 3-amino-5-[(4-methylphenyl)sulfonyl]-N-(3,3,3-trifluoro-2-hydroxypropyl)pyridine-2-carboxamide | 403 | 404 | 8 | B1, C1, E1 |
| 246 | 3-amino-5-{[4-(propan-2-yl)phenyl]sulfonyl}-N-(3,3,3-trifluoro-2-hydroxypropyl)pyridine-2-carboxamide | 431 | 432 | 8 | B1, C1, E1 |
| 247 | 3-amino-5-[(4-tert-butylphenyl)sulfonyl]-N-(3,3,3-trifluoro-2-hydroxypropyl)pyridine-2-carboxamide | 445 | 446 | 8 | B1, C1, E1 |
| 248 | 3-amino-N-[(2R)-2-hydroxy-3-(2,2,2-trifluoroethoxy)propyl]-5-{[4-(trifluoromethyl)phenyl]sulfonyl}pyridine-2-carboxamide | 501 | 502 | 5; 15 | A1, Chiral separation, first eluting |
| 249 | 3-amino-N-[(2S)-2-hydroxy-3-(2,2,2-trifluoroethoxy)propyl]-5-{[4-(trifluoromethyl)phenyl]sulfonyl}pyridine-2-carboxamide | 501 | 502 | 5; 15 | A1, Chiral separation, last eluting |
| 250 | 3-amino-6-bromo-5-[(4-fluorophenyl)sulfonyl]-N-[(2R)-3,3,3-trifluoro-2-hydroxypropyl]pyridine-2-carboxamide | 486 | 488-490 | Cpd 36 | F1 |

TABLE II-continued

List of final compounds

| Cpd Number | Name | MW | Mes | Intermediate | Method |
|---|---|---|---|---|---|
| 251 | 3-amino-N-[(2R)-3-(cyclopropylmethoxy)-2-hydroxypropyl]-5-{[4-(trifluoromethoxy)phenyl]sulfonyl}pyridine-2-carboxamide | 489 | 490 | 4 | A1, Chiral separation, last eluting |
| 252 | 3-amino-N-[(2R)-2-hydroxy-3-(propan-2-yloxy)propyl]-5-{[4-(trifluoromethyl)phenyl]sulfonyl}pyridine-2-carboxamide | 461 | 462 | 4 | A1, Chiral separation, last eluting |
| 253 | 3-amino-5-(phenylsulfonyl)-N-[(2R)-3,3,3-trifluoro-2-hydroxypropyl]pyridine-2-carboxamide | 389 | 390 | 12; 19 | A1 |
| 254 | 3-amino-5-[(3-fluorophenyl)sulfonyl]-N-[(2R)-3,3,3-trifluoro-2-hydroxypropyl]pyridine-2-carboxamide | 407 | 408 | 18; 19 | A1 |
| 255 | [3-amino-5-(phenylsulfonyl)pyridin-2-yl][3-hydroxy-3-(trifluoromethyl)azetidin-1-yl]methanone | 401 | 402 | 12 | A1 |
| 256 | {3-amino-5-[(3-fluorophenyl)sulfonyl]pyridin-2-yl}[3-hydroxy-3-(trifluoromethyl)azetidin-1-yl]methanone | 419 | 420 | 18 | A1 |
| 257 | 3-amino-N-[(3S,4R)-4-hydroxytetrahydro-2H-pyran-3-yl]-5-{[4-(trifluoromethyl)phenyl]sulfonyl}pyridine-2-carboxamide | 445 | 446 | 5 | A1, Chiral separation, last eluting |
| 258 | 3-amino-6-cyclopropyl-N-(2-hydroxyethyl)-5-{[4-(trifluoromethyl)phenyl]sulfonyl}pyridine-2-carboxamide | 429 | 430 | 22 | B1, C1, A1 |
| 259 | 3-amino-6-(4-fluorophenyl)-5-[(4-fluorophenyl)sulfonyl]-N-[(2R)-3,3,3-trifluoro-2-hydroxypropyl]pyridine-2-carboxamide | 501 | 502 | 21 | G1, B1, C1, A1 |
| 260 | 3-amino-6-cyclopropyl-N-(2-hydroxyethyl)-5-(phenylsulfonyl)pyridine-2-carboxamide | 361 | 362 | 21 | B1, G1, C1, A1 |
| 261 | 3-amino-5-(cyclopentylsulfonyl)-6-(4-fluorophenyl)-N-[(2S)-2-hydroxypropyl]pyridine-2-carboxamide | 421 | 422 | | B1, H1, C2, A1 |
| 262 | 3-amino-6-(4-fluorophenyl)-5-[(2-hydroxyethyl)sulfonyl]-N-[(2S)-2-hydroxypropyl]pyridine-2-carboxamide | 397 | 398 | | B1, C2, H1, A1 |
| 263 | 3-amino-5-(ethylsulfonyl)-6-(4-fluorophenyl)-N-[(2S)-2-hydroxypropyl]pyridine-2-carboxamide | 381 | 382 | | B1, H1, C2, A1 |
| 264 | 3-amino-6-(4-fluorophenyl)-N-[(2S)-2-hydroxypropyl]-5-(propan-2-ylsulfonyl)pyridine-2-carboxamide | 395 | 396 | | B1, H1, C2, A1 |
| 265 | 3-amino-6-(4-fluorophenyl)-N-[(2S)-2-hydroxypropyl]-5-[(2-methoxyethyl)sulfonyl]pyridine-2-carboxamide | 411 | 412 | | B1, H1, C2, A1 |
| 266 | 3-amino-N-[(2S)-2-hydroxypropyl]-5-{[(2S)-2-methylpyrrolidin-1-yl]sulfonyl}pyridine-2-carboxamide | 342 | 343 | 23 | D2 |
| 267 | 3-amino-5-[(4-fluorobenzyl)sulfamoyl]-N-[(2S)-2-hydroxypropyl]pyridine-2-carboxamide | 382 | 383 | 23 | D2 |
| 268 | 3-amino-5-{[2-(hydroxymethyl)pyrrolidin-1-yl]sulfonyl}-N-[(2S)-2-hydroxypropyl]pyridine-2-carboxamide | 358 | 359 | 23 | D2 |
| 269 | 3-amino-5-[(4-fluorobenzyl)(methyl)sulfamoyl]-N-[(2S)-2-hydroxypropyl]pyridine-2-carboxamide | 396 | 397 | 23 | D2 |
| 270 | 3-amino-5-{[(2S)-2-methylpyrrolidin-1-yl]sulfonyl}-N-[2-oxo-2-(propan-2-ylamino)ethyl]pyridine-2-carboxamide | 383 | 384 | 24 | A4 |

TABLE II-continued

List of final compounds

| Cpd Number | Name | MW | Mes | Intermediate | Method |
|---|---|---|---|---|---|
| 271 | 1-[(3-amino-5-{[(2S)-2-methylpyrrolidin-1-yl]sulfonyl}pyridin-2-yl)carbonyl]azetidine-3-carboxamide | 367 | 368 | 24 | A4 |
| 272 | (3-amino-5-{[(2S)-2-methylpyrrolidin-1-yl]sulfonyl}pyridin-2-yl)(3-hydroxyazetidin-1-yl)methanone | 340 | 341 | 24 | A4 |
| 273 | 3-amino-N-(3-fluoro-2-hydroxypropyl)-5-{[4-(trifluoromethoxy)phenyl]sulfonyl}pyridine-2-carboxamide | 437 | 438 | 4, 29 | A1 |
| 274 | 3-amino-6-cyclopropyl-5-[(4-fluorophenyl)sulfonyl]-N-[(2S)-2-hydroxypropyl]pyridine-2-carboxamide | 393 | 394 | 27 | B1, C2, A1 |
| 275 | 3-amino-6-cyclopropyl-5-(ethylsulfonyl)-N-[(2S)-2-hydroxypropyl]pyridine-2-carboxamide | 327 | 328 | 27 | B1, H1, C2, A1 |
| 276 | 3-amino-N-(2-hydroxy-3-methoxypropyl)-5-{[(2S)-2-methylpyrrolidin-1-yl]sulfonyl}pyridine-2-carboxamide | 372 | 373 | 24 | A4 |
| 277 | 3-amino-N-[(2S)-2-hydroxypropyl]-5-[(2-methoxyethyl)(methyl)sulfamoyl]pyridine-2-carboxamide | 346 | 347 | 23 | D2 |
| 278 | 3-amino-5-[cyclobutyl(methyl)sulfamoyl]-N-[(2S)-2-hydroxypropyl]pyridine-2-carboxamide | 342 | 343 | 23 | D2 |
| 279 | 3-amino-N-(3,3-difluoro-2-hydroxypropyl)-5-{[4-(trifluoromethoxy)phenyl]sulfonyl}pyridine-2-carboxamide | 455 | 456 | 1 | A1 |
| 280 | 3-amino-N-[(2S)-2-hydroxypropyl]-6-methoxy-5-{[4-(trifluoromethoxy)phenyl]sulfonyl}pyridine-2-carboxamide | 449 | 450 | 28 | B2, A4 |
| 281 | 3-amino-N-[(4-methoxypyrimidin-2-yl)methyl]-5-{[(2S)-2-methylpyrrolidin-1-yl]sulfonyl}pyridine-2-carboxamide | 406 | 407 | 25 | D2 |
| 282 | 3-amino-5-{[(2S)-2-methylpyrrolidin-1-yl]sulfonyl}-N-[(6-oxo-1,6-dihydropyrimidin-2-yl)methyl]pyridine-2-carboxamide | 392 | 393 | Compound 281 | Specific example |
| 283 | 3-amino-6-(dimethylamino)-N-[(2S)-2-hydroxypropyl]-5-{[4-(trifluoromethoxy)phenyl]sulfonyl}pyridine-2-carboxamide | 462 | 463 | 28 | B3, A4 |
| 284 | 3-amino-6-(3-fluorophenoxy)-N-[(2S)-2-hydroxypropyl]-5-{[4-(trifluoromethoxy)phenyl]sulfonyl}pyridine-2-carboxamide | 529 | 530 | 28 | B2, A4 |
| 285 | 3-amino-6-(cyclopropylamino)-N-[(2S)-2-hydroxypropyl]-5-{[4-(trifluoromethoxy)phenyl]sulfonyl}pyridine-2-carboxamide | 474 | 475 | 28 | B3, A4 |
| 286 | 3-amino-N'-(methoxyacetyl)-5-{[4-(trifluoromethoxy)phenyl]sulfonyl}pyridine-2-carbohydrazide | 448 | 449 | 4 | A3 |
| 287 | 3-amino-N'-(hydroxyacetyl)-5-{[4-(trifluoromethoxy)phenyl]sulfonyl}pyridine-2-carbohydrazide | 434 | 435 | 4 | A3 |
| 288 | 3-amino-N-[(2S)-2-hydroxypropyl]-6-(2-methoxyethoxy)-5-{[4-(trifluoromethoxy)phenyl]sulfonyl}pyridine-2-carboxamide | 493 | 494 | 28 | B2, A4 |
| 289 | 3-amino-6-[2-(dimethylamino)ethoxy]-N-[(2S)-2-hydroxypropyl]-5-{[4-(trifluoromethoxy)phenyl]sulfonyl}pyridine-2-carboxamide | 506 | 507 | 28 | B2, A4 |
| 290 | 3-amino-6-cyclopropyl-N-[(2S)-2-hydroxypropyl]-5-{[4-(trifluoromethoxy)phenyl]sulfonyl}pyridine-2-carboxamide | 459 | 460 | 22 | B1, C1, A1 |

TABLE II-continued

List of final compounds

| Cpd Number | Name | MW | Mes | Intermediate | Method |
|---|---|---|---|---|---|
| 291 | 3-amino-N-(1H-pyrazol-3-yl)-5-{[4-(trifluoromethoxy)phenyl]sulfonyl}pyridine-2-carboxamide | 427 | 428 | 4 | A1 |
| 292 | 3-amino-N-[1-(hydroxymethyl)cyclopropyl]-5-{[4-(trifluoromethyl)phenyl]sulfonyl}pyridine-2-carboxamide | 415 | 416 | 5 | A1 |
| 293 | 3-amino-N-[(1S,2S)-2-methoxycyclopentyl]-5-{[4-(trifluoromethyl)phenyl]sulfonyl}pyridine-2-carboxamide | 443 | 444 | 5 | A1 |
| 294 | (3-amino-5-{[4-(trifluoromethyl)phenyl]sulfonyl}pyridin-2-yl)(3-fluoro-3-methylazetidin-1-yl)methanone | 417 | 418 | 5 | A1 |
| 295 | (3-amino-5-{[4-(trifluoromethyl)phenyl]sulfonyl}pyridin-2-yl)(6-oxa-2-azaspiro[3.5]non-2-yl)methanone | 455 | 456 | 5 | A1 |
| 296 | 3-amino-N-[(2R)-2-hydroxy-3-methoxypropyl]-5-(phenylsulfonyl)pyridine-2-carboxamide | 365 | 366 | 12; 14 | A1 |
| 297 | 3-amino-5-{[4-(trifluoromethoxy)phenyl]sulfonyl}pyridine-2-carboxamide | 361 | 362 | 4 | A1 |
| 298 | 3-amino-6-bromo-5-[(4-fluorophenyl)sulfonyl]pyridine-2-carboxamide | 372 | 373 | 31 | F1 |

TABLE III

NMR Data of Representative Compounds

| Cpd # | $^1$H NMR data |
|---|---|
| 1 | (300 MHz, DMSO-$d_6$) δ ppm 8.39 (1 H, t), 8.24 (1 H, d), 8.13 (2 H, d), 7.74 (1 H, d), 7.65 (2 H, d), 7.27 (2 H, s br), 4.65 (1 H, s), 3.21 (2 H, d), 1.07 (6 H, s). |
| 2 | (400 MHz, DMSO-$d_6$) δ ppm 8.52 (1 H, t), 8.25 (1 H, d, J = 2.0 Hz), 8.14 (2 H, m), 7.76 (1 H, d, J = 2.0 Hz), 7.65 (2 H, d, J = 8.0 Hz), 7.27 (2 H, s br), 6.23 (1 H, s), 3.62 (1 H, dd), 3.43 (1 H, dd), 1.22 (3 H, s). |
| 3 | (400 MHz, DMSO-$d_6$) δ ppm 8.53 (1 H, m), 8.22 (1 H, J = 2.0 Hz, d), 8.12 (2 H, m), 7.73 (1 H, J = 2 Hz, d), 7.65 (2 H, J = 8 Hz, d), 7.27 (2 H, s), 5.03 (1 H, J = 5.2 Hz, d), 3.74 (1 H, m), 3.39 (1 H, m), 3.24 (5 H, m), 3.19 (1 H, m). |
| 4 | (400 MHz, DMSO-$d_6$) δ ppm 8.25 (1 H, t), 8.12 (2 H, m), 7.65 (3 H, m), 6.39 (2 H, d, J = 20 Hz), 4.92 (1 H, dd), 4.26 (1 H, dd), 3.60 (3 H, m), 3.40 (1 H, m), 1.88 (1 H, m), 1.78 (1 H, m). |
| 6 | (300 MHz, DMSO-$d_6$) δ ppm 8.39 (1 H, t), 8.24 (1 H, d), 8.13 (2 H, d), 7.74 (1 H, d), 7.65 (2 H, d), 7.27 (2 H, s br), 6.44 (1 H, d), 4.20 (1 H, m), 3.57 (1 H, m), 3.38 (1 H, m). |
| 10 | (400 MHz, DMSO-$d_6$) δ ppm 8.39 (1 H, t), 8.23 (1 H, d, J = 2.0 Hz), 8.07 (2 H, m), 7.72 (1 H, d, J = 2.0 Hz), 7.51 (2 H, m), 7.26 (2 H, s br), 4.66 (1 H, s), 3.21 (2 H, d, J = 6.0 Hz), 1.08 (6 H, s). |
| 11 | (400 MHz, DMSO-$d_6$) δ ppm 8.39 (1 H, t), 8.26 (1 H, d, J = 2.0 Hz), 8.21 (2 H, m), 8.04 (2 H, m), 7.76 (1 H, d, J = 2.0 Hz), 7.29 (2 H, s br), 4.66 (1 H, s), 3.21 (2 H, d, J = 6.0 Hz), 1.08 (6 H, s). |
| 13 | (300 MHz, DMSO-$d_6$) δ ppm 8.39 (1 H, t), 8.24 (1 H, d), 8.13 (2 H, d), 7.74 (1 H, d), 7.65 (2 H, d), 7.27 (2 H, s br), 4.69 (1 H, t), 3.70 (1 H, m), 3.53 (1 H, m), 3.45 (1 H, m), 1.90 (1 H, m), 0.89 (3 H, d), 0.83 (3 H, d). |
| 14 | (300 MHz, DMSO-$d_6$) δ ppm 8.59 (1 H, t), 8.21 (1 H, d), 8.13 (2 H, d), 7.72 (1 H, d), 7.66 (2 H, d), 7.27 (2 H, s br), 4.75 (1 H, t), 3.49 (2 H, t), 3.31 (2 H, t). |
| 18 | (400 MHz, DMSO-$d_6$) δ ppm 8.65 (1 H, t), 8.22 (1 H, d, J = 2.0 Hz), 8.13 (2 H, m), 7.73 (1 H, d, J = 2.0 Hz), 7.65 (2 H, m), 7.27 (2 H, s br), 4.72 (1 H, t), 3.15 (4 H, d, J = 6.4 Hz), 0.79 (6 H, m). |
| 19 | (400 MHz, DMSO-$d_6$) δ ppm 8.52 (1 H, t), 8.24 (1 H, d, J = 2.0 Hz), 8.07 (2 H, m), 7.74 (1 H, d, J = 2.0 Hz), 7.52 (2 H, m), 7.26 (2 H, s br), 6.24 (1 H, s), 3.62 (1 H, m), 3.43 (1 H, m), 1.22 (3 H, s). |
| 20 | (300 MHz, DMSO-$d_6$) δ ppm 8.52 (1H, t), 8.23 (1 H, d), 8.12 (2 H, d), 7.73 (1 H, d), 7.65 (2 H, d), 7.27 (2 H, s, br), 4.80 (1 H, d), 3.75 (1 H, m), 3.28 (1 H, m), 3.12 (1 H, m), 1.03 (1 H, d). |
| 21 | (300 MHz, DMSO-$d_6$) δ ppm 8.39 (1 H, t), 8.24 (1 H, d), 8.13 (2 H, d), 7.74 (1 H, d), 7.65 (2 H, d), 7.27 (2 H, s br), 3.75 (1 H, m), 3.25 (1 H, m), 3.13 (1 H, m), 1.03 (3 H, d). |

TABLE III-continued

NMR Data of Representative Compounds

| Cpd # | $^1$H NMR data |
|---|---|
| 25 | (400 MHz, DMSO-$d_6$) δ ppm 8.74 (1 H, t), 8.21 (1 H, d, J = 2.0 Hz), 8.07 (2 H, m), 7.72 (1 H, d, J = 2.0 Hz), 7.52 (2 H, m), 7.26 (2 H, s br), 6.45 (1 H, s), 4.21 (1 H, m), 3.56 (1 H, m), 3.39 (1 H, m). |
| 26 | (400 MHz, DMSO-$d_6$) δ ppm 8.74 (1 H, t), 8.23 (1 H, d, J = 2.0 Hz), 8.13 (2 H, m), 7.75 (1 H, d, J = 2.0 Hz), 7.65 (2 H, m), 7.27 (2 H, s br), 6.45 (1 H, d, J = 6.4 Hz), 4.21 (1 H, m), 3.56 (1 H, m), 3.39 (1 H, m). |
| 28 | (400 MHz, DMSO-$d_6$) δ ppm 8.53 (1 H, m), 8.22 (1 H, J = 2 Hz, d), 8.12 (2 H, m), 7.73 (1 H, J = 2 Hz, d), 7.65 (2 H, J = 8 Hz, d), 7.27 (2 H, s), 5.15 (1 H, s), 3.78 (1 H, m), 3.73 (1 H, m), 3.57 (1 H, J = 9.2 Hz, d), 3.44 (3 H, m), 1.86 (1 H, m), 1.79 (1 H, m). |
| 29 | (400 MHz, DMSO-$d_6$) δ ppm 8.53 (1 H, m), 8.22 (1 H, J = 2 Hz, d), 8.12 (2 H, m), 7.73 (1 H, J = 2.4 Hz, d), 7.65 (2 H, J = 8.4 Hz, d), 7.27 (2 H, s), 4.74 (1 H, s), 3.56 (4 H, m), 3.28 (2 H, J = 6.4 Hz, d), 1.47 (2 H, m), 1.38 (2 H, m). |
| 31 | (400 MHz, DMSO-$d_6$) δ ppm 8.54 (1 H, t), 8.22 (1 H, d, J = 2.0 Hz), 8.13 (2 H, m), 7.73 (1 H, d, J = 2.0 Hz), 7.66 (2 H, m), 7.28 (2 H, s br), 5.06 (1 H, d, J = 5.2 Hz), 3.40 (1 H, m), 3.30 (2 H, m), 3.19 (3 H, m), 0.97 (1 H, m), 0.41 (2 H, m), 0.13 (2 H, m). |
| 32 | (400 MHz, DMSO-$d_6$) δ ppm 8.20 (1 H, d, J = 2.0 Hz), 8.12 (2 H, m), 7.69 (1 H, d, J = 2.0 Hz), 7.65 (2 H, d, J = 8.0 Hz), 7.10 (2 H, s br), 5.65 (1 H, s br), 4.65 (1 H, m), 4.44 (1 H, m), 4.21 (2 H, m), 3.75 (1 H, dd). |
| 34 | (400 MHz, DMSO-$d_6$) δ ppm 8.53 (1 H, m), 8.22 (1 H, J = 2 Hz, d), 8.12 (2 H, m), 7.73 (1 H, J = 2 Hz, d), 7.65 (2 H, J = 8 Hz, d), 7.27 (2 H, s), 4.44 (1 H, m), 3.48 (2 H, m), 3.13 (2 H, J = 6.8 Hz, d), 1.38 (2 H, m), 0.85 (6 H, s). |
| 36 | (300 MHz, DMSO-$d_6$) δ ppm 8.74 (1 H, t), 8.21 (1 H, d), 8.07 (2 H, m), 7.73 (1 H, d), 7.50 (2 H, m), 7.26 (2 H, s, br), 6.45 (1 H, d), 4.21 (1 H, m), 3.56 (1 H, m), 3.38 (1 H, m). |
| 39 | (300 MHz, DMSO-$d_6$) δ ppm 8.39 (1H, t), 8.26 (1H, d), 7.51 (2H, m), 7.75 (2H, m), 7.63 (1H, m), 7.26 (2H, s), 4.65 (1H, s), 3.21 (2H, d), 1.08 (6H, s). |
| 40 | (300 MHz, DMSO-$d_6$) δ ppm 8.19 (1 H, d), 8.13 (2 H, d), 7.75 (1 H, d), 7.65 (2 H, d), 7.20 (2 H, s, br), 4.91 (2 H, t), 4.43 (2 H, t). |
| 41 | (400 MHz, DMSO-$d_6$) δ ppm 8.22 (d, J = 2.0 Hz, 1H), 8.16-8.05 (m, 2H), 7.72 (d, J = 2.1 Hz, 1H), 7.65-7.54 (m, 2H), 7.27-7.17 (m, 2H), 7.11 (d, J = 8.0 Hz, 2H), 5.02-4.90 (m, 1H), 3.73 (d, J = 5.7 Hz, 2H), 2.26 (s, 3H). |
| 42 | (400 MHz, DMSO-$d_6$) δ ppm 8.20 (1 H, d, J = 2.0 Hz), 8.13 (2 H, m), 7.70 (1 H, d, J = 2.0 Hz), 7.65 (2 H, m), 7.11 (2 H, s br), 4.66 (1 H, m), 4.28 (1 H, m), 4.18 (2 H, m), 3.82 (1 H, m), 3.21 (1 H, s). |
| 43 | (400 MHz, DMSO-$d_6$) δ ppm 8.21 (d, J = 2.1 Hz, 1H), 8.14-8.06 (m, 2H), 7.73 (d, J = 2.1 Hz, 1H), 7.60 (d, J = 8.5 Hz, 2H), 4.40 (q, J = 6.9 Hz, 1H), 3.11 (q, J = 7.2 Hz, 2H), 1.33 (d, J = 6.9 Hz, 3H), 1.03 (t, J = 7.2 Hz, 3H). |
| 44 | (400 MHz, DMSO-$d_6$) δ ppm 8.19 (d, J = 2.0 Hz, 1H), 8.14-8.01 (m, 2H), 7.72 (d, J = 2.1 Hz, 1H), 7.60 (d, J = 8.4 Hz, 2H), 3.92 (p, J = 5.4 Hz, 1H), 3.56 (qd, J = 10.9, 5.3 Hz, 4H). |
| 45 | (400 MHz, DMSO-$d_6$) δ ppm 8.18 (d, J = 1.9 Hz, 1H), 8.15-8.04 (m, 2H), 7.70 (d, J = 2.1 Hz, 1H), 7.65-7.54 (m, 2H), 3.43 (t, J = 6.4 Hz, 2H), 3.30 (d, J = 2.3 Hz, 2H), 1.64-1.39 (m, 4H). |
| 46 | (400 MHz, DMSO-$d_6$) δ ppm 8.18 (d, J = 2.0 Hz, 1H), 8.13-8.02 (m, 2H), 7.71 (d, J = 2.0 Hz, 1H), 7.62-7.50 (m, 2H), 4.00 (dq, J = 8.2, 5.2 Hz, 1H), 3.60-3.38 (m, 2H), 1.60 (dp, J = 13.4, 6.7 Hz, 1H), 1.43 (ddd, J = 8.7, 5.8, 3.2 Hz, 2H), 0.88 (d, J = 6.5 Hz, 6H). |
| 47 | (400 MHz, DMSO-$d_6$) δ ppm 8.23 (d, J = 2.0 Hz, 1H), 8.18-8.04 (m, 2H), 7.75 (d, J = 2.0 Hz, 1H), 7.60 (d, J = 8.4 Hz, 2H), 4.27 (s, 1H), 2.61 (s, 3H), 0.95 (s, 9H). |
| 48 | (400 MHz, DMSO-$d_6$) δ ppm 8.21 (d, J = 2.1 Hz, 1H), 8.17-8.05 (m, 2H), 7.73 (d, J = 2.0 Hz, 1H), 7.65-7.46 (m, 2H), 3.87 (s, 2H), 3.12 (q, J = 7.3 Hz, 2H), 1.03 (t, J = 7.2 Hz, 3H). |
| 49 | (400 MHz, DMSO-$d_6$) δ ppm 8.23 (d, J = 2.0 Hz, 1H), 8.17-8.06 (m, 2H), 7.75 (d, J = 2.1 Hz, 1H), 7.60 (d, J = 8.4 Hz, 2H), 4.37-4.26 (m, 1H), 2.11 (h, J = 6.7 Hz, 1H), 0.91 (dd, J = 14.7, 6.8 Hz, 6H). |
| 50 | (400 MHz, DMSO-$d_6$) δ ppm 8.19 (d, J = 2.1 Hz, 1H), 8.15-8.05 (m, 2H), 7.72 (d, J = 2.0 Hz, 1H), 7.60 (d, J = 8.4 Hz, 2H), 3.65 (p, J = 5.8 Hz, 1H), 3.52-3.34 (m, 3H). |
| 52 | (400 MHz, DMSO-$d_6$) δ ppm 8.84 (1 H, t), 8.20 (1 H, d, J = 2.0 Hz), 8.13 (2 H, m), 7.72 (1 H, d, J = 2.0 Hz), 7.65 (2 H, m), 7.27 (2 H, s br), 6.23 (1 H, m), 3.98 (1 H, m), 3.42 (2 H, m), 1.85 (1 H, m), 1.65 (1 H, m). |
| 55 | (400 MHz, DMSO-$d_6$) δ ppm 8.17 (d, J = 2.0 Hz, 1H), 8.14-8.04 (m, 2H), 7.71 (d, J = 2.1 Hz, 1H), 7.60 (d, J = 8.4 Hz, 2H), 4.27 (h, J = 6.3 Hz, 1H), 2.45-2.25 (m, 2H), 1.20 (d, J = 6.5 Hz, 3H). |
| 56 | (400 MHz, DMSO-$d_6$) δ ppm 8.21 (d, J = 2.0 Hz, 1H), 8.16-8.05 (m, 2H), 7.74 (d, J = 2.0 Hz, 1H), 7.60 (d, J = 8.4 Hz, 2H), 4.44 (t, J = 6.6 Hz, 1H), 1.63 (dd, J = 6.4, 2.6 Hz, 3H), 0.94-0.85 (m, 6H). |
| 57 | (400 MHz, DMSO-$d_6$) δ ppm 8.26 (d, J = 2.0 Hz, 1H), 8.20-8.12 (m, 2H), 7.75 (d, J = 2.0 Hz, 1H), 7.72-7.62 (m, 2H), 3.84 (d, J = 5.9 Hz, 2H), 1.06 (d, J = 6.5 Hz, 6H). |
| 58 | (400 MHz, DMSO-$d_6$) δ ppm 8.23 (d, J = 2.0 Hz, 1H), 8.17-8.05 (m, 2H), 7.79-7.67 (m, 1H), 7.67-7.52 (m, 2H), 3.88 (s, 2H), 2.66 (tt, J = 7.4, 3.9 Hz, 1H), 0.64 (t, J = 6.3 Hz, 2H), 0.47 (d, J = 4.4 Hz, 2H). |

TABLE III-continued

NMR Data of Representative Compounds

| Cpd # | $^1$H NMR data |
|---|---|
| 60 | (400 MHz, DMSO-$d_6$) δ ppm 8.19 (1 H, d, J = 2.0 Hz), 8.13 (2 H, m), 7.70 (1 H, d, J = 2.0 Hz), 7.65 (2 H, m), 7.12 (2 H, s br), 4.51 (1 H, m), 4.28 (1 H, m), 4.02 (1 H, m), 3.83 (1 H, m), 3.57 (4 H, m), 3.07 (1 H, m), 2.29 (4 H, m). |
| 62 | (400 MHz, DMSO-$d_6$) δ ppm 8.20 (1 H, d, J = 2.0 Hz), 8.12 (2 H, m), 7.70 (1 H, d, J = 2.0 Hz), 7.66 (2 H, m), 7.15 (2 H, s br), 4.68 (1 H, t), 4.53 (1 H, m), 4.17 (1 H, m), 4.08 (1 H, m), 3.70 (1 H, m), 2.84 (6 H, m). |
| 66 | (400 MHz, DMSO-$d_6$) δ ppm 8.20 (1 H, d, J = 2.0 Hz), 8.13 (2 H, m), 7.67 (3 H, m), 7.13 (2 H, s br), 4.79 (1 H, t), 4.50 (1 H, m), 4.22 (1 H, m), 4.00 (1 H, m), 3.73 (1 H, m), 3.51 (2 H, m), 2.66 (1 H, m). |
| 68 | (400 MHz, DMSO-$d_6$) δ ppm 8.20 (1 H, d, J = 2.0 Hz), 8.13 (2 H, m), 7.69 (1 H, d, J = 2.0 Hz), 7.66 (2 H, m), 7.13 (2 H, s br), 4.66 (6 H, s), 4.18 (2 H, s). |
| 69 | (400 MHz, DMSO-$d_6$) δ ppm 8.54 (1 H, t), 8.23 (1 H, d, J = 2.0 Hz), 8.13 (2 H, m), 7.73 (1 H, d, J = 2.0 Hz), 7.66 (2 H, m), 7.28 (2 H, s br), 5.06 (1 H, d, J = 5.2 Hz), 3.73 (1 H, m), 3.37 (1 H, m), 3.26 (2 H, d, J = 6.0 Hz), 3.24 (3 H, s), 3.17 (1 H, m). |
| 70 | (300 MHz, DMSO-$d_6$) δ ppm 8.53 (1 H, t), 8.24 (1 H, d), 8.20 (2 H, d), 8.04 (2 H, d), 7.75 (1 H, d), 7.28 (2 H, s br), 5.03 (1 H, d), 3.74 (1 H, m), 3.40 (1 H, m), 3.25 (2 H, d), 3.24 (3 H, s). |
| 71 | (400 MHz, DMSO-$d_6$) δ ppm 8.58 (1 H, t), 8.21 (1 H, d, J = 8.4 Hz), 8.17 (1 H, m), 7.77 (1 H, m), 7.72 (1 H, m), 7.55 (1 H, m), 7.33 (2 H, s br), 5.05 (1 H, m), 3.74 (1 H, m), 3.38 (1 H, m), 3.26 (2 H, d, J = 5.6 Hz), 3.24 (3 H, s), 3.18 (1 H, m). |
| 72 | (400 MHz, DMSO-$d_6$) δ ppm 8.81 (1 H, t), 8.18 (1 H, d, J = 2.4 Hz), 8.06 (1 H, m), 7.70 (1 H, d, J = 2.0 Hz), 7.50 (2 H, m), 7.24 (2 H, s br), 6.21 (1 H, d, J = 6.8 Hz), 3.98 (1 H, m), 3.40 (2 H, m), 1.85 (1 H, m), 1.65 (1 H, m). |
| 75 | (400 MHz, DMSO-$d_6$) δ ppm 8.64 (1 H, t), 8.24 (1 H, m), 8.11 (1 H, d, J = 2.0 Hz), 7.91 (1 H, m), 7.70 (2 H, m), 7.59 (1 H, m), 7.30 (2 H, s br), 4.76 (1 H, m), 3.49 (2 H, m), 3.30 (2 H, m). |
| 76 | (400 MHz, DMSO-$d_6$) δ ppm 8.24 (1 H, m), 8.08 (1 H, d, J = 2.4 Hz), 7.91 (1 H, m), 7.72 (1 H, m), 7.65 (1 H, d, J = 2.0 Hz), 7.60 (1 H, m), 7.11 (2 H, s br), 5.66 (1 H, m), 4.64 (1 H, m), 4.44 (1 H, m), 4.22 (2 H, m), 3.75 (1 H, m). |
| 77 | (300 MHz, DMSO-$d_6$) δ ppm 8.20 (1 H, t), 8.15 (1 H, d), 7.72 (3 H, m), 7.55 (1 H, d), 7.14 (2 H, s, br), 5.66 (1 H, d), 4.66 (1 H, m), 4.44 (1 H, m), 4.23 (2 H, m), 3.75 (1 H, m). |
| 78 | (300 MHz, DMSO-$d_6$) δ ppm 8.24 (1 H, d), 8.07 (1 H, d), 7.92 (1 H, t), 7.72 (2 H, m), 7.61 (1 H, d), 7.23 (2 H, s, br), 4.90 (2 H, t), 4.44 (2 H, t). |
| 79 | (400 MHz, DMSO-$d_6$) δ ppm 8.22 (1 H, d, J = 2.0 Hz), 8.13 (2 H, m), 7.74 (1 H, d, J = 2.0 Hz), 7.65 (2 H, m), 7.39 (1 H, s), 7.18 (2 H, s br), 4.75 (1 H, m), 4.50 (1 H, m), 4.24 (1 H, m), 4.00 (1 H, m). |
| 81 | (400 MHz, DMSO-$d_6$) δ ppm 8.79 (1 H, t), 8.25 (1 H, m), 8.12 (1 H, d, J = 2.0 Hz), 7.92 (1 H, m), 7.72 (2 H, m), 7.60 (1 H, m), 7.30 (2 H, s br), 6.44 (1 H, s br), 4.22 (1 H, m), 3.57 (1 H, m), 3.39 (1 H, m). |
| 82 | (400 MHz, DMSO-$d_6$) δ ppm 8.57 (1 H, t), 8.24 (1 H, m), 8.11 (1 H, d, J = 2.0 Hz), 7.92 (1 H, m), 7.71 (2 H, m), 7.60 (1 H, m), 7.30 (2 H, s br), 3.76 (1 H, m), 3.27 (2 H, m), 3.14 (1 H, m), 1.04 (1 H, d, J = 6.4 Hz). |
| 83 | (400 MHz, DMSO-$d_6$) δ ppm 8.24 (2 H, m), 8.11 (1 H, d, J = 2.4 Hz), 7.92 (1 H, m), 7.72 (2 H, m), 7.59 (1 H, m), 7.32 (2 H, s br), 3.93 (2 H, m), 3.65 (1 H, m), 3.51 (4 H, m), 1.77 (1 H, m), 1.64 (1 H, m). |
| 84 | (300 MHz, DMSO-$d_6$) δ ppm 8.77 (1 H, t), 8.04 (1 H, d), 7.58 (1 H, d), 7.24 (2 H, s), 6.47 (1 H, d), 4.23 (1 H, m), 3.60 (1 H, m), 3.39 (1 H, m), 3.17 (4 H, m), 2.09 (4 H, m). |
| 85 | (300 MHz, DMSO-$d_6$) δ ppm 8.24 (1 H, d), 8.09 (1 H, d), 7.92 (1 H, t), 7.72 (2 H, m), 7.60 (1 H, d), 7.21 (2 H, s, br), 4.73 (1 H, d), 4.49 (1 H, d), 4.25 (1 H, d), 4.01 (1 H, d). |
| 86 | (400 MHz, DMSO-$d_6$) δ ppm 8.20 (1 H, d, J = 2.0 Hz), 8.13 (2 H, m), 7.70 (1 H, d, J = 2.4 Hz), 7.65 (2 H, m), 7.11 (2 H, s br), 5.56 (1 H, s), 4.26 (2 H, m), 3.80 (2 H, m), 1.15 (1 H, m), 0.39 (2 H, m), 0.31 (2 H, m). |
| 87 | (400 MHz, DMSO-$d_6$) δ ppm 8.52 (1 H, t), 8.23 (1 H, d, J = 2.4 Hz), 8.13 (2 H, m), 7.73 (1 H, d, J = 2.0 Hz), 7.66 (2 H, m), 7.27 (2 H, s br), 4.72 (1 H, s), 3.63 (1 H, m), 3.33 (1 H, m), 3.10 (1 H, m), 1.73 (1 H, m), 1.26 (1 H, m), 1.13 (1 H, m), 0.84 (6 H, m). |
| 89 | (400 MHz, DMSO-$d_6$) δ ppm 8.20 (1 H, d, J = 2.0 Hz), 8.12 (2 H, m), 7.70 (1 H, d, J = 2.4 Hz), 7.65 (2 H, m), 7.11 (2 H, s br), 5.60 (1 H, s), 4.32 (2 H, m), 3.85 (2 H, m), 1.35 (3 H, s). |
| 90 | (400 MHz, DMSO-$d_6$) δ ppm 8.53 (1 H, t), 8.21 (1 H, d, J = 2.0 Hz), 8.14 (2 H, m), 7.73 (1 H, d, J = 2.4 Hz), 7.64 (1 H, m), 7.27 (2 H, s br), 4.99 (1 H, s), 3.69 (1 H, m), 3.52 (1 H, m), 3.60 (4 H, m br), 1.06 (6 H, dd). |
| 91 | (300 MHz, DMSO-$d_6$) δ ppm 8.22 (1 H, d), 8.20 (2 H, d), 8.05 (2 H, d), 7.71 (1 H, d), 7.13 (2 H, s br), 5.22 (1 H, s br), 4.32 (2 H, m), 3.87 (2 H, m), 1.35 (3 H, s). |
| 92 | (400 MHz, DMSO-$d_6$) δ ppm 8.52 (1 H, t), 8.23 (1 H, d, J = 2.0 Hz), 8.20 (2 H, d, J = 8.4 Hz), 8.04 (2 H, d, J = 8.4 Hz), 7.75 (1 H, d, J = 2.0 Hz), 7.28 (2 H, s br), 4.99 (1 H, s), 3.68 (1 H, m), 3.52 (1 H, m), 3.60 (4 H, m br), 1.06 (6 H, dd). |
| 93 | (400 MHz, DMSO-$d_6$) δ ppm 8.22 (d, J = 2.0 Hz, 1H), 8.16-8.05 (m, 2H), 7.74 (d, J = 2.1 Hz, 1H), 7.65-7.56 (m, 2H), 4.36 (dd, J = 7.3, 5.5 Hz, 1H), 1.92-1.67 (m, 2H), 0.87 (t, J = 7.4 Hz, 3H). |
| 96 | (400 MHz, DMSO-$d_6$) δ ppm 8.22 (d, J = 2.1 Hz, 1H), 8.20-8.00 (m, 2H), 7.72 (d, J = 2.1 Hz, 1H), 7.60 (d, J = 8.6 Hz, 2H), 7.38-7.19 (m, 2H), 6.93-6.79 (m, 2H), 4.94 (t, J = 5.8 Hz, 1H), 3.72 (d, J = 5.7 Hz, 5H). |

TABLE III-continued

NMR Data of Representative Compounds

| Cpd # | $^1$H NMR data |
|---|---|
| 98 | (300 MHz, DMSO-$d_6$) δ ppm 8.56 (1 H, t), 8.30 (1 H, t), 8.19 (1 H, d), 8.04 (1 H, d), 7.92 (1 H, d), 7.79 (1 H, d), 7.32 (2 H, s br), 4.79 (1 H, d), 3.76 (1 H, m), 3.28 (1 H, m), 3.12 (1 H, m), 1.03 (3 H, d). |
| 99 | (400 MHz, DMSO-$d_6$) δ ppm 8.57 (t, J = 5.6 Hz, 1 H), 8.28 (t, J = 7.6 Hz, 1 H), 8.20-8.18 (m, 1 H), 8.01 (dd, J = 10.4, 1.2 Hz, 1 H), 7.92 (dd, J = 8.4, 1.6 Hz, 1 H), 7.80-7.78 (m, 1 H), 7.33 (br s, 2 H), 5.03 (d, J = 5.2 Hz, 1 H), 3.78-3.71 (m, 1 H), 3.43-3.36 (m, 1 H), 3.27-3.24 (m, 3 H), 3.22-3.14 (m, 1 H). |
| 100 | (300 MHz, DMSO-$d_6$) δ ppm 8.53 (1 H, t), 8.24 (1 H, d), 8.20 (2 H, d), 8.04 (2 H, d), 7.75 (1 H, d), 7.28 (2 H, s br), 4.79 (1 H, d), 3.76 (1 H, m), 3.28 (1 H, m), 3.11 (1 H, m), 1.03 (3 H, d). |
| 101 | (400 MHz, DMSO-$d_6$) δ ppm 8.57 (t, J = 6 Hz, 1 H), 8.23 (d, J = 2 Hz, 1 H), 8.20 (d, J = 8.4 Hz, 2 H), 8.04 (d, J = 8.4 Hz, 2 H), 7.75 (d, J = 2 Hz, 1 H), 7.27 (br s, 2 H), 3.96-3.92 (m, 1 H), 3.78-3.72 (m, 1 H), 3.63-3.31 (m, 1 H), 3.40-3.31 (m, 2 H), 1.90-1.75 (m, 3 H), 1.58-1.50 (m, 1 H). |
| 103 | (400 MHz, DMSO-$d_6$) δ ppm 8.22-8.20 (m, 3 H), 8.05 (d, J = 8.4 Hz, 2 H), 7.77 (d, J = 2.4 Hz, 1 H), 7.20 (br s, 2 H), 4.91 (t, J = 12.4 Hz, 2 H), 4.44 (t, J = 12.4 Hz, 2 H). |
| 104 | (400 MHz, DMSO-$d_6$) δ ppm 8.72 (t, J = 6 Hz, 1 H), 8.26 (d, J = 2 Hz, 1 H), 8.20 (d, J = 8 Hz, 2 H), 8.05 (d, J = 8.4 Hz, 2 H), 7.80 (d, J = 8 Hz, 1 H), 7.75 (d, J = 2.4 Hz, 1 H), 7.18 (br s, 2 H), 3.91-3.80 (m, 3 H), 1.04 (d, J = 6.8 Hz, 6 H). |
| 105 | (400 MHz, DMSO-$d_6$) δ ppm 8.23 (d, J = 2 Hz, 1 H), 8.20 (d, J = 8 Hz, 2 H), 8.05 (d, J = 8 Hz, 2 H), 7.76 (d, J = 2 Hz, 1 H), 7.38 (br s, 1 H), 7.18 (br s, 2 H), 4.75 (d, J = 11.6 Hz, 1 H), 4.49 (d, J = 11.6 Hz, 1 H), 4.24 (d, J = 11.6 Hz, 1 H), 4.00 (d, J = 11.6 Hz, 1 H). |
| 106 | (400 MHz, DMSO-$d_6$) δ ppm 8.61 (t, J = 5.6 Hz, 1 H), 8.28 (t, J = 7.2 Hz, 1 H), 8.18 (d, J = 1.2 Hz, 2 H), 8.03 (d, J = 8.4 Hz, 1 H), 7.92 (d, J = 8 Hz, 1 H), 7.80-7.79 (m, 1 H), 3.98-3.92 (m, 1 H), 3.78-3.72 (m, 1 H), 3.63-3.57 (m, 1 H), 3.36-3.24 (m, 2 H), 1.91-1.74 (m, 3 H), 1.59-1.51 (m, 1 H). |
| 107 | (400 MHz, DMSO-$d_6$) δ ppm 8.79 (t, J = 6 Hz, 1 H), 8.29 (t, J = 7.2 Hz, 1 H), 8.19 (d, J = 1.2 Hz, 2 H), 8.03 (d, J = 10.4 Hz, 1 H), 7.92 (d, J = 8.4 Hz, 1 H), 7.80 (d, J = 1.2 Hz, 1 H), 7.33 (br s, 1 H), 6.45 (d, J = 6.4 Hz, 1 H), 4.29-4.15 (m, 1 H), 3.61-3.54 (m, 1 H), 3.-43-3.36 (m, 1 H). |
| 110 | (400 MHz, DMSO-$d_6$) δ ppm 8.20 (d, J = 2 Hz, 1 H), 8.19 (d, J = 8.4 Hz, 2 H), 8.48 (d, J = 8.4 Hz, 2 H), 7.70 (d, J = 2 Hz, 1 H), 7.12 (s, 2 H), 4.18 (s, 2 H), 3.70 (s, 2 H), 1.21 (s, 6 H). |
| 111 | (400 MHz, DMSO-$d_6$) δ ppm 8.28 (t, J = 7.6 Hz, 1 H), 8.14 (d, J = 2.4 Hz, 1 H), 8.04 (d, J = 10 Hz, 1 H), 7.92 (d, J = 8.4 Hz, 1 H), 7.75 (m, 1 H), 7.17 (s, 2 H), 4.19 (s, 2 H), 3.70 (s, 2 H), 1.22 (s, 6 H). |
| 112 | (400 MHz, DMSO-$d_6$) δ ppm 8.29 (t, J = 7.2 Hz, 1 H), 8.18 (d, J = 1.6 Hz, 1 H), 8.04 (d, J = 10 Hz, 1 H), 7.92 (d, J = 7.6 Hz, 1 H), 7.81 (m, 1 H), 7.40 (br s, 1 H), 7.22 (s, 2 H), 4.75 (dd, J = 11.6, 1.2 Hz, 1 H), 4.51 (d, J = 11.6 Hz, 1 H), 4.25 (dd, J = 11.2, 1.2 Hz, 1 H), 4.01 (dd, J = 12, 3.2 Hz, 1 H). |
| 113 | (400 MHz, DMSO-$d_6$) δ ppm 8.76 (t, J = 6.4 Hz, 1 H), 8.29 (t, J = 7.6 Hz, 1 H), 8.19 (d, J = 2 Hz, 1 H), 8.03 (d, J = 10.4 Hz, 1 H), 7.93 (d, J = 8 Hz, 1 H), 7.81-7.80 (m, 1 H), 7.31 (br s, 1 H), 7.04 (br s, 2 H), 3.89-3.77 (m, 3 H), 1.04 (d, J = 6.8 Hz, 6 H). |
| 116 | (400 MHz, DMSO-$d_6$) δ ppm 8.61 (t, J = 6 Hz, 1 H), 8.21 (t, J = 8.8 Hz, 1 H), 8.19 (d, J = 2 Hz, 1 H), 7.77 (d, J = 1.2 Hz, 1 H), 7.72-7.69 (m, 1 H), 7.56-7.54 (m, 1 H), 7.33 (br s, 1 H), 3.99-3.92 (m, 1 H), 3.78-3.72 (m, 1 H), 3.64-3.58 (m, 1 H), 3.36-3.24 (m, 2 H), 1.91-1.72 (m, 3 H), 1.59-1.51 (m, 1 H). |
| 117 | (400 MHz, DMSO-$d_6$) δ ppm 8.79 (t, J = 6 Hz, 1 H), 8.21 (t, J = 8.4 Hz, 1 H), 8.19-8.17 (m, 1 H), 7.79-7.77 (m, 1 H), 7.70 (d, J = 10.4 Hz, 1 H), 7.55 (d, J = 8.8 Hz, 1 H), 7.32 (br s, 1 H), 6.46 (d, J = 6.4 Hz, 1 H), 4.25-4.15 (m, 1 H), 3.61-3.54 (m, 1 H), 3.-43-3.36 (m, 1 H). |
| 118 | (400 MHz, DMSO-$d_6$) δ ppm 8.15 (d, J = 2.1 Hz, 1H), 8.13-8.04 (m, 2H), 7.71 (d, J = 2.0 Hz, 1H), 7.59 (d, J = 8.4 Hz, 2H), 3.48 (q, J = 7.0 Hz, 2H), 3.45-3.34 (m, 4H), 1.92-1.81 (m, 2H), 1.80-1.69 (m, 3H), 1.14 (t, J = 7.0 Hz, 3H). |
| 119 | (400 MHz, DMSO-$d_6$) δ ppm 8.18 (d, J = 2.1 Hz, 1H), 8.13-7.97 (m, 2H), 7.68 (d, J = 2.1 Hz, 1H), 7.60 (d, J = 8.4 Hz, 2H), 6.07 (tt, J = 54.8, 3.6 Hz, 1H), 4.57-4.12 (m, 4H), 3.71 (td, J = 15.3, 3.5 Hz, 2H). |
| 120 | (400 MHz, DMSO-$d_6$) δ ppm 8.18 (d, J = 2.1 Hz, 1H), 8.14-8.01 (m, 2H), 7.70 (d, J = 2.1 Hz, 1H), 7.60 (d, J = 8.4 Hz, 2H), 4.39 (dd, J = 7.9, 5.6 Hz, 1H), 4.02 (p, J = 5.3 Hz, 1H), 3.16 (s, 3H), 2.29 (dd, J = 7.2, 5.3 Hz, 4H). |
| 121 | (400 MHz, DMSO-$d_6$) δ ppm 8.18 (d, J = 2.1 Hz, 1H), 8.15-8.06 (m, 2H), 7.67 (d, J = 2.1 Hz, 1H), 7.60 (d, J = 8.2 Hz, 2H), 4.30-4.07 (m, 2H), 3.71 (q, J = 10.6 Hz, 2H), 3.57 (s, 2H), 3.51 (t, J = 5.3 Hz, 2H), 1.78 (t, J = 6.0 Hz, 2H), 1.50 (q, J = 5.3 Hz, 2H). |
| 122 | (400 MHz, DMSO-$d_6$) δ ppm 8.19 (d, J = 2.0 Hz, 1H), 8.13-8.03 (m, 2H), 7.72 (d, J = 2.1 Hz, 1H), 7.60 (d, J = 8.3 Hz, 2H), 4.23 (d, J = 7.6 Hz, 1H), 2.95-2.84 (m, 2H), 2.84-2.71 (m, 2H). |
| 123 | (400 MHz, DMSO-$d_6$) δ ppm 8.20 (d, J = 2.0 Hz, 1H), 8.14-8.05 (m, 2H), 7.73 (d, J = 2.0 Hz, 1H), 7.62 (d, J = 8.5 Hz, 2H), 3.42 (t, J = 6.3 Hz, 2H), 3.35 (q, J = 6.7 Hz, 2H), 3.26 (s, 3H), 1.78 (p, J = 6.6 Hz, 2H). |
| 124 | (400 MHz, DMSO-$d_6$) δ ppm 7.95 (d, J = 2.1 Hz, 1H), 7.92-7.83 (m, 2H), 7.48 (d, J = 2.1 Hz, 1H), 7.38 (d, J = 8.5 Hz, 2H), 3.14 (t, J = 7.4 Hz, 2H), 1.26 (t, J = 7.4 Hz, 2H), 0.07 (d, J = 4.0 Hz, 2H), 0.00 (d, J = 4.0 Hz, 2H). |

TABLE III-continued

NMR Data of Representative Compounds

| Cpd # | ¹H NMR data |
|---|---|
| 125 | (400 MHz, DMSO-$d_6$) δ ppm 8.13-8.02 (m, 2H), 7.63-7.52 (m, 2H), 4.47 (s, 2H), 3.77 (s, 2H), 3.72 (t, J = 6.8 Hz, 2H), 2.11 (t, J = 7.0 Hz, 2H). |
| 126 | (400 MHz, DMSO-$d_6$) δ ppm 8.17 (d, J = 2.1 Hz, 1H), 8.14-8.06 (m, 2H), 7.66 (d, J = 2.1 Hz, 1H), 7.59 (d, J = 8.4 Hz, 2H), 4.59 (s, 1H), 4.10 (d, J = 47.8 Hz, 2H), 3.59 (s, 1H), 2.84-2.62 (m, 1H), 1.19 (d, J = 6.9 Hz, 3H). |
| 127 | (400 MHz, DMSO-$d_6$) δ ppm 8.18 (d, J = 2.0 Hz, 1H), 8.14-8.01 (m, 2H), 7.72 (d, J = 2.0 Hz, 1H), 7.60 (d, J = 8.5 Hz, 2H), 4.43 (dq, J = 8.0, 4.8 Hz, 1H), 3.85 (td, J = 8.7, 6.4 Hz, 2H), 3.72 (td, J = 8.3, 5.9 Hz, 1H), 3.58 (dd, J = 8.9, 4.3 Hz, 1H), 2.19 (dq, J = 12.6, 7.6 Hz, 1H), 2.03-1.76 (m, 1H). |
| 128 | (400 MHz, DMSO-$d_6$) δ ppm 8.18 (d, J = 2.0 Hz, 1H), 8.14-8.01 (m, 2H), 7.72 (d, J = 2.0 Hz, 1H), 7.60 (d, J = 8.5 Hz, 2H), 4.50-4.37 (m, 1H), 3.84 (dd, J = 9.2, 6.4 Hz, 2H), 3.72 (td, J = 8.2, 5.9 Hz, 1H), 3.58 (dd, J = 9.0, 4.3 Hz, 1H), 2.28-2.07 (m, 1H), 1.90 (ddt, J = 12.7, 7.7, 5.2 Hz, 1H). |
| 129 | (400 MHz, DMSO-$d_6$) δ ppm 8.18 (d, J = 2.1 Hz, 1H), 8.13-8.00 (m, 2H), 7.71 (d, J = 2.2 Hz, 1H), 7.65-7.51 (m, 2H), 3.92-3.68 (m, 2H), 3.23-3.11 (m, 2H), 1.81 (m, J = 10.9, 7.8, 3.9 Hz, 1H), 1.56 (ddd, J = 13.3, 4.1, 2.1 Hz, 2H), 1.22 (m, J = 13.4, 11.5, 4.5 Hz, 2H). |
| 130 | (400 MHz, DMSO-$d_6$) δ ppm 8.14-8.00 (m, 2H), 7.66-7.49 (m, 2H), 4.55 (s, 2H), 1.98-1.75 (m, 2H), 0.93 (t, J = 7.4 Hz, 3H). |
| 131 | (400 MHz, DMSO-$d_6$) δ ppm 8.53 (t, J = 6 Hz, 1 H), 8.24 (d, J = 2 Hz, 1 H), 8.20 (d, J = 8 Hz, 2 H), 8.04 (d, J = 8 Hz, 2 H), 7.75 (d, J = 2 Hz, 1 H), 7.28 (br s, 2 H), 5.04 (d, J = 5.6 Hz, 1 H), 3.77-3.70 (m, 1 H), 3.44-3.16 (m, 7 H), 1.01-0.91 (m, 1 H), 0.44-0.39 (m, 2 H), 0.15-0.11 (m, 2 H). |
| 132 | (400 MHz, DMSO-$d_6$) δ ppm 8.57 (t, J = 6.4 Hz, 1 H), 8.29 (t, J = 7.2 Hz, 1 H), 8.18 (d, J = 2 Hz, 1 H), 8.04 (d, J = 10.4 Hz, 1 H), 7.92 (d, J = 8 Hz, 1 H), 7.80-7.79 (m, 1 H), 7.33 (br s, 2 H), 5.03 (d, J = 6 Hz, 1 H), 3.78-3.70 (m, 1 H), 3.45-3.29 (m, 3 H), 3.26-3.14 (m, 3 H), 1.02-0.92 (m, 1 H), 0.44-0.39 (m, 2 H), 0.16-0.12 (m, 2 H). |
| 133 | (400 MHz, DMSO-$d_6$) δ ppm 8.57 (t, J = 5.6 Hz, 1 H), 8.28 (t, J = 7.6 Hz, 1 H), 8.18-8.17 (m, 1 H), 8.03 (d, J = 9.6 Hz, 1 H), 7.92 (d, J = 8.4 Hz, 1 H), 7.79-7.78 (m, 1 H), 7.33 (br s, 2 H), 4.98 (br s, 1 H), 3.72-3.66 (m, 1 H), 3.57-3.16 (m, 5 H), 1.07 (dd, J = 6.4, 1.6 Hz, 6 H). |
| 134 | (400 MHz, DMSO-$d_6$) δ ppm 8.20 (t, J = 8.8 Hz, 1 H), 8.12 (d, J = 1.2 Hz, 1 H), 7.78 (d, J = 1.2 Hz, 1 H), 7.71 (d, J = 10.4 Hz, 1 H), 7.55 (d, J = 8.8 Hz, 1 H), 7.16 (br s, 2 H), 4.19 (s, 2 H), 3.70 (s, 2 H), 1.22 (s, 6 H). |
| 135 | (400 MHz, DMSO-$d_6$) δ ppm 8.75 (t, J = 5.6 Hz, 1 H), 8.22 (t, J = 8.8 Hz, 1 H), 8.20-8.18 (m, 1 H), 7.80 (d, J = 7.6 Hz, 1 H), 7.79-7.77 (m, 1 H), 7.71 (d, J = 10.4 Hz, 1 H), 7.57-7.54 (m, 1 H), 7.31 (br s, 2 H), 3.89-3.81 (m, 3 H), 1.04 (d, J = 6.4 Hz, 6 H). |
| 138 | (400 MHz, DMSO-$d_6$) δ ppm 8.78 (1 H, m), 8.09 (1 H, s), 7.64 (1 H, s), 7.23 (4 H, J = 8.8 Hz, d), 6.92 (2 H, J = 8.4 Hz, d), 6.49 (1 H, J = 6.4 Hz, d), 4.24 (1 H, m), 4.11 (2 H, s), 3.74 (3 H, s), 3.60 (1 H, m), 3.42 (1 H, m), 2.57 (3 H, s). |
| 139 | (400 MHz, DMSO-$d_6$) δ ppm 8.78 (1 H, m), 8.00 (1 H, J = 1.6 Hz, d), 7.55 (1 H, J = 2 Hz, d), 7.25 (2 H, s), 6.47 (1 H, J = 6.4 Hz, d), 4.23 (1 H, m), 3.64 (4 H, m), 3.59 (1 H, m), 3.41 (1 H, m), 2.96 (4 H, m).. |
| 140 | (400 MHz, DMSO-$d_6$) δ ppm 8.24 (d, J = 2.0 Hz, 1H), 8.20-8.08 (m, 2H), 7.73 (d, J = 2.0 Hz, 1H), 7.66 (d, J = 8.4 Hz, 2H), 4.00-3.82 (m, 1H), 3.66 (t, J = 4.3 Hz, 1H), 3.49-3.35 (m, 1H), 3.32 (dd, J = 10.9, 8.0 Hz, 1H), 1.83 (s, 1H), 1.68 (dd, J = 12.4, 8.3 Hz, 2H), 1.54 (dd, J = 9.2, 4.7 Hz, 1H). |
| 141 | (400 MHz, DMSO-$d_6$) δ ppm 8.83 (t, J = 6.1 Hz, 1H), 8.21 (d, J = 2.0 Hz, 1H), 8.18-8.09 (m, 2H), 7.72 (d, J = 2.0 Hz, 1H), 7.69-7.60 (m, 2H), 7.50 (d, J = 1.7 Hz, 1H), 6.35 (dd, J = 3.0, 1.8 Hz, 1H), 6.16 (d, J = 3.2 Hz, 1H), 3.52 (q, J = 6.9 Hz, 2H), 2.86 (t, J = 7.1 Hz, 2H). |
| 142 | (400 MHz, DMSO-$d_6$) δ ppm 8.31 (d, J = 9.2 Hz, 1H), 8.24 (d, J = 2.0 Hz, 1H), 8.20-8.10 (m, 2H), 7.73 (d, J = 2.0 Hz, 1H), 7.69-7.55 (m, 2H), 3.81 (tq, J = 10.1, 5.2 Hz, 1H), 3.55-3.34 (m, 2H), 1.61 (ddd, J = 13.4, 7.7, 5.8 Hz, 1H), 1.52-1.39 (m, 1H), 0.84 (t, J = 7.3 Hz, 3H). |
| 143 | (400 MHz, DMSO-$d_6$) δ ppm 8.79 (t, J = 6.3 Hz, 1H), 8.22 (d, J = 2.0 Hz, 1H), 8.19-8.05 (m, 2H), 7.72 (d, J = 2.0 Hz, 1H), 7.68-7.58 (m, 2H), 3.29 (td, J = 10.8, 2.7 Hz, 1H), 3.12 (tdd, J = 11.4, 9.7, 6.0 Hz, 3H), 1.91-1.62 (m, 2H), 1.57 (dt, J = 13.3, 3.6 Hz, 1H), 1.48-1.33 (m, 1H), 1.32-1.09 (m, 1H). |
| 144 | (400 MHz, DMSO-$d_6$) δ ppm 8.23 (d, J = 2.0 Hz, 1H), 8.19-8.09 (m, 2H), 7.73 (d, J = 2.0 Hz, 1H), 7.70-7.60 (m, 2H), 4.42 (ddt, J = 8.4, 6.0, 4.4 Hz, 1H), 3.89-3.78 (m, 2H), 3.57 (dd, J = 8.9, 4.4 Hz, 1H), 2.26-2.05 (m, 1H), 2.01-1.76 (m, 1H). |
| 145 | (400 MHz, DMSO-$d_6$) δ ppm 8.85 (d, J = 8.6 Hz, 1H), 8.29-8.09 (m, 3H), 7.81-7.50 (m, 3H), 7.30-7.06 (m, 2H), 6.92-6.74 (m, 2H), 5.20 (q, J = 7.1 Hz, 1H), 4.33-4.14 (m, 2H), 2.20-1.94 (m, 2H). |
| 146 | (400 MHz, DMSO-$d_6$) δ ppm 8.23 (d, J = 2.1 Hz, 1H), 8.19-8.09 (m, 2H), 7.72 (d, J = 2.1 Hz, 1H), 7.69-7.61 (m, 2H), 4.03-3.89 (m, 1H), 3.89-3.82 (m, 2H), 3.38 (td, J = 11.6, 2.4 Hz, 2H), 1.76-1.53 (m, 4H). |
| 147 | (400 MHz, DMSO-$d_6$) δ ppm 8.76 (t, J = 6.0 Hz, 1H), 8.22 (d, J = 2.1 Hz, 1H), 8.19-8.08 (m, 2H), 7.72 (d, J = 2.1 Hz, 1H), 7.66 (d, J = 8.4 Hz, 2H), 4.85 (t, J = 4.6 Hz, 1H), 3.98-3.82 (m, 2H), 3.80-3.74 (m, 4H), 3.43-3.31 (m, 2H), 1.84 (td, J = 7.0, 4.5 Hz, 2H). |

TABLE III-continued

NMR Data of Representative Compounds

| Cpd # | $^1$H NMR data |
|---|---|
| 148 | (400 MHz, DMSO-$d_6$) δ ppm 8.34-8.21 (m, 2H), 8.19-8.09 (m, 2H), 7.74 (d, J = 2.0 Hz, 1H), 7.66 (d, J = 8.3 Hz, 2H), 3.55 (dd, J = 11.2, 5.4 Hz, 1H), 3.47 (dd, J = 11.1, 4.5 Hz, 1H), 1.90 (h, J = 6.8 Hz, 1H), 0.90 (d, J = 6.7 Hz, 3H), 0.84 (d, J = 6.7 Hz, 3H). |
| 149 | (400 MHz, DMSO-$d_6$) δ ppm 8.59 (d, J = 7.5 Hz, 1H), 8.23 (d, J = 2.0 Hz, 1H), 8.19-8.09 (m, 2H), 7.73 (d, J = 2.0 Hz, 1H), 7.66 (d, J = 8.4 Hz, 2H), 4.50-4.37 (m, 1H), 3.90 (dd, J = 8.9, 6.2 Hz, 1H), 3.62 (dd, J = 8.9, 5.7 Hz, 1H), 2.06 (dd, J = 12.9, 8.0 Hz, 1H), 1.74 (dd, J = 12.8, 6.1 Hz, 1H), 1.56 (d, J = 9.7 Hz, 4H), 1.47 (d, J = 4.9 Hz, 2H), 1.33 (s, 4H). |
| 150 | (400 MHz, DMSO-$d_6$) δ ppm 8.61 (d, J = 7.4 Hz, 1H), 8.23 (d, J = 2.0 Hz, 1H), 8.20-8.09 (m, 2H), 7.74 (d, J = 2.0 Hz, 1H), 7.66 (d, J = 8.4 Hz, 2H), 4.44 (ddd, J = 13.3, 7.4, 5.5 Hz, 1H), 3.90 (dd, J = 9.0, 6.4 Hz, 1H), 3.59 (dd, J = 9.0, 5.3 Hz, 1H), 2.19 (dd, J = 12.8, 7.9 Hz, 1H), 1.95 (dd, J = 12.8, 5.9 Hz, 1H), 1.83-1.65 (m, 3H), 1.65-1.40 (m, 6H). |
| 151 | (400 MHz, DMSO-$d_6$) δ ppm 8.37-8.19 (m, 1H), 8.19-8.04 (m, 2H), 7.69-7.54 (m, 3H), 3.53-3.35 (m, 2H), 3.15 (d, J = 7.1 Hz, 2H). |
| 152 | (400 MHz, DMSO-$d_6$) δ ppm 8.73 (t, J = 6.2 Hz, 1H), 8.22 (d, J = 2.1 Hz, 1H), 8.19-8.11 (m, 2H), 7.72 (d, J = 2.0 Hz, 1H), 7.69-7.61 (m, 2H), 3.39-3.25 (m, 2H), 1.40 (q, J = 7.1 Hz, 2H), 0.76-0.58 (m, 1H), 0.50-0.22 (m, 2H). |
| 153 | (400 MHz, DMSO-$d_6$) δ ppm 8.22 (d, J = 2.1 Hz, 1H), 8.19-8.09 (m, 2H), 7.73 (d, J = 2.0 Hz, 1H), 7.70-7.61 (m, 2H), 3.38 (d, J = 5.9 Hz, 2H), 2.69-2.55 (m, 2H), 2.33 (dtd, J = 19.8, 9.6, 5.2 Hz, 3H). |
| 154 | (400 MHz, DMSO-$d_6$) δ ppm 8.20 (d, J = 2.1 Hz, 1H), 8.17-8.08 (m, 2H), 7.74-7.53 (m, 3H), 4.41-4.22 (m, 1H), 4.12 (d, J = 10.2 Hz, 1H), 3.85 (d, J = 10.2 Hz, 1H), 3.63 (d, J = 10.1 Hz, 1H), 3.30 (s, 3H), 1.21 (s, 3H). |
| 155 | (400 MHz, DMSO-$d_6$) δ ppm 8.78 (t, J = 6.1 Hz, 1H), 8.33-8.09 (m, 3H), 7.77-7.61 (m, 3 H), 3.18-3.06 (m, 2H), 1.09-0.93 (m, 1H), 0.48-0.35 (m, 2H), 0.30-0.16 (m, 2H). |
| 156 | (400 MHz, DMSO-$d_6$) δ ppm 8.22 (d, J = 2.0 Hz, 1H), 8.19-8.09 (m, 2H), 7.72 (d, J = 2.1 Hz, 1H), 7.69-7.61 (m, 2H), 3.41 (dt, J = 13.6, 4.4 Hz, 1H), 3.26 (td, J = 11.5, 2.4 Hz, 1H), 3.12-2.92 (m, 2H), 1.55 (dq, J = 13.2, 2.5 Hz, 1H), 1.49-1.29 (m, 2H), 1.28-1.08 (m, 1H), 0.99 (d, J = 6.1 Hz, 3H). |
| 157 | (400 MHz, DMSO-$d_6$) δ ppm 8.22 (d, J = 2 Hz, 1 H), 8.20 (d, J = 8 Hz, 2 H), 8.05 (d, J = 8.4 Hz, 2 H), 7.75 (d, J = 2 Hz, 1 H), 7.18 (br s, 2 H), 4.78-4.72 (m, 1 H), 4.55-4.50 (m, 1 H), 4.28-4.23 (m, 1 H), 4.01-3.96 (m, 1 H), 3.69-3.54 (m, 1 H). |
| 158 | (400 MHz, DMSO-$d_6$) δ ppm 8.22 (d, J = 2.4 Hz, 1 H), 8.20 (d, J = 8.4 Hz, 2 H), 8.04 (d, J = 8.4 Hz, 2 H), 7.74 (d, J = 2.4 Hz, 1 H), 7.16 (br s, 2 H), 6.75 (t, J = 74.8 Hz, 1 H), 5.00-4.94 (m, 1 H), 4.84-4.78 (m, 1 H), 4.48-4.43 (m, 1 H), 4.39-4.33 (m, 1H), 3.98-3.94 (m, 1 H). |
| 159 | (400 MHz, DMSO-$d_6$) δ ppm 8.23 (d, J = 2.4 Hz, 1 H), 8.20 (d, J = 8 Hz, 2 H), 8.04 (d, J = 8 Hz, 2 H), 7.72 (d, J = 2.4 Hz, 1 H), 7.11 (br s, 2 H), 5.46 (s, 1 H), 4.38 (dd, J = 10.8, 1.2 Hz, 1H), 4.21 (dd, J = 10.8, 1.2 Hz, 1 H), 3.94 (dd, J = 11.2, 1.2 Hz, 3 H), 3.73 (dd, J = 11.2, 1.2 Hz, 3 H), 1.84-1.76 (m, 1 H), 0.84 (d, J = 6.8 Hz, 3 H), 0.82 (d, J = 6.8 Hz, 3 H). |
| 160 | (300 MHz, DMSO-$d_6$) δ ppm 8.28 (1 H, t), 8.17 (1 H, d), 8.04 (1 H, d), 7.92 (1 H, d), 7.79 (1 H, d), 7.23 (2 H, s br), 4.76 (1 H, m), 4.54 (1 H, m), 4.27 (1 H, m), 4.00 (1 H, m), 3.61 (1 H, m). |
| 161 | (400 MHz, DMSO-$d_6$) δ ppm 8.28 (t, J = 7.2 Hz, 1 H), 8.17-8.16 (m, 1 H), 8.04 (d, J = 10.4 Hz, 1 H), 7.92 (d, J = 8.4 Hz, 1 H), 7.79-7.77 (m, 1 H), 7.21 (br s, 2 H), 6.76 (t, J = 74.8 Hz, 1 H), 5.00-4.94 (m, 1 H), 4.85-4.79 (m, 1 H), 4.49-4.44 (m, 1 H), 4.39-4.34 (m, 1 H), 3.99-3.95 (m, 1 H). |
| 162 | (300 MHz, DMSO-$d_6$) δ ppm 8.28 (1 H, t), 8.17 (1 H, d), 8.04 (1 H, d), 7.92 (1 H, d), 7.76 (1 H, d), 7.16 (2 H, s br), 5.45 (1 H, s br), 4.41 (1 H, d), 4.22 (1 H, d), 3.94 (1 H, d), 3.73 (1 H, d), 1.80 (1 H, m), 0.83 (6 H, m). |
| 164 | (300 MHz, DMSO-$d_6$) δ ppm 8.30 (1 H, t), 8.16 (1 H, d), 8.05 (1 H, d), 7.93 (1 H, d), 7.82 (1 H, d), 7.25 (2 H, s br), 4.92 (2 H, m), 4.45 (2 H, m). |
| 165 | (300 MHz, DMSO-$d_6$) δ ppm 8.23 (1 H, d), 8.22 (2 H, d), 8.06 (2 H, d), 7.70 (1 H, d), 7.13 (2 H, s br), 4.51 (1 H, s br), 4.38 (2 H, m), 3.90 (2 H, m), 2.54 (1 H, m), 1.02 (3 H, s), 1.00 (3 H, s). |
| 166 | (400 MHz, DMSO-$d_6$) δ ppm 8.52 (t, J = 5.6 Hz, 1 H), 8.22 (d, J = 2 Hz, 1 H), 8.20 (d, J = 8 Hz, 2 H), 8.04 (d, J = 8 Hz, 2 H), 7.74 (d, J = 2 hz, 1 H), 7.31 (br s, 2 H), 3.77-3.70 (m, 1 H), 3.45-3.09 (m, 6 H), 1.81-1.71 (m, 1 H), 0.82 (d, J = 7.6 Hz, 6 H). |
| 167 | (400 MHz, DMSO-$d_6$) δ ppm 8.42 (t, J = 6.4 Hz, 1 H), 8.26 (d, J = 2 Hz, 1 H), 8.20 (d, J = 8.4 Hz, 2 H), 8.04 (d, J = 8 Hz, 2 H), 7.76 (d, J = 2.4 Hz, 1 H), 7.29 (br s, 2 H), 3.45-3.36 (m, 2 H), 3.23 (d, J = 6.8 Hz, 2 H), 3.20 (s, 3 H), 1.62 (t, J = 7.6 Hz, 2 H), 1.05 (s, 3H). |
| 168 | (400 MHz, DMSO-$d_6$) δ ppm 8.56 (t, J = 5.6 Hz, 1 H), 8.21 (t, J = 8.4 Hz, 1 H), 8.16-8.15 (m, 1 H), 7.77-7.76 (m, 1 H), 7.69 (d, J = 10.8 Hz, 1 H), 7.54 (dd, J = 8.8, 1 H), 7.32 (br s, 2 H), 3.72-3.66 (m, 1 H), 3.57-3.47 (m, 1 H), 3.44-3.32 (m, 2 H), 3.29-3.18 (m, 2 H), 1.08-1.06 (m, 6 H). |
| 169 | (400 MHz, DMSO-$d_6$) δ ppm 8.56 (t, J = 5.6 Hz, 1 H), 8.37 (s, 1 H), 8.21 (t, J = 8.8 Hz, 1 H), 8.16 (d, J = 1.2 Hz, 1 H), 7.77 (d, J = 1.2 Hz, 1 H), 7.70 (d, J = 10.8 Hz, 1 H), 7.55 (d, J = 8.8 Hz, 1 H), 7.32 (br s, 2 H), 3.77-3.16 (m, 7 H), 1.02-0.93 (m, 1 H), 0.77-0.39 (m, 2 H), 0.16-0.12 (m, 2 H). |

TABLE III-continued

NMR Data of Representative Compounds

| Cpd # | $^1$H NMR data |
|---|---|
| 170 | (400 MHz, DMSO-d$_6$) δ ppm 8.56 (t, J = 6 Hz, 1 H), 8.28 (t, J = 8 Hz, 1 H), 8.18-8.16 (m, 1 H), 8.03 (d, J = 10 Hz, 1 H), 7.92 (d, J = 8 Hz, 1 H), 7.79-7.78 (m, 1 H), 7.32 (br s, 2 H), 5.01 (br s, 1 H), 3.78-3.72 (m, 1 H), 3.45-3.11 (m, 6 H), 1.82-1.72 (m, 1 H), 0.83 (d, J = 6.8 Hz, 6 H). |
| 171 | (400 MHz, DMSO-d$_6$) δ ppm 8.56 (t, J = 5.6 Hz, 1 H), 8.21 (t, J = 8.4 Hz, 1 H), 8.15 (d, J = 1.2 Hz, 1 H), 7.70 (d, J = 10.8 Hz, 1 H), 7.54 (d, J = 8.4 Hz, 1 H), 7.32 (br s, 2 H), 5.01 (br s, 1 H), 3.77-3.70 (m, 1 H), 3.45-3.11 (m, 6 H), 1.82-1.71 (m, 1 H), 0.83 (d, J = 6.8 Hz, 6 H). |
| 172 | (400 MHz, DMSO-d$_6$) δ ppm 8.21 (t, J = 8.8 Hz, 1 H), 8.14 (d, J = 1.2 Hz, 1 H), 7.80 (d, J = 1.2 Hz, 1 H), 7.71 (d, J = 9.2 Hz, 1 H), 7.55 (d, J = 8.8 Hz, 1 H), 7.24 (br s, 2 H), 4.92 (t, J = 12.4 Hz, 2 H), 4.44 (t, J = 12.4 Hz, 2 H). |
| 173 | (400 MHz, DMSO-d$_6$) δ ppm 8.20 (t, J = 8.8 Hz, 1 H), 8.16 (d, J = 2 Hz, 1 H), 7.78 (d, J = 1.2 Hz, 1 H), 7.71 (dd, J = 10.8, 2 Hz, 1 H), 7.55 (dd, J = 8.8, 1.2 Hz, 1 H), 7.22 (br s, 2 H), 4.76 (dd, J = 11.6, 1.2 Hz, 1 H), 4.51 (d, J = 11.6 Hz, 1 H), 4.24 (dd, J = 11.2, 1.2 Hz, 1 H), 4.01 (d, J = 11.6 Hz, 1 H). |
| 174 | (400 MHz, DMSO-d$_6$) δ ppm 8.20 (t, J = 8.4 Hz, 1 H), 8.15 (d, J = 1.2 Hz, 1 H), 7.73-7.72 (m, 1 H), 7.70 (d, J = 10.8, 1 H), 7.56-7.53 (m, 1 H), 7.16 (br s, 2 H), 4.45-4.35 (m, 2 H), 3.96-3.88 (m, 2 H), 2.59-2.52 (m, 1 H), 1.01 (d, J = 6 Hz, 6 H). |
| 175 | (400 MHz, DMSO-d$_6$) δ ppm 8.28 (s, 1 H), 8.20 (t, J = 8.4 Hz, 1 H), 8.15 (d, J = 2.4 Hz, 1 H), 7.74 (d, J = 1.2 Hz, 1 H), 7.70 (d, J = 10.4 Hz, 1 H), 7.55 (dd, J = 8.8, 1.2 Hz, 1 H), 7.16 (br s, 2 H), 4.41 (dd, J = 10.8, 1.6 Hz, 1 H), 4.22 (dd, J = 10.8, 0.8 Hz, 1 H), 3.95 (dd, J = 10.8, 0.8 Hz, 1 H), 3.75 (d, J = 10.8 Hz, 1 H), 1.84-1.77 (m, 1 H), 0.84 (d, J = 6.8 Hz, 3 H), 0.83 (d, J = 6.8 Hz, 3 H). |
| 176 | (400 MHz, DMSO-d$_6$) δ ppm 8.20 (1 H, d, J = 2.0 Hz), 8.06 (2 H, m), 7.72 (1 H, d, J = 2.0 Hz), 7.51 (2 H, m), 7.44 (1 H, s), 7.16 (2 H, s br), 4.75 (1 H, m), 4.50 (1 H, m), 4.24 (1 H, m), 4.00 (1 H, m). |
| 177 | (400 MHz, DMSO-d$_6$) δ ppm 8.59 (1 H, t), 8.24 (1 H, m), 8.11 (1 H, d, J = 2.0 Hz), 7.92 (1 H, m), 7.70 (2 H, m), 7.60 (1 H, m), 7.32 (2 H, s br), 5.07 (1 H, s), 3.75 (1 H, m), 3.41 (1 H, m), 3.26 (2 H, m), 3.24 (3 H, s), 3.17 (1 H, m). |
| 178 | (300 MHz, DMSO-d$_6$) δ ppm 8.28 (1 H, t), 8.17 (1 H, d), 8.04 (1 H, d), 7.92 (1 H, d), 7.75 (1 H, d), 7.17 (2 H, s br), 4.49 (1 H, s br), 4.39 (2 H, m), 3.92 (2 H, m), 2.54 (1 H, m), 1.03 (3 H, s), 1.01 (3 H, s). |
| 188 | (400 MHz, DMSO-d$_6$) δ ppm 8.28 (d, J = 9.2 Hz, 1 H), 8.23 (d, J = 2 Hz, 1 H), 8.20 (d, J = 7.6 Hz, 2 H), 8.04 (d, J = 8.4 Hz, 2 H), 7.74 (d, J = 1.2 Hz, 1 H), 7.26 (br s, 2 H), 3.79-3.72 (m, 1 H), 1.80-1.71 (m, 1 H), 1.08 (d, J = 6.4 Hz, 3 H), 0.85 (d, J = 6.8 Hz, 3 H), 0.83 (d, J = 6.4 Hz, 3 H). |
| 189 | (400 MHz, DMSO-d$_6$) δ ppm 8.68 (t, J = 6.4 Hz, 1 H), 8.22 (d, J = 2 Hz, 1 H), 8.20 (d, J = 8.4 Hz, 2 H), 8.04 (d, J = 8 Hz, 2 H), 7.74 (d, J = 2 Hz, 1 H), 7.27 (br s, 2 H), 3.06 (d, J = 6.8 Hz, 2 H), 1.86-1.79 (m, 1 H), 0.84 (d, J = 6.8 Hz, 6 H). |
| 190 | (400 MHz, DMSO-d$_6$) δ ppm 8.62 (t, J = 6 Hz, 1 H), 8.22 (d, J = 2 Hz, 1 H), 8.20 (d, J = 8.4 Hz, 2 H), 8.04 (d, J = 8.4 Hz, 2 H), 7.74 (d, J = 2.4 Hz, 1 H), 7.28 (br s, 2 H), 3.92-3.85 (m, 1 H), 3.72-3.66 (m, 1 H), 3.60-3.32 (m, 7 H), 1.88-1.68 (m, 3 H), 1.53-1.44 (m, 1 H). |
| 191 | (300 MHz, DMSO-d$_6$) δ ppm 8.49 (1 H, t), 8.26 (1 H, s), 8.21 (2 H, d), 8.04 (2 H, d), 7.75 (1 H, s), 7.29 (2 H, s), 3.08 (2 H, d), 0.86 (9 H, s). |
| 192 | (400 MHz, DMSO-d$_6$) δ ppm 8.59 (t, J = 6 Hz, 1 H), 8.22 (d, J = 2.4 Hz, 1 H), 8.20 (d, J = 8 Hz, 2 H), 8.04 (d, J = 8 Hz, 2 H), 7.74 (d, J = 2 Hz, 1 H), 7.23 (br s, 2 H), 3.58-3.31 (m, 5 H), 1.06 (g, J = 6 Hz, 6 H) |
| 193 | (400 MHz, DMSO-d$_6$) δ ppm 8.23 (d, J = 2.0 Hz, 1H), 8.19-8.10 (m, 2H), 7.81 (d, J = 2.0 Hz, 1H), 7.63 (d, J = 8.5 Hz, 2H), 3.87 (dd, J = 12.3, 4.4 Hz, 2H), 3.49 (t, J = 12.0 Hz, 2H), 2.59 (dd, J = 13.6, 2.1 Hz, 2H), 1.88 (td, J = 13.1, 4.7 Hz, 2H). |
| 196 | (300 MHz, DMSO-d$_6$) δ ppm 8.81 (1 H, t), 8.00 (1 H, d), 7.55 (1 H, d), 7.25 (2 H, s, br), 6.52 (1 H, s), 4.23 (1 H, m), 3.59 (1 H, m), 3.41 (1 H, m), 3.26 (1 H, m), 3.16 (1 H, s), 3.11 (1 H, m), 2.87 (2 H, m), 1.83 (2 H, m), 1.53 (2 H, m). |
| 198 | (400 MHz, DMSO-d$_6$) δ ppm 8.81 (1 H, t), 8.01 (1 H, d, J = 2.4 Hz), 7.56 (1 H, d, J = 2.0 Hz), 7.26 (2 H, s br), 6.49 (1 H, d, J = 6.0 Hz), 4.57 (1 H, m), 4.23 (1 H, m), 3.59 (1 H, m), 3.42 (2 H, m), 3.28 (1 H, m), 2.90 (2 H, m), 2.00 (2 H, m), 1.75 (2 H, m). |
| 201 | (300 MHz, DMSO-d$_6$) δ ppm 8.57 (1 H, t), 8.23 (1 H, d), 8.20 (2 H, d), 8.04 (2 H, d), 7.75 (1 H, d), 7.28 (2 H, s br), 4.06 (2 H, m), 3.77 (1 H, m), 3.52 (2 H, m), 3.39 (1 H, m), 3.21 (1 H, m). |
| 202 | (400 MHz, DMSO-d$_6$) δ ppm 8.63 (t, J = 5.6 Hz, 1H), 8.23 (d, J = 2.4 Hz, 1H), 8.20 (d, J = 8.4 Hz, 2H), 8.04 (d, J = 8.4 Hz, 2H), 7.74 (d, J = 2 Hz, 1H), 7.27 (br s, 2H), 3.44.3.34 (m, 4H), 3.23 (s, 3H). |
| 203 | (400 MHz, DMSO-d$_6$) δ ppm 8.23 (d, J = 2.1 Hz, 1H), 8.17-8.00 (m, 2H), 7.69 (d, J = 2.1 Hz, 1H), 7.65-7.46 (m, 2H), 2.42 (dt, J = 14.2, 6.9 Hz, 2H). |
| 204 | (400 MHz, DMSO-d$_6$) δ ppm 8.23 (d, J = 2.1 Hz, 1H), 8.18-8.05 (m, 2H), 7.67 (d, J = 2.1 Hz, 1H), 7.60 (d, J = 8.4 Hz, 2H), 5.32 (d, J = 51.3 Hz, 1H), 3.80 (d, J = 35.1 Hz, 4H), 2.22-2.05 (m, 2H). |
| 205 | (400 MHz, DMSO-d$_6$) δ ppm 8.36 (d, J = 8 Hz, 1H), 8.26 (d, J = 2 Hz, 1H), 8.19 (d, J = 8 Hz, 2H), 8.04 (d, J = 8.4 Hz, 2H), 7.75 (d, J = 2 Hz, 1H), 7.30 (br s, 2H), 5.05 (br s, 1H), 4.00-3.91 (m, 2H), 1.96-1.48 (m, 6H). |
| 206 | (400 MHz, DMSO-d$_6$) δ ppm 8.23 (d, J = 2.1 Hz, 1H), 8.15-8.04 (m, 2H), 7.67 (d, J = 2.1 Hz, 1H), 7.60 (d, J = 8.6 Hz, 2H), 5.25 (s, 1H), 3.79 (t, J = 19.4 Hz, 4H), 2.24-2.08 (m, 2H). |

TABLE III-continued

NMR Data of Representative Compounds

| Cpd # | ¹H NMR data |
|---|---|
| 207 | (400 MHz, DMSO-d$_6$) δ ppm 8.20 (d, J = 2.0 Hz, 1H), 8.14-8.03 (m, 2H), 7.74 (d, J = 2.0 Hz, 1H), 7.61 (d, J = 8.4 Hz, 2H), 4.64 (s, 1H), 3.55 (s, 2H), 2.89 (s, 3H), 2.42 (s, 1H), 2.09 (s, 1H). |
| 208 | (400 MHz, DMSO-d$_6$) δ ppm 8.24 (d, J = 2.0 Hz, 1H), 8.19-8.09 (m, 2H), 7.76 (d, J = 1.9 Hz, 1H), 7.67 (d, J = 8.4 Hz, 2H), 4.63 (d, J = 29.4 Hz, 1H), 3.57 (d, J = 11.1 Hz, 1H), 3.45-3.16 (m, 1H), 3.07 (q, J = 9.4 Hz, 1H), 2.88 (d, J = 11.7 Hz, 3H), 2.25 (s, 1H), 2.07-1.90 (m, 1H). |
| 209 | (400 MHz, DMSO-d$_6$) δ ppm 9.92 (t, J = 6.8 Hz, 1 H), 8.26 (d, J = 2 Hz, 1 H), 8.21 (d, J = 8.4 Hz, 2 H), 8.05 (d, J = 8.4 Hz, 2 H), 7.80 (d, J = 2 Hz, 1 H), 7.27 (br s, 2 H), 4.09-3.97 (s, 2 H) |
| 210 | (400 MHz, DMSO-d$_6$) δ ppm 8.25-8.16 (m, 1H), 8.15-8.06 (m, 2H), 7.75 (d, J = 2.1 Hz, 1H), 7.61 (d, J = 8.4 Hz, 2H), 4.78 (q, J = 7.7 Hz, 1H), 4.35 (t, J = 9.4 Hz, 2H), 4.24 (s, 2H), 2.89 (s, 3H). |
| 211 | (400 MHz, DMSO-d$_6$) δ ppm 8.79 (1 H, m), 8.13 (1 H, s), 7.75 (2 H, J = 8.0 Hz, d), 7.66 (1 H, J = 2.0 Hz, d), 7.56 (2 H, J = 8.0 Hz, d), 7.25 (2 H, s), 6.50 (1 H, J = 5.6 Hz, d), 4.32 (2 H, s), 4.24 (1 H, m), 3.62 (1 H, m), 3.42 (1 H, m), 2.65 (3 H, s). |
| 212 | (400 MHz, DMSO-d$_6$) δ ppm 8.92 (t, J = 6 Hz, 1 H), 8.22 (d, J = 2 Hz, 1 H), 8.20 (d, J = 8.4 Hz, 2 H), 8.04 (d, J = 8.4 Hz, 2 H), 7.75 (d, J = 2 Hz, 1 H), 7.25 (br s, 2 H), 3.52-3.46 (m, 2 H), 2.59-2.50 (m, 2 H). |
| 213 | (300 MHz, DMSO-d$_6$) δ ppm 8.61 (1 H, t), 8.298 (1 H, t), 8.18 (1 H, s), 8.03 (1 H, d), 7.92 (1 H, d), 7.79 (1 H, s), 7.32 (2 H, s), 4.07 (2 H, m), 3.79 (1 H, m), 3.54 (2 H, m), 3.40 (2H, m). |
| 214 | (400 MHz, DMSO-d$_6$) δ ppm 8.25 (d, J = 2.0 Hz, 1H), 8.19-8.03 (m, 2H), 7.78 (d, J = 2.1 Hz, 1H), 7.73-7.57 (m, 2H), 4.90 (d, J = 8.0 Hz, 2H), 4.73 (d, J = 8.1 Hz, 2H). |
| 215 | (400 MHz, DMSO-d$_6$) δ ppm 8.44 (d, J = 7.6 Hz, 1 H), 8.22 (d, J = 2.4 Hz, 1 H), 8.20 (d, J = 5 Hz, 2 H), 8.04 (d, J = 8.4 Hz, 2 H), 7.73 (d, J = 2 Hz, 1 H), 7.28 (br s, 2 H), 4.77 (d, J = 4.4 Hz, 1 H), 3.99-3.88 (m, 2 H), 2.00-1.90 (m, 1 H), 1.87-1.77 (m, 1 H), 1.67-1.57 (m, 2 H), 1.50-1.39 (m, 2 H). |
| 216 | (400 MHz, DMSO-d$_6$) δ ppm: 8.27 (1 H, d), 8.21 (3 H, m), 8.04 (2 H, d), 7.76 (1 H, d), 7.30 (2 H, s), 5.26 (1 H, d), 3.91 (2 H, m), 3.65 (1 H, m), 3.50 (3 H, m), 1.75(1 H, m), 1.61(1 H, m). |
| 217 | (300 MHz, DMSO-d$_6$) δ ppm 8.53 (1 H, t), 8.24 (1 H, d), 8.20 (2 H, d), 8.04 (2 H, d), 7.75) (1 H, d), 7.28 (2 H, s br), 4.77 (1 H, t), 3.48 (2 H, m), 3.31 (2 H, m). |
| 218 | (400 MHz, DMSO-d$_6$) δ ppm: 8.27 (2 H, m), 8.20 (1 H, d), 8.04(1 H, d), 7.92 (1 H, d), 7.81 (1 H, m), 7.35 (2 H, s), 5.26 (1 H, d), 3.91 (2 H, m), 3.65 (1 H, m), 3.50 (3 H, m), 1.75(1 H, m), 1.61(1 H, m). |
| 219 | (300 MHz, DMSO-d$_6$) δ ppm 8.65 (1 H, t), 8.28 (1 H, t), 8.18 (1 H, m), 8.05 (1 H, m), 7.92 (1 H, m), 7.78 (1 H, m), 7.33 (2 H, s br), 4.77 (1 H, t), 3.48 (2 H, m), 3.31 (2 H, m). |
| 220 | (400 MHz, DMSO-d$_6$) δ ppm 8.74 (1 H, t), 8.19 (1 H, d, J = 2.0 Hz), 7.91 (2 H, m), 7.67 (1 H, d, J = 2.0 Hz), 7.23 (2 H, s br), 7.18 (2 H, m), 6.45 (1 H, s br), 4.20 (1 H, m), 3.81 (3 H, s), 3.54 (1 H, m). |
| 221 | (400 MHz, DMSO-d$_6$) δ ppm 8.54 (1 H, t), 8.24 (1 H, d, J = 2.0 Hz), 8.20 (2 H, m), 8.04 (2 H, m), 7.75 (1 H, d, J = 2.0 Hz), 7.29 (2 H, s br), 5.06 (1 H, d, J = 4.8 Hz), 3.72 (1 H, m), 3.49 (2 H, m), 3.41 (4 H, m), 3.32 (1 H, m), 3.19 (3 H, s), 3.17 (1 H, m). |
| 222 | (400 MHz, DMSO-d$_6$) δ ppm 8.77 (t, J = 6 Hz, 1H), 8.21 (d, J = 2 Hz, 1H), 8.20 (d, J = 9 Hz, 2H), 8.04 (d, J = 8.4 Hz, 2H), 7.73 (d, J = 2 Hz, 1H), 7.28 (br s, 2H), 3.34-3.25 (m, 2H), 3.21 (s, 3H), 1.74-1.69 (m, 2H). |
| 223 | (400 MHz, DMSO-d$_6$) δ ppm 8.78 (t, J = 6.4 Hz, 1H), 8.23 (d, J = 2 Hz, 1H), 8.20 (d, J = 8.4 Hz, 2H), 8.04 (d, J = 8.4 Hz, 2H), 7.74 (d, J = 2.4 Hz, 1H), 7.29 (br s, 2H), 3.10 (t, J = 6.8 Hz, 1H), 1.06-0.96 (m, 1H), 0.41-0.36 (m, 2H), 0.23-0.19 (m, 2H). |
| 224 | (300 MHz, DMSO-d$_6$) δ ppm 8.58 (1 H, t), 8.29 (1 H, t), 8.16 (1 H, m), 8.05 (1 H, d), 7.92 (1 H, d), 7.79 (1 H, m), 7.34 (2 H, s br), 4.98 (1 H, d), 3.64 (1 H, m), 3.40 (1 H, m), 3.31 (1 H, m), 3.21 (2 H, m), 1.12 (9 H, s). |
| 225 | (400 MHz, DMSO-d$_6$) δ ppm 8.80 (1 H, t), 8.05 (1 H, d, J = 2.0 Hz), 7.61 (1 H, d, J = 1.6 Hz), 7.24 (2 H, s br), 6.50 (1 H, d, J = 6.4 Hz), 4.23 (1 H, m), 3.59 (1 H, m), 3.41 (1 H, m), 3.26 (2 H, m), 2.76 (3 H, s), 2.62 (2 H, m). |
| 227 | (400 MHz, DMSO-d$_6$) δ ppm 8.22 (d, J = 2 Hz, 1 H), 8.19 (d, J = 8.4 Hz, 2 H), 8.04 (d, J = 8.4 Hz, 2 H), 7.73 (d, J = 2 Hz, 1 H), 7.28 (br s, 2 H), 5.11 (t, J = 5.6 Hz, 1 H), 3.39 (d, J = 5.6 Hz, 2 H), 1.29 (s, 6 H). |
| 228 | (400 MHz, DMSO-d$_6$) δ ppm 8.56 (t, J = 6.4 Hz, 1 H), 8.27 (d, J = 2.4 Hz, 1 H), 8.21 (d, J = 8 Hz, 2 H), 8.05 (d, J = 8.4 Hz, 2 H), 7.75 (d, J = 2 Hz, 1 H), 7.29 (br s, 2 H), 5.50 (s, 1 H), 3.36 (d, J = 6 Hz, 2 H), 0.57-0.49 (m, 4 H). |
| 231 | (400 MHz, DMSO-d$_6$) δ ppm 8.22-8.19 (m, 3 H), 8.05 (d, J = 8.4 Hz, 2 H), 7.73 (d, J = 2 Hz, 1 H), 7.14 (br s, 2 H), 6.16 (tt, J = 54.8, 3.2 Hz, 1 H), 4.71-4.65 (m, 1 H), 4.44-4.38 (m, 1 H), 4.34-4.30 (m, 1 H), 4.25-4.20 (m, 1 H), 3.87-3.82 (m, 1 H), 3.75 (td, J = 15.6, 1.2, 2 H). |
| 232 | (300 MHz, DMSO-d$_6$) δ ppm 8.20 (1 H, d), 8.19 (2 H, d), 8.05 (2 H, d), 7.70 (1 H, d), 7.15 (2 H, s br), 4.31 (1 H, d), 4.10 (1 H, d), 3.82 (1 H, d), 3.60 (1 H, d), 3.31 (2 H, s), 3.28 (3 H, s), 1.20 (3 H, s). |
| 234 | (300 MHz, DMSO-d$_6$) δ ppm 8.39 (1 H, d), 8.24 (1 H, d), 8.20 (2 H, d), 8.05 (2 H, d), 7.74 (1 H, d), 7.29 (2 H, s br), 4.78 (1 H, t), 3.78 (1 H, m), 3.44 (2 H, m), 1.62 (1 H, m), 1.45 (1 H, m), 0.82 (3 H, t). |

TABLE III-continued

NMR Data of Representative Compounds

| Cpd # | ¹H NMR data |
|---|---|
| 236 | (300 MHz, DMSO-d₆) δ ppm 8.78 (1 H, t), 8.27 (1 H, d), 8.04 (1 H, m), 7.99 (1 H, s), 7.83 (2 H, m), 7.77 (1 H, d), 7.28 (2 H, br s), 6.47 (1 H, d), 4.21 (1 H, m), 3.55 (1 H, m), 3.39 (1 H, m). |
| 244 | (300 MHz, DMSO-d₆) δ ppm 8.74 (1 H, t), 8.20 (1 H, d), 7.98 (2 H, m), 7.76 (1 H, m), 7.73 (1 H, d), 7.68 (2 H, m), 7.25 (2 H, br s) 6.45 (1 H, br s), 4.21 (1 H, m), 3.58 (1 H, m), 3.38 (1 H, m). |
| 250 | (300 MHz, DMSO-d₆) δ ppm 8.51 (1 H, t), 8.17 (1 H, s), 8.03 (2 H, m), 7.51 (2 H, t), 7.42 (2 H, s, br), 6.47 (1 H, s), 4.21 (1 H, m), 3.54 (1 H, m), 3.37 (1 H, m). |
| 253 | (400 MHz, DMSO-d₆) δ ppm 8.77 (t, J = 6 Hz, 1H), 8.20 (d, J = 1.4 Hz, 1 H), 8.00-7.97 (m, 2 H), 7.78-7.63 (m, 3 H), 7.27 (br s, 2 H), 6.46 (d, J = 6 Hz, 1 H), 4.36-4.65 (m, 1 H), 3.59-3.52 (m, 1 H), 3.41-3.27. |
| 254 | (400 MHz, DMSO-d₆) δ ppm 8.74 (1 H, m), 8.25 (1 H, J = 2.0 Hz, d), 7.85 (2 H, m), 7.75 (2 H, m), 7.64 (1 H, m), 7.26 (2 H, s), 6.45 (1 H, J = 6.4 Hz, d), 4.20 (1 H, m), 3.57 (1 H, m), 3.38 (1 H, m). |
| 255 | (300 MHz, DMSO-d₆) δ ppm 8.19 (1 H, d), 7.99 (1 H, m), 7.97 (1 H, m), 7.76 (1 H, m), 7.72 (1 H, d), 7.67 (1 H, m), 7.39 (1 H, s), 7.16 (2 H, s), 4.75 (1 H, dd), 4.49 (1 H, d), 4.23 (1 H, dd), 3.99 (1 H, d). |
| 256 | (300 MHz, DMSO-d₆) δ ppm 8.26 (1H, d), 7.51 (2H, m), 7.75 (2H, m), 7.63 (1H m), 7.16 (2H, s), 4.75 (1H, d), 4.49 (1H, d), 4.24 (1H, d), 4.00 (1H, d). |
| 260 | (300 MHz, DMSO-d₆) δ ppm 0.65 (2 H, m), 0.81 (2 H, m), 2.41 (1 H, m), 3.29 (2 H, m), 3.46 (2 H, m), 4.75 (1 H, m), 7.07 (2 H, br s), 7.99 (1 H, s), 8.02 (2 H, d), 8.12 (2 H, m), 8.25 (1 H, m). |
| 261 | (400 MHz, CDCl₃) δ ppm 8.30 (t, J = 5.8 Hz, 1H), 7.85 (s, 1H), 7.65-7.55 (m, 2H), 7.20-7.10 (m, 2H), 6.26 (br s, 2H), 4.06-3.97 (m, 1H), 3.54 (ddd, J = 14.0, 6.6, 3.1 Hz, 1H), 3.32 (ddd, J = 13.9, 7.5, 6.0 Hz, 1H), 2.87 (tt, J = 8.9, 6.5 Hz, 1H), 2.54 (d, J = 4.2 Hz, 1H), 1.88-1.78 (m, 2H), 1.74-1.64 (m, 2H), 1.62-1.54 (m, 2H), 1.50-1.44 (m, 2H), 1.23 (d, J = 6.3 Hz, 3H). |
| 262 | (400 MHz, CDCl₃) δ ppm 8.29 (t, J = 5.9 Hz, 1H), 7.84 (s, 1H), 7.63-7.53 (m, 2H), 7.21-7.10 (m, 2H), 6.32 (br s, 2H), 4.05-3.98 (m, 1H), 3.80 (q, J = 6.0 Hz, 2H), 3.54 (ddd, J = 14.0, 6.6, 3.1 Hz, 1H), 3.32 (ddd, J = 13.8, 7.5, 6.0 Hz, 1H), 2.93-2.90 (m, 2H), 2.49 (d, J = 4.3 Hz, 1H), 2.24 (t, J = 6.3 Hz, 1H), 1.23 (d, J = 6.3 Hz, 3H). |
| 263 | (400 MHz, CDCl₃) δ ppm 8.30 (d, J = 6.0 Hz, 1H), 7.83 (s, 1H), 7.62-7.57 (m, 2H), 7.15 (t, J = 8.7 Hz, 2H), 6.29 (br s, 2H), 4.02 (s, 1H), 3.54 (ddd, J = 14.1, 6.6, 3.1 Hz, 1H), 3.33 (ddd, J = 13.8, 7.5, 6.0 Hz, 1H), 2.70-2.63 (m, 2H), 2.49 (d, J = 4.3 Hz, 1H), 1.24 (d, J = 6.3 Hz, 3H), 1.04 (t, J = 7.4 Hz, 3H). |
| 264 | (400 MHz, CDCl₃) δ ppm 8.31 (t, J = 5.6 Hz, 1H), 7.84 (s, 1H), 7.61-7.56 (m, 2H), 7.14 (t, J = 8.6 Hz, 2H), 4.03 (ddq, J = 10.3, 6.1, 3.2 Hz, 1H), 3.54 (ddd, J = 14.1, 6.6, 3.1 Hz, 1H), 3.33 (ddd, J = 13.8, 7.3, 6.1 Hz, 1H), 2.60 (hept, J = 6.8 Hz, 1H), 1.24 (d, J = 6.3 Hz, 3H), 1.09 (d, J = 6.8 Hz, 3H), 1.07 (d, J = 6.8 Hz, 3H). |
| 265 | (400 MHz, CDCl₃) δ ppm 8.30 (t, J = 6.0 Hz, 1H), 7.81 (s, 1H), 7.61-7.55 (m, 2H), 7.19-7.10 (m, 2H), 6.27 (br s, 2H), 4.06-3.97 (m, 1H), 3.53 (td, J = 6.6, 5.9, 2.7 Hz, 3H), 3.33 (ddd, J = 13.8, 7.5, 6.0 Hz, 1H), 3.10 (s, 3H), 2.93 (t, J = 5.9 Hz, 2H), 2.55 (d, J = 4.3 Hz, 1H), 1.23 (d, J = 6.3 Hz, 3H). |
| 266 | (400 MHz, CDCl₃) δ ppm 1.27 (d, J = 6.3 Hz, 3H), 1.32 (d, J = 6.4 Hz, 3H), 1.51-1.69 (m, 2H), 1.73-1.95 (m, 2H), 2.55-2.60 (m, 1H), 3.18 (ddd, J = 10.1, 7.6, 6.8 Hz, 1H), 3.34 (ddd, J = 13.7, 7.5, 5.8 Hz, 1H), 3.48 (ddd, J = 10.1, 7.0, 4.8 Hz, 1H), 3.58 (ddd, J = 14.0, 6.6, 3.2 Hz, 1H), 3.71-3.80 (m, 1H), 4.00-4.10 (m, 1H), 6.23 (br s, 2H), 7.42 (d, J = 1.9 Hz, 1H), 8.20 (d, J = 1.9 Hz, 1H), 8.35-8.44 (m, 1H). |
| 267 | (400 MHz, CD₂Cl₂) δ ppm 1.22 (d, J = 6.3 Hz, 3H), 3.27-3.36 (m, 1H), 3.53 (ddd, J = 13.9, 6.5, 3.2 Hz, 1H), 3.96-4.04 (m, 1H), 4.16 (d, J = 6.1 Hz, 2H), 5.20 (t, J = 6.1 Hz, 1H), 6.96-7.03 (m, 2H), 7.19-7.25 (m, 2H), 7.39 (d, J = 1.9 Hz, 1H), 8.17 (d, J = 1.9 Hz, 1H), 8.31-8.40 (m, 1H). |
| 268 | (400 MHz, CDCl₃) δ ppm 1.27 (d, J = 6.3 Hz, 3H), 1.54-1.61 (m, 1H), 1.74-1.92 (m, 3H), 3.25-3.39 (m, 2H), 3.47-3.54 (m, 1H), 3.55-3.76 (m, 4H), 4.01-4.09 (m, 1H), 7.42 (d, J = 1.9 Hz, 1H), 8.22 (d, J = 1.9 Hz, 1H), 8.39 (s, 1H). |
| 269 | (400 MHz, CD₂Cl₂) δ ppm 1.24 (d, J = 6.3 Hz, 3H), 2.64 (s, 3H), 3.34 (ddd, J = 13.9, 7.5, 5.9 Hz, 1H), 3.55 (ddd, J = 13.9, 6.5, 3.2 Hz, 1H), 3.97-4.07 (m, 1H), 4.16 (s, 2H), 4.51 (br s, 2H), 7.03-7.09 (m, 2H), 7.27-7.33 (m, 2H), 7.41 (d, J = 1.9 Hz, 1H), 8.18 (d, J = 1.9 Hz, 1H), 8.36-8.45 (m, 1H). |
| 270 | (400 MHz, DMSO-d₆) δ ppm 1.07 (d, J = 6.6 Hz, 6H), 1.24 (d, J = 6.3 Hz, 3H), 1.44-1.57 (m, 2H), 1.66-1.87 (m, 2H), 3.10-3.18 (m, 1H), 3.34-3.41 (m, 1H), 3.63-3.71 (m, 1H), 3.81-3.91 (m, 3H), 7.19 (br s, 2H), 7.64 (d, J = 1.9 Hz, 1H), 7.85 (d, J = 7.6 Hz, 1H), 8.10 (d, J = 1.9 Hz, 1H), 8.73 (t, J = 5.7 Hz, 1H). |
| 271 | (400 MHz, CD₃OD) δ ppm 1.30 (d, J = 6.3 Hz, 3H), 1.51-1.64 (m, 2H), 1.73-1.95 (m, 2H), 3.22 (dddd, J = 10.5, 7.2, 6.9, 3.4 Hz, 1H), 3.40-3.52 (m, 2H), 3.68-3.79 (m, 1H), 4.20-4.32 (m, 2H), 4.74 (dd, J = 10.8, 6.0 Hz, 1H), 4.85 (m, 1H), 7.54 (d, J = 2.0 Hz, 1H), 8.14 (d, J = 2.0 Hz, 1H). |
| 272 | (400 MHz, CD₃OD) δ ppm 1.30 (d, J = 6.3 Hz, 3H), 1.51-1.64 (m, 2H), 1.73-1.95 (m, 2H), 3.19-3.26 (m, 1H), 3.44 (ddd, J = 10.2, 6.8, 5.1 Hz, 1H), 3.69-3.78 (m, 1H), 3.92 (ddd, J = 11.1, 4.2, 1.7 Hz, 1H), 4.37 (ddd, J = 11.1, 6.8, 1.7 Hz, 1H), 4.43 (ddd, J = 11.4, 4.2, 1.7 Hz, 1H), 4.55-4.62 (m, 1H), 4.86 (ddd, J = 11.4, 6.6, 1.7 Hz, 1H), 7.54 (d, J = 2.0 Hz, 1H), 8.15 (d, J = 2.0 Hz, 1H). |

TABLE III-continued

NMR Data of Representative Compounds

| Cpd # | ¹H NMR data |
|---|---|
| 273 | (400 MHz, CDCl₃) δ ppm 8.36 (t, J = 5.7 Hz, 1H), 8.25 (d, J = 1.9 Hz, 1H), 8.03-7.98 (m, 2H), 7.51 (d, J = 1.9 Hz, 1H), 7.39-7.34 (m, 2H), 6.25 (s, 2H), 4.53-4.45 (m, 1H), 4.41-4.33 (m, 1H), 4.16-3.99 (m, 1H), 3.68 (dddd, J = 14.2, 6.4, 3.7, 1.2 Hz, 1H), 3.55-3.47 (m, 1H), 3.17 (d, J = 4.8 Hz, 1H). |
| 274 | (400 MHz, CDCl₃) δ ppm 8.12 (t, J = 5.0 Hz, 1H), 7.92-7.87 (m, 2H), 7.82 (s, 1H), 7.24-7.18 (m, 2H), 6.02 (br s, 2H), 4.04-3.95 (m, 1H), 3.54 (ddd, J = 13.9, 6.6, 3.1 Hz, 1H), 3.28 (ddd, J = 13.9, 7.4, 5.7 Hz, 1H), 2.62-2.55 (m, 1H), 2.37 (d, J = 4.2 Hz, 1H), 1.23 (d, J = 6.3 Hz, 3H), 0.85-0.76 (m, 4H). |
| 275 | (400 MHz, CDCl₃) δ ppm 8.19 (br s, 1H), 7.63 (s, 1H), 5.99 (br s, 2H), 4.07-4.00 (m, 1H), 3.58 (ddd, J = 13.8, 6.7, 3.2 Hz, 1H), 3.36-3.28 (m, 3H), 2.84-2.75 (m, 1H), 2.37 (d, J = 4.1 Hz, 1H), 1.30 (t, J = 7.4 Hz, 3H), 1.26 (d, J = 6.2 Hz, 3H), 1.09-1.02 (m, 4H). |
| 276 | (400 MHz, CDCl₃) δ ppm 1.32 (d, J = 6.3 Hz, 3H), 1.51 1.69 (m, 2H), 1.73-1.95 (m, 2H), 3.07 (br s, 1H), 3.15-3.22 (m, 1H), 3.39-3.52 (m, 7H), 3.67 (ddd, J = 14.1, 6.6, 3.8 Hz, 1H), 3.71-3.80 (m, 1H), 3.97-4.04 (m, 1H), 6.23 (br s, 2H), 7.42 (d, J = 1.9 Hz, 1H), 8.21 (d, J = 1.9 Hz, 1H), 8.41 (dd, 1H). |
| 277 | (400 MHz, CDCl₃) δ ppm 1.27 (d, J = 6.3 Hz, 3H), 2.66 (d, J = 4.4 Hz, 1H), 2.89 (s, 3H), 3.29 (t, J = 5.5 Hz, 2H), 3.31 (s, 3H), 3.32-3.39 (m, 1H), 3.52-3.61 (m, 3H), 4.00-4.10 (m, 1H), 6.25 (br s, 2H), 7.39 (d, J = 1.9 Hz, 1H), 8.15 (d, J = 1.9 Hz, 1H), 8.40 (dd, 1H). |
| 278 | (400 MHz, CDCl₃) δ ppm 1.27 (d, J = 6.3 Hz, 3H), 1.54-1.72 (m, 2H), 1.98-2.17 (m, 4H), 2.75 (s, 3H), 3.35 (ddd, J = 13.9, 7.4, 5.9 Hz, 1H), 3.57 (ddd, J = 13.9, 6.6, 3.3 Hz, 1H), 4.00-4.16 (m, 2H), 6.26 (br s, 2H), 7.36 (d, J = 1.9 Hz, 1H), 8.12 (d, J = 1.9 Hz, 1H), 8.36-8.43 (m, 1H). |
| 279 | (400 MHz, CDCl₃) δ ppm 8.37 (t, J = 5.9 Hz, 1H), 8.26 (d, J = 1.9 Hz, 1H), 8.03-7.98 (m, 2H), 7.52 (d, J = 1.9 Hz, 1H), 7.37 (d, J = 8.8 Hz, 2H), 6.23 (br s, 2H), 5.75 (td, J = 55.5, 4.2 Hz, 1H), 4.03-3.90 (m, 1H), 3.76 (ddd, J = 14.5, 6.3, 3.2 Hz, 1H), 3.64 (t, J = 6.5 Hz, 1H), 3.60 (d, J = 4.8 Hz, 1H). |
| 280 | (400 MHz, CDCl₃) δ ppm 8.07-8.02 (m, 2H), 7.99 (t, J = 5.9 Hz, 1H), 7.88 (s, 1H), 7.34 (d, J = 8.3 Hz, 2H), 5.85 (br s, 2H), 4.05-3.96 (m, 1H), 3.86 (s, 3H), 3.57 (ddd, J = 14.0, 6.8, 3.1 Hz, 1H), 3.28 (ddd, J = 13.5, 7.0, 5.8 Hz, 1H), 2.27 (d, J = 3.5 Hz, 1H), 1.23 (d, J = 6.3 Hz, 3H). |
| 281 | (400 MHz, CDCl₃) δ ppm 1.35 (d, J = 6.4 Hz, 3H), 1.53-1.71 (m, 2H), 1.75-1.98 (m, 2H), 3.22 (ddd, J = 10.1, 7.4, 7.2 Hz, 1H), 3.51 (ddd, J = 10.1, 7.0, 4.8 Hz, 1H), 3.74-3.83 (m, 1H), 4.04 (s, 3H), 4.78 (d, J = 5.2 Hz, 2H), 6.30 (br s, 2H), 6.66 (d, J = 5.8 Hz, 1H), 7.46 (d, J = 1.9 Hz, 1H), 8.29 (d, J = 1.9 Hz, 1H), 8.45 (d, J = 5.8 Hz, 1H), 9.09 9.16 (m, 1H). |
| 282 | (400 MHz, DMSO-d₆) δ ppm 1.24 1.25 (m, 3H), 1.44 1.57 (m, 2H), 1.66 1.86 (m, 2H), 3.10 3.18 (m, 1H), 3.34 3.42 (m, 1H), 3.63 3.72 (m, 1H), 4.37 (d, J = 5.9 Hz, 2H), 6.22 (d, J = 6.6 Hz, 1H), 7.18 (br s, 2H), 7.65 (d, J = 2.0 Hz, 1H), 7.85 (d, J = 6.6 Hz, 1H), 8.12 (d, J = 2.0 Hz, 1H), 9.08 (t, J = 5.9 Hz, 1H), 10.54 (br s, 1H), 12.55 (br s, 1H). |
| 283 | (501 MHz, CDCl₃) δ ppm 8.12 (t, J = 6.0 Hz, 1H), 7.98-7.94 (m, 2H), 7.88 (s, 1H), 7.29 (d, J = 8.3 Hz, 2H), 6.04 (br s, 2H), 4.04-3.97 (m, 1H), 3.54 (ddd, J = 14.0, 6.7, 3.2 Hz, 1H), 3.29 (ddd, J = 13.7, 7.5, 5.8 Hz, 1H), 2.48 (s, 6H), 2.38 (d, J = 4.2 Hz, 1H), 1.23 (d, J = 6.3 Hz, 3H). |
| 284 | (400 MHz, CDCl₃) δ ppm 8.09-8.05 (m, 2H), 7.95 (s, 1H), 7.54 (t, J = 6.0 Hz, 1H), 7.33 (d, J = 8.4 Hz, 2H), 7.29-7.24 (m, 1H), 6.92-6.86 (m, 1H), 6.63-6.59 (m, 2H), 6.03 (br s, 2H), 3.90-3.82 (m, 1H), 3.41 (ddd, J = 13.5, 6.5, 3.2 Hz, 1H), 3.13 (ddd, J = 13.2, 6.9, 5.6 Hz, 1H), 2.00 (d, J = 3.7 Hz, 1H), 1.12 (d, J = 6.3 Hz, 3H). |
| 285 | (400 MHz, CDCl₃) δ ppm 8.43 (t, J = 5.8 Hz, 1H), 7.95-7.90 (m, 2H), 7.61 (s, 1H), 7.32 (d, J = 8.2 Hz, 2H), 6.33 (br s, 1H), 5.52 (br s, 2H), 4.05-3.96 (m, 1H), 3.57 (ddd, J = 13.9, 6.7, 3.3 Hz, 1H), 3.28 (ddd, J = 13.9, 7.3, 5.6 Hz, 1H), 2.70-2.64 (m, 1H), 2.25 (d, J = 4.3 Hz, 1H), 1.24 (d, J = 6.3 Hz, 3H), 0.80-0.75 (m, 2H), 0.43-0.38 (m, 2H). |
| 286 | (400 MHz, DMSO-d₆) δ ppm 3.33 (s, 3H), 3.91 (s, 2H), 7.18 (s, 2H), 7.59 7.69 (m, 2H), 7.75 (d, J = 2.1 Hz, 1H), 8.08 8.16 (m, 2H), 8.21 (d, J = 2.0 Hz, 1H), 9.84 (s, 1H), 10.27 (s, 1H). |
| 287 | (501 MHz, DMSO-d₆) δ ppm 3.93 (d, J = 5.9 Hz, 2H), 5.48 (t, J = 6.0 Hz, 1H), 7.12-7.24 (m, 2H), 7.64 (dq, J = 7.8, 1.1 Hz, 2H), 7.75 (d, J = 2.0 Hz, 1H), 8.09-8.16 (m, 2H), 8.21 (d, J = 2.1 Hz, 1H), 9.70 (s, 1H), 10.23 (s, 1H). |
| 288 | (400 MHz, CDCl₃) δ ppm 8.12-8.08 (m, 2H), 7.97 (t, J = 6.0 Hz, 1H), 7.88 (s, 1H), 7.32 (d, J = 8.6 Hz, 2H), 5.84 (br s, 2H), 4.37-4.34 (m, 1H), 4.03-3.95 (m, 1H), 3.69-3.65 (m, 2H), 3.56 (ddd, J = 13.9, 6.6, 3.1 Hz, 1H), 3.39 (s, 3H), 3.27 (ddd, J = 13.6, 7.3, 5.7 Hz, 1H), 2.31 (d, J = 4.2 Hz, 1H), 1.23 (d, J = 6.3 Hz, 3H). |
| 289 | (501 MHz, CDCl₃) δ ppm 8.11-8.07 (m, 3H), 7.88 (s, 1H), 7.34-7.31 (m, 2H), 5.85 (br s, 2H), 4.34 (qt, J = 11.0, 6.3 Hz, 2H), 4.01-3.94 (m, 1H), 3.56 (ddd, J = 13.9, 6.8, 3.1 Hz, 1H), 3.25 (ddd, J = 13.9, 7.6, 5.4 Hz, 1H), 2.65-2.56 (m, 2H), 2.29 (s, 6H), 1.22 (d, J = 6.3 Hz, 3H). |
| 290 | (400 MHz, CDCl₃) δ ppm 8.12 (t, J = 6.0 Hz, 1H), 7.95-7.91 (m, 2H), 7.83 (s, 1H), 7.35 (d, J = 8.2 Hz, 2H), 6.04 (br s, 2H), 4.04-3.95 (m, 1H), 3.54 (ddd, J = 13.9, 6.7, 3.2 Hz, 1H), 3.28 (ddd, J = 13.8, 7.4, 5.7 Hz, 1H), 2.60-2.53 (m, 1H), 2.37 (d, J = 3.7 Hz, 1H), 1.23 (d, J = 6.3 Hz, 3H), 0.86-0.73 (m, 4H). |
| 297 | (400 MHz, DMSO-d₆) δ ppm 8.17 (d, J = 2.1 Hz, 1H), 8.13-8.09 (m, 2H), 8.02 (br s, 1H), 7.69 (d, J = 2.1 Hz, 1H), 7.63 (d, J = 8.1 Hz, 2H), 7.58 (br s, 1H), 7.25 (br s, 2H). |

TABLE III-continued

NMR Data of Representative Compounds

| Cpd # | $^1$H NMR data |
|---|---|
| 298 | (400 MHz, DMSO-$d_6$) δ ppm 7.37 (s, 2H), 7.43 7.52 (m, 2H), 7.59 (s, 1H), 7.77 (s, 1H), 7.96 8.03 (m, 2H), 8.10 (s, 1H). |

Biological Examples

List of abbreviations used in the biological examples section: cAMP for cyclic adenosine monophosphate; DMSO for dimethyl sulfoxide; FBS for fetal bovine serum; HEPES for 4-(2-hydroxyethyl)-1-piperazineethanesulfonic acid; LCMS for liquid chromatography-mass spectrometry; LC-MS/MS for liquid chromatography-tandem mass spectrometry; NADP+ for nicotinamide adenine dinucleotide phosphate; PEG for polyethylene glycol; and PBS for phosphate buffered saline.

In Vitro Assays

YFP-Halide Influx Assay for the CFTR-ΔF508 Mutation

The YFP halide influx assay measured the functionality of the cystic fibrosis Transmembrane Conductance regulator (CFTR) channels in the cystic fibrosis bronchial epithelium cell line CFBE41o-. The assay was used to evaluate the capacity of compounds to increase the open probability of existing CFTR channels in the membrane. It makes use of the observation that the yellow fluorescent protein (YFP) variant YFP H148Q, I152L, F47L has its fluorescence substantially quenched by halide ions like Cl⁻ and I⁻ (Galietta, L. J. V., Haggie, P. M., Verkman, A. S., 2001. Green fluorescent protein-based halide indicators with improved chloride and iodide affinities. FEBS Lett. 499, 220-224. doi:10.1016/S0014-5793(01)02561-3; Nagai, T., Ibata, K., Park, E. S., Kubota, M., Mikoshiba, K., Miyawaki, A., 2002. A variant of yellow fluorescent protein with fast and efficient maturation for cell-biological applications. Nat. Biotechnol. 20, 87-90. doi: 10.1038/nbt0102-87).

For this purpose, CFBE41o-cells were seeded in 384 well plates (3000 CFBE cells/well). One day after seeding, the CFBE cells were transduced with adenoviral vectors that direct the expression of the CFTR ΔF508 mutant and of the YFP reporter. Cells were incubated at 27° C., 5% $CO_2$ for 24 hours so as to allow for the proper folding and migration to the membrane of the CFTR channel or treated with a CFTR modulator during 24 hours at 37° C.

The next day the CFTR channels were activated by treatment with the cAMP inducer forskolin (10.67 μM) and test compound in 1×D-PBS in a total volume of 30 μL (from Gibco, Cat n#14090-041) for 10 minutes prior to addition of 30 μL of following iodide solution (375 mM NaI, 7.5 mM KI, 1.76 mM $KH_2PO_4$, 10.1 mM $Na_2HPO_4$, 13.75 mM glucose). The I-induced quenching of fluorescence was recorded on an immediately after injection of iodide for 2 minutes on an FDSS/μCell (Hamamatsu). The capacity of a compound to increase the channel opening was directly correlated with the decrease in fluorescence, and was expressed as (1−(fluorescence after 36 seconds (F)/fluorescence before injection (F0))) and an $EC_{50}$ was derived from a (1−F/F0) vs compound concentration plot.

TABLE IV

Illustrative $EC_{50}$ measured by YFP-halide influx assay for the CFTR- ΔF508 of the compounds of the invention.

| Compound # | % Activation | $EC_{50}$ (nM) |
|---|---|---|
| 1 | 97.9 | 31.4 |
| 2 | 104.5 | 4.3 |
| 3 | 109.7 | 17.7 |
| 4 | 92.1 | 206.0 |
| 5 | 14.8 | >2000 |
| 6 | 114.0 | 3.4 |
| 7 | 103.5 | 69.1 |
| 8 | 109.5 | 72.1 |
| 9 | 97.5 | 160.5 |
| 10 | 106.4 | 148.2 |
| 11 | 113.5 | 21.7 |
| 12 | 114.5 | 36.1 |
| 13 | 101.0 | 39.9 |
| 14 | 108.1 | 23.7 |
| 15 | 109.0 | 2.6 |
| 16 | 106.5 | 15.7 |
| 17 | 113.0 | 8.8 |
| 18 | 109.1 | 43.1 |
| 19 | 113.3 | 16.4 |
| 20 | 98.5 | 29.7 |
| 21 | 109.0 | 14.9 |
| 22 | 102.2 | 54.1 |
| 23 | 103.9 | 78.2 |
| 24 | 106.6 | 21.4 |
| 25 | 108.3 | 8.1 |
| 26 | 105.3 | 2.2 |
| 27 | 101.0 | 10.1 |
| 28 | 97.2 | 50.4 |
| 29 | 94.1 | 54.6 |
| 30 | 94.6 | 53.7 |
| 31 | 106.2 | 18.6 |
| 32 | 96.1 | 14.5 |
| 33 | 98.6 | 42.8 |
| 34 | 99.0 | 91.1 |
| 35 | 110.4 | 84.7 |
| 36 | 111.0 | 8.5 |
| 37 | 106.4 | 2.3 |
| 38 | 103.0 | 61.6 |
| 39 | 42.5 | 155.0 |
| 40 | 105.5 | 22.9 |
| 41 | 101.0 | 184.0 |
| 42 | 105.5 | 37.1 |
| 43 | 92.6 | 236.0 |
| 44 | 73.9 | 323.0 |
| 45 | 93.6 | 83.7 |
| 46 | 41.4 | 1155.0 |
| 47 | 84.8 | 503.0 |
| 48 | 103.0 | 21.1 |
| 49 | 132.0 | 125.0 |
| 50 | 90.8 | 57.5 |
| 51 | 96.8 | 30.2 |
| 52 | 96.6 | 8.0 |
| 53 | 95.6 | 41.4 |
| 54 | 89.2 | 72.9 |
| 55 | 37.6 | >2000 |
| 56 | 99.4 | 369.0 |
| 57 | 93.1 | 7.1 |
| 58 | 92.2 | 20.6 |
| 59 | 111.0 | 34.3 |
| 60 | 105.0 | 67.2 |
| 61 | 101.0 | 60.9 |
| 62 | 91.8 | 140.0 |
| 63 | 102.0 | 3.1 |

TABLE IV-continued

Illustrative $EC_{50}$ measured by YFP-halide influx assay for the CFTR-$\Delta$F508 of the compounds of the invention.

| Compound # | % Activation | $EC_{50}$ (nM) |
|---|---|---|
| 64 | 107.0 | 1.3 |
| 65 | 119.0 | 41.4 |
| 66 | 106.0 | 12.5 |
| 67 | 110.0 | 25.8 |
| 68 | 92.0 | 130.0 |
| 69 | 102.0 | 5.7 |
| 70 | 111.6 | 16.9 |
| 71 | 108.0 | 19.1 |
| 72 | 89.3 | 21.8 |
| 73 | 102.0 | 81.4 |
| 74 | 110.0 | 17.2 |
| 75 | 121.0 | 7.6 |
| 76 | 112.0 | 4.3 |
| 77 | 98.8 | 15.3 |
| 78 | 123.0 | 2.2 |
| 79 | 99.5 | 3.3 |
| 80 | 102.0 | 3.2 |
| 81 | 104.0 | 0.5 |
| 82 | 106.0 | 2.7 |
| 83 | 98.3 | 6.3 |
| 84 | 101.0 | 10.5 |
| 85 | 110.5 | 1.0 |
| 86 | 122.0 | 3.1 |
| 87 | 102.0 | 11.9 |
| 88 | 96.0 | 12.4 |
| 89 | 99.6 | 6.9 |
| 90 | 101.0 | 4.0 |
| 91 | 97.2 | 11.5 |
| 92 | 118.5 | 7.2 |
| 93 | 96.5 | 95.5 |
| 94 | 102.0 | 22.2 |
| 95 | 104.0 | 5.7 |
| 96 | 105.0 | 245.0 |
| 97 | 92.9 | 102.0 |
| 98 | 95.6 | 7.4 |
| 99 | 109.5 | 7.6 |
| 100 | 96.6 | 12.9 |
| 101 | 106.5 | 64.2 |
| 102 | 119.0 | 28.2 |
| 103 | 110.0 | 26.2 |
| 104 | 100.8 | 18.9 |
| 105 | 103.5 | 2.0 |
| 106 | 99.0 | 19.5 |
| 107 | 103.0 | 1.5 |
| 108 | 110.0 | 18.2 |
| 109 | 104.0 | 3.6 |
| 110 | 116.0 | 33.5 |
| 111 | 103.2 | 22.6 |
| 112 | 100.6 | 2.6 |
| 113 | 101.9 | 10.4 |
| 114 | 109.3 | 19.1 |
| 115 | 102.3 | 34.9 |
| 116 | 101.1 | 27.7 |
| 117 | 107.9 | 1.7 |
| 118 | 93.2 | 208.0 |
| 119 | 101.0 | 34.1 |
| 120 | 96.5 | 76.8 |
| 121 | 102 | 113.0 |
| 122 | 83.2 | 35.3 |
| 123 | 98.5 | 86.2 |
| 124 | 104.0 | 100.0 |
| 125 | 114.0 | 65.6 |
| 126 | 92.9 | 64.9 |
| 127 | 107.0 | 82.9 |
| 128 | 95.0 | 85.2 |
| 129 | 74.9 | 180.0 |
| 130 | 93.9 | 102.0 |
| 131 | 110.2 | 12.8 |
| 132 | 103.5 | 5.1 |
| 133 | 105.9 | 3.7 |
| 134 | 101.6 | 43.5 |
| 135 | 108.7 | 8.5 |
| 136 | 113.7 | 2.9 |
| 137 | 110.7 | 3.7 |
| 138 | 94.5 | 17.9 |
| 139 | 96.6 | 61.2 |
| 140 | 97.7 | 51.0 |
| 141 | 100.6 | 109.1 |
| 142 | 97.9 | 11.9 |
| 143 | 91.4 | 136.3 |
| 144 | 92.6 | 76.1 |
| 145 | 98.8 | 205.0 |
| 146 | 88.4 | 91.4 |
| 147 | 105.5 | 40.9 |
| 148 | 88.8 | 42.5 |
| 149 | 91.2 | 179.0 |
| 150 | 116.0 | 355.0 |
| 151 | 16.9 | >1000 |
| 152 | 93.3 | 119.0 |
| 153 | 105.0 | 75.4 |
| 154 | 98.1 | 66.3 |
| 155 | 108.0 | 81.2 |
| 156 | 94.0 | 238.0 |
| 157 | 101.2 | 33.7 |
| 158 | 114.3 | 31.6 |
| 159 | 111.1 | 4.4 |
| 160 | 113.9 | 23.6 |
| 161 | 97.3 | 21.5 |
| 162 | 101.8 | 2.7 |
| 163 | 97.0 | 22.6 |
| 164 | 102.0 | 8.2 |
| 165 | 115.2 | 10.9 |
| 166 | 111.7 | 17.5 |
| 167 | 98.3 | 41.7 |
| 168 | 103.5 | 9.6 |
| 169 | 95.5 | 13.8 |
| 170 | 108.6 | 6.6 |
| 171 | 103.7 | 8.7 |
| 172 | 95.9 | 13.4 |
| 173 | 98.3 | 2.6 |
| 174 | 118.3 | 5.9 |
| 175 | 103.0 | 6.3 |
| 176 | 93.4 | 1.0 |
| 177 | 102.1 | 3.6 |
| 178 | 109.7 | 5.6 |
| 179 | 100.4 | 27.7 |
| 180 | 97.0 | 107.1 |
| 181 | 90.6 | 19.8 |
| 182 | 112.7 | 4.7 |
| 183 | 103.7 | 20.8 |
| 184 | 111.0 | 6.9 |
| 185 | 111.3 | 2.9 |
| 186 | 108.2 | 29.9 |
| 187 | 99.1 | 2.8 |
| 188 | 88.8 | 378.4 |
| 189 | 99.9 | 112.0 |
| 190 | 96.6 | 135.4 |
| 191 | 99.7 | 157.1 |
| 192 | 101.5 | 38.8 |
| 193 | 26.7 | >2000 |
| 194 | 95.7 | 32.7 |
| 195 | 98.7 | 26.2 |
| 196 | 105.4 | 25.7 |
| 197 | 106.7 | 3.9 |
| 198 | 107.0 | 7.8 |
| 199 | 114.1 | 21.6 |
| 200 | 116.7 | 42.9 |
| 201 | 104.0 | 14.7 |
| 202 | 97.6 | 45.5 |
| 203 | 92.6 | 47.3 |
| 204 | 92.5 | 177.0 |
| 205 | 96.5 | 59.9 |
| 206 | 103.0 | 74.8 |
| 207 | 78.0 | >667 |
| 208 | 70.5 | 290.0 |
| 209 | 93.8 | 36.2 |
| 210 | 44.6 | >667 |
| 211 | 98.4 | 24.7 |
| 212 | 96.7 | 47.1 |
| 213 | 115.3 | 6.0 |

TABLE IV-continued

Illustrative $EC_{50}$ measured by YFP-halide influx assay for the CFTR- $\Delta$F508 of the compounds of the invention.

| Compound # | % Activation | $EC_{50}$ (nM) |
|---|---|---|
| 214 | 60.5 | >667 |
| 215 | 109.8 | 8.9 |
| 216 | 98.6 | 47.1 |
| 217 | 103.4 | 36.0 |
| 218 | 105.8 | 44.4 |
| 219 | 99.8 | 19.2 |
| 220 | 102.0 | 16.9 |
| 221 | 101.7 | 54.5 |
| 222 | 108.7 | 40.8 |
| 223 | 96.4 | 49.0 |
| 224 | 106.0 | 8.1 |
| 225 | 106.7 | 30.9 |
| 226 | 11.9 | >2000 |
| 227 | 81.0 | >667 |
| 228 | 123.3 | 8.5 |
| 229 | 24.0 | >2000 |
| 230 | 12.4 | >2000 |
| 231 | 103.3 | 52.3 |
| 232 | 94.5 | 68.4 |
| 233 | 44.9 | 1387.0 |
| 234 | 102.4 | 39.3 |
| 235 | 58.5 | >667 |
| 236 | 115.5 | 3.6 |
| 237 | 106.5 | 9.9 |
| 238 | 53.7 | 538.0 |
| 239 | 95.8 | 29.5 |
| 240 | 98.1 | 137.0 |
| 241 | 117.0 | 11.6 |
| 242 | 103.0 | 25.4 |
| 243 | 111.5 | 8.3 |
| 244 | 102.5 | 8.5 |
| 245 | 114.0 | 5.6 |
| 246 | 118.0 | 3.9 |
| 247 | 114.5 | 4.3 |
| 248 | 105.0 | 12.0 |
| 249 | 96.2 | 3.0 |
| 250 | 111.5 | 1.0 |
| 251 | 110.0 | 16.3 |
| 252 | 102.0 | 2.5 |
| 253 | 102.6 | 6.0 |
| 254 | 106.0 | 5.0 |
| 255 | 104.2 | 1.3 |
| 256 | 107.4 | 0.66 |
| 257 | 122.0 | 26.9 |
| 258 | 119.0 | 9.9 |
| 259 | 102.5 | 4.3 |
| 260 | 85.2 | 42.5 |
| 261 | 87.3 | 162.0 |
| 262 | 8.9 | >1000 |
| 263 | 97.2 | 141.7 |
| 264 | 76.0 | 213.3 |
| 265 | 92.4 | 141.2 |
| 266 | 105.0 | 180.0 |
| 267 | 59.3 | >667.0 |
| 268 | 37.1 | >667.0 |
| 269 | 107.0 | 7.8 |
| 270 | 100.0 | 143.0 |
| 271 | 20.4 | >2000 |
| 272 | 82.0 | >334 |
| 273 | 112.0 | 10.3 |
| 274 | 111.0 | 6.9 |
| 275 | 68.5 | >667 |
| 276 | 108.0 | 109.2 |
| 277 | 65.5 | >667 |
| 278 | 105.0 | 44.1 |
| 279 | 113.0 | 1.7 |
| 280 | 111.0 | 2.9 |
| 281 | 89.4 | 166.8 |
| 282 | 47.0 | >667 |
| 283 | 93.3 | 5.1 |
| 284 | 95.1 | 6.3 |
| 285 | 86.7 | 4.2 |
| 286 | 79.7 | 88.1 |
| 287 | 83.4 | 256.0 |
| 288 | 109.0 | 8.7 |
| 289 | 97.1 | 245.0 |
| 290 | 88.2 | 3.0 |
| 291 | 98.2 | 5.5 |
| 292 | 72.4 | 263.2 |
| 293 | 87.8 | 135.2 |
| 294 | 97.5 | 9.6 |
| 295 | 102.3 | 51.3 |
| 296 | 82.1 | 40.0 |
| 297 | 109 | 53.0 |

YFP-Halide Influx Assay for the CFTR-G551D Mutation

The YFP halide influx assay measured the functionality of the cystic fibrosis Transmembrane Conductance regulator (CFTR) channels. The assay was used to evaluate the capacity of compounds to increase the channel opening of existing mutant CFTR channels in the membrane. It makes use of the observation that the yellow fluorescent protein (YFP) variant YFP H148Q, I152L, F47L has its fluorescence substantially quenched by halide ions like Cl$^-$ and I$^-$ (Galietta, L. J. V., Haggie, P. M., Verkman, A. S., 2001. Green fluorescent protein-based halide indicators with improved chloride and iodide affinities. FEBS Lett. 499, 220-224. doi:10.1016/S0014-5793(01)02561-3).

For this purpose, HEK293-cells were seeded in 96 well plates. During seeding, the cells were reverse-transfected with plasmid vectors that direct the expression of the CFTR G551D mutant and of the YFP reporter. Cells were incubated at 37° C., 5% $CO_2$ for 24 hours so as to allow for sufficient expression of the CFTR protein.

The next day the CFTR channels were activated by treatment with the cAMP inducer forskolin (10.67 µM) and test compound in D-PBS (Gibco) for 10 minutes prior to addition of an I$^-$ solution (137 mM NaI, 2.7 mM KI, 1.76 mM $KH_2PO_4$, 10.1 mM $Na_2HPO_4$, 5 mM glucose). The I$^-$-induced quenching of fluorescence was recorded immediately after injection of I$^-$ for 7 seconds. The capacity of a compound to increase the channel opening was directly correlated with the decrease in fluorescence, and was expressed as (1−(fluorescence after 7 seconds (F)/fluorescence before injection (F0))) and an $EC_{50}$ was derived from a (1−F/F0) vs compound concentration plot.

Similar YHA assays were developed for other channel gating defective or channel conductance defective CFTR mutants to determine effect of compound on channel activity. Examples of mutants are G178R, G1349D, S549N, R117H, R334W. This assay is also used for additional class I CFTR mutants, including G542X, W1282X; class II mutants including N1303K, and for class III mutants including S1251N; or wild-type CFTR.

TABLE V

Illustrative $EC_{50}$ measured by YFP-halide influx assay for the CFTR-G551D of the compounds of the invention.

| Compound # | % Activation | $EC_{50}$ (nM) |
|---|---|---|
| 1 | 47.1 | 699.8 |
| 2 | 62.5 | 739.0 |
| 3 | 73.9 | 1980.8 |
| 4 | 43.6 | 5770.6 |
| 5 | 1.7 | >10000 |
| 6 | 82.5 | 350.0 |
| 7 | 73.5 | 722.8 |

TABLE V-continued

Illustrative EC$_{50}$ measured by YFP-halide influx assay for the CFTR-G551D of the compounds of the invention.

| Compound # | % Activation | EC$_{50}$ (nM) |
|---|---|---|
| 8 | 67.5 | 1200.0 |
| 9 | 59.5 | >3330 |
| 10 | 52.2 | >3330 |
| 11 | 75.7 | 835 |
| 12 | 43.8 | 692.0 |
| 13 | 21.3 | >10000 |
| 14 | 71.6 | 1328.2 |
| 15 | 69.3 | 361.0 |
| 16 | 96.2 | 1672.6 |
| 17 | 82.7 | 1640.0 |
| 18 | 79.2 | >3330 |
| 19 | 63.2 | 1076.4 |
| 20 | 64.8 | 893.3 |
| 21 | 85.1 | 1195.5 |
| 22 | 53.2 | 778.0 |
| 23 | 57.4 | 2147.5 |
| 24 | 52.2 | 423.0 |
| 25 | 67.2 | 976.2 |
| 26 | 80.8 | 315.2 |
| 27 | 55.0 | 1240.6 |
| 28 | 51.9 | 2330.0 |
| 29 | 58.7 | 1500.0 |
| 30 | 36.4 | 5770.6 |
| 31 | 71.7 | 424.6 |
| 32 | 65.8 | 1941.2 |
| 33 | 62.3 | 1391.2 |
| 34 | 70.2 | 1485.0 |
| 35 | 78.7 | 2385.8 |
| 36 | 58.4 | 667.1 |
| 37 | 83.7 | 271.2 |
| 38 | 86.0 | 1106.3 |
| 39 | 5.0 | >10000 |
| 40 | 70.2 | 655.9 |
| 42 | 64.3 | >3330 |
| 46 | 3.5 | >10000 |
| 50 | 23.5 | >10000 |
| 51 | 51.2 | 1131.0 |
| 52 | 48.8 | 458.0 |
| 53 | 54.0 | 1823.4 |
| 54 | 62.6 | 1655.0 |
| 57 | 51.8 | 385.0 |
| 58 | 42.3 | 1070.0 |
| 59 | 84.6 | 1629.4 |
| 60 | 71.1 | 3120.0 |
| 61 | 70.0 | 2730.0 |
| 62 | 49.3 | 1390.0 |
| 63 | 60.8 | 262.2 |
| 64 | 72.5 | 160.1 |
| 65 | 67.8 | 1160.0 |
| 66 | 60.8 | 1550.0 |
| 67 | 73.6 | 1586.8 |
| 68 | 54.0 | 1820.0 |
| 69 | 85.0 | 1083.0 |
| 70 | 75.3 | 864.4 |
| 71 | 70.2 | 1258.0 |
| 72 | 44.2 | >3330 |
| 73 | 61.0 | >3330 |
| 74 | 65.0 | 839.0 |
| 75 | 68.5 | 1505.5 |
| 76 | 54.3 | >3330 |
| 77 | 41.0 | >3330 |
| 78 | 55.9 | 609.0 |
| 79 | 48.9 | 256.0 |
| 80 | 95.1 | 946.0 |
| 81 | 108.0 | 239.0 |
| 82 | 89.9 | 795.0 |
| 83 | 90.4 | 1195.8 |
| 84 | 64.4 | 1944.2 |
| 85 | 51.7 | 28.9 |
| 86 | 69.3 | 332.0 |
| 87 | 67.5 | 996.6 |
| 88 | 82.0 | 762.2 |
| 89 | 53.6 | >3330 |
| 90 | 86.8 | 216.0 |
| 91 | 56.1 | 810.1 |
| 92 | 79.0 | 209.8 |
| 94 | 43.4 | 1140.0 |
| 95 | 54.2 | 299.5 |
| 97 | 23.8 | >10000 |
| 98 | 60.2 | 685.2 |
| 99 | 91.7 | 795.5 |
| 100 | 59.1 | 1135.9 |
| 101 | 71.2 | 1584.7 |
| 102 | 73.6 | 1359.8 |
| 103 | 52.6 | 368.2 |
| 104 | 26.1 | >10000 |
| 105 | 50.4 | 128.4 |
| 106 | 42.4 | >3330 |
| 107 | 81.7 | 164.0 |
| 108 | 56.8 | 1697.9 |
| 109 | 62.6 | 296.0 |
| 110 | 83.6 | 1138.3 |
| 111 | 99.2 | 850.9 |
| 112 | 74.1 | 157.5 |
| 113 | 41.1 | 296.6 |
| 114 | 37.9 | >10000 |
| 115 | 40.6 | 900.0 |
| 116 | 50.0 | 1402.9 |
| 117 | 79.8 | 218.4 |
| 118 | 49.5 | 419.2 |
| 119 | 64.6 | 554.0 |
| 120 | 54.0 | 1110.0 |
| 121 | 88.6 | 1330.0 |
| 122 | 50.9 | 425.0 |
| 123 | 60.5 | 880.0 |
| 124 | 57.0 | 824.0 |
| 125 | 84.1 | 2210.0 |
| 126 | 62.2 | 1470.0 |
| 127 | 61.2 | 1880.0 |
| 128 | 41.7 | >10000 |
| 129 | 25.9 | >10000 |
| 130 | 78.3 | 674.0 |
| 131 | 68.6 | 816.7 |
| 132 | 79.2 | 395.0 |
| 133 | 84.2 | 252.8 |
| 134 | 76.8 | 1128.1 |
| 135 | 43.5 | 5770.6 |
| 136 | 53.4 | >3330 |
| 137 | 69.6 | 420.5 |
| 138 | 49.6 | 683.9 |
| 139 | 40.6 | 5770.6 |
| 140 | 39.9 | >10000 |
| 141 | 60.4 | 795.0 |
| 142 | 44.7 | 399.0 |
| 143 | 80.6 | 2300.0 |
| 144 | 50.6 | 1120.0 |
| 145 | 53.9 | 836.0 |
| 146 | 58.4 | 3110.0 |
| 147 | 69.0 | 1280.0 |
| 148 | 60.2 | 510.0 |
| 149 | 42.7 | >1670 |
| 150 | 49.7 | 1070.0 |
| 151 | 3.0 | >5000 |
| 152 | 60.2 | 1130.0 |
| 153 | 47.6 | 760.0 |
| 154 | 81.9 | 881.0 |
| 155 | 80.2 | 987.0 |
| 156 | 63.5 | 1390.0 |
| 157 | 28.8 | >10000 |
| 158 | 29.2 | >10000 |
| 159 | 46.6 | 238.5 |
| 160 | 52.7 | 566.4 |
| 161 | 45.8 | 680.6 |
| 162 | 68.0 | 255.0 |
| 163 | 71.9 | 2295.7 |
| 164 | 71.5 | 683.0 |
| 165 | 55.0 | 287.4 |
| 166 | 69.3 | 661.0 |
| 167 | 71.5 | 1550.0 |
| 168 | 82.4 | 538.8 |

TABLE V-continued

Illustrative $EC_{50}$ measured by YFP-halide influx assay for the CFTR-G551D of the compounds of the invention.

| Compound # | % Activation | $EC_{50}$ (nM) |
|---|---|---|
| 169 | 81.3 | 1120.0 |
| 170 | 82.5 | 251.0 |
| 171 | 86.4 | 991.0 |
| 172 | 62.4 | 863.5 |
| 173 | 47.6 | 181.0 |
| 174 | 50.3 | 370.5 |
| 175 | 44.0 | >3330 |
| 176 | 46.0 | 69.4 |
| 177 | 91.4 | 430.0 |
| 178 | 75.8 | 322.3 |
| 179 | 52.6 | 1350.0 |
| 180 | 30.2 | >10000 |
| 181 | 61.4 | 1330.0 |
| 182 | 51.3 | 645.0 |
| 183 | 42.0 | 1130.0 |
| 184 | 66.4 | 392.0 |
| 185 | 69.4 | 1120.0 |
| 186 | 49.9 | >3330 |
| 187 | 71.8 | 705.0 |
| 188 | 13.4 | >10000 |
| 189 | 30.7 | >10000 |
| 190 | 67.4 | 1880.0 |
| 191 | 11.7 | >10000 |
| 192 | 58.4 | 868.1 |
| 194 | 62.3 | 1780.0 |
| 195 | 61.8 | 1245.4 |
| 196 | 65.4 | 1816.6 |
| 197 | 76.4 | 337.5 |
| 198 | 75.2 | 756.3 |
| 199 | 65.0 | 1430.9 |
| 200 | 59.5 | 2340.0 |
| 201 | 59.8 | 522.5 |
| 202 | 45.1 | 1595.7 |
| 203 | 57.3 | 1270.0 |
| 204 | 73.9 | >3330 |
| 205 | 37.6 | 10000 |
| 206 | 90.3 | 3150.0 |
| 207 | 15.0 | >10000 |
| 208 | 20.0 | >10000 |
| 209 | 39.3 | >10000 |
| 210 | 5.8 | >10000 |
| 211 | 24.0 | 10000 |
| 212 | 33.0 | 10000 |
| 213 | 71.0 | 414.0 |
| 214 | 39.1 | >10000 |
| 215 | 57.6 | 389.3 |
| 216 | 47.8 | 1140.0 |
| 217 | 51.8 | 3030.0 |
| 218 | 43.8 | 1520.0 |
| 219 | 44.7 | 1050.0 |
| 220 | 71.6 | 791.0 |
| 221 | 55.6 | 1840.0 |
| 222 | 48.4 | 816.0 |
| 223 | 19.0 | >10000 |
| 224 | 80.6 | 276.2 |
| 225 | 44.2 | 2210.0 |
| 226 | 1.4 | >10000 |
| 227 | 28.1 | >10000 |
| 228 | 62.6 | 1042.4 |
| 229 | 1.0 | >10000 |
| 230 | 1.5 | >10000 |
| 231 | 59.2 | 449.8 |
| 232 | 66.0 | 1490.0 |
| 233 | 5.4 | >10000 |
| 234 | 46.1 | 1090.0 |
| 235 | 14.4 | 10000 |
| 236 | 77.2 | 364.0 |
| 237 | 69.5 | 546.0 |
| 238 | 4.8 | >10000 |
| 239 | 76.5 | 1050.0 |
| 240 | 50.6 | 949.0 |
| 241 | 65.9 | 675.0 |
| 242 | 71.5 | 841.0 |
| 243 | 99.0 | 639.0 |
| 244 | 65.9 | 564.0 |
| 245 | 80.8 | 395.0 |
| 246 | 106.0 | 391.0 |
| 247 | 98.7 | 219.0 |
| 248 | 91.1 | 385.0 |
| 249 | 83.7 | 172.0 |
| 250 | 90.4 | 453.0 |
| 251 | 93.3 | 919.0 |
| 252 | 99.7 | 215.0 |
| 253 | 51.2 | 1069.8 |
| 254 | 56.0 | 1447.3 |
| 255 | 41.8 | 5770.6 |
| 256 | 45.6 | >3330 |
| 257 | 50.4 | 760.0 |
| 258 | 108.0 | 517.0 |
| 259 | 92.6 | 1118.5 |
| 261 | 16.6 | >1000 |
| 262 | 5.5 | >1000 |
| 263 | 5.99 | 2000 |
| 264 | 6.51 | 2000 |
| 265 | 11.24 | 2000 |
| 266 | 21.9 | >10000 |
| 267 | 0.9 | >10000 |
| 268 | 0.3 | 10000 |
| 269 | 44.8 | 1311.0 |
| 270 | 23.8 | >10000 |
| 271 | 2.5 | >10000 |
| 272 | 2.8 | >5000 |
| 273 | 39.5 | 1010.0 |
| 274 | 69.5 | >3330 |
| 275 | 4.2 | >10000 |
| 276 | 13.7 | >10000 |
| 277 | 0.8 | >10000 |
| 278 | 21.3 | >10000 |
| 279 | 57.2 | 662.0 |
| 280 | 57.6 | 1160.0 |
| 281 | 50.0 | >3330 |
| 282 | 1.8 | >10000 |
| 283 | 96.5 | 2620.0 |
| 284 | 67.0 | 1619.6 |
| 285 | 52.5 | 775.9 |
| 286 | 26.8 | 10000 |
| 287 | 24.3 | 10000 |
| 288 | 78.3 | >3330 |
| 289 | 31.0 | 10000 |
| 290 | 73.2 | 473.0 |
| 291 | 44.7 | 242.3 |
| 292 | 28.5 | >10000 |
| 293 | 40.8 | >3330 |
| 294 | 104.0 | 967.0 |
| 295 | 92.7 | 1970.0 |
| 297 | 85 | 518.0 |

TABLE VI

Illustrative $EC_{50}$ measured by YFP-halide influx assay for the CFTR-G178R of the compounds of the invention.

| Compound # | % Activation | $EC_{50}$ (nM) |
|---|---|---|
| 1 | 82.7 | 302.0 |
| 2 | 71.8 | 494.0 |
| 3 | 98.2 | 392.0 |
| 6 | 93.1 | 80.7 |
| 11 | 95.3 | 442.0 |
| 14 | 70.7 | 741.3 |
| 16 | 102.0 | 1010.0 |
| 19 | 89.9 | 561.0 |
| 21 | 86.1 | 284.0 |
| 25 | 76.8 | 211.0 |
| 31 | 84.3 | 348.0 |
| 32 | 78.0 | 522.0 |
| 33 | 81.8 | 514.0 |

TABLE VI-continued

Illustrative EC$_{50}$ measured by YFP-halide influx assay for the CFTR-G178R of the compounds of the invention.

| Compound # | % Activation | EC$_{50}$ (nM) |
|---|---|---|
| 36 | 79.3 | 229.7 |
| 40 | 81.76 | 391.6 |
| 70 | 96.0 | 424.6 |
| 74 | 84.3 | 348.0 |
| 75 | 94.3 | 323.0 |
| 78 | 73 | 58.12 |
| 79 | 74.5 | 31.3 |
| 80 | 95.08 | 81.08 |
| 81 | 104.8 | 12.62 |
| 82 | 106.7 | 84.7 |
| 85 | 77.69 | 3.295 |
| 86 | 78.08 | 32.54 |
| 92 | 104.9 | 145.4 |
| 95 | 80.8 | 225.8 |
| 100 | 78.7 | 546.0 |
| 176 | 79.1 | 12.7 |
| 177 | 104.0 | 77.8 |
| 217 | 63.9 | 933.0 |
| 231 | 98.4 | 305.0 |
| 241 | 84.5 | 502.0 |
| 259 | 97.2 | 149.0 |
| 291 | 79.3 | 109.0 |

TABLE VII

Illustrative EC$_{50}$ measured by YFP-halide influx assay for the CFTR-G1349D of the compounds of the invention.

| Compound # | % Activation | EC$_{50}$ (nM) |
|---|---|---|
| 1 | 69.6 | 265.0 |
| 2 | 69.4 | 567.0 |
| 3 | 83.2 | 291.0 |
| 6 | 87.4 | 158.0 |
| 7 | 63.0 | 549.0 |
| 11 | 90.4 | 1600.0 |
| 14 | 66.7 | 815.9 |
| 16 | 99.6 | 698.0 |
| 19 | 84.3 | 659.0 |
| 21 | 88.9 | 498.0 |
| 25 | 82.6 | 412.0 |
| 31 | 86.8 | 511.0 |
| 32 | 88.0 | 536.0 |
| 33 | 92.9 | 543.0 |
| 36 | 82.7 | 311.8 |
| 40 | 84.31 | 440.2 |
| 57 | 59.6 | 457.0 |
| 63 | 82.8 | 256.0 |
| 70 | 89.6 | 378.4 |
| 74 | 86.8 | 511.0 |
| 75 | 98.7 | 284.0 |
| 78 | 85.36 | 52.28 |
| 80 | 98.43 | 118.8 |
| 79 | 83.08 | 61.38 |
| 81 | 96.01 | 9.539 |
| 82 | 92.74 | 102 |
| 85 | 90.89 | 2.734 |
| 86 | 85.79 | 55.31 |
| 91 | 76.6 | 738.0 |
| 92 | 91.24 | 30.57 |
| 95 | 71.97 | 75.38 |
| 100 | 75.5 | 532.6 |
| 103 | 67.7 | 448.0 |
| 118 | 99.5 | 770.0 |
| 119 | 84.8 | 320.0 |
| 130 | 55.4 | 703.0 |
| 154 | 97.6 | 637.0 |
| 165 | 87.6 | 214.0 |
| 176 | 72.8 | 29.5 |
| 177 | 96.0 | 97.9 |
| 217 | 62.9 | 1350.0 |
| 231 | 83.9 | 129.0 |

TABLE VII-continued

Illustrative EC$_{50}$ measured by YFP-halide influx assay for the CFTR-G1349D of the compounds of the invention.

| Compound # | % Activation | EC$_{50}$ (nM) |
|---|---|---|
| 241 | 71.0 | 1110.0 |
| 259 | 91.0 | 173.0 |
| 291 | 79.8 | 149.0 |

TABLE VIII

Illustrative EC$_{50}$ measured by YFP-halide influx assay for the CFTR-S549N of the compounds of the invention.

| Compound # | % Activation | EC$_{50}$ (nM) |
|---|---|---|
| 1 | 72.7 | 580.0 |
| 2 | 70.3 | 331.0 |
| 3 | 91.8 | 839.0 |
| 6 | 87.1 | 390.0 |
| 11 | 84.1 | 945.0 |
| 14 | 68.9 | 1099.2 |
| 16 | 114.0 | >3330 |
| 19 | 79.6 | 1610.0 |
| 21 | 86.4 | 748.0 |
| 25 | 82.5 | 292.0 |
| 31 | 91.4 | 567.0 |
| 32 | 91.7 | 711.0 |
| 33 | 82.2 | 735.0 |
| 36 | 92.9 | 294.0 |
| 40 | 84.51 | 1197 |
| 70 | 104.7 | 526.1 |
| 74 | 91.4 | 567.0 |
| 75 | 107.0 | 251.0 |
| 75 | 107.2 | 251.4 |
| 78 | 80.37 | 115.6 |
| 79 | 88.09 | 44.34 |
| 80 | 108.5 | 143.6 |
| 81 | 107 | 11.05 |
| 82 | 106.9 | 121.6 |
| 85 | 104.8 | 3.292 |
| 86 | 98.52 | 138.7 |
| 92 | 98.96 | 130.7 |
| 95 | 65.61 | 86.37 |
| 100 | 103.0 | 648.0 |
| 176 | 92.0 | 25.7 |
| 177 | 104.0 | 80.4 |
| 217 | 55.9 | 401.0 |
| 231 | 88.2 | 256.0 |
| 241 | 90.7 | 691.0 |
| 259 | 105.0 | 74.4 |
| 291 | 75.6 | 92.1 |

TABLE IX

Illustrative EC$_{50}$ measured by YFP-halide influx assay for the CFTR-R117H of the compounds of the invention.

| Compound # | % Activation | EC$_{50}$ (nM) |
|---|---|---|
| 1 | 98.5 | 598.0 |
| 2 | 76.0 | 231.0 |
| 3 | 102.0 | 451.0 |
| 6 | 95.7 | 63.9 |
| 7 | 82.7 | 479.0 |
| 11 | 90.4 | 296.0 |
| 14 | 89.7 | 942.7 |
| 16 | 112.0 | 431.0 |
| 19 | 90.8 | 186.0 |
| 21 | 93.3 | 289.0 |
| 25 | 91.3 | 318.0 |
| 31 | 100.0 | 866.0 |
| 32 | 91.3 | 460.0 |
| 33 | 87.1 | 628.0 |
| 36 | 100.8 | 147.9 |

TABLE IX-continued

Illustrative $EC_{50}$ measured by YFP-halide influx assay
for the CFTR-R117H of the compounds of the invention.

| Compound # | % Activation | $EC_{50}$ (nM) |
|---|---|---|
| 40 | 86.71 | 290.9 |
| 57 | 72.8 | 356.0 |
| 63 | 89.3 | 152.0 |
| 70 | 98.8 | 539.7 |
| 74 | 100.0 | 866.0 |
| 75 | 98.4 | 472.0 |
| 78 | 89.74 | 59.55 |
| 79 | 103.1 | 22.16 |
| 80 | 111.5 | 408.1 |
| 81 | 113.2 | 21.84 |
| 82 | 128.3 | 1054 |
| 85 | 103 | 3.829 |
| 86 | 89.91 | 59.45 |
| 91 | 89.6 | 326.0 |
| 92 | 94.77 | 97.7 |
| 95 | 88.62 | 137.6 |
| 100 | 97.3 | 505.0 |
| 103 | 87.8 | 351.0 |
| 118 | 90.7 | 621.0 |
| 119 | 89.9 | 307.0 |
| 130 | 77.6 | 580.0 |
| 154 | 107.0 | 499.0 |
| 165 | 94.2 | 92.8 |
| 176 | 111.0 | 22.7 |
| 177 | 103.7 | 253.1 |
| 217 | 92.1 | 765.0 |
| 231 | 91.3 | 442.0 |
| 241 | 103.0 | 608.0 |
| 259 | 126.0 | 225.0 |
| 291 | 74.2 | 155.0 |

Cellular Assays

Electrophysiological measurements on primary human bronchial epithelial cell cultures are a useful preclinical surrogate of clinical efficacy (Rowe, S. M., Verkman, A. S., 2013. Cystic Fibrosis Transmembrane Regulator Correctors and Potentiators. Cold Spring Harb. Perspect. Med. 3, a009761. doi:10.1101/cshperspect.a009761), therefore compounds are evaluated in an Ussing chamber and/or TECC assay which are electrophysiological measurement assays.

Ussing Chambers Assay

Protocol

The Ussing chambers assay measures the functionality of the cystic fibrosis Transmembrane Conductance regulator (CFTR) by measuring the short circuit current ($I_{sc}$) generated over the basolateral and apical membrane of lung epithelial cells.

In order to measure the $I_{sc}$, the epithelium is short circuited by injecting a current that is adjusted by a feedback amplifier to keep the transepithelial potential ($V_t$) at 0 mV. The amount of current required is adjusted by a feedback circuit and continuously measured. Intermittently the voltage is clamped to values different from 0 mV thus enabling an estimate of the transepithelial resistance ($R_t$).

For this purpose, bronchial epithelial cells isolated from CF patients homozygous for the CFTR ΔF508 mutation (hAEC-CF, Epithelix) or heterozygous for CFTR G551D and ΔF508 mutations (University of Chapel Hill, N.C.) are plated on type IV collagen-coated Snapwell™ supports (Corning-Costar). Human airway epithelia are generated by provision of an air-liquid interface for 21 days to form well-differentiated polarized cultures that resemble in vivo pseudo-stratified ciliated epithelium (Fulcher, M. L., Gabriel, S., Burns, K. A., Yankaskas, J. R., Randell, S. H., 2005. Well-differentiated human airway epithelial cell cultures. Methods Mol. Med. 107, 183-206). In the case of the homozygous ΔF508 CFTR samples, the differentiated cells are treated with 3 μM VX809 (2626 South Loop West, Suite 225, Houston, Tex. 77054 USA, Cat n# S1565) to allow sufficient expression of properly folded CFTR protein on the membrane (48 hours basolateral treatment and 24 hours apical treatment), prior to electrophysiological recordings. For heterozygous G551D/ΔF508, differentiated cells are used as such for the recordings.

For electrophysiological recording, the human airway epithelia are mounted in Ussing chambers for measurement of short-circuit current ($I_{sc}$). The epithelia are bathed in a NaCl-Ringer solution (120 mM NaCl, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on the basolateral side and a glutamate-ringer solution (120 mM sodium glutamate, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on the apical side to generate a $Cl^-$ gradient. Both chambers are gassed with 95% $O_2$, 5% $CO_2$, and maintained at 27° C. Apical amiloride is used to inhibit the endogenous ENaC currents while forkolin is applied on both apical and basolateral side to stimulate CFTR. After forskolin triggering, compounds are added on both side to test their potential for increasing CFTR gating. The increase in $I_{sc}$ is used as a measure for the increased CFTR activity, $EC_{50}$ values can be generated by measuring impact of different concentrations of compound on Short circuit current on primary cells, for this purpose the same Snapwell™ is used for the addition of increasing amounts of compound and the increase in $I_{sc}$ signal at each step is then transformed into a dose response curve. Inh-172, an inhibitor specific for CFTR, is used to test the specificity of the tested compounds.

TECC Assay

Primary Bronchial Epithelial Cells Protocol

The TECC (Tranepithelial Clamp Circuit, EP-design) assay measures the functionality of the cystic fibrosis Transmembrane Conductance regulator (CFTR) by measuring the short circuit current ($I_{sc}$) generated over the basolateral and apical membrane of lung epithelial cells. In TECC the transepithelial potential PD and transepithelial resistance ($R_t$) are measured in an open circuit and transformed to $I_{sc}$ using Ohm's law. 24 Wells can be measured simultaneously allowing a higher throughput compared to Ussing chambers.

For this purpose, bronchial epithelial cells isolated from CF patients homozygous for the CFTR ΔF508 mutation (hAEC-CF, Epithelix) are plated on type IV collagen-coated Transwell® supports (Costar). Human airway epithelia are generated by provision of an air-liquid interface for 21 days to form well-differentiated polarized cultures that resemble in vivo pseudo-stratified ciliated epithelium (Fulcher, M. L., Gabriel, S., Burns, K. A., Yankaskas, J. R., Randell, S. H., 2005. Well-differentiated human airway epithelial cell cultures. Methods Mol. Med. 107, 183-206). In the case of the homozygous ΔF508 CFTR samples, the differentiated cells are treated with 3 μM VX809 (2626 South Loop West, Suite 225, Houston, Tex. 77054 USA, Cat n# S1565) to allow sufficient expression of properly folded CFTR protein on the membrane (48 hours basolateral treatment and 24 hours apical treatment), prior to electrophysiological recordings. For heterozygous G551D/ΔF508, differentiated cells are used as such for the recordings.

Information on the compounds can be retrieved on the homozygous ΔF508 CFTR samples looking at increased CFTR activity when compounds are added in an acute mode or in a chronic mode. On G551D/ΔF508 CFTR heterozygous samples compounds are added in an acute mode to the differentiated cells.

For the acute mode, for electrophysiological recording, the human airway epithelia are mounted in the TECC heating plate for electrophysiological measurement and kept at 37° C. The epithelia are bathed in a NaCl-Ringer solution (120 mM NaCl, 25 mM NaHCO$_3$, 1.2 mM CaCl$_2$, 1.2 mM MgCl$_2$, 0.8 mM KH$_2$PO$_4$, 0.8 mM K$_2$HPO$_4$, pH 7.4, 5 mM glucose) on both the basolateral and apical sides. Apical amiloride is used to inhibit the endogenous ENaC currents while forkolin is applied on both apical and basolateral side to stimulate CFTR. After forskolin triggering, compounds are added on both sides to test their potential for increasing CFTR gating. Measurements are done during a 20 minute timeframe with recordings every 2 minutes. The increase in I$_{sc}$ is used as a measure for the increased CFTR activity, EC$_{50}$ values can be generated by measuring impact of different concentrations of compound on I$_{sc}$ on primary cells, for this purpose each transwell is treated with a different compound concentration. Inh-172, an inhibitor specific for CFTR, is used to test the specificity of the tested compounds.

For the chronic mode, the differentiated cells are treated with 3 μM VX809 (2626 South Loop West, Suite 225, Houston, Tex. 77054 USA, Cat n# S1565) and potentiator compounds at different concentrations (48 hours basolateral treatment and 24 hours apical treatment), prior to electrophysiological recordings. For electrophysiological recording, the human airway epithelia are mounted in the TECC heating plate for electrophysiological measurement and kept at 37° C. The epithelia are bathed in a NaCl-Ringer solution (120 mM NaCl, 25 mM NaHCO$_3$, 1.2 mM CaCl$_2$, 1.2 mM MgCl$_2$, 0.8 mM KH$_2$PO$_4$, 0.8 mM K$_2$HPO$_4$, pH 7.4, 5 mM glucose) on both the basolateral and apical sides. Apical amiloride is used to inhibit the endogenous ENaC currents while forkolin is applied on both apical and basolateral side to stimulate CFTR. Measurements are done during a 20 minute timeframe with recordings every 2 minutes. The increase in I$_{sc}$ is used as a measure for the increased CFTR activity, EC$_{50}$ values can be generated by measuring impact of different concentrations of compound on I$_{sc}$ on primary cells, for this purpose each transwell is treated with a different compound concentration. Inh-172, an inhibitor specific for CFTR, is used to test the specificity of the tested compounds.

Similar TECC recordings are performed using primary cells for other channel gating defective or channel conductance defective CFTR mutants to determine effect of compound on channel activity. Examples of mutants include R117H, G178R. Similarly primary cells containing class I CFTR mutants, including G542X, W1282X; and additional class II mutants including N1303K can be used for electrophysiological recordings.

Results

When subjected to this protocol, the following values were obtained. The difference between ΔIsc measured as DMSO (baseline), and the ΔIsc measured with the compound tested.

CFTR ΔF508 TECC Assay EC$_{50}$ Measurements

TABLE X

TECC assay in CFTR ΔF508 EC$_{50}$ for illustrative compounds of the invention.

| Compound # | EC$_{50}$ (nM) |
|---|---|
| 1 | 95.9 |
| 2 | 47.06 |

TABLE X-continued

TECC assay in CFTR ΔF508 EC$_{50}$ for illustrative compounds of the invention.

| Compound # | EC$_{50}$ (nM) |
|---|---|
| 6 | 63.175 |
| 21 | 35.55 |
| 25 | 38.64 |
| 26 | 23.99 |
| 31 | 48.44 |
| 32 | 72.865 |
| 36 | 63 |
| 37 | 13.2415 |
| 38 | 91.28 |
| 40 | 62.18 |
| 52 | 38.29 |
| 59 | 50.4 |
| 70 | 38.7525 |
| 71 | 111.7 |
| 81 | 9.487 |

CFTR G551D/ΔF508 TECC Assay EC$_{50}$ Measurements

TABLE XI

TECC assay in CFTR G551D/ΔF508 EC$_{50}$ for illustrative compounds of the invention.

| Compound # | EC$_{50}$ (nM) |
|---|---|
| 7 | 7716 |
| 14 | 5302 |
| 21 | 846.9 |
| 31 | 632 |
| 36 | 1013 |
| 37 | 232 |
| 40 | 443 |
| 52 | 461 |
| 70 | 3522.667 |
| 85 | 9.5 |
| 92 | 144 |
| 95 | 487 |
| 99 | 358 |
| 100 | 2376 |
| 252 | 62.23 |
| 253 | 1439 |

FRT-CFTR G551D Protocol

For G551D recordings, Fischer Rat Thyroid (FRT) cells stably transfected with G551D CFTR (a low CFTR-G551D expressing cell line and a high expressing CFTR-G551D cell line from Rosalind Franklin University of Medicine and Science, North Chicago, Ill.) are plated on Transwell® supports (Costar 6.5 mm diameter, 0.4 μm pore size). The cells are grown for 8-10 days under liquid-liquid interface conditions prior to electrophysiological readings. For electrophysiological recording, the FRT-G551D cells are mounted in the TECC heating plate for electrophysiological measurement and kept at 37° C. The epithelia are bathed in HEPES buffered culturing medium without FBS on both the basolateral and apical sides. Apical amiloride is used to inhibit the endogenous ENaC currents while forkolin is applied on both apical and basolateral side to stimulate CFTR. After forskolin triggering, compounds are added on both sides to test their potential for increasing CFTR gating. Measurements are done during a 10 minute timeframe with recordings every 2 minutes. The increase in Isc is used as a measure for the increased CFTR activity, EC$_{50}$ values can be generated by measuring impact of different concentrations of compound on Isc on the cells, for this purpose each transwell is treated with a different compound concentration. Inh-172, an inhibitor specific for CFTR, is used to test the specificity of the tested compounds.

CFTR G551D TECC Assay EC$_{50}$ Measurements

When subjected to this protocol, the following EC$_{50}$ were measured.

TABLE XII

TECC assay in CFTR G551D EC$_{50}$ for illustrative compounds of the invention in high expression cells.

| Compound # | EC$_{50}$ (nM) |
|---|---|
| 1 | 645 |
| 3 | 1978 |
| 6 | 443 |
| 11 | 1351 |
| 14 | 11690 |
| 15 | 668.8 |
| 17 | 1127 |
| 18 | 1428 |
| 19 | 5475 |
| 20 | 3700 |
| 21 | 1635 |
| 24 | 2826 |
| 25 | 1201 |
| 26 | 1231 |
| 31 | 823.7 |
| 36 | 735.2 |
| 70 | 622 |
| 100 | 1188 |
| 165 | 116 |

FRT-CFTR ΔF508 Protocol

For ΔF508 recordings, Fischer Rat Thyroid (FRT) cells stably transfected with ΔF508 CFTR (cell line from Rosalind Franklin University of Medicine and Science, North Chicago, Ill.) are plated on Transwell® supports (Costar 6.5 mm diameter, 0.4 μm pore size Cat n#3378). The cells are grown for 8-10 days under liquid-liquid interface conditions prior to electrophysiological readings. The differentiated cells are treated with 3 μM VX809 (2626 South Loop West, Suite 225, Houston, Tex. 77054 USA, Cat n# S1565) to allow sufficient expression of properly folded CFTR protein on the membrane (24 hours basolateral treatment), prior to electrophysiological recordings. For electrophysiological recording, the FRT-ΔF508 cells are mounted in the TECC heating plate for electrophysiological measurement and kept at 37° C. The epithelia are bathed in HEPES buffered culturing medium without FBS on both the basolateral and apical sides. Apical amiloride is used to inhibit the endogenous ENaC currents while forkolin is applied on both apical and basolateral side to stimulate CFTR. After forskolin triggering, compounds are added on both sides to test their potential for increasing CFTR gating. Measurements are done during a 10 minute timeframe with recordings every 2 minutes. The increase in transepithelial conductance (Gt) is used as a measure for the increased CFTR activity, EC$_{50}$ values can be generated by measuring impact of different concentrations of compound on Gt of the cells, for this purpose each transwell is treated with a different compound concentration. Inh-172, an inhibitor specific for CFTR, is used to test the specificity of the tested compounds.

CFTR ΔF508 TECC Assay EC$_{50}$ Measurements

When subjected to this protocol, the following EC$_{50}$ were measured.

TABLE XIII

TECC assay in CFTR ΔF508 EC$_{50}$ for illustrative compounds of the invention and comparative compounds in high expression cells.

| Compound # | EC$_{50}$ (nM) |
|---|---|
| 1 | 179.7 |
| 2 | 70.05 |
| 36 | 63.24 |
| 37 | 10.45 |

The data provided in the present application demonstrate that the compounds of the invention demonstrate activity in vitro, and may be useful in vivo in the treatment of cystic fibrosis.

Further benefits of Applicants' invention will be apparent to one skilled in the art from reading this patent application.

It is understood that the foregoing detailed description and accompanying examples are merely illustrative and are not to be taken as limitations upon the scope of the invention, which is defined solely by the appended claims and their equivalents. Various changes and modifications to the embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

We claim:

1. A compound of Formula I or a pharmaceutically acceptable salt thereof

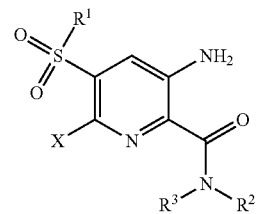

I wherein

X is

H;

halo;

C$_{1-4}$ alkyl optionally substituted with one or more independently selected halo;

C$_{1-4}$ alkoxy optionally substituted with one or more independently selected

—OH;

C$_{1-4}$ alkoxy; or

—NR$^{11A}$R$^{11B}$;

—NR$^{12A}$R$^{12B}$;

cyclopropyl optionally substituted with one or more independently selected R$^5$ groups;

phenoxy optionally substituted with one or more independently selected R$^5$ groups; or phenyl optionally substituted with one or more independently selected R$^5$ groups;

$R^1$ is
- $C_{1-4}$ alkyl optionally substituted with one or more independently selected
  - —OH;
  - $C_{1-4}$ alkoxy; or
  - 4-6 membered monocyclic heterocycle comprising 1 or 2 heteroatoms independently selected from the group consisting of O, S, and N;
- phenyl optionally substituted with one or more independently selected $R^4$ groups;
- N-linked 4-6 membered monocyclic heterocycle comprising 1, 2, or 3 heteroatoms independently selected from the group consisting of N, O, and S, wherein the monocyclic heterocycle is optionally substituted with one or more independently selected $R^5$ groups;
- N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with one or more independently selected $R^5$ groups;
- $C_{3-7}$ cycloalkyl optionally substituted with one or more independently selected $R^5$ groups; or
- —$NR^6R^7$;

$R^2$ is
- H;
- $C_{1-6}$ alkyl optionally substituted with one or more independently selected
  - —OH;
  - halo;
  - $C_{1-4}$ alkoxy optionally substituted with one or more independently selected
    - halo;
    - $C_{1-4}$ alkoxy;
  - $C_{3-7}$ cycloalkyl optionally substituted with one or more independently selected $R^5$ groups; or
  - 4-6 membered monocyclic heterocycle comprising 1 or 2 heteroatoms independently selected from the group consisting of N, O, and S, wherein the monocyclic heterocycle is optionally substituted with one or more independently selected $R^5$ groups;
- —C(=O)$NR^{8a}R^{8b}$;
- $C_{3-7}$ cycloalkyl optionally substituted with one or more independently selected
  - —OH;
  - halo;
  - $C_{1-4}$ alkoxy optionally substituted with one or more independently selected halo; or
  - $C_{1-4}$ alkyl optionally substituted with one or more independently selected —OH, halo, or $C_{1-4}$ alkoxy;
- 4-6 membered monocyclic heterocycle comprising 1 or 2 heteroatoms independently selected from the group consisting of N, O, and S, wherein the monocyclic heterocycle is optionally substituted with one or more independently selected
  - —OH;
  - halo;
  - $C_{1-4}$ alkoxy optionally substituted with one or more independently selected halo, or
  - $C_{1-4}$ alkyl optionally substituted with one or more independently selected halo;
- 5-6 membered monocyclic heteroaryl comprising 1, 2, or 3 heteroatoms independently selected from the group consisting of O, S, and N, wherein the monocyclic heteroaryl is optionally substituted with one or more independently selected $R^5$ groups; or
- phenyl optionally substituted with one or more independently selected $R^5$ groups;
- $C_{3-7}$ cycloalkyl optionally substituted with one or more
  - —OH;
  - halo;
  - $C_{1-4}$ alkyl optionally substituted with one or more independently selected halo or —OH; or
  - $C_{1-4}$ alkoxy optionally substituted with one or more independently selected halo;
- 4-6 membered monocyclic heterocycle comprising 1 or 2 heteroatoms independently selected from the group consisting of O, S, and N, wherein the monocyclic heterocycle is optionally substituted with one or more
  - —OH;
  - halo;
  - $C_{1-4}$ alkyl optionally substituted with one or more independently selected halo; or
  - $C_{1-4}$ alkoxy optionally substituted with one or more independently selected halo;
- 4-6 membered monocyclic heterocycle comprising 1 or 2 heteroatoms independently selected from the group consisting of O, S, and N, fused to a phenyl ring, wherein the monocyclic heterocycle and the phenyl are optionally substituted with one or more independently selected $R^5$ groups;
- 5-11 membered spirocyclic heterocycle comprising 1 or 2 heteroatoms independently selected from the group consisting of O, S, and N, wherein the spirocyclic heterocycle is optionally substituted with one or more independently selected $R^5$ groups;
- 5-6 membered monocyclic heteroaryl comprising 1, 2, or 3 heteroatoms independently selected from the group consisting of O, S, and N, wherein the monocyclic heteroaryl is optionally substituted with one or more independently selected $R^5$ groups; or
- —NHC(=O)$R^{13}$;

and $R^3$ is H; or $R^2$ and $R^3$, together with the nitrogen atom to which they are attached form
- an azetidine or a pyrrolidine ring, wherein the azetidine and the pyrrolidine are optionally substituted with one or more independently selected $R^9$ groups; or
- a 7-11 membered spirocyclic heterocycle comprising one or more heteroatoms independently selected from the group consisting of N, O, and S; wherein the spirocyclic heterocycle is optionally substituted with one or more independently selected $R^5$ groups;

each $R^4$ is independently selected from the group consisting of:
- halo;
- $C_{1-4}$ alkyl optionally substituted with one or more independently selected halo; and
- $C_{1-4}$ alkoxy optionally substituted with one or more independently selected halo;

each $R^5$ is independently selected from the group consisting of:
- —OH;
- halo;
- $C_{1-4}$ alkyl optionally substituted with one or more independently selected
  - $C_{1-4}$ alkoxy;
  - halo; or
  - —OH; and $C_{1-4}$ alkoxy optionally substituted with one or more independently selected halo;

$R^6$ is H, $C_{1-4}$ alkyl, or $C_{3-7}$ cycloalkyl wherein the $C_{3-7}$ cycloalkyl is optionally substituted with one or more independently selected $R^5$ groups;

$R^7$ is
  $C_{1-4}$ alkyl optionally substituted with one or more independently selected
    halo;
    phenyl optionally substituted with one or more independently selected
      halo;
      $C_{1-4}$ alkyl optionally substituted with one or more independently selected halo; or
      $C_{1-4}$ alkoxy optionally substituted with one or more independently selected halo;
  $C_{1-4}$ alkoxy optionally substituted with one or more independently selected halo; or
  4-6 membered monocyclic heterocycle comprising 1 or 2 heteroatoms independently selected from the group consisting of O, S, and N; wherein the monocyclic heterocycle is optionally substituted with one or more independently selected $R^5$ groups;

each $R^{8a}$ and $R^{8b}$ is independently selected from the group consisting of
  H;
  $C_{1-4}$ alkyl optionally substituted with one or more independently selected halo; and
  $C_{3-7}$ cycloalkyl optionally substituted with one or more independently selected $R^5$ groups;

each $R^9$ is independently selected from the group consisting of:
  —OH;
  halo;
  —CN;
  $C_{1-4}$ alkyl optionally substituted with one or more independently selected
    —OH;
    halo; or
    $C_{1-4}$ alkoxy;
  $C_{1-4}$ alkoxy optionally substituted with one or more independently selected halo;
  $C_{3-7}$ cycloalkyl optionally substituted with one or more independently selected $R^5$ groups;
  —C(=O)NR$^{10a}$R$^{10b}$; and
  4-6 membered monocyclic heterocycle comprising 1 or 2 heteroatoms independently selected from the group consisting of O, S, and N, wherein the monocyclic heterocycle is optionally substituted with one or more independently selected $R^5$ groups;

each $R^{10a}$ and $R^{10b}$ is independently selected from the group consisting of H and $C_{1-4}$ alkyl;

each $R^{11a}$ and $R^{11b}$ is independently selected from the group consisting of
  H; and
  $C_{1-4}$ alkyl;

$R^{12a}$ and $R^{12b}$ are independently selected from the group consisting of
  H;
  $C_{1-4}$ alkyl; and
  $C_{3-7}$ cycloalkyl; and $R^{13}$ is independently $C_{1-4}$ alkyl optionally substituted with one or more independently selected
  —OH;
  halo; or
  $C_{1-4}$ alkoxy.

2. The compound of claim 1 or a pharmaceutically acceptable salt thereof, wherein
  $R^1$ is phenyl optionally substituted with one, two, or three independently selected $R^4$ groups.

3. The compound of claim 1 or a pharmaceutically acceptable salt thereof, wherein
  $R^1$ is N-linked 4-6 membered monocyclic heterocycle comprising 1, 2, or 3 heteroatoms independently selected from the group consisting of N, O, and S, wherein the monocyclic heterocycle is optionally substituted with 1, 2, or 3 independently selected $R^5$ groups.

4. The compound of claim 1 or a pharmaceutically acceptable salt thereof, wherein
  $R^1$ is —NR$^6$R$^7$.

5. The compound of claim 1 or a pharmaceutically acceptable salt thereof, wherein X is H, halo, or unsubstituted cyclopropyl.

6. The compound of claim 1 or a pharmaceutically acceptable salt thereof, wherein
  $R^2$ is $C_{1-6}$ alkyl optionally substituted with 1, 2, or 3 independently selected
    —OH;
    fluoro;
    $C_{1-4}$ alkoxy optionally substituted with 1, 2, or 3 independently selected
      fluoro;
      $C_{1-4}$ alkoxy;
    $C_{3-7}$ cycloalkyl optionally substituted with 1, 2, or 3 independently selected $R^5$ groups; or
    4-6 membered monocyclic heterocycle comprising 1 or 2 heteroatoms independently selected from the group consisting of N, O, and S, wherein the monocyclic heterocycle is optionally substituted with 1, 2, or 3 independently selected $R^5$ groups;
  4-6 membered monocyclic heterocycle comprising 1 or 2 heteroatoms independently selected from the group consisting of N, O, and S, wherein the monocyclic heterocycle is optionally substituted with 1, 2, or 3 independently selected
    —OH;
    fluoro;
    $C_{1-4}$ alkoxy optionally substituted with 1, 2, or 3 fluoro, or
    $C_{1-4}$ alkyl optionally substituted with 1, 2, or 3 fluoro;
  or
  phenyl optionally substituted with 1, 2, or 3 independently selected $R^5$ groups.

7. The compound of claim 1 or a pharmaceutically acceptable salt thereof, wherein
  $R^2$ is $C_{3-6}$ alkyl substituted with one or two —OH, and optionally further substituted with 1, 2, or 3 fluoro; or optionally further substituted with one $C_{1-4}$ alkoxy which is optionally substituted with
    1, 2, or 3 fluoro;
    one $C_{1-4}$ alkoxy; or
    one $C_{3-7}$ cycloalkyl optionally substituted with 1, 2, or 3 independently selected $R^5$ groups.

8. The compound of claim 1 or a pharmaceutically acceptable salt thereof, wherein
  $R^2$ is $C_{1-6}$ alkyl substituted with one substituent wherein the substituent is
    —C(=O)NR$^{8a}$R$^{8b}$;

$C_{3-7}$ cycloalkyl optionally substituted with 1, 2, or 3 independently selected
—OH;
fluoro;
$C_{1-4}$ alkoxy optionally substituted with 1, 2, or 3 fluoro; or
$C_{1-4}$ alkyl optionally substituted with 1, 2, or 3 independently selected —OH, fluoro, or $C_{1-4}$ alkoxy;
4-6 membered monocyclic heterocycle comprising 1 or 2 heteroatoms independently selected from the group consisting of N, O, and S, wherein the monocyclic heterocycle is optionally substituted with 1, 2, or 3 independently selected
—OH;
fluoro;
$C_{1-4}$ alkoxy optionally substituted with 1, 2, or 3 fluoro, or
$C_{1-4}$ alkyl optionally substituted with 1, 2, or 3 fluoro;
or
5-6 membered monocyclic heteroaryl comprising 1, 2, or 3 heteroatoms independently selected from the group consisting of O, S, and N, wherein the monocyclic heteroaryl is optionally substituted with 1, 2, or 3 independently selected $R^5$ groups.

9. The compound of claim 1 or a pharmaceutically acceptable salt thereof, wherein
$R^2$ is $C_{3-6}$ cycloalkyl optionally substituted with 1, 2, or 3 independently selected —OH; fluoro; $C_{1-4}$ alkyl optionally substituted with 1, 2, or 3 fluoro; or $C_{1-4}$ alkoxy optionally substituted with 1, 2, or 3 fluoro.

10. The compound of claim 1 or a pharmaceutically acceptable salt thereof, wherein
$R^2$ is 4-6 membered monocyclic heterocycle comprising 1 or 2 heteroatoms independently selected from the group consisting of O, S, and N, wherein the monocyclic heterocycle is optionally substituted with 1, 2, or 3 independently selected —OH; fluoro; $C_{1-4}$ alkyl optionally substituted with 1, 2, or 3 fluoro; or $C_{1-4}$ alkoxy optionally substituted with 1, 2, or 3 fluoro.

11. The compound of claim 1 or a pharmaceutically acceptable salt thereof, wherein
$R^2$ and $R^3$, together with the nitrogen atom to which they are attached form an azetidine or a pyrrolidine ring, wherein the azetidine and the pyrrolidine are optionally substituted with 1, 2, or 3 independently selected $R^9$ groups.

12. The compound of claim 1 or a pharmaceutically acceptable salt thereof, wherein
$R^2$ and $R^3$, together with the nitrogen atom to which they are attached form an azetidine ring which is optionally substituted with 1, 2, or 3 independently selected $R^9$ groups.

13. The compound of claim 1 or a pharmaceutically acceptable salt thereof, wherein
$R^1$ is phenyl optionally substituted with one, two, or three independently selected $R^4$ groups; and
$R^2$ is $C_{1-6}$ alkyl optionally substituted with 1, 2, or 3 independently selected
—OH;
fluoro;
$C_{1-4}$ alkoxy optionally substituted with 1, 2, or 3 independently selected
fluoro;
$C_{1-4}$ alkoxy;
$C_{3-7}$ cycloalkyl optionally substituted with 1, 2, or 3 independently selected $R^5$ groups; or
4-6 membered monocyclic heterocycle comprising 1 or 2 heteroatoms independently selected from the group consisting of N, O, and S, wherein the monocyclic heterocycle is optionally substituted with 1, 2, or 3 independently selected $R^5$ groups;
4-6 membered monocyclic heterocycle comprising 1 or 2 heteroatoms independently selected from the group consisting of N, O, and S, wherein the monocyclic heterocycle is optionally substituted with 1, 2, or 3 independently selected
—OH;
fluoro;
$C_{1-4}$ alkoxy optionally substituted with 1, 2, or 3 fluoro, or
$C_{1-4}$ alkyl optionally substituted with 1, 2, or 3 fluoro;
or
phenyl optionally substituted with 1, 2, or 3 independently selected $R^5$ groups.

14. The compound of claim 1 or a pharmaceutically acceptable salt thereof, wherein
$R^1$ is phenyl optionally substituted with one, two, or three independently selected $R^4$ groups; and
$R^2$ is $C_{3-6}$ alkyl substituted with one or two —OH, and optionally further substituted with 1, 2, or 3 fluoro; or optionally further substituted with one $C_{1-4}$ alkoxy which is optionally substituted with
1, 2, or 3 fluoro;
one $C_{1-4}$ alkoxy; or
one $C_{3-7}$ cycloalkyl optionally substituted with 1, 2, or 3 independently selected
$R^5$ groups.

15. The compound of claim 1 or a pharmaceutically acceptable salt thereof, wherein
$R^1$ is phenyl optionally substituted with one, two, or three independently selected $R^4$ groups; and
$R^2$ is $C_{1-6}$ alkyl substituted with one substituent wherein the substituent is
—C(=O)NR$^{8a}$R$^{8b}$;
$C_{3-7}$ cycloalkyl optionally substituted with 1, 2, or 3 independently selected
—OH;
fluoro;
$C_{1-4}$ alkoxy optionally substituted with 1, 2, or 3 fluoro; or
$C_{1-4}$ alkyl optionally substituted with 1, 2, or 3 independently selected —OH, fluoro, or $C_{1-4}$ alkoxy;
4-6 membered monocyclic heterocycle comprising 1 or 2 heteroatoms independently selected from the group consisting of N, O, and S, wherein the monocyclic heterocycle is optionally substituted with 1, 2, or 3 independently selected
—OH;
fluoro;
$C_{1-4}$ alkoxy optionally substituted with 1, 2, or 3 fluoro, or
$C_{1-4}$ alkyl optionally substituted with 1, 2, or 3 fluoro;
or
5-6 membered monocyclic heteroaryl comprising 1, 2, or 3 heteroatoms independently selected from the group consisting of O, S, and N, wherein the monocyclic heteroaryl is optionally substituted with 1, 2, or 3 independently selected $R^5$ groups.

16. The compound of claim 1 or a pharmaceutically acceptable salt thereof, wherein
  $R^1$ is phenyl optionally substituted with one, two, or three independently selected $R^4$ groups; and
  $R^2$ is $C_{3-6}$ cycloalkyl optionally substituted with 1, 2, or 3 independently selected —OH; fluoro; $C_{1-4}$ alkyl optionally substituted with 1, 2, or 3 fluoro; or $C_{1-4}$ alkoxy optionally substituted with 1, 2, or 3 fluoro.

17. The compound of claim 1 or a pharmaceutically acceptable salt thereof, wherein
  $R^1$ is phenyl optionally substituted with one, two, or three independently selected $R^4$ groups; and
  $R^2$ is 4-6 membered monocyclic heterocycle comprising 1 or 2 heteroatoms independently selected from the group consisting of O, S, and N, wherein the monocyclic heterocycle is optionally substituted with 1, 2, or 3 independently selected —OH; fluoro; $C_{1-4}$ alkyl optionally substituted with 1, 2, or 3 fluoro; or $C_{1-4}$ alkoxy optionally substituted with 1, 2, or 3 fluoro.

18. The compound of claim 1 or a pharmaceutically acceptable salt thereof, wherein
  $R^1$ is phenyl optionally substituted with one, two, or three independently selected $R^4$ groups; and
  $R^2$ and $R^3$, together with the nitrogen atom to which they are attached form an azetidine or a pyrrolidine ring, wherein the azetidine and the pyrrolidine are optionally substituted with 1, 2, or 3 independently selected $R^9$ groups.

19. The compound of claim 1 or a pharmaceutically acceptable salt thereof, wherein
  $R^1$ is N-linked 4-6 membered monocyclic heterocycle comprising 1, 2, or 3 heteroatoms independently selected from the group consisting of N, O, and S, wherein the monocyclic heterocycle is optionally substituted with 1, 2, or 3 independently selected $R^5$ groups; and
  $R^2$ is $C_{3-6}$ alkyl substituted with one —OH and optionally further substituted with 1, 2, or 3 fluoro; or optionally further substituted with one $C_{1-4}$ alkoxy wherein the $C_{1-4}$ alkoxy is optionally substituted with 1, 2, or 3 fluoro.

20. The compound of claim 1 or a pharmaceutically acceptable salt thereof, wherein
  $R^1$ is —$NR^6R^7$; and
  $R^2$ is $C_{3-6}$ alkyl substituted with one —OH and optionally further substituted with 1, 2, or 3 fluoro; or optionally further substituted with one $C_{1-4}$ alkoxy wherein the $C_{1-4}$ alkoxy is optionally substituted with 1, 2, or 3 fluoro.

21. The compound of claim 1, or a pharmaceutically acceptable salt thereof, wherein
  $R^2$ and $R^3$ are H.

22. The compound of claim 1 of Formula I-a, or a pharmaceutically acceptable salt thereof

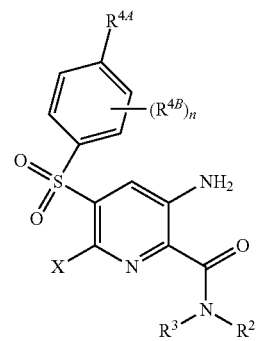

I-a wherein
  n is 0, 1, or 2;
  $R^{4A}$ is H, F, $CH_3$, —$CH(CH_3)_2$, t-Bu, $CF_3$, —$OCH_3$, —O—$CH(CH_3)_2$, or —$OCF_3$;
  each $R^{4B}$ is independently F or —$OCF_3$; and
  X, $R^2$, and $R^3$, are as set forth in claim 1.

23. The compound of claim 22 or a pharmaceutically acceptable salt thereof, wherein X is H.

24. The compound of claim 22 or a pharmaceutically acceptable salt thereof wherein
  n is 0 or 1;
  $R^{4A}$ is F, $CF_3$, or —$OCF_3$; and
  $R^{4B}$ is F.

25. The compound of claim 22 or a pharmaceutically acceptable salt thereof wherein
  $R^2$ is $C_{3-6}$ alkyl substituted with one or two —OH, and optionally further substituted with 1, 2, or 3 fluoro; or optionally further substituted with one $C_{1-4}$ alkoxy which is optionally substituted with
  1, 2, or 3 fluoro;
  one $C_{1-4}$ alkoxy; or
  one $C_{3-7}$ cycloalkyl optionally substituted with 1, 2, or 3 independently selected $R^5$ groups.

26. The compound of claim 22 or a pharmaceutically acceptable salt thereof wherein
  $R^2$ is $C_{3-6}$ alkyl substituted with one —OH, and optionally further substituted with 1, 2, or 3 fluoro or optionally further substituted with one $C_{1-4}$ alkoxy wherein the $C_{1-4}$ alkoxy is optionally substituted with one cyclopropyl or 1, 2, or 3 fluoro.

27. The compound of claim 22 or a pharmaceutically acceptable salt thereof wherein
  $R^2$ is $C_{1-6}$ alkyl substituted with one —C(=O)$NR^{8a}R^{8b}$ wherein $R^{8a}$ and $R^{8b}$ are independently selected from the group consisting of H; $C_{1-4}$ alkyl optionally substituted with 1, 2, or 3 fluoro; and cyclopropyl optionally substituted with 1, 2, or 3 independently selected $R^5$ groups.

28. The compound of claim 22 or a pharmaceutically acceptable salt thereof wherein
  $R^2$ is $C_{3-6}$ cycloalkyl optionally substituted with 1 or 2 independently selected fluoro, $CH_3$, $CF_3$, —OH, or —$OCH_3$.

29. The compound of claim 22 or a pharmaceutically acceptable salt thereof wherein
  $R^2$ is oxetanyl, tetrahydrofuranyl, tetrahydropyranyl, azetidinyl, pyrrolidinyl, or piperidinyl; each of which is optionally substituted with 1 or 2 independently selected fluoro, $CH_3$, $CF_3$, —OH, or —$OCH_3$.

30. The compound of claim 22 or a pharmaceutically acceptable salt thereof wherein R² and R³, together with the nitrogen atom to which they are attached form an azetidine ring which is optionally substituted with 1, 2, or 3 independently selected $R^9$ groups.

31. The compound of claim 22 or a pharmaceutically acceptable salt thereof wherein
R² is

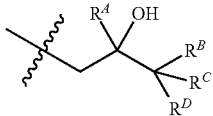

wherein
$R^A$ is H or $CH_3$; and
$R^B$, $R^C$, and $R^D$ are H; or
$R^B$, $R^C$, and $R^D$ are fluoro; or
$R^B$ and $R^C$ are H, and $R^D$ is $C_{1-4}$ alkoxy, —$OCH_2$-cyclopropyl, or —$OCH_2CF_3$.

32. The compound of claim 31 or a pharmaceutically acceptable salt thereof wherein
n is 0 or 1;
$R^{4A}$ is F, $CF_3$, or —$OCF_3$,
$R^4$ is H; and
$R^B$, $R^C$, and $R^D$ are fluoro; or
$R^B$ and $R^C$ are H, and $R^D$ is —$OCH_3$, —$OCH_2CH_3$, —$OCH(CH_3)_2$, —$OC(CH_3)_3$, —$OCH_2$-cyclopropyl, or —$OCH_2CF_3$.

33. The compound of claim 31 or a pharmaceutically acceptable salt thereof wherein
X is H;
n is 0; and
$R^{4A}$ is F.

34. The compound of claim 1, or a pharmaceutically acceptable salt thereof, wherein the compound is selected from the group consisting of:
3-amino-N-(2-hydroxy-2-methylpropyl)-5-{[4-(trifluoromethoxy)phenyl]sulfonyl}pyridine-2-carboxamide;
3-amino-N-(3,3,3-trifluoro-2-hydroxy-2-methylpropyl)-5-{[4-(trifluoromethoxy)phenyl]sulfonyl}pyridine-2-carboxamide;
3-amino-N-(2-hydroxy-3-methoxypropyl)-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(3-hydroxypyrrolidin-1-yl)methanone;
3-amino-N-[(4-hydroxy-1-methylpiperidin-4-yl)methyl]-5-{[4-(trifluoromethoxy)phenyl]sulfonyl}pyridine-2-carboxamide;
3-amino-N-(3,3,3-trifluoro-2-hydroxypropyl)-5-{[4-(trifluoromethoxy)phenyl]sulfonyl}pyridine-2-carboxamide;
3-amino-N-(tetrahydrofuran-2-ylmethyl)-5-{[4-(trifluoromethoxy)phenyl]sulfonyl}pyridine-2-carboxamide;
3-amino-N-(1,4-dioxan-2-ylmethyl)-5-{[4-(trifluoromethoxy)phenyl]sulfonyl}pyridine-2-carboxamide;
3-amino-N-[2-(morpholin-4-yl)ethyl]-5-{[4-(trifluoromethoxy)phenyl]sulfonyl}pyridine-2-carboxamide;
3-amino-5-[(4-fluorophenyl)sulfonyl]-N-(2-hydroxy-2-methylpropyl)pyridine-2-carboxamide;
3-amino-N-(2-hydroxy-2-methylpropyl)-5-{[4-(trifluoromethyl)phenyl]sulfonyl}pyridine-2-carboxamide;
3-amino-N-(1-hydroxybutan-2-yl)-5-{[4-(trifluoromethoxy)phenyl]sulfonyl}pyridine-2-carboxamide;
3-amino-N-(1-hydroxy-3-methylbutan-2-yl)-5-{[4-(trifluoromethoxy)phenyl]sulfonyl}pyridine-2-carboxamide;
3-amino-N-(2-hydroxyethyl)-5-{[4-(trifluoromethoxy)phenyl]sulfonyl}pyridine-2-carboxamide;
3-amino-N-[(1-hydroxycyclopropyl)methyl]-5-{[4-(trifluoromethoxy)phenyl]sulfonyl}pyridine-2-carboxamide;
3-amino-N-(2-hydroxy-3,3-dimethylbutyl)-5-{[4-(trifluoromethoxy)phenyl]sulfonyl}pyridine-2-carboxamide;
rac-3-amino-N-[(1R,2R)-2-hydroxycyclohexyl]-5-{[4-(trifluoromethoxy)phenyl]sulfonyl}pyridine-2-carboxamide;
3-amino-N-(3-hydroxy-2,2-dimethylpropyl)-5-{[4-(trifluoromethoxy)phenyl]sulfonyl}pyridine-2-carboxamide;
3-amino-5-[(4-fluorophenyl)sulfonyl]-N-(3,3,3-trifluoro-2-hydroxy-2-methylpropyl)pyridine-2-carboxamide;
3-amino-N-[(2R)-2-hydroxypropyl]-5-{[4-(trifluoromethoxy)phenyl]sulfonyl}pyridine-2-carboxamide;
3-amino-N-[(2S)-2-hydroxypropyl]-5-{[4-(trifluoromethoxy)phenyl]sulfonyl}pyridine-2-carboxamide;
3-amino-N-{[1-(hydroxymethyl)cyclopropyl]methyl}-5-{[4-(trifluoromethoxy)phenyl]sulfonyl}pyridine-2-carboxamide;
3-amino-N-{[1-(hydroxymethyl)cyclobutyl]methyl}-5-{[4-(trifluoromethoxy)phenyl]sulfonyl}pyridine-2-carboxamide;
3-amino-N-(3-hydroxy-2-methylpropyl)-5-{[4-(trifluoromethoxy)phenyl]sulfonyl}pyridine-2-carboxamide;
3-amino-5-[(4-fluorophenyl)sulfonyl]-N-[(2S)-3,3,3-trifluoro-2-hydroxypropyl]pyridine-2-carboxamide;
3-amino-N-[(2S)-3,3,3-trifluoro-2-hydroxypropyl]-5-{[4-(trifluoromethoxy)phenyl]sulfonyl}pyridine-2-carboxamide;
3-amino-5-[(4-fluorophenyl)sulfonyl]-N-(3,3,3-trifluoro-2-hydroxypropyl)pyridine-2-carboxamide;
3-amino-N-[(3-hydroxytetrahydrofuran-3-yl)methyl]-5-{[4-(trifluoromethoxy)phenyl]sulfonyl}pyridine-2-carboxamide;
3-amino-N-[(4-hydroxytetrahydro-2H-pyran-4-yl)methyl]-5-{[4-(trifluoromethoxy)phenyl]sulfonyl}pyridine-2-carboxamide;
3-amino-5-[(4-fluorophenyl)sulfonyl]-N-[(1-hydroxycyclopropyl)methyl]pyridine-2-carboxamide;
3-amino-N-[3-(cyclopropylmethoxy)-2-hydroxypropyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(3-hydroxyazetidin-1-yl)methanone;
rac-3-amino-N-[(3R,4S)-4-hydroxytetrahydro-2H-pyran-3-yl]-5-{[4-(trifluoromethoxy)phenyl]sulfonyl}pyridine-2-carboxamide;
3-amino-N-(4-hydroxy-2,2-dimethylbutyl)-5-{[4-(trifluoromethoxy)phenyl]sulfonyl}pyridine-2-carboxamide;
3-amino-N-[2-hydroxy-2-(tetrahydro-2H-pyran-4-yl)ethyl]-5-{[4-(trifluoromethoxy)phenyl]sulfonyl}pyridine-2-carboxamide;
3-amino-5-[(4-fluorophenyl)sulfonyl]-N-[(2R)-3,3,3-trifluoro-2-hydroxypropyl]pyridine-2-carboxamide;
3-amino-N-[(2R)-3,3,3-trifluoro-2-hydroxypropyl]-5-{[4-(trifluoromethoxy)phenyl]sulfonyl}pyridine-2-carboxamide;

3-amino-N-[3-(2-ethoxyethoxy)-2-hydroxypropyl]-5-{[4-(trifluoromethoxy)phenyl]sulfonyl}pyridine-2-carboxamide;
3-amino-5-[(3-fluorophenyl)sulfonyl]-N-(2-hydroxy-2-methylpropyl)pyridine-2-carboxamide;
(3-amino-5-{[4-(trifluoromethoxy)phenyl]sulfonyl}pyridin-2-yl)(3,3-difluoroazetidin-1-yl)methanone;
3-amino-N-[2-hydroxy-1-(4-methylphenyl)ethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(3-methoxyazetidin-1-yl)methanone;
3-amino-N-[1-(ethylamino)-1-oxopropan-2-yl]-5-{[4-(trifluoromethoxy)phenyl]sulfonyl}pyridine-2-carboxamide;
3-amino-N-(1,3-dihydroxypropan-2-yl)-5-{[4-(trifluoromethoxy)phenyl]sulfonyl}pyridine-2-carboxamide;
3-amino-N-(4-hydroxybutyl)-5-{[4-(trifluoromethoxy)phenyl]sulfonyl}pyridine-2-carboxamide;
3-amino-N-[(2R)-1-hydroxy-4-methylpentan-2-yl]-5-{[4-(trifluoromethoxy)phenyl]sulfonyl}pyridine-2-carboxamide;
3-amino-N-[(2S)-3,3-dimethyl-1-(methylamino)-1-oxobutan-2-yl]-5-{[4-(trifluoromethoxy)phenyl]sulfonyl}pyridine-2-carboxamide;
3-amino-N-[2-(ethylamino)-2-oxoethyl]-5-{[4-(trifluoromethoxy)phenyl]sulfonyl}pyridine-2-carboxamide;
3-amino-N-[(2S)-1-amino-3-methyl-1-oxobutan-2-yl]-5-{[4-(trifluoromethoxy)phenyl]sulfonyl}pyridine-2-carboxamide;
3-amino-N-[(2R)-2,3-dihydroxypropyl]-5-{[4-(trifluoromethoxy)phenyl]sulfonyl}pyridine-2-carboxamide;
3-amino-N-(3-hydroxy-3-methylbutyl)-5-{[4-(trifluoromethoxy)phenyl]sulfonyl}pyridine-2-carboxamide;
3-amino-N-(4,4,4-trifluoro-3-hydroxybutyl)-5-{[4-(trifluoromethoxy)phenyl]sulfonyl}pyridine-2-carboxamide;
3-amino-N-[(3S)-3-hydroxybutyl]-5-{[4-(trifluoromethoxy)phenyl]sulfonyl}pyridine-2-carboxamide;
3-amino-N-(3-hydroxy-4-methoxybutyl)-5-{[4-(trifluoromethoxy)phenyl]sulfonyl}pyridine-2-carboxamide;
3-amino-N-(4-amino-4-oxobutan-2-yl)-5-{[4-(trifluoromethoxy)phenyl]sulfonyl}pyridine-2-carboxamide;
$N^2$-[(3-amino-5-{[4-(trifluoromethoxy)phenyl]sulfonyl}pyridin-2-yl)carbonyl]-L-leucinamide;
3-amino-N-[2-oxo-2-(propan-2-ylamino)ethyl]-5-{[4-(trifluoromethoxy)phenyl]sulfonyl}pyridine-2-carboxamide;
3-amino-N-[2-(cyclopropylamino)-2-oxoethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(3,3-dimethylazetidin-1-yl)methanone;
(3-amino-5-{[4-(trifluoromethoxy)phenyl]sulfonyl}pyridin-2-yl)[3-(morpholin-4-yl)azetidin-1-yl]methanone;
1-[(3-amino-5-{[4-(trifluoromethoxy)phenyl]sulfonyl}pyridin-2-yl)carbonyl]azetidine-3-carbonitrile;
1-[(3-amino-5-{[4-(trifluoromethoxy)phenyl]sulfonyl}pyridin-2-yl)carbonyl]-N,N-dimethylazetidine-3-carboxamide;
3-amino-N-[(2R)-3,3,3-trifluoro-2-hydroxypropyl]-5-{[4-(trifluoromethyl)phenyl]sulfonyl}pyridine-2-carboxamide;
3-amino-N-[(2S)-3,3,3-trifluoro-2-hydroxypropyl]-5-{[4-(trifluoromethyl)phenyl]sulfonyl}pyridine-2-carboxamide;
(3-amino-5-{[4-(trifluoromethoxy)phenyl]sulfonyl}pyridin-2-yl)(azetidin-1-yl)methanone;
(3-amino-5-{[4-(trifluoromethoxy)phenyl]sulfonyl}pyridin-2-yl)[3-(hydroxymethyl)azetidin-1-yl]methanone;
(3-amino-5-{[4-(trifluoromethoxy)phenyl]sulfonyl}pyridin-2-yl)(3-fluoroazetidin-1-yl)methanone;
(3-amino-5-{[4-(trifluoromethoxy)phenyl]sulfonyl}pyridin-2-yl)(2-oxa-6-azaspiro[3.3]hept-6-yl)methanone;
3-amino-N-[(2R)-2-hydroxy-3-methoxypropyl]-5-{[4-(trifluoromethoxy)phenyl]sulfonyl}pyridine-2-carboxamide;
3-amino-N-[(2R)-2-hydroxy-3-methoxypropyl]-5-{[4-(trifluoromethyl)phenyl]sulfonyl}pyridine-2-carboxamide;
3-amino-5-{[2-fluoro-4-(trifluoromethoxy)phenyl]sulfonyl}-N-(2-hydroxy-3-methoxypropyl)pyridine-2-carboxamide;
3-amino-5-[(4-fluorophenyl)sulfonyl]-N-(4,4,4-trifluoro-3-hydroxybutyl)pyridine-2-carboxamide;
3-amino-N-[2-hydroxy-2-(tetrahydrofuran-3-yl)ethyl]-5-{[4-(trifluoromethoxy)phenyl]sulfonyl}pyridine-2-carboxamide;
rac-3-amino-N-[(3R,4S)-4-hydroxytetrahydrofuran-3-yl]-5-{[4-(trifluoromethoxy)phenyl]sulfonyl}pyridine-2-carboxamide;
3-amino-N-(2-hydroxyethyl)-5-{[2-(trifluoromethoxy)phenyl]sulfonyl}pyridine-2-carboxamide;
(3-amino-5-{[2-(trifluoromethoxy)phenyl]sulfonyl}pyridin-2-yl)(3-hydroxyazetidin-1-yl)methanone;
(3-amino-5-{[2-fluoro-4-(trifluoromethoxy)phenyl]sulfonyl}pyridin-2-yl)(3-hydroxyazetidin-1-yl)methanone;
(3-amino-5-{[2-(trifluoromethoxy)phenyl]sulfonyl}pyridin-2-yl)(3,3-difluoroazetidin-1-yl)methanone;
(3-amino-5-{[4-(trifluoromethoxy)phenyl]sulfonyl}pyridin-2-yl)[3-hydroxy-3-(trifluoromethyl)azetidin-1-yl]methanone;
3-amino-N-(2-hydroxy-3-methoxypropyl)-5-{[2-(trifluoromethoxy)phenyl]sulfonyl}pyridine-2-carboxamide;
3-amino-N-[(2R)-3,3,3-trifluoro-2-hydroxypropyl]-5-{[2-(trifluoromethoxy)phenyl]sulfonyl}pyridine-2-carboxamide;
3-amino-N-[(2S)-2-hydroxypropyl]-5-{[2-(trifluoromethoxy)phenyl]sulfonyl}pyridine-2-carboxamide;
rac-3-amino-N-[(3R,4S)-4-hydroxytetrahydro-2H-pyran-3-yl]-5-{[2-(trifluoromethoxy)phenyl]sulfonyl}pyridine-2-carboxamide;
3-amino-5-[(4,4-difluoropiperidin-1-yl)sulfonyl]-N-(3,3,3-trifluoro-2-hydroxypropyl)pyridine-2-carboxamide;
(3-amino-5-{[2-(trifluoromethoxy)phenyl]sulfonyl}pyridin-2-yl)[3-hydroxy-3-(trifluoromethyl)azetidin-1-yl]methanone;
(3-amino-5-{[4-(trifluoromethoxy)phenyl]sulfonyl}pyridin-2-yl)(3-cyclopropyl-3-hydroxyazetidin-1-yl)methanone;

3-amino-N-(2-hydroxy-4-methylpentyl)-5-{[4-(trifluoromethoxy)phenyl]sulfonyl}pyridine-2-carboxamide;
3-amino-N-(3-ethoxy-2-hydroxypropyl)-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(3-hydroxy-3-methylazetidin-1-yl)methanone;
3-amino-N-[2-hydroxy-3-(propan-2-yloxy)propyl]-5-{[4-(trifluoromethoxy)phenyl]sulfonyl}pyridine-2-carboxamide;
(3-amino-5-{[4-(trifluoromethyl)phenyl]sulfonyl}pyridin-2-yl)(3-hydroxy-3-methylazetidin-1-yl)methanone;
3-amino-N-[2-hydroxy-3-(propan-2-yloxy)propyl]-5-{[4-(trifluoromethyl)phenyl]sulfonyl}pyridine-2-carboxamide;
3-amino-N-[(2S)-1-amino-1-oxobutan-2-yl]-5-{[4-(trifluoromethoxy)phenyl]sulfonyl}pyridine-2-carboxamide;
3-amino-5-[cyclopropyl(methyl)sulfamoyl]-N-(3,3,3-trifluoro-2-hydroxypropyl)pyridine-2-carboxamide;
3-amino-N-(3,3,3-trifluoro-2-hydroxypropyl)-5-{[4-(trifluoromethyl)piperidin-1-yl]sulfonyl}pyridine-2-carboxamide;
3-amino-N-[2-hydroxy-1-(4-methoxyphenyl)ethyl]-5-{[4-(trifluoromethoxy)phenyl]sulfonyl}pyridine-2-carboxamide;
3-amino-5-[(3,3-difluoroazetidin-1-yl)sulfonyl]-N-(3,3,3-trifluoro-2-hydroxypropyl)pyridine-2-carboxamide;
3-amino-5-{[2-fluoro-4-(trifluoromethyl)phenyl]sulfonyl}-N-[(2S)-2-hydroxypropyl]pyridine-2-carboxamide;
3-amino-5-{[2-fluoro-4-(trifluoromethyl)phenyl]sulfonyl}-N-[(2R)-2-hydroxy-3-methoxypropyl]pyridine-2-carboxamide;
3-amino-N-[(2S)-2-hydroxypropyl]-5-{[4-(trifluoromethyl)phenyl]sulfonyl}pyridine-2-carboxamide;
3-amino-N-[(3R)-tetrahydrofuran-3-ylmethyl]-5-{[4-(trifluoromethyl)phenyl]sulfonyl}pyridine-2-carboxamide;
3-amino-N-[(3S)-tetrahydrofuran-3-ylmethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)(3,3-difluoroazetidin-1-yl)methanone;
3-amino-N-[2-oxo-2-(propan-2-ylamino)ethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3R)-tetrahydrofuran-3-ylmethyl]pyridine-2-carboxamide;
3-amino-5-{[2-fluoro-4-(trifluoromethyl)phenyl]sulfonyl}-N-[(2R)-3,3,3-trifluoro-2-hydroxypropyl]pyridine-2-carboxamide;
3-amino-5-[cyclopropyl(2-methoxyethyl)sulfamoyl]-N-(3,3,3-trifluoro-2-hydroxypropyl)pyridine-2-carboxamide;
3-amino-5-(2,3-dihydro-4H-1,4-benzoxazin-4-yl sulfonyl)-N-(3,3,3-trifluoro-2-hydroxypropyl)pyridine-2-carboxamide;
(3-amino-5-{[4-(trifluoromethyl)phenyl]sulfonyl}pyridin-2-yl)(3,3-dimethylazetidin-1-yl)methanone;
(3-amino-5-{[2-fluoro-4-(trifluoromethyl)phenyl]sulfonyl}pyridin-2-yl)(3,3-dimethylazetidin-1-yl)methanone;
(3-amino-5-{[2-fluoro-4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[2-oxo-2-(propan-2-ylamino)ethyl]pyridine-2-carboxamide;
3-amino-5-{[2-fluoro-4-(trifluoromethyl)phenyl]sulfonyl}-N-[(3S)-tetrahydrofuran-3-ylmethyl]pyridine-2-carboxamide;
3-amino-5-{[2-fluoro-4-(trifluoromethoxy)phenyl]sulfonyl}-N-[(3R)-tetrahydrofuran-3-ylmethyl]pyridine-2-carboxamide;
3-amino-5-{[2-fluoro-4-(trifluoromethoxy)phenyl]sulfonyl}-N-[(3S)-tetrahydrofuran-3-ylmethyl]pyridine-2-carboxamide;
3-amino-5-{[2-fluoro-4-(trifluoromethoxy)phenyl]sulfonyl}-N-[(2R)-3,3,3-trifluoro-2-hydroxypropyl]pyridine-2-carboxamide;
3-amino-N-{[1-(ethoxymethyl)cyclobutyl]methyl}-5-{[4-(trifluoromethoxy)phenyl]sulfonyl}pyridine-2-carboxamide;
(3-amino-5-{[4-(trifluoromethoxy)phenyl]sulfonyl}pyridin-2-yl)[3-(2,2-difluoroethoxy)azetidin-1-yl]methanone;
3-amino-N-(trans-3-methoxycyclobutyl)-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(6-oxa-2-azaspiro[3.5]non-2-yl)methanone;
3-amino-N-(3,3-difluorocyclobutyl)-5-{[4-(trifluoromethoxy)phenyl]sulfonyl}pyridine-2-carboxamide;
3-amino-N-(3-methoxypropyl)-5-{[4-(trifluoromethoxy)phenyl]sulfonyl}pyridine-2-carboxamide;
3-amino-N-[2-(1-methylcyclopropyl)ethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(6-oxa-2-azaspiro[3.4]oct-2-yl)methanone;
(3-amino-5-{[4-(trifluoromethoxy)phenyl]sulfonyl}pyridin-2-yl)(3-methylazetidin-1-yl)methanone;
3-amino-N-(tetrahydrofuran-3-yl)-5-{[4-(trifluoromethoxy)phenyl]sulfonyl}pyridine-2-carboxamide;
3-amino-N-[(3R)-tetrahydrofuran-3-yl]-5-{[4-(trifluoromethoxy)phenyl]sulfonyl}pyridine-2-carboxamide;
3-amino-N-(tetrahydro-2H-pyran-4-ylmethyl)-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(3-ethyl-3-fluoroazetidin-1-yl)methanone;
3-amino-N-[3-(cyclopropylmethoxy)-2-hydroxypropyl]-5-{[4-(trifluoromethyl)phenyl]sulfonyl}pyridine-2-carboxamide;
3-amino-N-[3-(cyclopropylmethoxy)-2-hydroxypropyl]-5-{[2-fluoro-4-(trifluoromethyl)phenyl]sulfonyl}pyridine-2-carboxamide;
3-amino-5-{[2-fluoro-4-(trifluoromethyl)phenyl]sulfonyl}-N-[2-hydroxy-3-(propan-2-yloxy)propyl]pyridine-2-carboxamide;
(3-amino-5-{[2-fluoro-4-(trifluoromethoxy)phenyl]sulfonyl}pyridin-2-yl)(3,3-dimethylazetidin-1-yl)methanone;

3-amino-5-{[2-fluoro-4-(trifluoromethoxy)phenyl]sulfonyl}-N-[2-oxo-2-(propan-2-ylamino)ethyl]pyridine-2-carboxamide;

3-amino-5-[(3,4-difluorobenzyl)(methyl)sulfamoyl]-N-(3,3,3-trifluoro-2-hydroxypropyl)pyridine-2-carboxamide;

3-amino-5-[(2,4-difluorobenzyl)(methyl)sulfamoyl]-N-(3,3,3-trifluoro-2-hydroxypropyl)pyridine-2-carboxamide;

3-amino-5-[(4-methoxybenzyl)(methyl)sulfamoyl]-N-(3,3,3-trifluoro-2-hydroxypropyl)pyridine-2-carboxamide;

3-amino-5-(morpholin-4-yl sulfonyl)-N-(3,3,3-trifluoro-2-hydroxypropyl)pyridine-2-carboxamide;

3-amino-N-[(3R)-tetrahydro-2H-pyran-3-yl]-5-{[4-(trifluoromethoxy)phenyl]sulfonyl}pyridine-2-carboxamide;

3-amino-N-[2-(furan-2-yl)ethyl]-5-{[4-(trifluoromethoxy)phenyl]sulfonyl}pyridine-2-carboxamide;

3-amino-N-[(2S)-1-hydroxybutan-2-yl]-5-{[4-(trifluoromethoxy)phenyl]sulfonyl}pyridine-2-carboxamide;

3-amino-N-(tetrahydro-2H-pyran-3-ylmethyl)-5-{[4-(trifluoromethoxy)phenyl]sulfonyl}pyridine-2-carboxamide;

3-amino-N-[(3S)-tetrahydrofuran-3-yl]-5-{[4-(trifluoromethoxy)phenyl]sulfonyl}pyridine-2-carboxamide;

3-amino-N-[(4R)-3,4-dihydro-2H-chromen-4-yl]-5-{[4-(trifluoromethoxy)phenyl]sulfonyl}pyridine-2-carboxamide;

3-amino-N-(tetrahydro-2H-pyran-4-yl)-5-{[4-(trifluoromethoxy)phenyl]sulfonyl}pyridine-2-carboxamide;

3-amino-N-[2-(1,3-dioxolan-2-yl)ethyl]-5-{[4-(trifluoromethoxy)phenyl]sulfonyl}pyridine-2-carboxamide;

3-amino-N-[(2S)-1-hydroxy-3-methylbutan-2-yl]-5-{[4-(trifluoromethoxy)phenyl]sulfonyl}pyridine-2-carboxamide;

3-amino-N-(1-oxaspiro[4.5]dec-3-yl)-5-{[4-(trifluoromethoxy)phenyl]sulfonyl}pyridine-2-carboxamide;

3-amino-N-(1-oxaspiro[4.4]non-3-yl)-5-{[4-(trifluoromethoxy)phenyl]sulfonyl}pyridine-2-carboxamide;

3-amino-N-(oxetan-3-yl)-5-{[4-(trifluoromethoxy)phenyl]sulfonyl}pyridine-2-carboxamide;

3-amino-N-(2-cyclopropylethyl)-5-{[4-(trifluoromethoxy)phenyl]sulfonyl}pyridine-2-carboxamide;

3-amino-N-[(3,3-difluorocyclobutyl)methyl]-5-{[4-(trifluoromethoxy)phenyl]sulfonyl}pyridine-2-carboxamide;

(3-amino-5-{[4-(trifluoromethoxy)phenyl]sulfonyl}pyridin-2-yl)[3-(methoxymethyl)-3-methylazetidin-1-yl]methanone;

3-amino-N-(cyclopropylmethyl)-5-{[4-(trifluoromethoxy)phenyl]sulfonyl}pyridine-2-carboxamide;

3-amino-N-[(4-methyltetrahydro-2H-pyran-3-yl)methyl]-5-{[4-(trifluoromethoxy)phenyl]sulfonyl}pyridine-2-carboxamide;

(3-amino-5-{[4-(trifluoromethyl)phenyl]sulfonyl}pyridin-2-yl)[3-(trifluoromethyl)azetidin-1-yl]methanone;

(3-amino-5-{[4-(trifluoromethyl)phenyl]sulfonyl}pyridin-2-yl)[3-(difluoromethoxy)azetidin-1-yl]methanone;

(3-amino-5-{[4-(trifluoromethyl)phenyl]sulfonyl}pyridin-2-yl)[3-hydroxy-3-(propan-2-yl)azetidin-1-yl]methanone;

(3-amino-5-{[2-fluoro-4-(trifluoromethyl)phenyl]sulfonyl}pyridin-2-yl)[3-(trifluoromethyl)azetidin-1-yl]methanone;

(3-amino-5-{[2-fluoro-4-(trifluoromethyl)phenyl]sulfonyl}pyridin-2-yl)[3-(difluoromethoxy)azetidin-1-yl]methanone;

(3-amino-5-{[2-fluoro-4-(trifluoromethyl)phenyl]sulfonyl}pyridin-2-yl)[3-hydroxy-3-(propan-2-yl)azetidin-1-yl]methanone;

3-amino-5-{[2-fluoro-4-(trifluoromethyl)phenyl]sulfonyl}-N-(2-hydroxy-4-methoxy-2-methylbutyl)pyridine-2-carboxamide;

(3-amino-5-{[2-fluoro-4-(trifluoromethyl)phenyl]sulfonyl}pyridin-2-yl)(3,3-difluoroazetidin-1-yl)methanone;

(3-amino-5-{[4-(trifluoromethyl)phenyl]sulfonyl}pyridin-2-yl)[3-(2-hydroxypropan-2-yl)azetidin-1-yl]methanone;

3-amino-N-[2-hydroxy-3-(2-methylpropoxy)propyl]-5-{[4-(trifluoromethyl)phenyl]sulfonyl}pyridine-2-carboxamide;

3-amino-N-(2-hydroxy-4-methoxy-2-methylbutyl)-5-{[4-(trifluoromethyl)phenyl]sulfonyl}pyridine-2-carboxamide;

3-amino-5-{[2-fluoro-4-(trifluoromethoxy)phenyl]sulfonyl}-N-[2-hydroxy-3-(propan-2-yloxy)propyl]pyridine-2-carboxamide;

3-amino-N-[3-(cyclopropylmethoxy)-2-hydroxypropyl]-5-{[2-fluoro-4-(trifluoromethoxy)phenyl]sulfonyl}pyridine-2-carboxamide;

3-amino-5-{[2-fluoro-4-(trifluoromethyl)phenyl]sulfonyl}-N-[2-hydroxy-3-(2-methylpropoxy)propyl]pyridine-2-carboxamide;

3-amino-5-{[2-fluoro-4-(trifluoromethoxy)phenyl]sulfonyl}-N-[2-hydroxy-3-(2-methylpropoxy)propyl]pyridine-2-carboxamide;

(3-amino-5-{[2-fluoro-4-(trifluoromethoxy)phenyl]sulfonyl}pyridin-2-yl)(3,3-difluoroazetidin-1-yl)methanone;

(3-amino-5-{[2-fluoro-4-(trifluoromethoxy)phenyl]sulfonyl}pyridin-2-yl)[3-hydroxy-3-(trifluoromethyl)azetidin-1-yl]methanone;

(3-amino-5-{[2-fluoro-4-(trifluoromethoxy)phenyl]sulfonyl}pyridin-2-yl)[3-(2-hydroxypropan-2-yl)azetidin-1-yl]methanone;

(3-amino-5-{[2-fluoro-4-(trifluoromethoxy)phenyl]sulfonyl}pyridin-2-yl)[3-hydroxy-3-(propan-2-yl)azetidin-1-yl]methanone;

{3-amino-5-[(4-fluorophenyl)sulfonyl]pyridin-2-yl}[3-hydroxy-3-(trifluoromethyl)azetidin-1-yl]methanone;

3-amino-N-[(2R)-2-hydroxy-3-methoxypropyl]-5-{[2-(trifluoromethoxy)phenyl]sulfonyl}pyridine-2-carboxamide;

(3-amino-5-{[2-fluoro-4-(trifluoromethyl)phenyl]sulfonyl}pyridin-2-yl)[3-(2-hydroxypropan-2-yl)azetidin-1-yl]methanone;

3-amino-5-{[(2R)-2-methylpyrrolidin-1-yl]sulfonyl}-N-(3,3,3-trifluoro-2-hydroxypropyl)pyridine-2-carboxamide;

3-amino-5-{[(3S)-3-fluoropyrrolidin-1-yl]sulfonyl}-N-(3,3,3-trifluoro-2-hydroxypropyl)pyridine-2-carboxamide;

3-amino-5-{[(2S)-2-methylpyrrolidin-1-yl]sulfonyl}-N-(3,3,3-trifluoro-2-hydroxypropyl)pyridine-2-carboxamide;

3-amino-5-[(3-methylpiperidin-1-yl)sulfonyl]-N-(3,3,3-trifluoro-2-hydroxypropyl)pyridine-2-carboxamide;

3-amino-5-[(3,3-difluoropiperidin-1-yl)sulfonyl]-N-(3,3,3-trifluoro-2-hydroxypropyl)pyridine-2-carboxamide;

3-amino-5-[(4-methylpiperidin-1-yl)sulfonyl]-N-(3,3,3-trifluoro-2-hydroxypropyl)pyridine-2-carboxamide;
3-amino-5-[(3,5-dimethylpiperidin-1-yl)sulfonyl]-N-(3,3,3-trifluoro-2-hydroxypropyl)pyridine-2-carboxamide;
3-amino-5-[(3,3-difluoropyrrolidin-1-yl)sulfonyl]-N-(3,3,3-trifluoro-2-hydroxypropyl)pyridine-2-carboxamide;
3-amino-5-[(4-fluorobenzyl)(methyl)sulfamoyl]-N-(3,3,3-trifluoro-2-hydroxypropyl)pyridine-2-carboxamide;
3-amino-N-(3-methylbutan-2-yl)-5-{[4-(trifluoromethyl)phenyl]sulfonyl}pyridine-2-carboxamide;
3-amino-N-(2-methylpropyl)-5-{[4-(trifluoromethyl)phenyl]sulfonyl}pyridine-2-carboxamide;
3-amino-N-[2-(tetrahydrofuran-2-ylmethoxy)ethyl]-5-{[4-(trifluoromethyl)phenyl]sulfonyl}pyridine-2-carboxamide;
3-amino-N-(2,2-dimethylpropyl)-5-{[4-(trifluoromethyl)phenyl]sulfonyl}pyridine-2-carboxamide;
3-amino-N-[2-(propan-2-yloxy)ethyl]-5-{[4-(trifluoromethyl)phenyl]sulfonyl}pyridine-2-carboxamide;
3-amino-5-{[4-(trifluoromethoxy)phenyl]sulfonyl}-N-[4-(trifluoromethyl)tetrahydro-2H-pyran-4-yl]pyridine-2-carboxamide;
3-amino-5-[(3-fluoropiperidin-1-yl)sulfonyl]-N-(3,3,3-trifluoro-2-hydroxypropyl)pyridine-2-carboxamide;
3-amino-5-[(4-fluoropiperidin-1-yl)sulfonyl]-N-(3,3,3-trifluoro-2-hydroxypropyl)pyridine-2-carboxamide;
3-amino-5-[(4-methoxypiperidin-1-yl)sulfonyl]-N-(3,3,3-trifluoro-2-hydroxypropyl)pyridine-2-carboxamide;
3-amino-5-[(4-tert-butylpiperidin-1-yl)sulfonyl]-N-(3,3,3-trifluoro-2-hydroxypropyl)pyridine-2-carboxamide;
3-amino-N-(3,3,3-trifluoro-2-hydroxypropyl)-5-{[4-(trifluoromethoxy)piperidin-1-yl]sulfonyl}pyridine-2-carboxamide;
3-amino-5-[(3,3-dimethylazetidin-1-yl)sulfonyl]-N-(3,3,3-trifluoro-2-hydroxypropyl)pyridine-2-carboxamide;
3-amino-5-{[(3R)-tetrahydrofuran-3-ylmethyl]sulfamoyl}-N-(3,3,3-trifluoro-2-hydroxypropyl)pyridine-2-carboxamide;
3-amino-N-[2-hydroxy-3-(2,2,2-trifluoroethoxy)propyl]-5-{[4-(trifluoromethyl)phenyl]sulfonyl}pyridine-2-carboxamide;
3-amino-N-(2-methoxyethyl)-5-{[4-(trifluoromethyl)phenyl]sulfonyl}pyridine-2-carboxamide;
(3-amino-5-{[4-(trifluoromethoxy)phenyl]sulfonyl}pyridin-2-yl)(3,3-difluoropyrrolidin-1-yl)methanone;
(3-amino-5-{[4-(trifluoromethoxy)phenyl]sulfonyl}pyridin-2-yl)[(3R)-3-fluoropyrrolidin-1-yl]methanone;
3-amino-N-[(1R,2S)-2-hydroxycyclopentyl]-5-{[4-(trifluoromethyl)phenyl]sulfonyl}pyridine-2-carboxamide;
(3-amino-5-{[4-(trifluoromethoxy)phenyl]sulfonyl}pyridin-2-yl)[(3S)-3-fluoropyrrolidin-1-yl]methanone;
3-amino-N-[(3S)-1-methylpyrrolidin-3-yl]-5-{[4-(trifluoromethoxy)phenyl]sulfonyl}pyridine-2-carboxamide;
3-amino-N-[(3R)-1-methylpyrrolidin-3-yl]-5-{[4-(trifluoromethoxy)phenyl]sulfonyl}pyridine-2-carboxamide;
3-amino-N-(2,2,2-trifluoroethyl)-5-{[4-(trifluoromethyl)phenyl]sulfonyl}pyridine-2-carboxamide;
3-amino-N-(1-methylazetidin-3-yl)-5-{[4-(trifluoromethoxy)phenyl]sulfonyl}pyridine-2-carboxamide;
3-amino-5-{methyl[4-(trifluoromethyl)benzyl]sulfamoyl}-N-(3,3,3-trifluoro-2-hydroxypropyl)pyridine-2-carboxamide;
3-amino-5-{[4-(trifluoromethyl)phenyl]sulfonyl}-N-(3,3,3-trifluoropropyl)pyridine-2-carboxamide;
3-amino-5-{[2-fluoro-4-(trifluoromethyl)phenyl]sulfonyl}-N-[2-hydroxy-3-(2,2,2-trifluoroethoxy)propyl]pyridine-2-carboxamide;
3-amino-5-{[4-(trifluoromethoxy)phenyl]sulfonyl}-N-[3-(trifluoromethyl)oxetan-3-yl]pyridine-2-carboxamide;
3-amino-N-[(1S,2S)-2-hydroxycyclopentyl]-5-{[4-(trifluoromethyl)phenyl]sulfonyl}pyridine-2-carboxamide;
rac-3-amino-N-[(3R,4S)-4-hydroxytetrahydro-2H-pyran-3-yl]-5-{[4-(trifluoromethyl)phenyl]sulfonyl}pyridine-2-carboxamide;
3-amino-N-(2-hydroxyethyl)-5-{[4-(trifluoromethyl)phenyl]sulfonyl}pyridine-2-carboxamide;
rac-3-amino-5-{[2-fluoro-4-(trifluoromethyl)phenyl]sulfonyl}-N-[(3R,4S)-4-hydroxytetrahydro-2H-pyran-3-yl]pyridine-2-carboxamide;
3-amino-5-{[2-fluoro-4-(trifluoromethyl)phenyl]sulfonyl}-N-(2-hydroxyethyl)pyridine-2-carboxamide;
3-amino-5-[(4-methoxyphenyl)sulfonyl]-N-(3,3,3-trifluoro-2-hydroxypropyl)pyridine-2-carboxamide;
3-amino-N-[2-hydroxy-3-(2-methoxyethoxy)propyl]-5-{[4-(trifluoromethyl)phenyl]sulfonyl}pyridine-2-carboxamide;
3-amino-N-(3-methoxypropyl)-5-{[4-(trifluoromethyl)phenyl]sulfonyl}pyridine-2-carboxamide;
3-amino-N-(cyclopropylmethyl)-5-{[4-(trifluoromethyl)phenyl]sulfonyl}pyridine-2-carboxamide;
3-amino-N-(3-tert-butoxy-2-hydroxypropyl)-5-{[2-fluoro-4-(trifluoromethyl)phenyl]sulfonyl}pyridine-2-carboxamide;
3-amino-5-[methyl(3,3,3-trifluoropropyl)sulfamoyl]-N-(3,3,3-trifluoro-2-hydroxypropyl)pyridine-2-carboxamide;
(3-amino-5-{[4-(trifluoromethyl)phenyl]sulfonyl}pyridin-2-yl)[(2S)-2-(hydroxymethyl)pyrrolidin-1-yl]methanone;
3-amino-N-(1-hydroxy-2-methylpropan-2-yl)-5-{[4-(trifluoromethyl)phenyl]sulfonyl}pyridine-2-carboxamide;
3-amino-N-[(1-hydroxycyclopropyl)methyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)[(3R,4R)-3,4-dihydroxypyrrolidin-1-yl]methanone;
3-amino-N-[(4-hydroxy-1-methylpiperidin-4-yl)methyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)[3-(2,2-difluoroethoxy)azetidin-1-yl]methanone;
(3-amino-5-{[4-(trifluoromethyl)phenyl]sulfonyl}pyridin-2-yl)[3-(methoxymethyl)-3-methylazetidin-1-yl]methanone;
(3-amino-5-{[4-(trifluoromethyl)phenyl]sulfonyl}pyridin-2-yl)[(2R)-2-(hydroxymethyl)pyrrolidin-1-yl]methanone;
3-amino-N-[(2S)-1-hydroxybutan-2-yl]-5-{[4-(trifluoromethyl)phenyl]sulfonyl}pyridine-2-carboxamide;
3-amino-N-[(3R,4S)-4-hydroxytetrahydro-2H-pyran-3-yl]-5-{[4-(trifluoromethyl)phenyl]sulfonyl}pyridine-2-carboxamide;

3-amino-N-(3,3,3-trifluoro-2-hydroxypropyl)-5-{[3-(trifluoromethoxy)phenyl]sulfonyl}pyridine-2-carboxamide;

3-amino-5-{[4-(propan-2-yloxy)phenyl]sulfonyl}-N-(3,3,3-trifluoro-2-hydroxypropyl)pyridine-2-carboxamide;

3-amino-5-[(tetrahydrofuran-2-ylmethyl)sulfonyl]-N-(3,3,3-trifluoro-2-hydroxypropyl)pyridine-2-carboxamide;

3-amino-N-(2-hydroxy-3-methoxypropyl)-5-{[4-(trifluoromethyl)phenyl]sulfonyl}pyridine-2-carboxamide;

3-amino-N-[2-(trifluoromethoxy)ethyl]-5-{[4-(trifluoromethyl)phenyl]sulfonyl}pyridine-2-carboxamide;

3-amino-N-(2,2-difluoro-3-hydroxypropyl)-5-{[4-(trifluoromethyl)phenyl]sulfonyl}pyridine-2-carboxamide;

3-amino-N-[(2S)-3-(cyclopropylmethoxy)-2-hydroxypropyl]-5-{[4-(trifluoromethoxy)phenyl]sulfonyl}pyridine-2-carboxamide;

3-amino-N-[(2S)-2-hydroxy-3-(propan-2-yloxy)propyl]-5-{[4-(trifluoromethyl)phenyl]sulfonyl}pyridine-2-carboxamide;

3-amino-5-(phenyl sulfonyl)-N-(3,3,3-trifluoro-2-hydroxypropyl)pyridine-2-carboxamide;

3-amino-5-[(4-methylphenyl)sulfonyl]-N-(3,3,3-trifluoro-2-hydroxypropyl)pyridine-2-carboxamide;

3-amino-5-{[4-(propan-2-yl)phenyl]sulfonyl}-N-(3,3,3-trifluoro-2-hydroxypropyl)pyridine-2-carboxamide;

3-amino-5-[(4-tert-butylphenyl)sulfonyl]-N-(3,3,3-trifluoro-2-hydroxypropyl)pyridine-2-carboxamide;

3-amino-N-[(2R)-2-hydroxy-3-(2,2,2-trifluoroethoxy)propyl]-5-{[4-(trifluoromethyl)phenyl]sulfonyl}pyridine-2-carboxamide;

3-amino-N-[(2S)-2-hydroxy-3-(2,2,2-trifluoroethoxy)propyl]-5-{[4-(trifluoromethyl)phenyl]sulfonyl}pyridine-2-carboxamide;

3-amino-6-bromo-5-[(4-fluorophenyl)sulfonyl]-N-[(2R)-3,3,3-trifluoro-2-hydroxypropyl]pyridine-2-carboxamide;

3-amino-N-[(2R)-3-(cyclopropylmethoxy)-2-hydroxypropyl]-5-{[4-(trifluoromethoxy)phenyl]sulfonyl}pyridine-2-carboxamide;

3-amino-N-[(2R)-2-hydroxy-3-(propan-2-yloxy)propyl]-5-{[4-(trifluoromethyl)phenyl]sulfonyl}pyridine-2-carboxamide;

3-amino-5-(phenylsulfonyl)-N-[(2R)-3,3,3-trifluoro-2-hydroxypropyl]pyridine-2-carboxamide;

3-amino-5-[(3-fluorophenyl)sulfonyl]-N-[(2R)-3,3,3-trifluoro-2-hydroxypropyl]pyridine-2-carboxamide;

[3-amino-5-(phenylsulfonyl)pyridin-2-yl][3-hydroxy-3-(trifluoromethyl)azetidin-1-yl]methanone;

{3-amino-5-[(3-fluorophenyl)sulfonyl]pyridin-2-yl}[3-hydroxy-3-(trifluoromethyl)azetidin-1-yl]methanone;

3-amino-N-[(3S,4R)-4-hydroxytetrahydro-2H-pyran-3-yl]-5-{[4-(trifluoromethyl)phenyl]sulfonyl}pyridine-2-carboxamide;

3-amino-6-cyclopropyl-N-(2-hydroxyethyl)-5-{[4-(trifluoromethyl)phenyl]sulfonyl}pyridine-2-carboxamide;

3-amino-6-(4-fluorophenyl)-5-[(4-fluorophenyl)sulfonyl]-N-[(2R)-3,3,3-trifluoro-2-hydroxypropyl]pyridine-2-carboxamide;

3-amino-6-cyclopropyl-N-(2-hydroxyethyl)-5-(phenylsulfonyl)pyridine-2-carboxamide;

3-amino-5-(cyclopentylsulfonyl)-6-(4-fluorophenyl)-N-[(2S)-2-hydroxypropyl]pyridine-2-carboxamide;

3-amino-6-(4-fluorophenyl)-5-[(2-hydroxyethyl)sulfonyl]-N-[(2S)-2-hydroxypropyl]pyridine-2-carboxamide;

3-amino-5-(ethyl sulfonyl)-6-(4-fluorophenyl)-N-[(2S)-2-hydroxypropyl]pyridine-2-carboxamide;

3-amino-6-(4-fluorophenyl)-N-[(2S)-2-hydroxypropyl]-5-(propan-2-ylsulfonyl)pyridine-2-carboxamide;

3-amino-6-(4-fluorophenyl)-N-[(2S)-2-hydroxypropyl]-5-[(2-methoxyethyl)sulfonyl]pyridine-2-carboxamide;

3-amino-N-[(2S)-2-hydroxypropyl]-5-{[(2S)-2-methylpyrrolidin-1-yl]sulfonyl}pyridine-2-carboxamide;

3-amino-5-[(4-fluorobenzyl)sulfamoyl]-N-[(2S)-2-hydroxypropyl]pyridine-2-carboxamide;

3-amino-5-{[2-(hydroxymethyl)pyrrolidin-1-yl]sulfonyl}-N-[(2S)-2-hydroxypropyl]pyridine-2-carboxamide;

3-amino-5-[(4-fluorobenzyl)(methyl)sulfamoyl]-N-[(2S)-2-hydroxypropyl]pyridine-2-carboxamide;

3-amino-5-{[(2S)-2-methylpyrrolidin-1-yl]sulfonyl}-N-[2-oxo-2-(propan-2-ylamino)ethyl]pyridine-2-carboxamide;

1-[(3-amino-5-{[(2S)-2-methylpyrrolidin-1-yl]sulfonyl}pyridin-2-yl)carbonyl]azetidine-3-carboxamide;

(3-amino-5-{[(2S)-2-methylpyrrolidin-1-yl]sulfonyl}pyridin-2-yl)(3-hydroxyazetidin-1-yl)methanone;

3-amino-N-(3-fluoro-2-hydroxypropyl)-5-{[4-(trifluoromethoxy)phenyl]sulfonyl}pyridine-2-carboxamide;

3-amino-6-cyclopropyl-5-[(4-fluorophenyl)sulfonyl]-N-[(2S)-2-hydroxypropyl]pyridine-2-carboxamide;

3-amino-6-cyclopropyl-5-(ethylsulfonyl)-N-[(2S)-2-hydroxypropyl]pyridine-2-carboxamide;

3-amino-N-(2-hydroxy-3-methoxypropyl)-5-{[(2S)-2-methylpyrrolidin-1-yl]sulfonyl}pyridine-2-carboxamide;

3-amino-N-[(2S)-2-hydroxypropyl]-5-[(2-methoxyethyl)(methyl)sulfamoyl]pyridine-2-carboxamide;

3-amino-5-[cyclobutyl(methyl)sulfamoyl]-N-[(2S)-2-hydroxypropyl]pyridine-2-carboxamide;

3-amino-N-(3,3-difluoro-2-hydroxypropyl)-5-{[4-(trifluoromethoxy)phenyl]sulfonyl}pyridine-2-carboxamide;

3-amino-N-[(2S)-2-hydroxypropyl]-6-methoxy-5-{[4-(trifluoromethoxy)phenyl]sulfonyl}pyridine-2-carboxamide;

3-amino-N-[(4-methoxypyrimidin-2-yl)methyl]-5-{[(2S)-2-methylpyrrolidin-1-yl]sulfonyl}pyridine-2-carboxamide;

3-amino-5-{[(2S)-2-methylpyrrolidin-1-yl]sulfonyl}-N-[(6-oxo-1,6-dihydropyrimidin-2-yl)methyl]pyridine-2-carboxamide;

3-amino-6-(dimethylamino)-N-[(2S)-2-hydroxypropyl]-5-{[4-(trifluoromethoxy)phenyl]sulfonyl}pyridine-2-carboxamide;

3-amino-6-(3-fluorophenoxy)-N-[(2S)-2-hydroxypropyl]-5-{[4-(trifluoromethoxy)phenyl]sulfonyl}pyridine-2-carboxamide;

3-amino-6-(cyclopropylamino)-N-[(2S)-2-hydroxypropyl]-5-{[4-(trifluoromethoxy)phenyl]sulfonyl}pyridine-2-carboxamide;

3-amino-N-(methoxyacetyl)-5-{[4-(trifluoromethoxy)phenyl]sulfonyl}pyridine-2-carbohydrazide;

3-amino-N-(hydroxyacetyl)-5-{[4-(trifluoromethoxy)phenyl]sulfonyl}pyridine-2-carbohydrazide;

3-amino-N-[(2S)-2-hydroxypropyl]-6-(2-methoxyethoxy)-5-{[4-(trifluoromethoxy)phenyl]sulfonyl}pyridine-2-carboxamide;

3-amino-6-[2-(dimethylamino)ethoxy]-N-[(2S)-2-hydroxypropyl]-5-{[4-(trifluoromethoxy)phenyl]sulfonyl}pyridine-2-carboxamide;
3-amino-6-cyclopropyl-N-[(2S)-2-hydroxypropyl]-5-{[4-(trifluoromethoxy)phenyl]sulfonyl}pyridine-2-carboxamide;
3-amino-N-(1H-pyrazol-3-yl)-5-{[4-(trifluoromethoxy)phenyl]sulfonyl}pyridine-2-carboxamide;
3-amino-N-[1-(hydroxymethyl)cyclopropyl]-5-{[4-(trifluoromethyl)phenyl]sulfonyl}pyridine-2-carboxamide;
3-amino-N-[(1S,2S)-2-methoxycyclopentyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)(3-fluoro-3-methylazetidin-1-yl)methanone;
(3-amino-5-{[4-(trifluoromethyl)phenyl]sulfonyl}pyridin-2-yl)(6-oxa-2-azaspiro[3.5]non-2-yl)methanone;
3-amino-N-[(2R)-2-hydroxy-3-methoxypropyl]-5-(phenylsulfonyl)pyridine-2-carboxamide;
3-amino-5-{[4-(trifluoromethoxy)phenyl]sulfonyl}pyridine-2-carboxamide; and
3-amino-6-bromo-5-[(4-fluorophenyl)sulfonyl]pyridine-2-carboxamide.

35. A pharmaceutical composition comprising a therapeutically effective amount of a compound of Formula I according to claim 1, or a pharmaceutically acceptable salt thereof, in combination with a pharmaceutically acceptable carrier.

36. A compound of claim 1 or a pharmaceutically acceptable salt thereof, or a pharmaceutical composition of claim 34, for use in medicine.

37. A compound of claim 1 or a pharmaceutically acceptable salt thereof, or a pharmaceutical composition of claim 34, for use in treatment of cystic fibrosis.

38. A method for treating cystic fibrosis in a subject comprising administering a therapeutically effective amount of a compound of Formula I according to claim 1, or a pharmaceutically acceptable salt thereof, to a subject in need thereof.

39. A pharmaceutical composition comprising a compound of claim 1, or a pharmaceutically acceptable salt thereof, and one or more correctors.

40. A method for treating cystic fibrosis in a subject comprising administering a compound of claim 1 or a pharmaceutically acceptable salt thereof, and one or more correctors, to a subject in need thereof.

41. A pharmaceutical composition comprising a compound of claim 1 or a pharmaceutically acceptable salt thereof, and one or more additional therapeutic agents.

42. The pharmaceutical composition of claim 41 wherein the additional therapeutic agents are selected from the group consisting of CFTR modulators and CFTR amplifiers.

43. The pharmaceutical composition of claim 41 wherein the additional therapeutic agents are CFTR modulators.

44. A method for treating cystic fibrosis in a subject comprising administering a compound of claim 1 or a pharmaceutically acceptable salt thereof, and one or more additional therapeutic agents.

45. The method of claim 44 wherein the additional therapeutic agents are selected from the group consisting of CFTR modulators and CFTR amplifiers.

46. The method of claim 44 the wherein the additional therapeutic agents are CFTR modulators.

47. 3-amino-N-[(2S)-2-hydroxypropyl]-5-{[4-(trifluoromethoxy)phenyl]sulfonyl}pyridine-2-carboxamide or a pharmaceutically acceptable salt thereof.

* * * * *